US011193127B2

(12) United States Patent
Terns et al.

(10) Patent No.: US 11,193,127 B2
(45) Date of Patent: Dec. 7, 2021

(54) METHODS FOR CLEAVING DNA AND RNA MOLECULES

(71) Applicant: UNIVERSITY OF GEORGIA RESEARCH FOUNDATION, INC., Athens, GA (US)

(72) Inventors: Rebecca M. Terns, Athens, GA (US); Michael P. Terns, Athens, GA (US); Joshua R. Elmore, Knoxville, TN (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 58 days.

(21) Appl. No.: 16/065,236

(22) PCT Filed: Jan. 6, 2017

(86) PCT No.: PCT/US2017/012443
§ 371 (c)(1),
(2) Date: Jun. 22, 2018

(87) PCT Pub. No.: WO2017/120410
PCT Pub. Date: Jul. 13, 2017

(65) Prior Publication Data
US 2019/0161753 A1  May 30, 2019

Related U.S. Application Data

(60) Provisional application No. 62/276,526, filed on Jan. 8, 2016.

(51) Int. Cl.
| *C12N 9/22* | (2006.01) |
|---|---|
| *C12N 15/113* | (2010.01) |
| *C12N 15/11* | (2006.01) |
| *C12N 1/20* | (2006.01) |
| *C12Q 1/6806* | (2018.01) |
| *C12Q 1/686* | (2018.01) |
| *C07K 14/195* | (2006.01) |

(52) U.S. Cl.
CPC .............. *C12N 15/113* (2013.01); *C12N 1/20* (2013.01); *C12N 9/22* (2013.01); *C12N 15/111* (2013.01); *C07K 14/195* (2013.01); *C12N 2310/10* (2013.01); *C12N 2310/20* (2017.05); *C12N 2510/00* (2013.01); *C12Q 1/686* (2013.01); *C12Q 1/6806* (2013.01)

(58) Field of Classification Search
CPC ............................ C12N 9/22; C12N 2310/20
See application file for complete search history.

(56) References Cited

U.S. PATENT DOCUMENTS 8,546,553 B2  10/2013  Terns et al.
9,404,098 B2  8/2016  Terns et al.
9,422,553 B2  8/2016  Terns et al.

FOREIGN PATENT DOCUMENTS

| WO | WO 2010/011961 A2 | 1/2010 |
| WO | WO 2012/164565 A1 | 12/2012 |
| WO | WO 2017/120410 A1 | 7/2017 |

OTHER PUBLICATIONS

Benda Christian et al.: "Structural Model of a CRISPR RNA-Silencing Complex Reveals the RNA-Target Cleavage Activity in Cmr4", Molecular Cell, vol. 56, No. 1,Oct. 2, 2014 (Oct. 2, 2014), pp. 43-54 (Year: 2014).*
Cocozaki et al., Structure. Mar. 7, 2012; 20(3): 545-553 (Year: 2012).*
Hale et al., Cell. Nov. 25, 2009; 139(5): 945-956 (Year: 2009).*
International Application No. PCT/US2017/012443, filed Jan. 6, 2017; International Search Report and Written Opinion issued dated Mar. 27, 2017; 15 pages.
International Application No. PCT/US2017/012443, filed Jan. 6, 2017; International Preliminary Report on Patentability dated Jul. 19, 2018; 9 pages.
Almendros et al., "Target motifs affecting natural immunity by a constitutive CRISPR-Cas system in *Escherichia coli*" PloS One, 2012; 7(11):e50797. Epub Nov. 26, 2012.
Anantharaman et al., "Presence of a classical RRM-fold palm domain in Thg1-type 3'-5'nucleic acid polymerases and the origin of the GGDEF and CRISPR polymerase domains" Biol Direct, Jun. 30, 2010; 5:43.
Barrangou et al., "CRISPR-Cas systems: Prokaryotes upgrade to adaptive immunity" Mol Cell, Apr. 24, 2014; 54(2): 234-44.
Benda et al., "Structural model of a CRISPR RNA-silencing complex reveals the RNA-target cleavage activity in Cmr4" Molecular Cell, Oct. 2, 2014; 56(1):43-54.
Bolotin et al., "Clustered regularly interspaced short palindrome repeats (CRISPRs) have spacers of extrachromosomal origin" Microbiology, Aug. 2005; 151(Pt 8):2551-61.
Bowie et al., "Deciphering the Message in Protein Sequences: Tolerance to Amino Acid Substitutions" *Science*, 1990; 247:1306-1310.
Carte et al., "Binding and cleavage of CRISPR RNA by Cas6" RNA, Nov. 2010;16(11):2181-8.
Cocozaki et al., "Structure of the Cmr2 subunit of the CRISPR-Cas RNA silencing complex" Structure, Jan. 15, 2012; 20(3):545-53.

(Continued)

*Primary Examiner* — Antonio Galisteo Gonzalez
(74) *Attorney, Agent, or Firm* — Mueting Raasch Group

(57) ABSTRACT

Provided herein is a programmable RNA-activated DNA endonuclease activity associated with a Cmr complex. In one embodiment, the enzyme is a general double-stranded DNA endonuclease. Also provided is a programmable RNA endonuclease activity associated with a Cmr complex. In one embodiment, a Cmr2 protein present in a Cmr complex includes a mutation that reduces RNA-activated DNAse activity of the Cmr complex. In one embodiment, a Cmr4 protein present in a Cmr complex includes a mutation that reduces the RNase activity of the Cmr complex. Compositions including components of a Cmr complex and a CRISPR-RNA, and an optional activating RNA, are provided. Also provided are methods for using the compositions, and genetically engineered cells that include components of a Cmr complex and a CRISPR-RNA, and an optional activating RNA.

9 Claims, 23 Drawing Sheets
Specification includes a Sequence Listing.

(56) References Cited

OTHER PUBLICATIONS

Crooks et al., "WebLogo: a sequence logo generator" Genome Res, Jun. 2004; 14(6):1188-90.
Deng et al., "A novel interference mechanism by a type IIIB CRISPR-Cmr module in Sulfolobus" Molecular Microbiology, Feb. 3, 2013; 87(5): 1088-99.
Elmore et al., "Programmable plasmid interference by the CRISPR-Cas system in Thermococcus kodakarensis" RNA Biology, May 2013; 10(5):828-40. Epub Mar. 27, 2013.
Elmore et al., "DNA targeting by the Type 1-G and Type I-A CRISPR-Cas systems of Pyrococcus furiosus" Nucleic Acids Res, Dec. 2, 2015; 43(21): 10353-63. Epub Oct. 30, 2015.
Elmore et al., "Bipartite recognition of target RNAs activates DNA cleavage by the Type III-B CRISPR-Cas system" Genes Dev, Feb. 15, 2016; 30(4):447-59. Epub Feb. 4, 2016.
Elmore et al., Supplementary Material For "Bipartite recognition of target RNAs activates DNA cleavage by the Type III-B CRISPR-Cas system" Genes Dev, Feb. 15, 2016; 30(4):447-59. 19 pages.
Estrella et al., "RNA-activated DNA cleavage by the Type III-B CRISPR-Cas effector complex" Genes Dev, Feb. 4, 2016; 30(4):460-70.
Farkas et al., "Defining components of the chromosomal origin of replication of the hyperthermophilic archaeon Pyrococcus furiosus needed for construction of a stable replicating shuttle vector" Applied Environ Microbiol, Sep. 2011; 77(18):6343-9.
Farkas et al., "Recombinogenic Properties of Pyrococcus furiosus Strain COM1 Enable Rapid Selection of Targeted Mutants" *Appl Environ Microb*, Jul. 2012; 78(13):4669-76.
Fischer et al., "An archaeal immune system can detect multiple protospacer adjacent motifs (PAMs) to target invader DNA" J Biol Chem, Sep. 28, 2012; 287(40): 33351-63.
Garrett et al., "Archaeal CRISPR-based immune systems: exchangeable functional modules" Trends Microbiol, Nov. 2011; 19(11):549-56, Epub Sep. 22, 2011.
Glazer et al., "Energy-transfer fluorescent reagents for DNA analyses" Curr Opin Biotechnol, Feb. 1997; 8(1):94-102.
Goldberg et al., "Conditional tolerance of temperate phages via transcription-dependent CRISPR-Cas targeting" Nature. Oct. 30, 2014; 514(7524):633-7. Epub Aug. 31, 2014.
Haft et al., "A guild of 45 CRISPR-associated (Cas) protein families and multiple CRISPR/Cas subtypes exist in prokaryotic genomes." *PLoS Computational Biology*, Nov. 2005, 1(6)e60:0474-83.
Hale et al., "Prokaryotic silencing (psi) RNAs in Pyrococcus furiosus", *RNA* (New York, NY), Dec. 2008, 14(12):2572-2579.
Hale et al., "RNA-Guided RNA Cleavage by a CRISPR RNA-Cas Protein Complex" *Cell*, 2009; 139:945-956.
Hale et al., "Essential features and rational design of CRISPR RNAs that function with the Cas RAMP module complex to cleave RNAs" Mol Cell, Feb. 10, 2012; 45(3):292-302.
Hale et al., "Target RNA capture and cleavage by the Cmr type III-B CRISPR-Cas effector complex" Genes Dev, Nov. 1, 2014; 28(21):2432-43.
Hatoum-Aslan et al., "Genetic characterization of antiplasmid immunity through a type III-A CRISPR-Cas system" J Bacteriol, Jan. 2014; 196(2):310-7. Epub Nov. 1, 2013.
Hochstrasser et al., "CasA mediates Cas3-catalyzed target degradation during CRISPR RNA-guided interference" Proc Natl Acad Sci USA, May 6, 2014; 111(18):6618-23. Epub Apr. 18, 2014.
Jackson et al., "A Conserved Structural Chassis for Mounting Versatile CRISPR RNA-Guided Immune Responses" Mol Cell, Jun. 4, 2015; 58(5):722-8. Epub May 28, 2015.
Jinek et al., "A programmable dual-RNA-guided DNA endonuclease in adaptive bacterial immunity" Science, Aug. 17, 2012; 337(6096):816-21.
Jung et al., "Crystal Structure of the Csm1 Subunit of the Csm Complex and Its Single-Stranded DNA-Specific Nuclease Activity" Structure, Apr. 7, 2015; 23(4):782-90, Epub Mar. 12, 2015.
Kunin et al., "Evolutionary conservation of sequence and secondary structures in CRISPR repeats" Genome Biol., 2007; 8(4) Article R61. R61.1-R61.7.
Labrie et al., "Bacteriophage resistance mechanisms" Nat Rev Microbiol, May 2010; 8(5):317-27. Epub Mar. 29, 2010.
Li et al., "Harnessing Type I and Type III CRISPR-Cas Systems for Genome Editing" Nucleic Acids Research, Oct. 13, 2015; 44(4):e34-e34.
Lipscomb et al., "Natural Competence in the Hyperthermophilic Archaeon Pyrococcus furiosus, Facilitates Genetic Manipulation: Construction of Markerless Deletions of Genes Encoding the Two Cytoplasmic Hydrogenases," Appl. Environ Microbiol., Apr. 2011;77(7):2232-2238.
Majumdar et al., "Three CRISPR-Cas immune effector complexes coexist in Pyrococcus furiosus" RNA, Jun. 2015; 21(6): 1147-58. Epub Apr. 22, 2015.
Makarova et al. "A DNA repair system specific for thermophilic Archaea and bacteria predicted by genomic contest analysis" 2002. *Nucleic Acids Res.* 30(2):482-496.
Makarova et al., "A putative RNA-interference-based immune system in prokaryotes: computational analysis of the predicted enzymatic machinery, functional analogies with eukaryotic RNAi, and hypothetical mechanisms of action" Biology direct 2006; 1: 7.
Makarova et al., "Evolution and classification of the CRISPR-Cas systems" Nat Rev Microbiol, Jun. 2011; 9(6):467-77, Epub May 9, 2011.
Makarova and Koonin, "Evolution and Classification of CRISPR-Cas Systems and Cas Protein Families" in CRISPR-Cas Systems. Barrangou and van der Oost (Eds.) Springer: Berlin, Heidelberg; 2013, Cover page, publisher's page. and pp. 61-91.
Makarova et al., "CARF and WYL domains: ligand-binding regulators of prokaryotic defense systems" Front Genet, Apr. 30, 2014; 5:102, eCollection 2014.
Makarova et al., "An updated evolutionary classification of CRISPR-Cas systems" Nature Rev Microbiol, Nov. 2015; 13:722-36.
Marmur et al., "Determination of the base composition of deoxyribonucleic acid from its thermal denaturation temperature" J Mol Biol, Jul. 1962; 5:109-18.
Marraffini et al., "Self versus non-self discrimination during CRISPR RNA-directed immunity" Nature, Jan. 28, 2010; 463(7280):568-71, Epub Jan. 13, 2010.
Mojica et al., "Intervening Sequences of Regularly Spaced Prokaryotic Repeats Derive from Foreign Genetic Elements" *Mol. Evol.*, 2005; 60:174-182.
Mojica et al., "Short motif sequences determine the targets of the prokaryotic CRISPR defence system" Microbiology, Mar. 2009; 15 5(Pt 3):733-40.
Osawa et al., "Crystal structure of the Cmr2-Cmr3 subcomplex in the CRISPR-Cas RNA silencing effector complex" J Mol Biol, Oct. 23, 2013; 425(20):3 811-23. Epub Apr. 10, 2013.
Osawa et al., "Crystal Structure of the CRISPR-Cas RNA Silencing Cmr Complex Bound to a Target Analog" Molecular Cell, 2015; 58: 418-430.
Park et al., "Crystal structure of Cmr5 from Pyrococcus furiosus and its functional implications" FEBS Lett, Mar. 18, 2013; 587(6):562-8, Epub Jan. 28, 2013.
Plagens et al., "In vitro assembly and activity of an archaeal CRISPR-Cas type I-A Cascade interference complex" Nucleic Acids Res, Apr. 2014; 42(8):5125-38. Epub Feb. 5, 2014.
Pourcel et al., "CRISPR elements in Yersinia pestis acquire new repeats by preferential uptake of bacteriophage DNA, and provide additional tools for evolutionary studies" Microbiol, 2005; 151:653-663.
Ramia et al., "Essential structural and functional roles of the Cmr4 subunit in RNA cleavage by the Cmr CRISPR-Cas complex" Cell Reports, Dec. 4, 2014; 9(5): 1610-17.
Ramia et al., "Staphylococcus epidermidis Csm1 is a 3'-5' exonuclease" Nucleic Acids Res, Jan. 2014; 42(2): 1129-38, Epub Oct. 10, 2013.
Rollins et al., "Mechanism of foreign DNA recognition by a CRISPR RNA-guided surveillance complex from Pseudomonas aeruginosa" Nucleic Acids Res, Feb. 27, 2015; 43(4):2216-22, Epub Feb. 8, 2015.

(56) References Cited

OTHER PUBLICATIONS

Samai et al., "Co-transcriptional DNA and RNA Cleavage during Type III CRISPR-Cas Immunity" Cell, May 21, 2015; 161(5): 1164-74, Epub May 7, 2015.
Samson et al., "Revenge of the phages: defeating bacterial defences" Nat Rev Microbiol, Oct. 2013; 11(10):675-87. Epub Aug. 27, 2013.
Schneider et al., "Sequence logos: a new way to display consensus sequences" Nucleic Acids Res, Oct. 25, 1990; 18(20):6097-100.
Shah et al., "Protospacer recognition motifs: mixed identities and functional diversity" RNA Biology, May 2013; 10(5):891-9. Epub Feb. 12, 2013.
Shao et al., "Structure of the Cmr2-Cmr3 subcomplex of the Cmr RNA silencing complex" Structure, Mar. 5, 2013; 21(3):376-84, Epub Feb. 7, 2013.
Sinkunas et al., "In vitro reconstitution of Cascade-mediated CRISPR immunity in Streptococcus thermophilus" EMBO J, Feb. 6, 2013; 32(3): 385-94. Epub Jan. 18, 2013.
Spilman et al., "Structure of an RNA silencing complex of the CRISPR-Cas immune system" Mol Cell, Oct. 10, 2013; 52(1): 146-52.
Spoel et al., "How do plants achieve immunity? Defence without specialized immune cells" Nat Rev Immunol, Jan. 25, 2012; 12(2):89-100.
Staals et al., "Structure and activity of the RNA-targeting Type III-B CRISPR-Cas complex of Thermus thermophilus" Mol Cell, Oct. 10, 2013; 52(1):135-45.
Staals et al., "RNA targeting by the type III-A CRISPR-Cas Csm complex of Thermus thermophilus" Mol Cell, Nov. 20, 2014; 56(4):518-30, Epub Nov. 6, 2014.
Sun et al., "Crystal structure and CRISPR RNA-binding site of the Cmr1 subunit of the Cmr interference complex" Acta Crystallogr D Biol Crystallogr, Feb. 2014; 70(Pt 2):535-43, Epub Jan. 31, 2014.
Tamulaitis et al., "Programmable RNA shredding by the type III-A CRISPR-Cas system of Streptococcus thermophilus" Mol Cell, Nov. 20, 2014; 56(4):506-17. Epub Nov. 6, 2014.
Tatusov et al. "A Genomic Perspective on Protein Families" Science. Oct. 24, 1997; 278:631-7.
Tatusov et al. "The COG database: an updated version includes eukaryotes" BMC Bioinformatics. 2003; 4(1):41. 14 pages.
Tatusova et al., "BLAST 2 Sequences, a new tool for comparing protein and nucleotide sequences," FEMS Microbiol Lett, 1999;174:247-250.
Taylor et al., "Structures of the CRISPR-Cmr complex reveal mode of RNA target positioning" Science, May 1, 2015; 348(6234):581-5, Epub Apr. 2, 2015.
Terns et al., "The RNA- and DNA-targeting CRISPR-Cas immune systems of Pyrococcus furiosus" Biochemical Society Transactions, 2013; 41(6): 1416-1421.
Terns et al., "CRISPR-based technologies: prokaryotic defense weapons repurposed" Trends Genet. Mar. 2014;30(3):111-8, Epub Feb. 18, 2014.
Tyagi et al., "Multicolor molecular beacons for allele discrimination" Nat Biotechnol, Jan. 1998; 16(1):49-53.
Van der Oost et al., "Unravelling the structural and mechanistic basis of CRISPR-Cas systems" Nat Rev Microbiol, Jul. 2014; 12(7):479-92, Epub Jun. 9, 2014.
Vestergaard et al., "CRISPR adaptive immune systems of Archaea" RNA Biol, 2014; 11(2):156-67. Epub Feb. 7, 2014.
Wang et al., "Interaction of the Cas6 riboendonuclease with CRISPR RNAs: recognition and cleavage" Structure, Feb. 9, 2011; 19(2):257-64.
Westra et al., "CRISPR immunity relies on the consecutive binding and degradation of negatively supercoiled invader DNA by Cascade and Cas3" Mol Cell, Jun. 8, 2012; 46(5):595-605, Epub Apr. 19, 2012.
Westra et al., "Type I-E CRISPR-cas systems discriminate target from non-target DNA through base pairing-independent PAM recognition" PLoS Genetics, 2013; 9(9):e1003742, Epub Sep. 5, 2013.
Wiedenheft et al., "Structures of the RNA-guided surveillance complex from a bacterial immune system" Nature, Sep. 21, 2011; 477(7365):486-9.
Zhang et al., "Structure and mechanism of the CMR complex for CRISPR-mediated antiviral immunity" Mol Cell, Feb. 10, 2012; 45(3):303-13, Epub Jan. 5, 2012.
Zhu et al., "Cmr4 is the slicer in the RNA-targeting Cmr CRISPR complex" Nucleic Acids Research, Dec. 24, 2014; 43(2): 1257-67.

\* cited by examiner

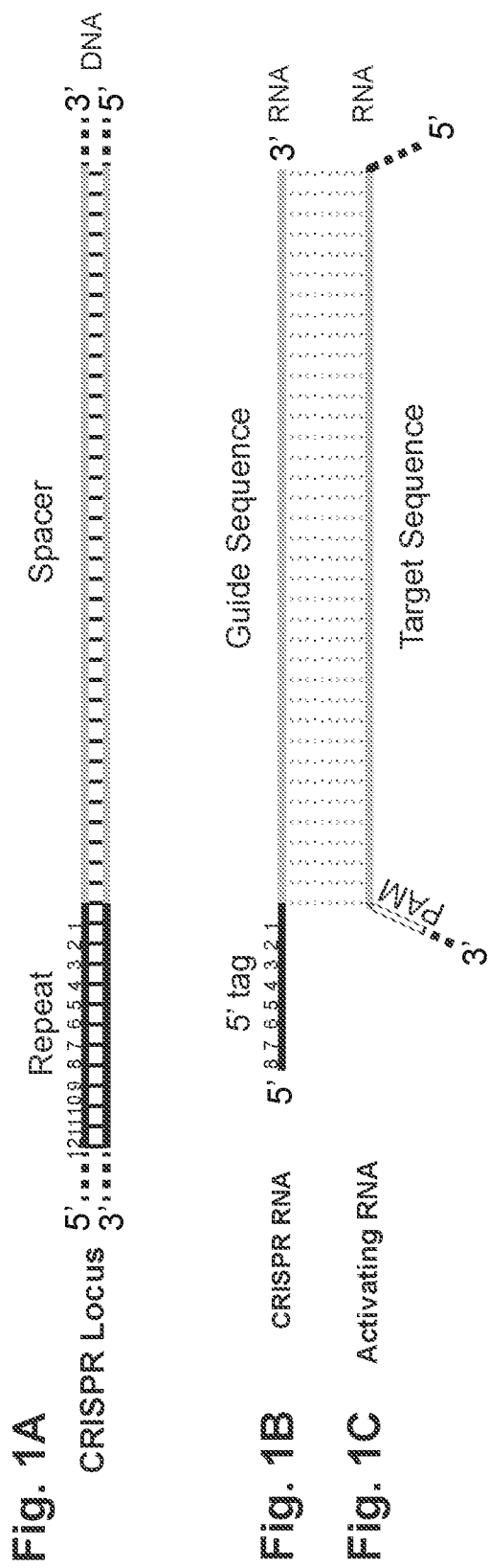

FIG. 2A

Pyrococcus furiosus Cmr (Type III-B) Gene and Protein Information
All information refers to COM1 strain Cmr genes/proteins (Bridger
et al., J Bacteriol. 2012, 194(15):4097-106).

Cmr1 - PFC_04870
GI: 397651632
Genome coordinates: 882853..883866
Open Reading Frame sequence:
>PFC_04870 (SEQ ID NO:7)
ATGTTTATTGAAGAATTTGAAATTGAGTTCATAACTCCAGCATTTATTAG
AGGTGCTGACCAGAGAATACCAGAAGTGAGAAGTCCTTCAATAAAGGGAG
CAATGAGATGGTGGTTCAGAGCTTTGGCTGGCTCATATTTTGGAGACGAT
GCTCAAAAACTTAAAGAAATAGAAAACCAAGTTTTTGGGAGCACAAAGGA
AAGAAGCAGAGTAAAAATTTCTGTTACACCGCTTAGTTCTCCAAAAAGAT
TAAACCTTAAAGAGTTTAAGGATAAAAATGTTGGGTACATCTGGTTTTCA
ATAAATCTGCTCGGAAAAGAGGGACTATAACTCACTATTATCCTCCTGG
GAGCAGATTTAGAGTAGTTCTAGAATCACCTAGCGAAAGGGTTATTAAGC
TGGCAACTTTATCTCTCTGGGCTCTTGTGAGCTTAGGTAGTGTTGGATTT
AGAAGTAGACGGGGAACAGGTTCAATGAAAATCGTTAGGGCAAGTAGCGA
AGTTCTGGAGGATTTGGGACTCACAACAGAATTCAATTCTATAGATGAAT
TTAAAGATTCTTTGAAAGGGTGTTAGATGTCACAGGCGAAATTTTAGGA
GTAAAAAATAGCGAAACTAATAAGTCCCTCCCTTCTTACGCTACTTTAAA
GTTTTCAGACGTTGAAGTATTTGGGCCAGGGAAGAATACTTGGGAGGTAT
TAGCTCAGTTCAACAACTCTTACAAGGAATACCTAAGGAGGAGAATTAAG
AAGTATCAAAGGATAATATTTGGATTGCCTCGATTTAAGCTTAGAGGCGT
GAGGAAAGACCTAAGGAGAGCTTCTCCCCTTTGGTTTGGCGTTGTAGAGA
TAGGCGGAAAGCCATATGGAAGGATAATCAAGTTCTTCCAATCTACATTT
CATCCAGAAGTAAGAAGCAAACATATAGTTGATTGGAACGTTCTTTCAAA
TTTTGATTGGTTTATATCCTCTAGACTTCCTGTGACTAAGGTGTGGGGTG
GTTGGAGTGGTTAA Protein sequence:
>PFC_04870 length=337 (SEQ ID NO:1)
MFIEEFEIEFITPAFIRGADQRIPEVRSPSIKGAMRWWFRALAGSYFGDD
AQKLKEIENQVFGSTKERSRVKISVTPLSSPKRLNLKEFKDKNVGYIWFS
INLLGKRGTITHYYPPGSRFVVLESPSERVIKLATLSLWALVSLGSVGF
RSRRGTGSMKIVRASSEVLEDLGLTTEFNSIDEFKDSLKRVLDVTGEILG
VKNSETNKSLPSYATLKFSDVEVFGPGKNTWEVLAQFNNSYKEYLRRRIK
KYQRIIFGLPRFKLRGVRKDLRRASPLWFGVVEIGGKPYGRIIKFFQSTF
HPEVRSKHIVDWNVLSNFDWFISSRLPVTKVWGGWSG Cmr2 - PFC_04865
GI: 397651631
Genome coordinates: 880245..882860
Open Reading Frame sequence:

FIG. 2B

\>PFC_04865 (SEQ ID NO:8)
GTGGTTAACATCAAAGAGAAACTTTTTGTATACCTTCATGATCCACCAGA
CAAGGCTCTAAAAATTGAAAATCATGAGGAAGGTCAAAAAGATATTAA
GTTCTGGCAATATCCAGTACTCGAGAACGGACAAAGTTAAACAAGCAGAT
GCACTTTCTTCTAAGACTCAGAGATTTATAATTCGAACAAAGGAAAATAA
AGAGCCAGTAATAGATTTTTTGGGTAGATCTTCAGGAAAGTACTTCCATG
TTGGATATCCTGTTTTTATACACCCCATATCCACAGAAATTAAGAGGTAT
GAAACACTTGAAAAGTACATAGACCTTGGCAGGAGTAATAGAGGGGAAAG
ATTTGTTAACGAGTTTTTGGAAAGGGTTTCAAAGCTTGAAGGCGATGTTC
TCAAAGAGGTCTTTGAAGATGCTAGTAACAAATTTAAAGGAGAAGAGAGT
AAACAGTGGGCCTACATCTGGCAGTTTTATCCCGTAAAACTCAAAGAAGG
AGTCAAGGAATTTGCCAAGTCAGAGTTAAAACTTAAGAGGAAGAAGCAG
AAAAGTTTGCAGAGGAATTTGTTAACCTCCCAGCTGATACAAGATTTCCA
GATCATGCAATTTGGACCCATTTAGACTTAACTTCCGCATTATCCGTTAA
GGATCCCACTTTGCTCAGGATCAAAATAGTTCCAGTTCAACCTTTTATTG
CCAATTCAAGAAAGCAGTTAGATCTCTGGGCCTCCAGTCATCTCCTTTCA
ATGCTTATGTATAAAGCTTTAGAGGTGATAGTGGACAAGTTCGGGCCAGA
ACATGTAATCTATCCATCTCTAAGGGATCAACCCTTCTTCTTGAAGTTCT
ACCTGGGGGAAAACATAGGTGATGAAATCTTAGTTGCAAACTTGCCTAAC
AAAGCGCTTGCAATAGTCTCAGGAAGGAGGCTGAAAAGATTGAAGAAGA
AATCAAGAAAGAATTAGGGATTTCCTACTCCAACTGTACAGAGAAGCTG
TTGATTGGGCAGTTGAAAATGGAGTAGTAAAAGTGGATAGAAGTGAAAAG
GATAGCATGCTCAAGGAAGCATATCTTAAAATTGTGAGGGAGTACTTCAC
CGTCTCGATAACCTGGGTATCTCTTTCCGAAAGGAGGATATCTATCAAG
TAACAGAGAACGCGGGTCTCTCGGATGAAGATGTTAAGAAGTGGCTAAAG
TTTGCAGAAAAGAAAGAAAATAGTAGAGTTCTCGAGAGGATTGCAATATA
CCCACTTTTGGTAAAGATATTGGATAGCCTGGGAGAGAGAAAAGTTACAG
AAGAAAGGTTCGAAAAAGCGAACAACTCAAAGGATGGAAGTGCCACGTT
TGTGGTGAGAATCTTGCAATTTTTGGAGACATGTACGATCACGATAATCT
TAAGAGTTTGTGGCTTGATGAGGAACCATTATGTCCCATGTGTTTGATAA
AAAGGTATTATCCAGTGTGGATTAGGAGTAAAACTGGACAGAAAATAAGG
TTTGAGTCGGTGGTAGATGTTGCACTTCTGTACAAGAACTGGAGGAAGAT
ATTTGACGAGAAGTATGGAAAAGACCTAGTCTCAAAGGCTAGGGAAGTTA
GTGAAGACTTCGTAAAGGACAATATGCTAGTAGATTCGGATCTATACTAT
TCTTCAACCTGGGAATCTGGACTTTCTAAAAAGCTCAAAAATAAGAAAGA
GATTGATGAGGAAAAAGTTAAGGAAGTTGTTGACTTCTTAAATGCGGCTT
ATAAAGAAATCGGTAATCCACCAAAGTACTATGCTATTCTAGTTATGGAT
GGCGACGATATGGGGAAAGTTATTTCAGGAGAGGTGCTTGGAGAAATATC
AACTAGAATTCATCCAAATATTAGGGATTACGTTGAAATTCCAGAAGCAA
AATATTACTCCACCCCGCAGGTTCACGTGGCTATAAGCCAAGCATTGGCT
AACTTTTCGATAAGGGAAGTTAGATCCGTAGTTAAAGACGAGGGATTGCT
AATATACGCTGGAGGGATGATGTCCTAGCAATTTGCCAGTCGACAAAG
CTTTAGAAGTTGCATATAAGATAAGGAAAGAATTTGGCAAGAGCTTTGAA
AATGGTTCTCTTCTCCCAGGTTGGAAGTTGAGTGCTGGAATTTTGATAGT
CCATTATAAGCATCCATTGTATGACGCCCTAGAAAAGGCAAGAGATCTTC
TCAATAATAAAGCAAAAAACGTTCCAGGAAAAGATACACTAGCTATAGGC

FIG. 2C

```
CTACTTAAGAGGAGTGGTTCCTACTATATCTCCCTAGTGGGATGGGAATT
AATTAGGGTCTTCTACAACTCAGAGCTGAGGAAAAAGCTATTGGAAGAGA
AAGGTGGAGTGGGAAAGAGGTTCATTTATCATGTGCTCAGAGAAGTTGAT
ACTTGGCCAAAAGTTGGAATAGACGAGATGCTTAAGTTTGAGGTGATTAG
ACATATCAGGGGAAGGAACAAAGAAGAAACTAAAGAGCTCAGAGAAAAGA
TCTATGGAGAAATAAAGGATCTTCTTGAGCATGTAAGAGGGAACAATGAA
GTTGAAAAAGTTAGAGGCTTATTCACATTTCTAAAAATAATCACGGACGC
GGAGGTGTTTCCATGA
```

Protein sequence:

>PFC_04865 length=871 (SEQ ID NO:2)
```
MVNIKEKLFVYLHDPPDKALKIENHEERSKKILSSGNIQYSRTDKVKQAD
ALSSKTQRFIIRTKENKEPVIDFLGRSSGKYFHVGYPVFIHPISTEIKRY
ETLEKYIDLGRSNRGERFVNEFLERVSKLEGDVLKEVFEDASNKFKGEES
KQWAYIWQFYPVKLKEGVKEFAKSELKLKEEEAEKFAEEFVNLPADTRFP
DHAIWTHLDLTSALSVKDPTLLRIKIVPVQPFIANSRKQLDLWASSHLLS
MLMYKALEVIVDKFGPEHVIYPSLRDQPFFLKFYLGENIGDEILVANLPN
KALAIVSGKEAEKIEEEIKKRIRDFLLQLYREAVDWAVENGVVKVDRSEK
DSMLKEAYLKIVREYFTVSITWVSLSEKEDIYQVTENAGLSDEDVKKWLK
FAEKKENSRVLERIAIYPLLVKILDSLGERKVTEERFEKSEQLKGWKCHV
CGENLAIFGDMYDHDNLKSLWLDEEPLCPMCLIKRYYPVWIRSKTGQKIR
FESVVDVALLYKNWRKIFDEKYGKDLVSKAREVSEDFVKDNMLVDSDLYY
SSTWESGLSKKLKNKKEIDEEKVKEVVDFLNAAYKEIGNPPKYYAILVMD
GDDMGKVISGEVLGEISTRIHPNIRDYVEIPEAKYYSTPQVHVAISQALA
NFSIREVRSVVKDEGLLIYAGGDDVLAILPVDKALEVAYKIRKEFGKSFE
NGSLLPGWKLSAGILIVHYKHPLYDALEKARDLLNNKAKNVPGKDTLAIG
LLKRSGSYYISLVGWELIRVFYNSELRKKLLEEKGGVGKRFIYHVLREVD
TWPKVGIDEMLKFEVIRHIRGRNKEETKELREKIYGEIKDLLEHVRGNNE
VEKVRGLFTFLKIITDAEVFP
```

Cmr3 - PFC_04860
GI:    397651630
Genome coordinates: 879280..880248
Open Reading Frame sequence:

>PFC_04860 (SEQ ID NO:9)
```
ATGATTGAGGTTACTTTTACTCCTTATGATGTCCTCTTATTTAGAGAAAG
TAGGCCTTTTGATGCAGGAAGTGAAAGTGTGGCAAGATCAATTATTCCTC
TTCCCCAAACAGTCGCTGGCGCTATAAGGACTCTTTTATTCTACAAAGGC
CTCAAGAATTGTGTTGGAGTGGGTGAGGAGGAACCCGAATTTACGTTAGT
TGGGATTGCAATTGGAACAGAGAAAGGCAGAATTTACCCCCTTCCCTTCA
ATATCATAAAAGCGAGAAATTCTACAAGTTGTCAACCCAGGTAGATTT
TTAGGGAAGTTAATTCTTCCTCCAAAAGGAAAGTACAAGAGTGGCTATGT
AACTGAAGCATATTGGAAAGTATTTGAAGGGAGAATTAAAAGAAGTAG
```

FIG. 2D

AAGAAAATAAAGTAATAAGGATTGAAAAGGAAAAAGGATTGGCATTAAG
CTTTCTAGAGAGAAGAAAGTAGTTGAAGAGGGAATGCTATATACTGTTGA
ATTCCTAAGAATTGAGAAATTTACGCTTGGATAGAAGACCCAGGATGCG
GAATCAAGATATTTTGTCATCATATGAGTTCTTAACGTTAGGAGGAGAA
AGTAGAGTTGCTTTTGTGGAAGTGGACGACAAACACCCGATATATTTAA
TAGAGAATTAGGATCAACAAGAAAGCCCTCTTCTATTTCTAACTCCCA
CAATAGGGAAAGTTGGAGAAATAGTACAAGAACTTGAGAAAGATTGAAT
GCAAAATTGATGATTATCTTCTTGTTTCCTCTAGACCTACAGCAATTTC
TGGGTGGGATATGCATGAAAGAAGCCAAAAGGTACTAAATTTGCGATAC
CTCCTGGTTCAGTTCTCTTTGTAGAGTTTAAGGAGGAAGTAGAAGTTCCC
CCCTACATTAAGCTTGGTAAGTTAAAGAAACTTGGCTATGGGCTTGCTTT
AGGAGGGATATGGGAATGA

Protein sequence:
>PFC_04860 length=322 (SEQ ID NO:3)
MIEVTFTPYDVLLFRESRPFDAGSESVARSIIPLPQTVAGAIRTLLFYKG
LKNCVGVGEEEPEFTLVGIAIGTEKGRIYPLPFNIIKSEKFYKVVNPGRF
LGKLILPPKGKYKSGYVTESILEKYLKGELKEVEENKVIRIEKEKRIGIK
LSREKKVVEEGMLYTVEFLRIEKIYAWIEDPGCGIKDILSSYEFLTLGGE
SRVAFVEVDDKTPDIFNRELGSTKKALFYFSTPTIGKVGEIVQELEKRLN
AKIDDYLLVSSRPTAISGWDMHEKKPKGTKFAIPPGSVLFVEFKEEVEVP
PYIKLGKLKKLGYGLALGGIWE Cmr4 - PFC_04850
GI: 397651628
Genome coordinates: 876963..877850
Open Reading Frame sequence:

>PFC_04850 (SEQ ID NO:10)
ATGAAGGCATATTTAGTTGGGTTATATACCTTAACTCCAACCCACCCGGG
AAGTGGAACTGAGCTTGGAGTGGTAGACCAACCAATTCAGAGAGAAAGAC
ACACAGGATTTCCAGTAATTTGGGGCCAGAGTCTCAAGGGTGTATTAAGG
AGCTACCTTAAATTGGTAGAAAAGGTTGATGAGGAGAAGATAAACAAAAT
ATTTGGCCCACCGACAGAAAAGCTCATGAGCAGGCTGGGCTAATAAGTG
TCGGAGATGCAAAGATACTATTCTTCCTGTTAGAAGTCTAAAAGGTGTT
TACGCATACGTAACTTCTCCACTAGTTCTTAACAGGTTCAAAAGAGACTT
AGAGCTAGCTGGGGTTAAGAATTTTCAGACAGAATTCCCGAGTTAACAG
ATACCGCAATTGCAAGTGAAGAAATTACAGTTGATAACAAGGTGATTCTT
GAAGAATTTGCAATTCTCATTCAAAAGGATGACAAAGGAATTTTGGAAAG
TGTAGTTAAAGCTATTGAACAAGCCTTTGGAAATGAAATGGCAGAGAAAA
TAAAGGGTAGAATTGCCATAATCCCAGATGACGTGTTTAGAGATTTAGTG
GAGCTGTCGACAGAAATAGTAGCTAGGATAAGAATTAATGCTGAGACAGG
AACTGTAGAAACTGGAGGACTGTGGTATGAGGAGTATATTCCTTCGGACA
CATTGTTCTACTCACTAATACTTGTAACTCCCAGGGCAAGGATAATGAT
ATGGCCCTAATCAAAGAAGTTCTAGGAAAGATTAACGGCAAATATCTCCA

FIG. 2E

```
GATTGGAGGTAATGAAACCGTTGGGAAGGGCTTCGTCAAAGTTACTCTTA
AAGAGGTGACCAACAATGGAGGTACACATGCTAAGTAA
```

Protein sequence:
>PFC_04850 length=295 (SEQ ID NO:4)
MKAYLVGLYTLTPTHPGSGTELGVVDQPIQRERHTGFPVIWGQSLKGVLR
SYLKLVEKVDEEKINKIFGPPTEKAHEQAGLISVGDAKILFFPVRSLKGV
YAYVTSPLVLNRFKRDLELAGVKNFQTEIPELTDTAIASEEITVDNKVIL
EEFAILIQKDDKGILESVVKAIEQAFGNEMAEKIKGRIAIIPDDVFRDLV
ELSTEIVARIRINAETGTVETGGLWYEEYIPSDTLFYSLILVTPRAKDND
MALIKEVLGKINGKYLQIGGNETVGKGFVKVTLKEVTNNGGTHAK <u>Cmr5 - PFC_04845</u>
GI: 397651627
Genome coordinates: 876476..876973
Open Reading Frame sequence:
>PFC_04845 (SEQ ID NO:11)
```
ATGCTAAGTAAAGATAACAAGAAAAGCATAAGAAAAACTCTAGAACAGCG
GAGGGGCGAGTATGCTTACTATGTGATAAAAGAAGTGGCAGATCTTAATG
ACAAGCAACTTGAGGAAAAGTATGCCTCCCTAGTTAAGAAAGCCCCAGTC
ATGATATTGTCCAATGGTCTCCTTCAGACGCTTGCATTTTACTTGCAAA
GGCCGAGACTTCACCAGAAAAGCTAATCAGATCTTGAGTAGAGTCAATG
AATACCCACCTAGGTTCATCGAAAAGCTTGGGAATGACAAAGACGAGCAC
CTTCTCCTGTACCTTCACATAGTCTACTGGTTGAGGGAAAATGTAGACAG
AAACATCGATGTGAAAACTCTATTATCCAGGATTATTCAAAAGTTCTGT
GGGCAACAAAAGAAGCAATAGCGCTCCTGAACTGGATGAGGAGATTCGCT
GTTGCAATGCTCAAGGAAGAGGGGAAAGAGAATGAAGGAAGTAGTTAA
```

Protein sequence:
>PFC_04845 length=165 (SEQ ID NO:5)
MLSKDNKKSIRKTLEQRRGEYAYYVIKEVADLNDKQLEEKYASLVKKAPV
MILSNGLLQTLAFLLAKAETSPEKANQILSRVNEYPPRFIEKLGNDKDEH
LLLYLHIVYWLRENVDRNIDVKTLLSQDYSKVLWATKEAIALLNWMRRFA
VAMLKEEGKENEGSS <u>Cmr6 - PFC_04840</u>
GI: 397651626
Genome coordinates: 875470..876492
Open Reading Frame sequence:
>PFC_04840 (SEQ ID NO:12)
```
ATGAAGGAAGTAGTTAAATTGGTTCTCCTGGGGGAGAGACAGAACTCCCT
TAACCTCTCACTATACTTCAACAAATATCCTCCAACCATAATCTATCCAG
AGGTACTGGAAGATAGGAACAAGAAACTTGCTTCACCCTCAGGATCACAG
AGAAAGATATCCCTCTTGGTCTTAAATCAAGGGGTTCTTCAGTTTAACAA
```

FIG. 2F

```
AATAAAAGAGACAATAGAAAAGTCGTTGCCAATTGAAACTAAGGTAAAAC
TTCCTCAAAAAGCATATGAATTGTACAAGAAATACTACCAGGATTACACT
GACATGCTTAACTCATTACACGCCATTACTGGAAAGTTTAAGACTCAATC
AAGGCTCGTAGTTGGGCTTGGTGATGAAAGCGTTTATGAGACAAGCATAA
GGCTTCTTAGAAACTATGGAGTGCCTTACATTCTGGGTCCGCAATTAAG
GGAGTTACTAGGCACTTAACTTACTACGTTCTAGCAGAATTTATCAATGA
AGGAAATGATTTCTATAAGAGGGCAAAGACTGTTCAGGATGCATTTATGA
AAGGTGATCCTAAAGAATTCTTTCCAATGCTAAGGTACCGGAAAGGTGT
AGTAGGCTTTGTAAAGAATTTCTCAGAATATTTGGAGAGAAAAAGGTTCC
AGAGATTATAGATGAACTCATAAGAATCTTCGGAACCCAGAAAAAAGAAG
GAGAAGTTGTATTCTTTGATGCAATACCCATAGCTGAAGAGATAGCAGAT
AAGCCGATCTTGGAGTTAGACATAATGAATCCTCACTATGGGCCGTATTA
TCAAAGTGGAGAGAAAAATGTCCCACCTCCTGGGGACTGGTATGATCCCA
TCCCAATATTCTTCCTCACAGTACCAAAGGATGTCCCCTTCCTAGTTGCC
GTTGGTGGCAGAGATAGAGAACTTACAGAAAGGCCTTTAGCCTCGTTAA
GTTGGCCCTTAGAGACCTTGGTGTTGGTGCAAAAACTTCTCTTGGCTATG
GGAGGCTTGTTGAATATGTTTAG

Protein sequence:
>PFC_04840 length=340 (SEQ ID NO:6)
MKEVVKLVLLGERQNSLNLSLYFNKYPPTIIYPEVLEDRNKKLASPSGSQ
RKISLLVLNQGVLQFNKIKETIEKSLPIETKVKLPQKAYELYKKYYQDYT
DMLNSLHAITGKFKTQSRLVVGLGDESVYETSIRLLRNYGVPYIPGSAIK
GVTRHLTYYVLAEFINEGNDFYKRAKTVQDAFMKGDPKEILSNAKVPERC
SRLCKEFLRIFGEKKVPEIIDELIRIFGTQKKEGEVVFFDAIPIAEEIAD
KPILELDIMNPHYGPYYQSGEKNVPPPGDWYDPIPIFFLTVPKDVPFLVA
VGGRDRELTEKAFSLVKLALRDLGVGAKTSLGYGRLVEYV
```

Fig. 3
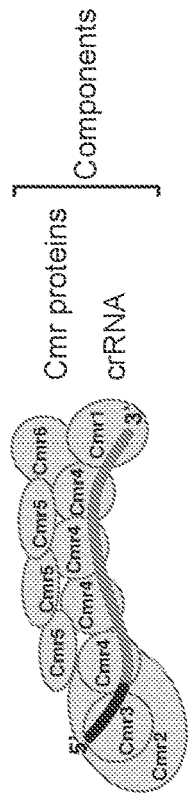
Fig. 3A
Cmr Complex
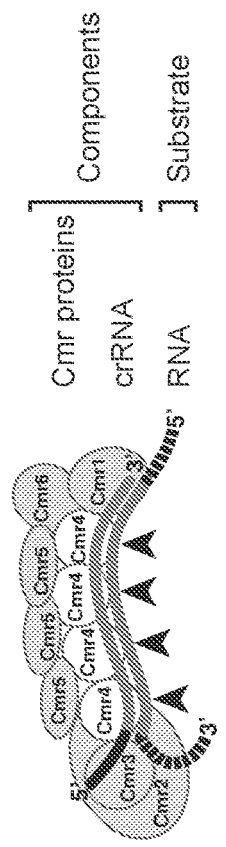
Fig. 3B
RNA-activated DNase
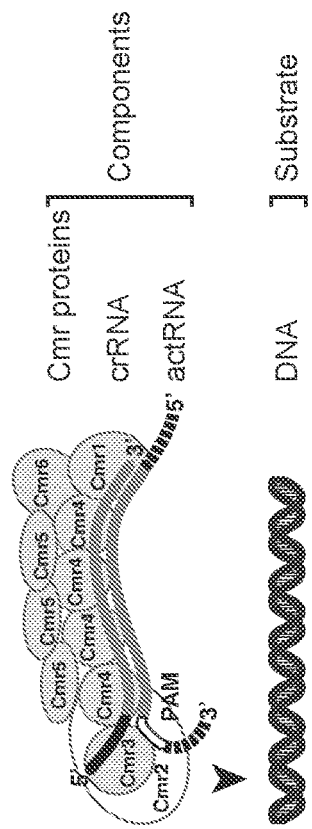
Fig. 3C
RNase

SEQUENCE LISTING

```
<160> NUMBER OF SEQ ID NOS: 189

<210> SEQ ID NO 1
<211> LENGTH: 337
<212> TYPE: PRT
<213> ORGANISM: Pyrococcus furiosus

<400> SEQUENCE: 1

Met Phe Ile Glu Glu Phe Glu Ile Glu Phe Ile Thr Pro Ala Phe Ile
1               5                   10                  15

Arg Gly Ala Asp Gln Arg Ile Pro Glu Val Arg Ser Pro Ser Ile Lys
            20                  25                  30

Gly Ala Met Arg Trp Trp Phe Arg Ala Leu Ala Gly Ser Tyr Phe Gly
        35                  40                  45

Asp Asp Ala Gln Lys Leu Lys Glu Ile Glu Asn Gln Val Phe Gly Ser
    50                  55                  60
```

Thr Lys Glu Arg Ser Arg Val Lys Ile Ser Val Thr Pro Leu Ser Ser
65                  70                  75                  80

Pro Lys Arg Leu Asn Leu Lys Glu Phe Lys Asp Lys Asn Val Gly Tyr
                85                  90                  95

Ile Trp Phe Ser Ile Asn Leu Leu Gly Lys Arg Gly Thr Ile Thr His
            100                 105                 110

Tyr Tyr Pro Pro Gly Ser Arg Phe Arg Val Val Leu Glu Ser Pro Ser
        115                 120                 125

Glu Arg Val Ile Lys Leu Ala Thr Leu Ser Leu Trp Ala Leu Val Ser
    130                 135                 140

Leu Gly Ser Val Gly Phe Arg Ser Arg Arg Gly Thr Gly Ser Met Lys
145                 150                 155                 160

Ile Val Arg Ala Ser Ser Glu Val Leu Glu Asp Leu Gly Leu Thr Thr
                165                 170                 175

Glu Phe Asn Ser Ile Asp Glu Phe Lys Asp Ser Leu Lys Arg Val Leu
            180                 185                 190

Asp Val Thr Gly Glu Ile Leu Gly Val Lys Asn Ser Glu Thr Asn Lys
        195                 200                 205

Ser Leu Pro Ser Tyr Ala Thr Leu Lys Phe Ser Asp Val Glu Val Phe
    210                 215                 220

Gly Pro Gly Lys Asn Thr Trp Glu Val Leu Ala Gln Phe Asn Asn Ser
225                 230                 235                 240

Tyr Lys Glu Tyr Leu Arg Arg Ile Lys Lys Tyr Gln Arg Ile Ile
                245                 250                 255

Phe Gly Leu Pro Arg Phe Lys Leu Arg Gly Val Arg Lys Asp Leu Arg
            260                 265                 270

Arg Ala Ser Pro Leu Trp Phe Gly Val Val Glu Ile Gly Gly Lys Pro
        275                 280                 285

Tyr Gly Arg Ile Ile Lys Phe Phe Gln Ser Thr Phe His Pro Glu Val
    290                 295                 300

Arg Ser Lys His Ile Val Asp Trp Asn Val Leu Ser Asn Phe Asp Trp
305                 310                 315                 320

Phe Ile Ser Ser Arg Leu Pro Val Thr Lys Val Trp Gly Gly Trp Ser
                325                 330                 335

Gly

<210> SEQ ID NO 2
<211> LENGTH: 871
<212> TYPE: PRT
<213> ORGANISM: Pyrococcus furiosus

<400> SEQUENCE: 2

Met Val Asn Ile Lys Glu Lys Leu Phe Val Tyr Leu His Asp Pro Pro
1               5                   10                  15

Asp Lys Ala Leu Lys Ile Glu Asn His Glu Glu Arg Ser Lys Lys Ile
            20                  25                  30

Leu Ser Ser Gly Asn Ile Gln Tyr Ser Arg Thr Asp Lys Val Lys Gln
        35                  40                  45

Ala Asp Ala Leu Ser Ser Lys Thr Gln Arg Phe Ile Ile Arg Thr Lys
    50                  55                  60

Glu Asn Lys Glu Pro Val Ile Asp Phe Leu Gly Arg Ser Ser Gly Lys
65                  70                  75                  80

Tyr Phe His Val Gly Tyr Pro Val Phe Ile His Pro Ile Ser Thr Glu
                85                  90                  95

```
Ile Lys Arg Tyr Glu Thr Leu Glu Lys Tyr Ile Asp Leu Gly Arg Ser
            100                 105                 110

Asn Arg Gly Glu Arg Phe Val Asn Glu Phe Leu Glu Arg Val Ser Lys
            115                 120                 125

Leu Glu Gly Asp Val Leu Lys Glu Val Phe Glu Asp Ala Ser Asn Lys
            130                 135                 140

Phe Lys Gly Glu Glu Ser Lys Gln Trp Ala Tyr Ile Trp Gln Phe Tyr
145                 150                 155                 160

Pro Val Lys Leu Lys Glu Gly Val Lys Glu Phe Ala Lys Ser Glu Leu
                165                 170                 175

Lys Leu Lys Glu Glu Ala Glu Lys Phe Ala Glu Glu Phe Val Asn
            180                 185                 190

Leu Pro Ala Asp Thr Arg Phe Pro Asp His Ala Ile Trp Thr His Leu
            195                 200                 205

Asp Leu Thr Ser Ala Leu Ser Val Lys Asp Pro Thr Leu Leu Arg Ile
            210                 215                 220

Lys Ile Val Pro Val Gln Pro Phe Ile Ala Asn Ser Arg Lys Gln Leu
225                 230                 235                 240

Asp Leu Trp Ala Ser Ser His Leu Leu Ser Met Leu Met Tyr Lys Ala
                245                 250                 255

Leu Glu Val Ile Val Asp Lys Phe Gly Pro Glu His Val Ile Tyr Pro
            260                 265                 270

Ser Leu Arg Asp Gln Pro Phe Phe Leu Lys Phe Tyr Leu Gly Glu Asn
            275                 280                 285

Ile Gly Asp Glu Ile Leu Val Ala Asn Leu Pro Asn Lys Ala Leu Ala
            290                 295                 300

Ile Val Ser Gly Lys Glu Ala Glu Lys Ile Glu Glu Ile Lys Lys
305                 310                 315                 320

Arg Ile Arg Asp Phe Leu Leu Gln Leu Tyr Arg Glu Ala Val Asp Trp
                325                 330                 335

Ala Val Glu Asn Gly Val Val Lys Val Asp Arg Ser Glu Lys Asp Ser
            340                 345                 350

Met Leu Lys Glu Ala Tyr Leu Lys Ile Val Arg Glu Tyr Phe Thr Val
            355                 360                 365

Ser Ile Thr Trp Val Ser Leu Ser Glu Lys Glu Asp Ile Tyr Gln Val
            370                 375                 380

Thr Glu Asn Ala Gly Leu Ser Asp Glu Asp Val Lys Lys Trp Leu Lys
385                 390                 395                 400

Phe Ala Glu Lys Lys Glu Asn Ser Arg Val Leu Glu Arg Ile Ala Ile
                405                 410                 415

Tyr Pro Leu Leu Val Lys Ile Leu Asp Ser Leu Gly Arg Lys Val
            420                 425                 430

Thr Glu Glu Arg Phe Glu Lys Ser Glu Gln Leu Lys Gly Trp Lys Cys
            435                 440                 445

His Val Cys Gly Glu Asn Leu Ala Ile Phe Gly Asp Met Tyr Asp His
            450                 455                 460

Asp Asn Leu Lys Ser Leu Trp Leu Asp Glu Glu Pro Leu Cys Pro Met
465                 470                 475                 480

Cys Leu Ile Lys Arg Tyr Tyr Pro Val Trp Ile Arg Ser Lys Thr Gly
                485                 490                 495

Gln Lys Ile Arg Phe Glu Ser Val Val Asp Val Ala Leu Leu Tyr Lys
            500                 505                 510
```

```
Asn Trp Arg Lys Ile Phe Asp Glu Lys Tyr Gly Lys Asp Leu Val Ser
            515                 520                 525

Lys Ala Arg Glu Val Ser Glu Asp Phe Val Lys Asp Asn Met Leu Val
        530                 535                 540

Asp Ser Asp Leu Tyr Tyr Ser Ser Thr Trp Glu Ser Gly Leu Ser Lys
545                 550                 555                 560

Lys Leu Lys Asn Lys Lys Glu Ile Asp Glu Lys Val Lys Glu Val
                565                 570                 575

Val Asp Phe Leu Asn Ala Ala Tyr Glu Ile Gly Asn Pro Pro Lys
                580                 585                 590

Tyr Tyr Ala Ile Leu Val Met Asp Gly Asp Met Gly Lys Val Ile
                595                 600                 605

Ser Gly Glu Val Leu Gly Glu Ile Ser Thr Arg Ile His Pro Asn Ile
        610                 615                 620

Arg Asp Tyr Val Glu Ile Pro Glu Ala Lys Tyr Tyr Ser Thr Pro Gln
625                 630                 635                 640

Val His Val Ala Ile Ser Gln Ala Leu Ala Asn Phe Ser Ile Arg Glu
                645                 650                 655

Val Arg Ser Val Val Lys Asp Glu Gly Leu Leu Ile Tyr Ala Gly Gly
                660                 665                 670

Asp Asp Val Leu Ala Ile Leu Pro Val Asp Lys Ala Leu Glu Val Ala
                675                 680                 685

Tyr Lys Ile Arg Lys Glu Phe Gly Lys Ser Phe Glu Asn Gly Ser Leu
                690                 695                 700

Leu Pro Gly Trp Lys Leu Ser Ala Gly Ile Leu Ile Val His Tyr Lys
705                 710                 715                 720

His Pro Leu Tyr Asp Ala Leu Glu Lys Ala Arg Asp Leu Leu Asn Asn
                725                 730                 735

Lys Ala Lys Asn Val Pro Gly Lys Asp Thr Leu Ala Ile Gly Leu Leu
                740                 745                 750

Lys Arg Ser Gly Ser Tyr Tyr Ile Ser Leu Val Gly Trp Glu Leu Ile
            755                 760                 765

Arg Val Phe Tyr Asn Ser Glu Leu Arg Lys Lys Leu Leu Glu Glu Lys
        770                 775                 780

Gly Gly Val Gly Lys Arg Phe Ile Tyr His Val Leu Arg Glu Val Asp
785                 790                 795                 800

Thr Trp Pro Lys Val Gly Ile Asp Glu Met Leu Lys Phe Glu Val Ile
                805                 810                 815

Arg His Ile Arg Gly Arg Asn Lys Glu Glu Thr Lys Glu Leu Arg Glu
                820                 825                 830

Lys Ile Tyr Gly Glu Ile Lys Asp Leu Leu Glu His Val Arg Gly Asn
            835                 840                 845

Asn Glu Val Glu Lys Val Arg Gly Leu Phe Thr Phe Leu Lys Ile Ile
        850                 855                 860

Thr Asp Ala Glu Val Phe Pro
865                 870

<210> SEQ ID NO 3
<211> LENGTH: 322
<212> TYPE: PRT
<213> ORGANISM: Pyrococcus furiosus

<400> SEQUENCE: 3

Met Ile Glu Val Thr Phe Thr Pro Tyr Asp Val Leu Leu Phe Arg Glu
1               5                   10                  15
```

```
Ser Arg Pro Phe Asp Ala Gly Ser Glu Ser Val Ala Arg Ser Ile Ile
         20                  25                  30

Pro Leu Pro Gln Thr Val Ala Gly Ala Ile Arg Thr Leu Leu Phe Tyr
         35                  40                  45

Lys Gly Leu Lys Asn Cys Val Gly Val Gly Glu Glu Pro Glu Phe
 50                  55                  60

Thr Leu Val Gly Ile Ala Ile Gly Thr Glu Lys Gly Arg Ile Tyr Pro
 65                  70                  75                  80

Leu Pro Phe Asn Ile Ile Lys Ser Glu Lys Phe Tyr Lys Val Val Asn
                 85                  90                  95

Pro Gly Arg Phe Leu Gly Lys Leu Ile Leu Pro Pro Lys Gly Lys Tyr
             100                 105                 110

Lys Ser Gly Tyr Val Thr Glu Ser Ile Leu Glu Lys Tyr Leu Lys Gly
         115                 120                 125

Glu Leu Lys Glu Val Glu Glu Asn Lys Val Ile Arg Ile Glu Lys Glu
 130                 135                 140

Lys Arg Ile Gly Ile Lys Leu Ser Arg Glu Lys Lys Val Val Glu Glu
145                 150                 155                 160

Gly Met Leu Tyr Thr Val Glu Phe Leu Arg Ile Glu Lys Ile Tyr Ala
                 165                 170                 175

Trp Ile Glu Asp Pro Gly Cys Gly Ile Lys Asp Ile Leu Ser Ser Tyr
             180                 185                 190

Glu Phe Leu Thr Leu Gly Gly Glu Ser Arg Val Ala Phe Val Glu Val
         195                 200                 205

Asp Asp Lys Thr Pro Asp Ile Phe Asn Arg Glu Leu Gly Ser Thr Lys
 210                 215                 220

Lys Ala Leu Phe Tyr Phe Ser Thr Pro Thr Ile Gly Lys Val Gly Glu
225                 230                 235                 240

Ile Val Gln Glu Leu Glu Lys Arg Leu Asn Ala Lys Ile Asp Asp Tyr
                 245                 250                 255

Leu Leu Val Ser Ser Arg Pro Thr Ala Ile Ser Gly Trp Asp Met His
             260                 265                 270

Glu Lys Lys Pro Lys Gly Thr Lys Phe Ala Ile Pro Pro Gly Ser Val
         275                 280                 285

Leu Phe Val Glu Phe Lys Glu Glu Val Glu Val Pro Pro Tyr Ile Lys
 290                 295                 300

Leu Gly Lys Leu Lys Lys Leu Gly Tyr Gly Leu Ala Leu Gly Gly Ile
305                 310                 315                 320

Trp Glu

<210> SEQ ID NO 4
<211> LENGTH: 295
<212> TYPE: PRT
<213> ORGANISM: Pyrococcus furiosus

<400> SEQUENCE: 4

Met Lys Ala Tyr Leu Val Gly Leu Tyr Thr Leu Thr Pro Thr His Pro
1               5                   10                  15

Gly Ser Gly Thr Glu Leu Gly Val Asp Gln Pro Ile Gln Arg Glu
         20                  25                  30

Arg His Thr Gly Phe Pro Val Ile Trp Gly Gln Ser Leu Lys Gly Val
         35                  40                  45

Leu Arg Ser Tyr Leu Lys Leu Val Glu Lys Val Asp Glu Glu Lys Ile
 50                  55                  60
```

Asn Lys Ile Phe Gly Pro Pro Thr Glu Lys Ala His Glu Gln Ala Gly
 65                  70                  75                  80

Leu Ile Ser Val Gly Asp Ala Lys Ile Leu Phe Phe Pro Val Arg Ser
                 85                  90                  95

Leu Lys Gly Val Tyr Ala Tyr Val Thr Ser Pro Leu Val Leu Asn Arg
            100                 105                 110

Phe Lys Arg Asp Leu Glu Leu Ala Gly Val Lys Asn Phe Gln Thr Glu
        115                 120                 125

Ile Pro Glu Leu Thr Asp Thr Ala Ile Ala Ser Glu Glu Ile Thr Val
130                 135                 140

Asp Asn Lys Val Ile Leu Glu Glu Phe Ala Ile Leu Ile Gln Lys Asp
145                 150                 155                 160

Asp Lys Gly Ile Leu Glu Ser Val Val Lys Ala Ile Glu Gln Ala Phe
                165                 170                 175

Gly Asn Glu Met Ala Glu Lys Ile Lys Gly Arg Ile Ala Ile Ile Pro
            180                 185                 190

Asp Asp Val Phe Arg Asp Leu Val Glu Leu Ser Thr Glu Ile Val Ala
        195                 200                 205

Arg Ile Arg Ile Asn Ala Glu Thr Gly Thr Val Glu Thr Gly Gly Leu
210                 215                 220

Trp Tyr Glu Glu Tyr Ile Pro Ser Asp Thr Leu Phe Tyr Ser Leu Ile
225                 230                 235                 240

Leu Val Thr Pro Arg Ala Lys Asp Asn Asp Met Ala Leu Ile Lys Glu
                245                 250                 255

Val Leu Gly Lys Ile Asn Gly Lys Tyr Leu Gln Ile Gly Gly Asn Glu
            260                 265                 270

Thr Val Gly Lys Gly Phe Val Lys Val Thr Leu Lys Glu Val Thr Asn
        275                 280                 285

Asn Gly Gly Thr His Ala Lys
            290                 295

<210> SEQ ID NO 5
<211> LENGTH: 165
<212> TYPE: PRT
<213> ORGANISM: Pyrococcus furiosus

<400> SEQUENCE: 5

Met Leu Ser Lys Asp Asn Lys Lys Ser Ile Arg Lys Thr Leu Glu Gln
1               5                   10                  15

Arg Arg Gly Glu Tyr Ala Tyr Tyr Val Ile Lys Glu Val Ala Asp Leu
            20                  25                  30

Asn Asp Lys Gln Leu Glu Glu Lys Tyr Ala Ser Leu Val Lys Lys Ala
        35                  40                  45

Pro Val Met Ile Leu Ser Asn Gly Leu Leu Gln Thr Leu Ala Phe Leu
 50                  55                  60

Leu Ala Lys Ala Glu Thr Ser Pro Glu Lys Ala Asn Gln Ile Leu Ser
 65                  70                  75                  80

Arg Val Asn Glu Tyr Pro Pro Arg Phe Ile Glu Lys Leu Gly Asn Asp
                 85                  90                  95

Lys Asp Glu His Leu Leu Leu Tyr Leu His Ile Val Tyr Trp Leu Arg
            100                 105                 110

Glu Asn Val Asp Arg Asn Ile Asp Val Lys Thr Leu Leu Ser Gln Asp
        115                 120                 125

Tyr Ser Lys Val Leu Trp Ala Thr Lys Glu Ala Ile Ala Leu Leu Asn

```
            130                 135                 140
Trp Met Arg Arg Phe Ala Val Ala Met Leu Lys Glu Glu Gly Lys Glu
145                 150                 155                 160

Asn Glu Gly Ser Ser
                165

<210> SEQ ID NO 6
<211> LENGTH: 340
<212> TYPE: PRT
<213> ORGANISM: Pyrococcus furiosus

<400> SEQUENCE: 6

Met Lys Glu Val Val Lys Leu Val Leu Leu Gly Glu Arg Gln Asn Ser
1               5                   10                  15

Leu Asn Leu Ser Leu Tyr Phe Asn Lys Tyr Pro Pro Thr Ile Ile Tyr
                20                  25                  30

Pro Glu Val Leu Glu Asp Arg Asn Lys Lys Leu Ala Ser Pro Ser Gly
            35                  40                  45

Ser Gln Arg Lys Ile Ser Leu Leu Val Leu Asn Gln Gly Val Leu Gln
        50                  55                  60

Phe Asn Lys Ile Lys Glu Thr Ile Glu Lys Ser Leu Pro Ile Glu Thr
65                  70                  75                  80

Lys Val Lys Leu Pro Gln Lys Ala Tyr Glu Leu Tyr Lys Lys Tyr Tyr
                85                  90                  95

Gln Asp Tyr Thr Asp Met Leu Asn Ser Leu His Ala Ile Thr Gly Lys
            100                 105                 110

Phe Lys Thr Gln Ser Arg Leu Val Val Gly Leu Gly Asp Glu Ser Val
        115                 120                 125

Tyr Glu Thr Ser Ile Arg Leu Leu Arg Asn Tyr Gly Val Pro Tyr Ile
130                 135                 140

Pro Gly Ser Ala Ile Lys Gly Val Thr Arg His Leu Thr Tyr Tyr Val
145                 150                 155                 160

Leu Ala Glu Phe Ile Asn Gly Asn Asp Phe Tyr Lys Arg Ala Lys
                165                 170                 175

Thr Val Gln Asp Ala Phe Met Lys Gly Asp Pro Lys Glu Ile Leu Ser
            180                 185                 190

Asn Ala Lys Val Pro Glu Arg Cys Ser Arg Leu Cys Lys Glu Phe Leu
        195                 200                 205

Arg Ile Phe Gly Glu Lys Lys Val Pro Glu Ile Ile Asp Glu Leu Ile
210                 215                 220

Arg Ile Phe Gly Thr Gln Lys Lys Glu Gly Glu Val Val Phe Phe Asp
225                 230                 235                 240

Ala Ile Pro Ile Ala Glu Glu Ile Ala Asp Lys Pro Ile Leu Glu Leu
                245                 250                 255

Asp Ile Met Asn Pro His Tyr Gly Pro Tyr Tyr Gln Ser Gly Glu Lys
            260                 265                 270

Asn Val Pro Pro Gly Asp Trp Tyr Asp Pro Ile Pro Ile Phe Phe
        275                 280                 285

Leu Thr Val Pro Lys Asp Val Pro Phe Leu Val Ala Val Gly Gly Arg
290                 295                 300

Asp Arg Glu Leu Thr Glu Lys Ala Phe Ser Leu Val Lys Leu Ala Leu
305                 310                 315                 320

Arg Asp Leu Gly Val Gly Ala Lys Thr Ser Leu Gly Tyr Gly Arg Leu
                325                 330                 335
```

Val Glu Tyr Val
340

<210> SEQ ID NO 7
<211> LENGTH: 1014
<212> TYPE: DNA
<213> ORGANISM: Pyrococcus furiosus

<400> SEQUENCE: 7

```
atgtttattg aagaatttga aattgagttc ataactccag catttattag aggtgctgac      60
cagagaatac agaagtgag aagtccttca ataagggag caatgagatg gtggttcaga       120
gctttggctg gctcatattt tggagacgat gctcaaaaac ttaaagaaat agaaaaccaa     180
gttttgga gcacaaagga aagaagcaga gtaaaattt ctgttacacc gcttagttct        240
ccaaaaagat taaaccttaa agagtttaag gataaaaatg ttgggtacat ctggttttca     300
ataaatctgc tcggaaaaag agggactata actcactatt atcctcctgg gagcagattt    360
agagtagttc tagaatcacc tagcgaaagg gttattaagc tggcaacttt atctctctgg     420
gctcttgtga gcttaggtag tgttggattt agaagtagac ggggaacagg ttcaatgaaa     480
atcgttaggg caagtagcga agttctggag gatttgggac tcacaacaga attcaattct     540
atagatgaat ttaaagattc tttgaaaagg gtgttagatg tcacaggcga aatttttagga     600
gtaaaaaata gcgaaactaa taagtccctc ccttcttacg ctactttaaa gttttcagac     660
gttgaagtat ttgggccagg aagaatact tgggaggtat tagctcagtt caacaactct      720
tacaaggaat acctaaggag gagaattaag aagtatcaaa ggataatatt tggattgcct     780
cgatttaagc ttagaggcgt gaggaaagac ctaaggagag cttctccct ttggtttggc      840
gttgtgaaga taggcggaaa gccatatgga aggataatca agttcttcca atctacattt     900
catccagaag taagaagcaa acatatagtt gattggaacg ttctttcaaa ttttgattgg     960
tttatatcct ctagacttcc tgtgactaag gtgtggggtg gttggagtgg ttaa          1014
```

<210> SEQ ID NO 8
<211> LENGTH: 2616
<212> TYPE: DNA
<213> ORGANISM: Pyrococcus furiosus

<400> SEQUENCE: 8

```
gtggttaaca tcaaagagaa actttttgta taccttcatg atccaccaga caaggctcta     60
aaaattgaaa atcatgagga aaggtcaaaa aagatattaa gttctggcaa tatccagtac    120
tcgagaacgg acaagttaa acaagcagat gcactttctt ctaagactca gagatttata    180
attcgaacaa aggaaaataa agagccagta atagattttt gggtagatc ttcaggaaag     240
tacttccatg ttgatatcc tgttttata caccccatat ccacagaaat taagaggtat      300
gaaacacttg aaaagtacat agaccttggc aggagtaata gagggaaag atttgttaac    360
gagttttttgg aaagggtttc aaagcttgaa ggcgatgttc tcaaagaggt ctttgaagat    420
gctagtaaca aatttaaagg agaagagagt aaacagtggg cctacatctg gcagttttat    480
cccgtaaaac tcaagaagg agtcaaggaa tttgccaagt cagagttaaa acttaaagag     540
gaagaagcag aaaagtttgc agaggaattt gttaacctcc cagctgatac aagatttcca     600
gatcatgcaa tttggaccca tttagactta acttccgcat tatccgttaa ggatcccact    660
ttgctcagga tcaaaatagt tccagttcaa ccttttattg ccaattcaag aaagcagtta     720
gatctctggg cctccagtca tctcctttca atgcttatgt ataaagcttt agaggtgata    780
```

| | |
|---|---:|
| gtggacaagt tcgggccaga acatgtaatc tatccatctc taagggatca acccttcttc | 840 |
| ttgaagttct acctggggga aaacataggt gatgaaatct tagttgcaaa cttgcctaac | 900 |
| aaagcgcttg caatagtctc aggaaaggag gctgaaaaga ttgaagaaga aatcaagaaa | 960 |
| agaattaggg atttcctact ccaactgtac agagaagctg ttgattgggc agttgaaaat | 1020 |
| ggagtagtaa aagtggatag aagtgaaaag gatagcatgc tcaaggaagc atatcttaaa | 1080 |
| attgtgaggg agtacttcac cgtctcgata acctgggtat ctctttccga aaaggaggat | 1140 |
| atctatcaag taacagagaa cgcgggtctc tcggatgaag atgttaagaa gtggctaaag | 1200 |
| tttgcagaaa agaaagaaaa tagtagagtt ctcgagagga ttgcaatata cccactttg | 1260 |
| gtaaagatat tggatagcct gggagagaga aaagttacag aagaaaggtt cgaaaaaagc | 1320 |
| gaacaactca aaggatggaa gtgccacgtt tgtggtgaga tcttgcaat ttttggagac | 1380 |
| atgtacgatc acgataatct taagagtttg tggcttgatg aggaaccatt atgtcccatg | 1440 |
| tgtttgataa aaaggtatta tccagtgtgg attaggagta aaactggaca gaaaataagg | 1500 |
| tttgagtcgg tggtagatgt tgcacttctg tacaagaact ggaggaagat atttgacgag | 1560 |
| aagtatggaa aagacctagt ctcaaaggct agggaagtta gtgaagactt cgtaaaggac | 1620 |
| aatatgctag tagattcgga tctatactat tcttcaacct gggaatctgg actttctaaa | 1680 |
| aagctcaaaa ataagaaaga gattgatgag gaaaaagtta aggaagttgt tgacttctta | 1740 |
| aatgcggctt ataagaaat cggtaatcca ccaaagtact atgctattct agttatggat | 1800 |
| ggcgacgata tggggaaagt tatttcagga gaggtgcttg agaaaatatc aactagaatt | 1860 |
| catccaaata ttagggatta cgttgaaatt ccagaagcaa aatattactc cacccccgcag | 1920 |
| gttcacgtgg ctataagcca agcattggct aacttttcga taagggaagt tagatccgta | 1980 |
| gttaaagacg agggattgct aatatacgct ggaggggatg atgtcctagc aattttgcca | 2040 |
| gtcgacaaag cttagaagt tgcatataag ataaggaaag aatttggcaa gagctttgaa | 2100 |
| aatggttctc ttctcccagg ttggaagttg agtgctggaa ttttgatagt ccattataag | 2160 |
| catccattgt atgacgccct agaaaaggca agagatcttc tcaataataa agcaaaaaac | 2220 |
| gttccaggaa aagatacact agctataggc ctacttaaga ggagtggttc ctactatatc | 2280 |
| tccctagtgg gatgggaatt aattagggtc ttctacaact cagagctgag gaaaaagcta | 2340 |
| ttggaagaga aaggtggagt gggaaagagg ttcatttatc atgtgctcag agaagttgat | 2400 |
| acttggccaa aagttggaat agacgagatg cttaagtttg aggtgattag acatatcagg | 2460 |
| ggaaggaaca aagaagaaac taaagagctc agagaaaaga tctatggaga aataaaggat | 2520 |
| cttcttgagc atgtaagagg gaacaatgaa gttgaaaaag ttagaggctt attcacatttt | 2580 |
| ctaaaaataa tcacggacgc ggaggtgttt ccatga | 2616 |

<210> SEQ ID NO 9
<211> LENGTH: 969
<212> TYPE: DNA
<213> ORGANISM: Pyrococcus furiosus

<400> SEQUENCE: 9

| | |
|---|---:|
| atgattgagg ttactttac tccttatgat gtcctcttat ttagagaaag taggccttt | 60 |
| gatgcaggaa gtgaaagtgt ggcaagatca attattcctc ttccccaaac agtcgctggc | 120 |
| gctataagga ctctttttatt ctacaaaggc ctcaagaatt gtgttggagt gggtgaggag | 180 |
| gaacccgaat ttacgttagt tgggattgca attggaacag agaaaggcag aatttacccc | 240 |
| cttcccttca atatcataaa aagcgagaaa ttctacaaag ttgtcaaccc aggtagattt | 300 |

-continued

```
ttagggaagt taattcttcc tccaaaagga aagtacaaga gtggctatgt aactgaaagc    360
atattggaaa agtatttgaa gggagaatta aagaagtag aagaaaataa agtaataagg     420
attgaaaagg aaaaaaggat tggcattaag ctttctagag agaagaaagt agttgaagag    480
ggaatgctat atactgttga attcctaaga attgagaaaa tttacgcttg gatagaagac    540
ccaggatgcg gaatcaaaga tattttgtca tcatatgagt tcttaacgtt aggaggagaa    600
agtagagttg cttttgtgga agtggacgac aaaacacccg atatatttaa tagagaatta    660
ggatcaacaa agaaagccct cttctatttc tcaactccca caataggaa agttggagaa     720 atagtacaag aacttgagaa aagattgaat gcaaaaattg atgattatct tcttgtttcc    780
tctagaccta cagcaatttc tgggtgggat atgcatgaaa agaagccaaa aggtactaaa    840
tttgcgatac ctcctggttc agttctcttt gtagagttta aggaggaagt agaagttccc    900
ccctacatta agcttggtaa gttaaagaaa cttggctatg ggcttgcttt aggagggata    960
tgggaatga                                                            969

<210> SEQ ID NO 10
<211> LENGTH: 888
<212> TYPE: DNA
<213> ORGANISM: Pyrococcusfuriosus

<400> SEQUENCE: 10
atgaaggcat atttagttgg gttatatacc ttaactccaa cccacccggg aagtggaact    60
gagcttggag tggtagacca accaattcag agagaaagac acacaggatt tccagtaatt    120
tggggccaga gtctcaaggg tgtattaagg agctacctta aattggtaga aaaggttgat    180
gaggagaaga taaacaaaat atttggccca ccgacagaaa aagctcatga gcaggctggg    240
ctaataagtg tcggagatgc aaagatacta ttcttccctg ttagaagtct aaaaggtgtt    300
tacgcatacg taacttctcc actagttctt aacaggttca aaagagactt agagctagct    360
ggggttaaga attttcagac agaaattccc gagttaacag ataccgcaat tgcaagtgaa    420
gaaattacag ttgataacaa ggtgattctt gaagaatttg caattctcat tcaaaaggat    480
gacaaaggaa ttttggaaag tgtagttaaa gctattgaac aagcctttgg aaatgaaatg    540
gcagagaaaa taagggtag aattgccata atcccagatg acgtgtttag agatttagtg    600
gagctgtcga cagaaatagt agctaggata agaattaatg ctgagacagg aactgtagaa    660
actggaggac tgtggtatga ggagtatatt ccttcggaca cattgttcta ctcactaata    720
cttgtaactc ccagggcaaa ggataatgat atggccctaa tcaaagaagt tctaggaaag    780
attaacggca aatatctcca gattggaggt aatgaaaccg ttgggaaggg cttcgtcaaa    840
gttactctta aagaggtgac caacaatgga ggtacacatg ctaagtaa                 888

<210> SEQ ID NO 11
<211> LENGTH: 498
<212> TYPE: DNA
<213> ORGANISM: Pyrococcus furiosus

<400> SEQUENCE: 11
atgctaagta aagataacaa gaaaagcata agaaaaactc tagaacagcg gagggggcgag   60 tatgcttact atgtgataaa agaagtggca gatcttaatg acaagcaact tgaggaaaag   120
tatgcctccc tagttaagaa agccccagtc atgatattgt ccaatggtct ccttcagacg   180
cttgcatttt tacttgcaaa ggccgagact tcaccagaaa aagctaatca gatcttgagt   240
```

| | |
|---|---|
| agagtcaatg aataccccacc taggttcatc gaaaagcttg ggaatgacaa agacgagcac | 300 |
| cttctcctgt accttcacat agtctactgg ttgagggaaa atgtagacag aaacatcgat | 360 |
| gtgaaaactc tattatccca ggattattca aaagttctgt gggcaacaaa agaagcaata | 420 |
| gcgctcctga actggatgag gagattcgct gttgcaatgc tcaaggaaga ggggaaagag | 480 |
| aatgaaggaa gtagttaa | 498 |

<210> SEQ ID NO 12
<211> LENGTH: 1023
<212> TYPE: DNA
<213> ORGANISM: Pyrococcus furiosus

<400> SEQUENCE: 12

| | |
|---|---|
| atgaaggaag tagttaaatt ggttctcctg ggggagagac agaactccct taacctctca | 60 |
| ctatacttca acaaatatcc tccaaccata atctatccag aggtactgga agataggaac | 120 |
| aagaaacttg cttcaccctc aggatcacag agaaagatat ccctcttggt cttaaatcaa | 180 |
| ggggttcttc agtttaacaa aataaaagag acaatagaaa agtcgttgcc aattgaaact | 240 |
| aaggtaaaac ttcctcaaaa agcatatgaa ttgtacaaga aatactacca ggattacact | 300 |
| gacatgctta actcattaca cgccattact ggaaagttta agactcaatc aaggctcgta | 360 |
| gttgggcttg gtgatgaaag cgtttatgag acaagcataa ggcttcttag aaactatgga | 420 |
| gtgccttaca ttcctgggtc cgcaattaag ggagttacta ggcacttaac ttactacgtt | 480 |
| ctagcagaat ttatcaatga aggaaatgat ttctataaga gggcaaagac tgttcaggat | 540 |
| gcatttatga aggtgatcc taagaaaatt ctttccaatg ctaaggtacc ggaaaggtgt | 600 |
| agtaggcttt gtaaagaatt tctcagaata tttggagaga aaaaggttcc agagattata | 660 |
| gatgaactca taagaatctt cggaacccag aaaaaagaag gagaagttgt attctttgat | 720 |
| gcaataccca tagctgaaga gatagcagat aagccgatct tggagttaga cataatgaat | 780 |
| cctcactatg ggccgtatta tcaaagtgga gagaaaaatg tcccacctcc tggggactgg | 840 |
| tatgatccca tcccaatatt cttcctcaca gtaccaaagg atgtccccctt cctagttgcc | 900 |
| gttggtggca gagatagaga acttacagaa aaggcctttta gcctcgttaa gttggccctt | 960 |
| agagaccttg gtgttggtgc aaaaaacttct cttggctatg ggaggcttgt tgaatatgtt | 1020 |
| tag | 1023 |

<210> SEQ ID NO 13
<211> LENGTH: 5
<212> TYPE: PRT
<213> ORGANISM: Pyrococcus furiosus

<400> SEQUENCE: 13

Gly Gly Asp Glu Phe
1               5

<210> SEQ ID NO 14
<211> LENGTH: 4
<212> TYPE: PRT
<213> ORGANISM: Pyrococcus furiosus

<400> SEQUENCE: 14

Gly Gly Asp Asp
1

<210> SEQ ID NO 15
<211> LENGTH: 25

```
<212> TYPE: DNA
<213> ORGANISM: artificial
<220> FEATURE:
<223> OTHER INFORMATION: oligo

<400> SEQUENCE: 15
gctctcagcc gcaaggaccg catac                                    25

<210> SEQ ID NO 16
<211> LENGTH: 25
<212> TYPE: DNA
<213> ORGANISM: artificial
<220> FEATURE:
<223> OTHER INFORMATION: oligo

<400> SEQUENCE: 16
gtatgcggtc cttgcggctg agagc                                    25

<210> SEQ ID NO 17
<211> LENGTH: 20
<212> TYPE: DNA
<213> ORGANISM: artificial
<220> FEATURE:
<223> OTHER INFORMATION: oligo

<400> SEQUENCE: 17
cccggcttcc cgcccctct                                           20

<210> SEQ ID NO 18
<211> LENGTH: 23
<212> TYPE: DNA
<213> ORGANISM: artificial
<220> FEATURE:
<223> OTHER INFORMATION: oligo

<400> SEQUENCE: 18
gattgaaaat ggagtgagct gag                                      23

<210> SEQ ID NO 19
<211> LENGTH: 25
<212> TYPE: DNA
<213> ORGANISM: artificial
<220> FEATURE:
<223> OTHER INFORMATION: oligo

<400> SEQUENCE: 19
ttatcttgag ctccattctt tcacc                                    25

<210> SEQ ID NO 20
<211> LENGTH: 20
<212> TYPE: DNA
<213> ORGANISM: artificial
<220> FEATURE:
<223> OTHER INFORMATION: oligo

<400> SEQUENCE: 20
ggcagaattt accccctccc                                          20

<210> SEQ ID NO 21
<211> LENGTH: 47
<212> TYPE: DNA
<213> ORGANISM: artificial
<220> FEATURE:
<223> OTHER INFORMATION: oligo

<400> SEQUENCE: 21
```
ctcagctcac tccattttca atctcattcc catatccctc ctaaagc                47

<210> SEQ ID NO 22
<211> LENGTH: 46
<212> TYPE: DNA
<213> ORGANISM: artificial
<220> FEATURE:
<223> OTHER INFORMATION: oligo

<400> SEQUENCE: 22
ggtgaaagaa tggagctcaa gataatccca caatagggaa agttgg             46

<210> SEQ ID NO 23
<211> LENGTH: 24
<212> TYPE: DNA
<213> ORGANISM: artificial
<220> FEATURE:
<223> OTHER INFORMATION: oligo

<400> SEQUENCE: 23
tcattcccat atccctccta aagc                                      24

<210> SEQ ID NO 24
<211> LENGTH: 45
<212> TYPE: DNA
<213> ORGANISM: artificial
<220> FEATURE:
<223> OTHER INFORMATION: oligo

<400> SEQUENCE: 24
gctttaggag ggatatggga atgactgcaa atctcgctta tgaag               45

<210> SEQ ID NO 25
<211> LENGTH: 20
<212> TYPE: DNA
<213> ORGANISM: artificial
<220> FEATURE:
<223> OTHER INFORMATION: oligo

<400> SEQUENCE: 25
cctttgccct gggagttaca                                           20

<210> SEQ ID NO 26
<211> LENGTH: 22
<212> TYPE: DNA
<213> ORGANISM: artificial
<220> FEATURE:
<223> OTHER INFORMATION: oligo

<400> SEQUENCE: 26
tgttacaccg cttagttctc ca                                        22

<210> SEQ ID NO 27
<211> LENGTH: 42
<212> TYPE: DNA
<213> ORGANISM: artificial
<220> FEATURE:
<223> OTHER INFORMATION: oligo

<400> SEQUENCE: 27
ctcagctcac tccattttca atcgttaacc actccaacca cc                  42

<210> SEQ ID NO 28
<211> LENGTH: 45
<212> TYPE: DNA
<213> ORGANISM: artificial

```
<220> FEATURE:
<223> OTHER INFORMATION: oligo

<400> SEQUENCE: 28
ggtgaaagaa tggagctcaa gataatggat tgcctcgatt taagc           45

<210> SEQ ID NO 29
<211> LENGTH: 19
<212> TYPE: DNA
<213> ORGANISM: artificial
<220> FEATURE:
<223> OTHER INFORMATION: oligo

<400> SEQUENCE: 29
gttaaccact ccaaccacc                                        19

<210> SEQ ID NO 30
<211> LENGTH: 40
<212> TYPE: DNA
<213> ORGANISM: artificial
<220> FEATURE:
<223> OTHER INFORMATION: oligo

<400> SEQUENCE: 30
ggtggttgga gtggttaacg ttaaggatcc cactttgctc                 40

<210> SEQ ID NO 31
<211> LENGTH: 20
<212> TYPE: DNA
<213> ORGANISM: artificial
<220> FEATURE:
<223> OTHER INFORMATION: oligo

<400> SEQUENCE: 31
ggcacttcca tcctttgagt                                       20

<210> SEQ ID NO 32
<211> LENGTH: 20
<212> TYPE: DNA
<213> ORGANISM: artificial
<220> FEATURE:
<223> OTHER INFORMATION: oligo

<400> SEQUENCE: 32
tggatagcct gggagagaga                                       20

<210> SEQ ID NO 33
<211> LENGTH: 42
<212> TYPE: DNA
<213> ORGANISM: artificial
<220> FEATURE:
<223> OTHER INFORMATION: oligo

<400> SEQUENCE: 33
ctcagctcac tccattttca atcccctcca gcgtatatta gc              42

<210> SEQ ID NO 34
<211> LENGTH: 45
<212> TYPE: DNA
<213> ORGANISM: artificial
<220> FEATURE:
<223> OTHER INFORMATION: oligo

<400> SEQUENCE: 34
ggtgaaagaa tggagctcaa gataattatg gatggcgacg atatg           45
```

<210> SEQ ID NO 35
<211> LENGTH: 19
<212> TYPE: DNA
<213> ORGANISM: artificial
<220> FEATURE:
<223> OTHER INFORMATION: oligo

<400> SEQUENCE: 35
ccctccagcg tatattagc                                               19

<210> SEQ ID NO 36
<211> LENGTH: 46
<212> TYPE: DNA
<213> ORGANISM: artificial
<220> FEATURE:
<223> OTHER INFORMATION: oligo

<400> SEQUENCE: 36
gctaatatac gctggagggg cagcagtcct agcaattttg ccagtc                 46

<210> SEQ ID NO 37
<211> LENGTH: 20
<212> TYPE: DNA
<213> ORGANISM: artificial
<220> FEATURE:
<223> OTHER INFORMATION: oligo

<400> SEQUENCE: 37
aaattcgggt tcctcctcac                                              20

<210> SEQ ID NO 38
<211> LENGTH: 20
<212> TYPE: DNA
<213> ORGANISM: artificial
<220> FEATURE:
<223> OTHER INFORMATION: oligo

<400> SEQUENCE: 38
atcctcctgg gagcagattt                                              20

<210> SEQ ID NO 39
<211> LENGTH: 51
<212> TYPE: DNA
<213> ORGANISM: artificial
<220> FEATURE:
<223> OTHER INFORMATION: oligo

<400> SEQUENCE: 39
ctcagctcac tccattttca atcaaggtat acaaaaagtt tctctttgat g           51

<210> SEQ ID NO 40
<211> LENGTH: 45
<212> TYPE: DNA
<213> ORGANISM: artificial
<220> FEATURE:
<223> OTHER INFORMATION: oligo

<400> SEQUENCE: 40
ggtgaaagaa tggagctcaa gataaaggag agcttctccc ctttg                  45

<210> SEQ ID NO 41
<211> LENGTH: 28
<212> TYPE: DNA
<213> ORGANISM: artificial
<220> FEATURE:
<223> OTHER INFORMATION: oligo

<400> SEQUENCE: 41
aaggtataca aaaagtttct ctttgatg                                        28

<210> SEQ ID NO 42
<211> LENGTH: 53
<212> TYPE: DNA
<213> ORGANISM: artificial
<220> FEATURE:
<223> OTHER INFORMATION: oligo

<400> SEQUENCE: 42
catcaaagag aaacttttg tataccttgc agcaccacca gacaaggctc taa             53

<210> SEQ ID NO 43
<211> LENGTH: 21
<212> TYPE: DNA
<213> ORGANISM: artificial
<220> FEATURE:
<223> OTHER INFORMATION: oligo

<400> SEQUENCE: 43
ccgaacttgt ccactatcac c                                               21

<210> SEQ ID NO 44
<211> LENGTH: 23
<212> TYPE: DNA
<213> ORGANISM: artificial
<220> FEATURE:
<223> OTHER INFORMATION: oligo

<400> SEQUENCE: 44
tccaatccga agcttgcaac ata                                             23

<210> SEQ ID NO 45
<211> LENGTH: 49
<212> TYPE: DNA
<213> ORGANISM: artificial
<220> FEATURE:
<223> OTHER INFORMATION: oligo

<400> SEQUENCE: 45
ctcagctcac tccattttca atcgctacct caccgagcca aataaagtg                 49

<210> SEQ ID NO 46
<211> LENGTH: 47
<212> TYPE: DNA
<213> ORGANISM: artificial
<220> FEATURE:
<223> OTHER INFORMATION: oligo

<400> SEQUENCE: 46
ggtgaaagaa tggagctcaa gataactggg cttcggaatg gttaagg                   47

<210> SEQ ID NO 47
<211> LENGTH: 26
<212> TYPE: DNA
<213> ORGANISM: artificial
<220> FEATURE:
<223> OTHER INFORMATION: oligo

<400> SEQUENCE: 47
gctacctcac cgagccaaat aaagtg                                          26

<210> SEQ ID NO 48

```
<211> LENGTH: 48
<212> TYPE: DNA
<213> ORGANISM: artificial
<220> FEATURE:
<223> OTHER INFORMATION: oligo

<400> SEQUENCE: 48
cactttattt ggctcggtga ggtagcttgc cgttggtggc agagatag                    48

<210> SEQ ID NO 49
<211> LENGTH: 22
<212> TYPE: DNA
<213> ORGANISM: artificial
<220> FEATURE:
<223> OTHER INFORMATION: oligo

<400> SEQUENCE: 49
gcctttggta ccctctccca ga                                                22

<210> SEQ ID NO 50
<211> LENGTH: 54
<212> TYPE: DNA
<213> ORGANISM: artificial
<220> FEATURE:
<223> OTHER INFORMATION: oligo

<400> SEQUENCE: 50
cactttattt ggctcggtga ggtagcatga aaccgtgctt tgcaaaattt cttc             54

<210> SEQ ID NO 51
<211> LENGTH: 23
<212> TYPE: DNA
<213> ORGANISM: artificial
<220> FEATURE:
<223> OTHER INFORMATION: oligo

<400> SEQUENCE: 51
tcgttgccaa ttgaaactaa ggt                                               23

<210> SEQ ID NO 52
<211> LENGTH: 51
<212> TYPE: DNA
<213> ORGANISM: artificial
<220> FEATURE:
<223> OTHER INFORMATION: oligo

<400> SEQUENCE: 52
ctcagctcac tccattttca atcctaaaca tattcaacaa gcctcccata g                51

<210> SEQ ID NO 53
<211> LENGTH: 46
<212> TYPE: DNA
<213> ORGANISM: artificial
<220> FEATURE:
<223> OTHER INFORMATION: oligo

<400> SEQUENCE: 53
ggtgaaagaa tggagctcaa gataaatgtc ccacctcctg gggact                      46

<210> SEQ ID NO 54
<211> LENGTH: 28
<212> TYPE: DNA
<213> ORGANISM: artificial
<220> FEATURE:
<223> OTHER INFORMATION: oligo

<400> SEQUENCE: 54
```

```
ctaaacatat tcaacaagcc tcccatag                                          28

<210> SEQ ID NO 55
<211> LENGTH: 56
<212> TYPE: DNA
<213> ORGANISM: artificial
<220> FEATURE:
<223> OTHER INFORMATION: oligo

<400> SEQUENCE: 55
ctatgggagg cttgttgaat atgtttagat gaaaccgtgc tttgcaaaat ttcttc          56

<210> SEQ ID NO 56
<211> LENGTH: 22
<212> TYPE: DNA
<213> ORGANISM: artificial
<220> FEATURE:
<223> OTHER INFORMATION: oligo

<400> SEQUENCE: 56
gggccgcttc agtctttcca ta                                               22

<210> SEQ ID NO 57
<211> LENGTH: 24
<212> TYPE: DNA
<213> ORGANISM: artificial
<220> FEATURE:
<223> OTHER INFORMATION: oligo

<400> SEQUENCE: 57
ggattttgta ttgcctcacg gtta                                             24

<210> SEQ ID NO 58
<211> LENGTH: 52
<212> TYPE: DNA
<213> ORGANISM: artificial
<220> FEATURE:
<223> OTHER INFORMATION: oligo

<400> SEQUENCE: 58
ctcagctcac tccattttca atcgttttc tgtatcgaat attccccgaa tg              52

<210> SEQ ID NO 59
<211> LENGTH: 47
<212> TYPE: DNA
<213> ORGANISM: artificial
<220> FEATURE:
<223> OTHER INFORMATION: oligo

<400> SEQUENCE: 59
ggtgaaagaa tggagctcaa gataatccca ggttctggtt tgacaag                   47

<210> SEQ ID NO 60
<211> LENGTH: 29
<212> TYPE: DNA
<213> ORGANISM: artificial
<220> FEATURE:
<223> OTHER INFORMATION: oligo

<400> SEQUENCE: 60
gtttttctgt atcgaatatt ccccgaatg                                        29

<210> SEQ ID NO 61
<211> LENGTH: 57
<212> TYPE: DNA
```

```
<213> ORGANISM: artificial
<220> FEATURE:
<223> OTHER INFORMATION: oligo

<400> SEQUENCE: 61
cattcgggga atattcgata cagaaaaaca gctttatctt ttcccataac cattagg      57

<210> SEQ ID NO 62
<211> LENGTH: 21
<212> TYPE: DNA
<213> ORGANISM: artificial
<220> FEATURE:
<223> OTHER INFORMATION: oligo

<400> SEQUENCE: 62 tggctcccttt aactcgctgg a                                            21

<210> SEQ ID NO 63
<211> LENGTH: 20
<212> TYPE: DNA
<213> ORGANISM: artificial
<220> FEATURE:
<223> OTHER INFORMATION: oligo

<400> SEQUENCE: 63
gtgttggagt gggtgaggag                                               20

<210> SEQ ID NO 64
<211> LENGTH: 23
<212> TYPE: DNA
<213> ORGANISM: artificial
<220> FEATURE:
<223> OTHER INFORMATION: oligo

<400> SEQUENCE: 64
tctggagata tttgccgtta atc                                           23

<210> SEQ ID NO 65
<211> LENGTH: 21
<212> TYPE: DNA
<213> ORGANISM: artificial
<220> FEATURE:
<223> OTHER INFORMATION: oligo

<400> SEQUENCE: 65
tcccacaata gggaaagttg g                                             21

<210> SEQ ID NO 66
<211> LENGTH: 20
<212> TYPE: DNA
<213> ORGANISM: artificial
<220> FEATURE:
<223> OTHER INFORMATION: oligo

<400> SEQUENCE: 66
gtttttggga gcacaaagga                                               20

<210> SEQ ID NO 67
<211> LENGTH: 20
<212> TYPE: DNA
<213> ORGANISM: artificial
<220> FEATURE:
<223> OTHER INFORMATION: oligo

<400> SEQUENCE: 67
ggttcctcat caagccacaa                                               20
```

<210> SEQ ID NO 68
<211> LENGTH: 20
<212> TYPE: DNA
<213> ORGANISM: artificial
<220> FEATURE:
<223> OTHER INFORMATION: oligo

<400> SEQUENCE: 68
tggattgcct cgatttaagc                                              20

<210> SEQ ID NO 69
<211> LENGTH: 20
<212> TYPE: DNA
<213> ORGANISM: artificial
<220> FEATURE:
<223> OTHER INFORMATION: oligo

<400> SEQUENCE: 69
gggtctctcg gatgaagatg                                              20

<210> SEQ ID NO 70
<211> LENGTH: 21
<212> TYPE: DNA
<213> ORGANISM: artificial
<220> FEATURE:
<223> OTHER INFORMATION: oligo

<400> SEQUENCE: 70
ttctgccttt ctctgttcca a                                            21

<210> SEQ ID NO 71
<211> LENGTH: 20
<212> TYPE: DNA
<213> ORGANISM: artificial
<220> FEATURE:
<223> OTHER INFORMATION: oligo

<400> SEQUENCE: 71
ttatggatgg cgacgatatg                                              20

<210> SEQ ID NO 72
<211> LENGTH: 27
<212> TYPE: DNA
<213> ORGANISM: artificial
<220> FEATURE:
<223> OTHER INFORMATION: oligo

<400> SEQUENCE: 72
gactggcaaa attgctagga ctgctgc                                      27

<210> SEQ ID NO 73
<211> LENGTH: 27
<212> TYPE: DNA
<213> ORGANISM: artificial
<220> FEATURE:
<223> OTHER INFORMATION: oligo

<400> SEQUENCE: 73
gactggcaaa attgctagga catcatc                                      27

<210> SEQ ID NO 74
<211> LENGTH: 20
<212> TYPE: DNA
<213> ORGANISM: artificial
<220> FEATURE:

<223> OTHER INFORMATION: oligo

<400> SEQUENCE: 74
gtttttggga gcacaaagga                                            20

<210> SEQ ID NO 75
<211> LENGTH: 20
<212> TYPE: DNA
<213> ORGANISM: artificial
<220> FEATURE:
<223> OTHER INFORMATION: oligo

<400> SEQUENCE: 75
ttcagcctcc tttcctgaga                                            20

<210> SEQ ID NO 76
<211> LENGTH: 20
<212> TYPE: DNA
<213> ORGANISM: artificial
<220> FEATURE:
<223> OTHER INFORMATION: oligo

<400> SEQUENCE: 76
aggagagctt ctccctttg                                             20

<210> SEQ ID NO 77
<211> LENGTH: 25
<212> TYPE: DNA
<213> ORGANISM: artificial
<220> FEATURE:
<223> OTHER INFORMATION: oligo

<400> SEQUENCE: 77
ttagagcctt gtctggtggt gctgc                                      25

<210> SEQ ID NO 78
<211> LENGTH: 25
<212> TYPE: DNA
<213> ORGANISM: artificial
<220> FEATURE:
<223> OTHER INFORMATION: oligo

<400> SEQUENCE: 78
ttagagcctt gtctggtgga tcatg                                      25

<210> SEQ ID NO 79
<211> LENGTH: 21
<212> TYPE: DNA
<213> ORGANISM: artificial
<220> FEATURE:
<223> OTHER INFORMATION: oligo

<400> SEQUENCE: 79
ttggagatag gttcacgtgg t                                          21

<210> SEQ ID NO 80
<211> LENGTH: 20
<212> TYPE: DNA
<213> ORGANISM: artificial
<220> FEATURE:
<223> OTHER INFORMATION: oligo

<400> SEQUENCE: 80
aaatccctga tgagctgtgg                                            20

```
<210> SEQ ID NO 81
<211> LENGTH: 22
<212> TYPE: DNA
<213> ORGANISM: artificial
<220> FEATURE:
<223> OTHER INFORMATION: oligo

<400> SEQUENCE: 81
ctgggcttcg gaatggttaa gg                                              22

<210> SEQ ID NO 82
<211> LENGTH: 21
<212> TYPE: DNA
<213> ORGANISM: artificial
<220> FEATURE:
<223> OTHER INFORMATION: oligo

<400> SEQUENCE: 82
ttggagatag gttcacgtgg t                                               21

<210> SEQ ID NO 83
<211> LENGTH: 21
<212> TYPE: DNA
<213> ORGANISM: artificial
<220> FEATURE:
<223> OTHER INFORMATION: oligo

<400> SEQUENCE: 83
gcgtgagcca caaatctagt c                                               21

<210> SEQ ID NO 84
<211> LENGTH: 20
<212> TYPE: DNA
<213> ORGANISM: artificial
<220> FEATURE:
<223> OTHER INFORMATION: oligo

<400> SEQUENCE: 84
cgagattgaa acaggagctg                                                 20

<210> SEQ ID NO 85
<211> LENGTH: 20
<212> TYPE: DNA
<213> ORGANISM: artificial
<220> FEATURE:
<223> OTHER INFORMATION: oligo

<400> SEQUENCE: 85
ttgggaggag ctgtaattgg                                                 20

<210> SEQ ID NO 86
<211> LENGTH: 22
<212> TYPE: DNA
<213> ORGANISM: artificial
<220> FEATURE:
<223> OTHER INFORMATION: oligo

<400> SEQUENCE: 86
tcccaggttc tggtttgaca ag                                              22

<210> SEQ ID NO 87
<211> LENGTH: 20
<212> TYPE: DNA
<213> ORGANISM: artificial
<220> FEATURE:
<223> OTHER INFORMATION: oligo
```

```
<400> SEQUENCE: 87 cctggggag agacagaact                                            20

<210> SEQ ID NO 88
<211> LENGTH: 20
<212> TYPE: DNA
<213> ORGANISM: artificial
<220> FEATURE:
<223> OTHER INFORMATION: oligo

<400> SEQUENCE: 88
aaatccctga tgagctgtgg                                           20

<210> SEQ ID NO 89
<211> LENGTH: 21
<212> TYPE: DNA
<213> ORGANISM: artificial
<220> FEATURE:
<223> OTHER INFORMATION: oligo

<400> SEQUENCE: 89
atgtcccacc tcctggggac t                                         21

<210> SEQ ID NO 90
<211> LENGTH: 59
<212> TYPE: DNA
<213> ORGANISM: artificial
<220> FEATURE:
<223> OTHER INFORMATION: oligo

<400> SEQUENCE: 90
tatgggatcc tctgaagtgc tctcagccgc aaggaccgca tactacaagg gatccgagg    59

<210> SEQ ID NO 91
<211> LENGTH: 61
<212> TYPE: DNA
<213> ORGANISM: artificial
<220> FEATURE:
<223> OTHER INFORMATION: oligo

<400> SEQUENCE: 91
gatccctcgg atcccttgta gtatgcggtc cttgcggctg agagcacttc agaggatccc    60
a                                                                   61

<210> SEQ ID NO 92
<211> LENGTH: 59
<212> TYPE: DNA
<213> ORGANISM: artificial
<220> FEATURE:
<223> OTHER INFORMATION: oligo

<400> SEQUENCE: 92
tatgctcgga tcccttgtag tatgcggtcc ttgcggctga gagcacttca gaggatccg     59

<210> SEQ ID NO 93
<211> LENGTH: 61
<212> TYPE: DNA
<213> ORGANISM: artificial
<220> FEATURE:
<223> OTHER INFORMATION: oligo

<400> SEQUENCE: 93
gatccggatc ctctgaagtg ctctcagccg caaggaccgc atactacaag ggatccgagc    60
a                                                                   61
```

<210> SEQ ID NO 94
<211> LENGTH: 59
<212> TYPE: DNA
<213> ORGANISM: artificial
<220> FEATURE:
<223> OTHER INFORMATION: oligo

<400> SEQUENCE: 94
tatgggatcc tctgaagtgc tctcagccgc aaggaccgca tactacaact ttcaatagg    59

<210> SEQ ID NO 95
<211> LENGTH: 61
<212> TYPE: DNA
<213> ORGANISM: artificial
<220> FEATURE:
<223> OTHER INFORMATION: oligo

<400> SEQUENCE: 95
gatccctatt gaaagttgta gtatgcggtc cttgcggctg agagcacttc agaggatccc    60
a                                                                   61

<210> SEQ ID NO 96
<211> LENGTH: 59
<212> TYPE: DNA
<213> ORGANISM: artificial
<220> FEATURE:
<223> OTHER INFORMATION: oligo

<400> SEQUENCE: 96
tatgggatcc tctgaagtgc tctcagccgc aaggaccgca tactacaact ttcaaaagg    59

<210> SEQ ID NO 97
<211> LENGTH: 61
<212> TYPE: DNA
<213> ORGANISM: artificial
<220> FEATURE:
<223> OTHER INFORMATION: oligo

<400> SEQUENCE: 97 gatcccttt t gaaagttgta gtatgcggtc cttgcggctg agagcacttc agaggatccc    60
a                                                                   61

<210> SEQ ID NO 98
<211> LENGTH: 59
<212> TYPE: DNA
<213> ORGANISM: artificial
<220> FEATURE:
<223> OTHER INFORMATION: oligo

<400> SEQUENCE: 98
tatgggatcc tctgaagtgc tctcagccgc aaggaccgca tactacaact ttcataagg    59

<210> SEQ ID NO 99
<211> LENGTH: 61
<212> TYPE: DNA
<213> ORGANISM: artificial
<220> FEATURE:
<223> OTHER INFORMATION: oligo

<400> SEQUENCE: 99
gatcccttat gaaagttgta gtatgcggtc cttgcggctg agagcacttc agaggatccc    60
a                                                                   61

```
<210> SEQ ID NO 100
<211> LENGTH: 59
<212> TYPE: DNA
<213> ORGANISM: artificial
<220> FEATURE:
<223> OTHER INFORMATION: oligo

<400> SEQUENCE: 100
tatgggatcc tctgaagtgc tctcagccgc aaggaccgca tactacaact ttcttaagg      59

<210> SEQ ID NO 101
<211> LENGTH: 61
<212> TYPE: DNA
<213> ORGANISM: artificial
<220> FEATURE:
<223> OTHER INFORMATION: oligo

<400> SEQUENCE: 101
gatcccttaa gaaagttgta gtatgcggtc cttgcggctg agagcacttc agaggatccc      60
a                                                                     61

<210> SEQ ID NO 102
<211> LENGTH: 59
<212> TYPE: DNA
<213> ORGANISM: artificial
<220> FEATURE:
<223> OTHER INFORMATION: oligo

<400> SEQUENCE: 102
tatgggatcc tctgaagtgc tctcagccgc aaggaccgca tactacaact ttgttaagg      59

<210> SEQ ID NO 103
<211> LENGTH: 61
<212> TYPE: DNA
<213> ORGANISM: artificial
<220> FEATURE:
<223> OTHER INFORMATION: oligo

<400> SEQUENCE: 103
gatcccttaa caaagttgta gtatgcggtc cttgcggctg agagcacttc agaggatccc      60
a                                                                     61

<210> SEQ ID NO 104
<211> LENGTH: 59
<212> TYPE: DNA
<213> ORGANISM: artificial
<220> FEATURE:
<223> OTHER INFORMATION: oligo

<400> SEQUENCE: 104
tatgggatcc tctgaagtgc tctcagccgc aaggaccgca tactacaact tagttaagg      59

<210> SEQ ID NO 105
<211> LENGTH: 61
<212> TYPE: DNA
<213> ORGANISM: artificial
<220> FEATURE:
<223> OTHER INFORMATION: oligo

<400> SEQUENCE: 105
gatcccttaa ctaagttgta gtatgcggtc cttgcggctg agagcacttc agaggatccc      60
a                                                                     61
```

```
<210> SEQ ID NO 106
<211> LENGTH: 59
<212> TYPE: DNA
<213> ORGANISM: artificial
<220> FEATURE:
<223> OTHER INFORMATION: oligo

<400> SEQUENCE: 106
tatgggatcc tctgaagtgc tctcagccgc aaggaccgca tactacaact aagttaagg      59

<210> SEQ ID NO 107
<211> LENGTH: 61
<212> TYPE: DNA
<213> ORGANISM: artificial
<220> FEATURE:
<223> OTHER INFORMATION: oligo

<400> SEQUENCE: 107
gatcccttaa cttagttgta gtatgcggtc cttgcggctg agagcacttc agaggatccc     60
a                                                                     61

<210> SEQ ID NO 108
<211> LENGTH: 59
<212> TYPE: DNA
<213> ORGANISM: artificial
<220> FEATURE:
<223> OTHER INFORMATION: oligo

<400> SEQUENCE: 108
tatgggatcc tctgaagtgc tctcagccgc aaggaccgca tactacaaca aagttaagg      59

<210> SEQ ID NO 109
<211> LENGTH: 61
<212> TYPE: DNA
<213> ORGANISM: artificial
<220> FEATURE:
<223> OTHER INFORMATION: oligo

<400> SEQUENCE: 109
gatcccttaa ctttgttgta gtatgcggtc cttgcggctg agagcacttc agaggatccc     60
a                                                                     61

<210> SEQ ID NO 110
<211> LENGTH: 59
<212> TYPE: DNA
<213> ORGANISM: artificial
<220> FEATURE:
<223> OTHER INFORMATION: oligo

<400> SEQUENCE: 110
tatgggatcc tctgaagtgc tctcagccgc aaggaccgca tactacaaga aagttaagg      59

<210> SEQ ID NO 111
<211> LENGTH: 61
<212> TYPE: DNA
<213> ORGANISM: artificial
<220> FEATURE:
<223> OTHER INFORMATION: oligo

<400> SEQUENCE: 111
gatcccttaa ctttcttgta gtatgcggtc cttgcggctg agagcacttc agaggatccc     60
a                                                                     61

<210> SEQ ID NO 112
```

<211> LENGTH: 59
<212> TYPE: DNA
<213> ORGANISM: artificial
<220> FEATURE:
<223> OTHER INFORMATION: oligo

<400> SEQUENCE: 112
tatgggatcc tctgaagtgc tctcagccgc aaggaccgca tactacaaga atcaatagg    59

<210> SEQ ID NO 113
<211> LENGTH: 61
<212> TYPE: DNA
<213> ORGANISM: artificial
<220> FEATURE:
<223> OTHER INFORMATION: oligo

<400> SEQUENCE: 113
gatccctatt gattcttgta gtatgcggtc cttgcggctg agagcacttc agaggatccc    60
a    61

<210> SEQ ID NO 114
<211> LENGTH: 59
<212> TYPE: DNA
<213> ORGANISM: artificial
<220> FEATURE:
<223> OTHER INFORMATION: oligo

<400> SEQUENCE: 114
tatgggatcc tctgaagtgc tctcagccgc aaggaccgca tactacaagt tagttaagg    59

<210> SEQ ID NO 115
<211> LENGTH: 61
<212> TYPE: DNA
<213> ORGANISM: artificial
<220> FEATURE:
<223> OTHER INFORMATION: oligo

<400> SEQUENCE: 115
gatcccttaa ctaacttgta gtatgcggtc cttgcggctg agagcacttc agaggatccc    60
a    61

<210> SEQ ID NO 116
<211> LENGTH: 59
<212> TYPE: DNA
<213> ORGANISM: artificial
<220> FEATURE:
<223> OTHER INFORMATION: oligo

<400> SEQUENCE: 116
tatgctcgga tcccagtcct gtagagacta ataccttcaa tacgcagcac caggatccg    59

<210> SEQ ID NO 117
<211> LENGTH: 61
<212> TYPE: DNA
<213> ORGANISM: artificial
<220> FEATURE:
<223> OTHER INFORMATION: oligo

<400> SEQUENCE: 117
gatccggatc ctggtgctgc gtattgaagg tattagtctc tacaggactg ggatccgagc    60
a    61

<210> SEQ ID NO 118
<211> LENGTH: 59

```
<212> TYPE: DNA
<213> ORGANISM: artificial
<220> FEATURE:
<223> OTHER INFORMATION: oligo

<400> SEQUENCE: 118
tatgctcgga tcccagtgaa gaatttgacg tacaaatgtc cttagtggaa caggatccg    59

<210> SEQ ID NO 119
<211> LENGTH: 61
<212> TYPE: DNA
<213> ORGANISM: artificial
<220> FEATURE:
<223> OTHER INFORMATION: oligo

<400> SEQUENCE: 119
gatccggatc ctgttccact aaggacattt gtacgtcaaa ttcttcactg ggatccgagc    60
a                                                                  61

<210> SEQ ID NO 120
<211> LENGTH: 61
<212> TYPE: DNA
<213> ORGANISM: artificial
<220> FEATURE:
<223> OTHER INFORMATION: oligo

<400> SEQUENCE: 120
tatgctcgga tccctgttca tcgcacttct tcttctgact ctgctccact tagaggatcc    60
g                                                                  61

<210> SEQ ID NO 121
<211> LENGTH: 63
<212> TYPE: DNA
<213> ORGANISM: artificial
<220> FEATURE:
<223> OTHER INFORMATION: oligo

<400> SEQUENCE: 121
gatccggatc ctctaagtgg agcagagtca gaagaagaag tgcgatgaac agggatccga    60
gca                                                                63

<210> SEQ ID NO 122
<211> LENGTH: 81
<212> TYPE: DNA
<213> ORGANISM: artificial
<220> FEATURE:
<223> OTHER INFORMATION: oligo
<220> FEATURE:
<221> NAME/KEY: misc_feature
<222> LOCATION: (59)..(61)
<223> OTHER INFORMATION: n is a, c, g, or t

<400> SEQUENCE: 122
ggtgttgtca tatgggttcc tctgaagtgc tctcagccgc aaggaccgca tactacaann    60
nttccgaggg atccccctc t                                              81

<210> SEQ ID NO 123
<211> LENGTH: 19
<212> TYPE: DNA
<213> ORGANISM: artificial
<220> FEATURE:
<223> OTHER INFORMATION: oligo

<400> SEQUENCE: 123
``` agaggggga tccctcgga        19

<210> SEQ ID NO 124
<211> LENGTH: 59
<212> TYPE: DNA
<213> ORGANISM: artificial
<220> FEATURE:
<223> OTHER INFORMATION: oligo

<400> SEQUENCE: 124
tatgggttcc tctgaagtgc tctcagccgc aaggaccgca tactacaatc cttccgagg        59

<210> SEQ ID NO 125
<211> LENGTH: 61
<212> TYPE: DNA
<213> ORGANISM: artificial
<220> FEATURE:
<223> OTHER INFORMATION: oligo

<400> SEQUENCE: 125
gatccctcgg aaggattgta gtatgcggtc cttgcggctg agagcacttc agaggaaccc        60
a        61

<210> SEQ ID NO 126
<211> LENGTH: 59
<212> TYPE: DNA
<213> ORGANISM: artificial
<220> FEATURE:
<223> OTHER INFORMATION: oligo

<400> SEQUENCE: 126
tatgggttcc tctgaagtgc tctcagccgc aaggaccgca tactacaacc tttccgagg        59

<210> SEQ ID NO 127
<211> LENGTH: 61
<212> TYPE: DNA
<213> ORGANISM: artificial
<220> FEATURE:
<223> OTHER INFORMATION: oligo

<400> SEQUENCE: 127
gatccctcgg aaaggttgta gtatgcggtc cttgcggctg agagcacttc agaggaaccc        60
a        61

<210> SEQ ID NO 128
<211> LENGTH: 59
<212> TYPE: DNA
<213> ORGANISM: artificial
<220> FEATURE:
<223> OTHER INFORMATION: oligo

<400> SEQUENCE: 128
tatgggttcc tctgaagtgc tctcagccgc aaggaccgca tactacaaca cttccgagg        59

<210> SEQ ID NO 129
<211> LENGTH: 61
<212> TYPE: DNA
<213> ORGANISM: artificial
<220> FEATURE:
<223> OTHER INFORMATION: oligo

<400> SEQUENCE: 129
gatccctcgg aagtgttgta gtatgcggtc cttgcggctg agagcacttc agaggaaccc        60
a        61

<210> SEQ ID NO 130
<211> LENGTH: 59
<212> TYPE: DNA
<213> ORGANISM: artificial
<220> FEATURE:
<223> OTHER INFORMATION: oligo

<400> SEQUENCE: 130
tatgggttcc tctgaagtgc tctcagccgc aaggaccgca tactacaaat cttccgagg    59

<210> SEQ ID NO 131
<211> LENGTH: 61
<212> TYPE: DNA
<213> ORGANISM: artificial
<220> FEATURE:
<223> OTHER INFORMATION: oligo

<400> SEQUENCE: 131
gatccctcgg aagatttgta gtatgcggtc cttgcggctg agagcacttc agaggaaccc    60
a                                                                   61

<210> SEQ ID NO 132
<211> LENGTH: 59
<212> TYPE: DNA
<213> ORGANISM: artificial
<220> FEATURE:
<223> OTHER INFORMATION: oligo

<400> SEQUENCE: 132
tatgggttcc tctgaagtgc tctcagccgc aaggaccgca tactacaaac cttccgagg    59

<210> SEQ ID NO 133
<211> LENGTH: 61
<212> TYPE: DNA
<213> ORGANISM: artificial
<220> FEATURE:
<223> OTHER INFORMATION: oligo

<400> SEQUENCE: 133
gatccctcgg aaggtttgta gtatgcggtc cttgcggctg agagcacttc agaggaaccc    60
a                                                                   61

<210> SEQ ID NO 134
<211> LENGTH: 59
<212> TYPE: DNA
<213> ORGANISM: artificial
<220> FEATURE:
<223> OTHER INFORMATION: oligo

<400> SEQUENCE: 134
tatgggttcc tctgaagtgc tctcagccgc aaggaccgca tactacaaaa tttccgagg    59

<210> SEQ ID NO 135
<211> LENGTH: 61
<212> TYPE: DNA
<213> ORGANISM: artificial
<220> FEATURE:
<223> OTHER INFORMATION: oligo

<400> SEQUENCE: 135
gatccctcgg aaattttgta gtatgcggtc cttgcggctg agagcacttc agaggaaccc    60
a                                                                   61

<210> SEQ ID NO 136
<211> LENGTH: 59
<212> TYPE: DNA
<213> ORGANISM: artificial
<220> FEATURE:
<223> OTHER INFORMATION: oligo

<400> SEQUENCE: 136
tatgggttcc tctgaagtgc tctcagccgc aaggaccgca tactacaata cttccgagg      59

<210> SEQ ID NO 137
<211> LENGTH: 61
<212> TYPE: DNA
<213> ORGANISM: artificial
<220> FEATURE:
<223> OTHER INFORMATION: oligo

<400> SEQUENCE: 137
gatccctcgg aagtattgta gtatgcggtc cttgcggctg agagcacttc agaggaaccc      60
a                                                                     61

<210> SEQ ID NO 138
<211> LENGTH: 59
<212> TYPE: DNA
<213> ORGANISM: artificial
<220> FEATURE:
<223> OTHER INFORMATION: oligo

<400> SEQUENCE: 138
tatgggttcc tctgaagtgc tctcagccgc aaggaccgca tactacaact tttccgagg      59

<210> SEQ ID NO 139
<211> LENGTH: 61
<212> TYPE: DNA
<213> ORGANISM: artificial
<220> FEATURE:
<223> OTHER INFORMATION: oligo

<400> SEQUENCE: 139
gatccctcgg aaaagttgta gtatgcggtc cttgcggctg agagcacttc agaggaaccc      60
a                                                                     61

<210> SEQ ID NO 140
<211> LENGTH: 59
<212> TYPE: DNA
<213> ORGANISM: artificial
<220> FEATURE:
<223> OTHER INFORMATION: oligo

<400> SEQUENCE: 140
tatgggttcc tctgaagtgc tctcagccgc aaggaccgca tactacaacc attccgagg      59

<210> SEQ ID NO 141
<211> LENGTH: 61
<212> TYPE: DNA
<213> ORGANISM: artificial
<220> FEATURE:
<223> OTHER INFORMATION: oligo

<400> SEQUENCE: 141
gatccctcgg aatggttgta gtatgcggtc cttgcggctg agagcacttc agaggaaccc      60
a                                                                     61

```
<210> SEQ ID NO 142
<211> LENGTH: 59
<212> TYPE: DNA
<213> ORGANISM: artificial
<220> FEATURE:
<223> OTHER INFORMATION: oligo

<400> SEQUENCE: 142
tatgggttcc tctgaagtgc tctcagccgc aaggaccgca tactacaaca gttccgagg        59

<210> SEQ ID NO 143
<211> LENGTH: 61
<212> TYPE: DNA
<213> ORGANISM: artificial
<220> FEATURE:
<223> OTHER INFORMATION: oligo

<400> SEQUENCE: 143
gatccctcgg aactgttgta gtatgcggtc cttgcggctg agagcacttc agaggaaccc        60
a                                                                        61

<210> SEQ ID NO 144
<211> LENGTH: 59
<212> TYPE: DNA
<213> ORGANISM: artificial
<220> FEATURE:
<223> OTHER INFORMATION: oligo

<400> SEQUENCE: 144
tatgggttcc tctgaagtgc tctcagccgc aaggaccgca tactacaaac tttccgagg        59

<210> SEQ ID NO 145
<211> LENGTH: 61
<212> TYPE: DNA
<213> ORGANISM: artificial
<220> FEATURE:
<223> OTHER INFORMATION: oligo

<400> SEQUENCE: 145
gatccctcgg aaagtttgta gtatgcggtc cttgcggctg agagcacttc agaggaaccc        60
a                                                                        61

<210> SEQ ID NO 146
<211> LENGTH: 59
<212> TYPE: DNA
<213> ORGANISM: artificial
<220> FEATURE:
<223> OTHER INFORMATION: oligo

<400> SEQUENCE: 146
tatgggttcc tctgaagtgc tctcagccgc aaggaccgca tactacaaac attccgagg        59

<210> SEQ ID NO 147
<211> LENGTH: 61
<212> TYPE: DNA
<213> ORGANISM: artificial
<220> FEATURE:
<223> OTHER INFORMATION: oligo

<400> SEQUENCE: 147
gatccctcgg aatgtttgta gtatgcggtc cttgcggctg agagcacttc agaggaaccc        60
a                                                                        61

<210> SEQ ID NO 148
```

```
<211> LENGTH: 59
<212> TYPE: DNA
<213> ORGANISM: artificial
<220> FEATURE:
<223> OTHER INFORMATION: oligo

<400> SEQUENCE: 148
tatgggttcc tctgaagtgc tctcagccgc aaggaccgca tactacaaaa attccgagg    59

<210> SEQ ID NO 149
<211> LENGTH: 61
<212> TYPE: DNA
<213> ORGANISM: artificial
<220> FEATURE:
<223> OTHER INFORMATION: oligo

<400> SEQUENCE: 149
gatccctcgg aattttttgta gtatgcggtc cttgcggctg agagcacttc agaggaaccc    60
a                                                                    61

<210> SEQ ID NO 150
<211> LENGTH: 59
<212> TYPE: DNA
<213> ORGANISM: artificial
<220> FEATURE:
<223> OTHER INFORMATION: oligo

<400> SEQUENCE: 150
tatgggttcc tctgaagtgc tctcagccgc aaggaccgca tactacaaaa gttccgagg    59

<210> SEQ ID NO 151
<211> LENGTH: 61
<212> TYPE: DNA
<213> ORGANISM: artificial
<220> FEATURE:
<223> OTHER INFORMATION: oligo

<400> SEQUENCE: 151
gatccctcgg aacttttgta gtatgcggtc cttgcggctg agagcacttc agaggaaccc    60
a                                                                    61

<210> SEQ ID NO 152
<211> LENGTH: 59
<212> TYPE: DNA
<213> ORGANISM: artificial
<220> FEATURE:
<223> OTHER INFORMATION: oligo

<400> SEQUENCE: 152
tatgggttcc tctgaagtgc tctcagccgc aaggaccgca tactacaaag tttccgagg    59

<210> SEQ ID NO 153
<211> LENGTH: 61
<212> TYPE: DNA
<213> ORGANISM: artificial
<220> FEATURE:
<223> OTHER INFORMATION: oligo

<400> SEQUENCE: 153
gatccctcgg aaactttgta gtatgcggtc cttgcggctg agagcacttc agaggaaccc    60
a                                                                    61

<210> SEQ ID NO 154
<211> LENGTH: 59
```

```
<212> TYPE: DNA
<213> ORGANISM: artificial
<220> FEATURE:
<223> OTHER INFORMATION: oligo

<400> SEQUENCE: 154
tatgggttcc tctgaagtgc tctcagccgc aaggaccgca tactacaagt tttccgagg      59

<210> SEQ ID NO 155
<211> LENGTH: 61
<212> TYPE: DNA
<213> ORGANISM: artificial
<220> FEATURE:
<223> OTHER INFORMATION: oligo

<400> SEQUENCE: 155
gatccctcgg aaaacttgta gtatgcggtc cttgcggctg agagcacttc agaggaaccc      60
a                                                                     61

<210> SEQ ID NO 156
<211> LENGTH: 59
<212> TYPE: DNA
<213> ORGANISM: artificial
<220> FEATURE:
<223> OTHER INFORMATION: oligo

<400> SEQUENCE: 156
tatgggttcc tctgaagtgc tctcagccgc aaggaccgca tactacaaga cttccgagg      59

<210> SEQ ID NO 157
<211> LENGTH: 61
<212> TYPE: DNA
<213> ORGANISM: artificial
<220> FEATURE:
<223> OTHER INFORMATION: oligo

<400> SEQUENCE: 157
gatccctcgg aagtcttgta gtatgcggtc cttgcggctg agagcacttc agaggaaccc      60
a                                                                     61

<210> SEQ ID NO 158
<211> LENGTH: 59
<212> TYPE: DNA
<213> ORGANISM: artificial
<220> FEATURE:
<223> OTHER INFORMATION: oligo

<400> SEQUENCE: 158
tatgggttcc tctgaagtgc tctcagccgc aaggaccgca tactacaaga attccgagg      59

<210> SEQ ID NO 159
<211> LENGTH: 61
<212> TYPE: DNA
<213> ORGANISM: artificial
<220> FEATURE:
<223> OTHER INFORMATION: oligo

<400> SEQUENCE: 159
gatccctcgg aattcttgta gtatgcggtc cttgcggctg agagcacttc agaggaaccc      60
a                                                                     61

<210> SEQ ID NO 160
<211> LENGTH: 59
<212> TYPE: DNA
```

<213> ORGANISM: artificial
<220> FEATURE:
<223> OTHER INFORMATION: oligo

<400> SEQUENCE: 160
tatgggatcc tgttccacta aggacatttg tacgtcaaat tcttcactgg gatccgagg    59

<210> SEQ ID NO 161
<211> LENGTH: 61
<212> TYPE: DNA
<213> ORGANISM: artificial
<220> FEATURE:
<223> OTHER INFORMATION: oligo

<400> SEQUENCE: 161
gatccctcgg atcccagtga agaatttgac gtacaaatgt ccttagtgga acaggatccc    60
a                                                                   61

<210> SEQ ID NO 162
<211> LENGTH: 59
<212> TYPE: DNA
<213> ORGANISM: artificial
<220> FEATURE:
<223> OTHER INFORMATION: oligo

<400> SEQUENCE: 162
tatgggatcc tgttccacta aggacatttg tacgtcaaat tcttcactaa aatccgagg    59

<210> SEQ ID NO 163
<211> LENGTH: 61
<212> TYPE: DNA
<213> ORGANISM: artificial
<220> FEATURE:
<223> OTHER INFORMATION: oligo

<400> SEQUENCE: 163
gatccctcgg attttagtga agaatttgac gtacaaatgt ccttagtgga acaggatccc    60
a                                                                   61

<210> SEQ ID NO 164
<211> LENGTH: 59
<212> TYPE: DNA
<213> ORGANISM: artificial
<220> FEATURE:
<223> OTHER INFORMATION: oligo

<400> SEQUENCE: 164
tatgggatcc tgttccacta aggacatttg tacgtcaaat tcttcactcc catccgagg    59

<210> SEQ ID NO 165
<211> LENGTH: 61
<212> TYPE: DNA
<213> ORGANISM: artificial
<220> FEATURE:
<223> OTHER INFORMATION: oligo

<400> SEQUENCE: 165
gatccctcgg atgggagtga agaatttgac gtacaaatgt ccttagtgga acaggatccc    60
a                                                                   61

<210> SEQ ID NO 166
<211> LENGTH: 59
<212> TYPE: DNA
<213> ORGANISM: artificial

```
<220> FEATURE:
<223> OTHER INFORMATION: oligo

<400> SEQUENCE: 166
tatgggatcc tgttccacta aggacatttg tacgtcaaat tcttcacttt tatccgagg      59

<210> SEQ ID NO 167
<211> LENGTH: 61
<212> TYPE: DNA
<213> ORGANISM: artificial
<220> FEATURE:
<223> OTHER INFORMATION: oligo

<400> SEQUENCE: 167
gatccctcgg ataaaagtga agaatttgac gtacaaatgt ccttagtgga acaggatccc    60
a                                                                    61

<210> SEQ ID NO 168
<211> LENGTH: 27
<212> TYPE: DNA
<213> ORGANISM: artificial
<220> FEATURE:
<223> OTHER INFORMATION: oligo

<400> SEQUENCE: 168
aacgaagcgg ccgctatcgg caaaagg                                         27

<210> SEQ ID NO 169
<211> LENGTH: 32
<212> TYPE: DNA
<213> ORGANISM: artificial
<220> FEATURE:
<223> OTHER INFORMATION: oligo

<400> SEQUENCE: 169
aacgaagata tcgaggaagc ggaggttcca ag                                   32

<210> SEQ ID NO 170
<211> LENGTH: 39
<212> TYPE: DNA
<213> ORGANISM: artificial
<220> FEATURE:
<223> OTHER INFORMATION: oligo

<400> SEQUENCE: 170
ggatccgatt cgttcatatg acaacacctc cttgggttg                            39

<210> SEQ ID NO 171
<211> LENGTH: 46
<212> TYPE: DNA
<213> ORGANISM: artificial
<220> FEATURE:
<223> OTHER INFORMATION: oligo

<400> SEQUENCE: 171
gttgtcatat gaacgaatcg gatcccccct ctcttctcct cttttg                    46

<210> SEQ ID NO 172
<211> LENGTH: 46
<212> TYPE: DNA
<213> ORGANISM: artificial
<220> FEATURE:
<223> OTHER INFORMATION: oligo

<400> SEQUENCE: 172
```

```
gctaatatac gctggagggg cagcagtcct agcaattttg ccagtc                46
```

<210> SEQ ID NO 173
<211> LENGTH: 46
<212> TYPE: DNA
<213> ORGANISM: artificial
<220> FEATURE:
<223> OTHER INFORMATION: oligo

<400> SEQUENCE: 173

```
gactggcaaa attgctagga ctgctgcccc tccagcgtat attagc                46
```

<210> SEQ ID NO 174
<211> LENGTH: 53
<212> TYPE: DNA
<213> ORGANISM: artificial
<220> FEATURE:
<223> OTHER INFORMATION: oligo

<400> SEQUENCE: 174

```
catcaaagag aaacttttg tataccttgc agcaccacca gacaaggctc taa          53
```

<210> SEQ ID NO 175
<211> LENGTH: 53
<212> TYPE: DNA
<213> ORGANISM: artificial
<220> FEATURE:
<223> OTHER INFORMATION: oligo

<400> SEQUENCE: 175

```
ttagagcctt gtctggtggt gctgcaaggt atacaaaaag tttctctttg atg         53
```

<210> SEQ ID NO 176
<211> LENGTH: 117
<212> TYPE: DNA
<213> ORGANISM: artificial
<220> FEATURE:
<223> OTHER INFORMATION: oligo

<400> SEQUENCE: 176

```
ggcgaccgta tgcgcgtagt gccgtgcagt cgccgtaccc ctgaagtgct ctcagccgca   60
aggaccgcat actacaaggg agttactcgc gtgcactccg ccttggtgga gcactga     117
```

<210> SEQ ID NO 177
<211> LENGTH: 117
<212> TYPE: DNA
<213> ORGANISM: artificial
<220> FEATURE:
<223> OTHER INFORMATION: oligo

<400> SEQUENCE: 177

```
tcagtgctcc accaaggcgg agtgcacgcg agtaactccc ttgtagtatg cggtccttgc   60
ggctgagagc acttcagggg tacggcgact gcacggcact acgcgcatac ggtcgcc     117
```

<210> SEQ ID NO 178
<211> LENGTH: 117
<212> TYPE: DNA
<213> ORGANISM: artificial
<220> FEATURE:
<223> OTHER INFORMATION: oligo

<400> SEQUENCE: 178

```
tcagtgctcc accaaggcgg agtgcacgcg agtaactccc aacatcatac gccaggaacg   60
ccgactctcg tgaagtcggg tacggcgact gcacggcact acgcgcatac ggtcgcc     117
```

<210> SEQ ID NO 179
<211> LENGTH: 117
<212> TYPE: DNA
<213> ORGANISM: artificial
<220> FEATURE:
<223> OTHER INFORMATION: oligo

<400> SEQUENCE: 179
ggcgaccgta tgcgcgtagt gccgtgcagt cgccgtaccc agtcctgtag agactaatac    60
cttcaatacg cagcaccggg agttactcgc gtgcactccg ccttggtgga gcactga      117

<210> SEQ ID NO 180
<211> LENGTH: 117
<212> TYPE: DNA
<213> ORGANISM: artificial
<220> FEATURE:
<223> OTHER INFORMATION: oligo

<400> SEQUENCE: 180
tcagtgctcc accaaggcgg agtgcacgcg agtaactccc ggtgctgcgt attgaaggta    60
ttagtctcta caggactggg tacggcgact gcacggcact acgcgcatac ggtcgcc      117

<210> SEQ ID NO 181
<211> LENGTH: 45
<212> TYPE: RNA
<213> ORGANISM: artificial
<220> FEATURE:
<223> OTHER INFORMATION: oligo

<400> SEQUENCE: 181
auugaaaguu guaguaugcg guccuugcgg cugagagcac uucag                    45

<210> SEQ ID NO 182
<211> LENGTH: 37
<212> TYPE: RNA
<213> ORGANISM: artificial
<220> FEATURE:
<223> OTHER INFORMATION: oligo

<400> SEQUENCE: 182
cugaagugcu cucagccgca aggaccgcau acuacaa                             37

<210> SEQ ID NO 183
<211> LENGTH: 34
<212> TYPE: DNA
<213> ORGANISM: artificial
<220> FEATURE:
<223> OTHER INFORMATION: primer

<400> SEQUENCE: 183
tcgatgtaac gtatgcaaat gacaattatt acta                                34

<210> SEQ ID NO 184
<211> LENGTH: 49
<212> TYPE: DNA
<213> ORGANISM: artificial
<220> FEATURE:
<223> OTHER INFORMATION: primer

<400> SEQUENCE: 184
aagcaagaat tctaatacga ctcactatag ggagaggcga ccgtatgcg                49

<210> SEQ ID NO 185

```
<211> LENGTH: 16
<212> TYPE: DNA
<213> ORGANISM: artificial
<220> FEATURE:
<223> OTHER INFORMATION: primer

<400> SEQUENCE: 185
tcagtgctcc accaag                                                     16

<210> SEQ ID NO 186
<211> LENGTH: 14
<212> TYPE: DNA
<213> ORGANISM: artificial
<220> FEATURE:
<223> OTHER INFORMATION: primer

<400> SEQUENCE: 186
ggcgaccgta tgcg                                                       14

<210> SEQ ID NO 187
<211> LENGTH: 51
<212> TYPE: DNA
<213> ORGANISM: artificial
<220> FEATURE:
<223> OTHER INFORMATION: primer

<400> SEQUENCE: 187
aagcaaggat cctaatacga ctcactatag ggagatcagt gctccaccaa g               51

<210> SEQ ID NO 188
<211> LENGTH: 42
<212> TYPE: DNA
<213> ORGANISM: artificial
<220> FEATURE:
<223> OTHER INFORMATION: primer

<400> SEQUENCE: 188
taatacgact cactataggg agacaacact tagtaggggc ta                         42

<210> SEQ ID NO 189
<211> LENGTH: 21
<212> TYPE: DNA
<213> ORGANISM: artificial
<220> FEATURE:
<223> OTHER INFORMATION: primer

<400> SEQUENCE: 189
gcttccttag ctgtttctcc a                                               21
```

METHODS FOR CLEAVING DNA AND RNA MOLECULES

CROSS-REFERENCE TO RELATED APPLICATIONS

This application is the § 371 U.S. National Stage of International Application No. PCT/US2017/012443, filed Jan. 6, 2017, which claims the benefit of U.S. Provisional Application Ser. No. 62/276,526, filed Jan. 8, 2016, the disclosures of which are incorporated by reference herein in their entireties.

GOVERNMENT FUNDING

This invention was made with government support R01 GM54682, awarded by the National Institutes of Health. The government has certain rights in the invention. 37 CFR Sec. 401.14(f) (4)

SEQUENCE LISTING

This application contains a Sequence Listing electronically submitted via EFS-Web to the United States Patent and Trademark Office as an ASCII text file entitled "235_02600201_SeqList_ST25.txt" having a size of 64,076 bytes and created on Jan. 3, 2017. The information contained in the Sequence Listing is incorporated by reference herein.

SUMMARY

Provided herein are non-naturally occurring compositions. In one embodiment, a composition includes a CRISPR-RNA (crRNA) and a Cmr complex. In one embodiment, the crRNA is a single stranded RNA that includes a tag region including at least 5 to no greater than 12 nucleotides, and a guide region including a nucleotide sequence of at least 15 nucleotides, wherein the tag region is immediately upstream of the guide region. The Cmr complex includes at least 4 proteins including Cmr2, Cmr3, Cmr4, and Cmr5, wherein the Cmr4 protein includes a mutation that reduces the RNase activity of the Cmr complex.

In one embodiment, the tag is selected from a microbe in Table 2, and the proteins of the Cmr complex are selected from the same microbe as described in Table 1. In one embodiment, the tag is selected from a microbe in Table 2, and the Cmr2, Cmr3, Cmr4, and Cmr5 proteins of the Cmr complex have at least 80% identity with the Cmr2, Cmr3, Cmr4, and Cmr5 protein of the same microbe as described in Table 1. In one embodiment, the Cmr2, Cmr3, Cmr4, and Cmr5 protein are selected from a microbe described in Table 1, and the nucleotide sequence of the tag is substantially identical to the nucleotide sequence of the tag from the same microbe in Table 2. In one embodiment, the mutation includes a mutation of the Cmr4 active site. In one embodiment, the composition does not include a Csx1 protein. In one embodiment, the Cmr complex further includes a Cmr1 protein, a Cmr6 protein, or both a Cmr1 and a Cmr6 protein. In one embodiment, the tag is selected from a microbe in Table 2, and the Cmr1, Cmr2, Cmr3, Cmr4, Cmr5, and Cmr6 proteins of the Cmr complex have at least 80% identity with the Cmr1, Cmr2, Cmr3, Cmr4, Cmr5, and Cmr6 protein of the same microbe as described in Table 1. In one embodiment, the Cmr1, Cmr2, Cmr3, Cmr4, Cmr5, and Cmr6 protein are selected from a microbe described in Table 1, and the nucleotide sequence of the tag is substantially identical to the nucleotide sequence of the tag from the same microbe in Table 2.

In one embodiment, the complex further includes an activating RNA (actRNA), wherein the actRNA is a single stranded RNA. In one embodiment, the actRNA includes a target region including a nucleotide sequence of at least 12 nucleotides, wherein the nucleotide sequence of the target region is substantially complementary to at least a portion of the guide region of the crRNA, and a PAM region immediately downstream of the target region. In one embodiment, the PAM includes a sequence 5'-NGN, 5'-NNG, 5'-NAA, or 5'-NAC, wherein N is A, U, G, or C. In one embodiment, the nucleotide sequence of the target region is complementary to at least a portion of the guide region of the crRNA. in another embodiment, the nucleotide sequence of the target region is complementary to the entire guide region of the crRNA.

In another embodiment, a composition includes a CRISPR-RNA (crRNA) and a Cmr complex. In one embodiment, the crRNA is a single stranded RNA including a tag region that includes at least 5 to no greater than 12 nucleotides, and a guide region including a nucleotide sequence of at least 15 nucleotides, wherein the tag region is immediately upstream of the guide region. In one embodiment, the Cmr complex includes at least 6 proteins including Cmr1, Cmr2, Cmr3, Cmr4, Cmr5, and Cmr6, and the Cmr2 protein includes a mutation that reduces RNA-activated DNAse activity of the Cmr complex. In one embodiment, the mutation includes a mutation of the HD superfamily hydrolase domain. In one embodiment, the tag is selected from a microbe in Table 2, and the proteins of the Cmr complex are selected from the same microbe as described in Table 1. In one embodiment, the tag is selected from a microbe in Table 2, and the Cmr1, Cmr2, Cmr3, Cmr4, Cmr5, and Cmr6 proteins of the Cmr complex have at least 80% identity with the Cmr1, Cmr2, Cmr3, Cmr4, Cmr5, and Cmr6 protein of the same microbe as described in Table 1. In one embodiment, the Cmr1, Cmr2, Cmr3, Cmr4, Cmr5, and Cmr6 protein are selected from a microbe described in Table 1, and the nucleotide sequence of the tag is substantially identical to the nucleotide sequence of the tag from the same microbe in Table 2. In one embodiment, the nucleotide sequence of the target region is complementary to at least a portion of the guide region of the crRNA. In one embodiment, the nucleotide sequence of the target region is complementary to the entire guide region of the crRNA.

Also provided is a genetically modified cell that includes at least one exogenous coding region. The exogenous coding region encodes a CRISPR-RNA (crRNA) or a Cmr complex. In one embodiment, the crRNA is a single stranded RNA including a tag region including at least 5 to no greater than 12 nucleotides, and a guide region including a nucleotide sequence of at least 15 nucleotides, wherein the tag region is immediately upstream of the guide region. In one embodiment, the Cmr complex includes at least 4 proteins including Cmr2, Cmr3, Cmr4, and Cmr5, wherein either i) the Cmr2 protein includes a mutation of the HD superfamily hydrolase domain to reduce RNA-activated DNAse activity of the Cmr complex, or ii) the Cmr4 protein includes a mutation of the active site to reduce single stranded RNAse activity of the Cmr complex. In one embodiment, the genetically modified cell is a microbe or a eukaryotic cell.

In one embodiment, the at least one exogenous coding region encodes an activating RNA (actRNA). In one embodiment, the actRNA is a single stranded RNA that includes a target region including a nucleotide sequence of at least 12 nucleotides, and a PAM region immediately downstream of the target region. In one embodiment, the PAM includes a sequence 5'-NGN, 5'-NNG, 5'-NAA, or 5'-NAC, wherein N is A, U, G, or C. In one embodiment, the nucleotide sequence of the target region is substantially complementary to at least a portion of the guide region of the crRNA. In one embodiment, the at least one coding region encoding the crRNA or a protein of the Cmr complex are encoded by one or more vectors. In one embodiment, the tag is selected from a microbe in Table 2, and the proteins of the Cmr complex are selected from the same microbe as described in Table 1. In one embodiment, the tag is selected from a microbe in Table 2, and the Cmr2, Cmr3, Cmr4, and Cmr5 proteins of the Cmr complex have at least 80% identity with the Cmr2, Cmr3, Cmr4, and Cmr5 protein of the same microbe as described in Table 1. In one embodiment, the Cmr2, Cmr3, Cmr4, and Cmr5 protein are selected from a microbe described in Table 1, and the nucleotide sequence of the tag is substantially identical to the nucleotide sequence of the tag from the same microbe in Table 2. In one embodiment, the Cmr complex further includes a Cmr1 protein, a Cmr6 protein, or both a Cmr1 and a Cmr6 protein. In one embodiment, the tag is selected from a microbe in Table 2, and the Cmr1, Cmr2, Cmr3, Cmr4, Cmr5, and Cmr6 proteins of the Cmr complex have at least 80% identity with the Cmr1, Cmr2, Cmr3, Cmr4, Cmr5, and Cmr6 protein of the same microbe as described in Table 1. In one embodiment, the Cmr1, Cmr2, Cmr3, Cmr4, Cmr5, and Cmr6 protein are selected from a microbe described in Table 1, and the nucleotide sequence of the tag is substantially identical to the nucleotide sequence of the tag from the same microbe in Table 2.

In one embodiment, the nucleotide sequence of the target region is complementary to at least a portion of the guide region of the crRNA. In one embodiment, the nucleotide sequence of the target region is complementary to the entire guide region of the crRNA. In one embodiment, the at least one exogenous coding region is present on a vector within the cell. In one embodiment, the at least one exogenous coding region is integrated in the genome of the cell.

Also provided herein are methods. In one embodiment, a method is for determining whether a predetermined RNA is present or absent in a sample. In one embodiment, the method includes incubating a composition with a sample. In one embodiment, the composition includes a CRISPR-RNA (crRNA), a Cmr complex, and a substrate DNA. In one embodiment, the crRNA is a single stranded RNA including a tag region that includes at least 5 to no greater than 12 nucleotides, and a guide region including a nucleotide sequence of at least 15 nucleotides, wherein the tag region is immediately upstream of the guide region. In one embodiment, the Cmr complex includes at least 4 proteins including Cmr2, Cmr3, Cmr4, and Cmr5. The sample is suspected of including a predetermined RNA that includes a nucleotide sequence that is substantially complementary to at least a portion of the guide region of the crRNA, and the incubating includes incubating the sample under suitable conditions for cleavage of the substrate DNA when the predetermined RNA is present. In one embodiment, the sample does not include a predetermined RNA.

In one embodiment, the method further includes detecting the presence or absence of cleavage of the substrate DNA. In one embodiment, the sample is a biological sample. In one embodiment, the predetermined RNA is a viral RNA. In one embodiment, the predetermined RNA is a fetal RNA present in a biological sample of maternal plasma. In one embodiment, the substrate DNA includes a label. In one embodiment, the label includes a fluorescent label and an optional quencher. In one embodiment, the Cmr4 protein includes a mutation that reduces the RNAse activity of the Cmr2 protein. In one embodiment, the biological sample is a cell, and the predetermined RNA is present in the cell, wherein cleavage of the substrate DNA results in cell death.

In one embodiment, a method is for cleaving a predetermined RNA molecule. In one embodiment, the method includes incubating a composition with a sample. In one embodiment, the composition includes a CRISPR-RNA (crRNA) and a Cmr complex. In one embodiment, the crRNA is a single stranded RNA that includes a tag region including at least 5 to no greater than 12 nucleotides, and a guide region including a nucleotide sequence of at least 15 nucleotides, wherein the tag region is immediately upstream of the guide region. In one embodiment, the Cmr complex includes at least 6 proteins including Cmr1, Cmr2, Cmr3, Cmr4, Cmr5, and Cmr6, wherein the Cmr2 protein includes a mutation that reduces RNA-activated DNAse activity of the Cmr complex. The sample is suspected of including a predetermined RNA molecule that includes a nucleotide sequence that is substantially complementary to at least a portion of the guide region of the crRNA, and the incubating includes incubating the sample under suitable conditions for cleavage of the predetermined RNA molecule. In one embodiment, the sample does not include a predetermined RNA.

In one embodiment, the mutation includes a mutation of the HD superfamily hydrolase domain. In one embodiment, the method also includes detecting the presence or absence of cleavage of the predetermined RNA molecule. In one embodiment, the sample is a biological sample. In one embodiment, the tag is selected from a microbe in Table 2, and the proteins of the Cmr complex are selected from the same microbe as described in Table 1. In one embodiment, the tag is selected from a microbe in Table 2, and the Cmr1, Cmr2, Cmr3, Cmr4, Cmr5, and Cmr6 proteins of the Cmr complex have at least 80% identity with the Cmr1, Cmr2, Cmr3, Cmr4, Cmr5, and Cmr6 protein of the same microbe as described in Table 1. In one embodiment, the Cmr1, Cmr2, Cmr3, Cmr4, Cmr5, and Cmr6 protein are selected from a microbe described in Table 1, and the nucleotide sequence of the tag is substantially identical to the nucleotide sequence of the tag from the same microbe in Table 2.

As used herein, the term "protein" refers broadly to a polymer of two or more amino acids joined together by peptide bonds. The term "protein" also includes molecules which contain more than one protein joined by a disulfide bond, or complexes of proteins that are joined together, covalently or noncovalently, as multimers (e.g., dimers, tetramers). Thus, the terms peptide, oligopeptide, enzyme, and polypeptide are all included within the definition of protein and these terms are used interchangeably. It should be understood that these terms do not connote a specific length of a polymer of amino acids, nor are they intended to imply or distinguish whether the protein is produced using recombinant techniques, chemical or enzymatic synthesis, or is naturally occurring.

As used herein, an "isolated" substance is one that has been removed from its natural environment, produced using recombinant techniques, or chemically or enzymatically synthesized. For instance, a protein or a polynucleotide can be isolated. Preferably, a substance is purified, i.e., is at least 60% free, preferably at least 75% free, and most preferably at least 90% free from other components with which they are naturally associated.

As used herein, the term "polynucleotide" refers to a polymeric form of nucleotides of any length, either ribonucleotides or deoxynucleotides, and includes both double- and single-stranded RNA and DNA. A polynucleotide can be obtained directly from a natural source, or can be prepared with the aid of recombinant, enzymatic, or chemical techniques. A polynucleotide can be linear or circular in topology. A polynucleotide may be, for example, a portion of a vector, such as an expression or cloning vector, or a fragment. A polynucleotide may include nucleotide sequences having different functions, including, for instance, coding regions, and non-coding regions such as regulatory regions.

As used herein, an "exogenous polynucleotide" refers to a polynucleotide that is not normally or naturally found in a cell. An exogenous polynucleotide includes a coding region that is not normally found in a cell, and a coding region that is normally found in a cell but is operably linked to a regulatory region to which it is not normally linked. An "endogenous polynucleotide" is also referred to as a "native polynucleotide."

A polynucleotide described herein, such as a crRNA or an actRNA, may be "modified." Such modifications can be useful to increase stability of the polynucleotide in certain environments. Modifications can include a nucleic acid sugar, base, or backbone, or any combination thereof. The modifications can be synthetic, naturally occurring, or non-naturally occurring. A polynucleotide can include modifications at one or more of the nucleic acids present in the polynucleotide. Examples of backbone modifications include, but are not limited to, phosphonoacetates, thio-phosphonoacetates, phosphorothioates, phosphorodithioates, phosphoramidates, methyl phosphonates, chiral-methyl phosphonates, 2-O-methyl ribonucleotides, and peptide-nucleic acids. Examples of nucleic acid base modifications include, but are not limited to, inosine, purine, pyridin-4-one, pyridin-2-one, phenyl, pseudouracil, 2,4,6-trimethoxy benzene, 3-methyl uracil, dihydrouridine, naphthyl, amino-phenyl, 5-alkylcytidines (e.g., 5-methylcytidine), 5-alkylu-ridines (e.g., ribothymidine), 5-halouridine (e.g., 5-bromou-ridine) or 6-azapyrimidines or 6-alkylpyrimidines (e.g. 6-methyluridine), or propyne modifications. Examples of nucleic acid sugar modifications include, but are not limited to, 2'-sugar modification, e.g., 2'-O-methyl nucleotides, 2'-deoxy-2'-fluoro nucleotides, 2'-deoxy-2'-fluoroarabino, 2'-O-methoxyethyl nucleotides, 2'-O-trifluoromethyl nucleotides, 2'-O-ethyl-trifluoromethoxy nucleotides, 2'-O-difluoromethoxy-ethoxy nucleotides, or 2'-deoxy nucleotides.

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. The sequence similarity between two proteins is determined by aligning the residues of the two proteins (e.g., a candidate amino acid sequence and a reference amino acid sequence, such as SEQ ID NO:2) to optimize the number of identical amino acids along the lengths of their sequences; gaps in either or both sequences are permitted in making the alignment in order to optimize the number of shared amino acids, although the amino acids in each sequence must nonetheless remain in their proper order. Sequence similarity may be determined, for example, using sequence techniques such as the BEST-FIT algorithm in the GCG package (Madison Wis.), or the Blastp program of the BLAST 2 search algorithm, as described by Tatusova, et al. (*FEMS Microbiol Lett* 1999, 174:247-250), and available through the World Wide Web, for instance at the internet site maintained by the National Center for Biotechnology Information, National Institutes of Health. Preferably, sequence similarity between two amino acid sequences is determined using the Blastp program of the BLAST 2 search algorithm. Preferably, the default values for all BLAST 2 search parameters are used. In the comparison of two amino acid sequences using the BLAST search algorithm, structural similarity is referred to as "identities." Thus, reference to a protein described herein, such as SEQ ID NO:2, can include a protein with at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity with the reference protein. Alternatively, reference to a protein described herein, such as SEQ ID NO:2, can include a protein at least 80% similarity, at least 81% similarity, at least 82% similarity, at least 83% similarity, at least 84% similarity, at least 85% similarity, at least 86% similarity, at least 87% similarity, at least 88% similarity, at least 89% similarity, at least 90% similarity, at least 91% similarity, at least 92% similarity, at least 93% similarity, at least 94% similarity, at least 95% similarity, at least 96% similarity, at least 97% similarity, at least 98% similarity, or at least 99% similarity with the reference protein.

The sequence similarity between two polynucleotides is determined by aligning the residues of the two polynucleotides (e.g., a candidate nucleotide sequence and a reference nucleotide sequence, such as SEQ ID NO:1) to optimize the number of identical nucleotides along the lengths of their sequences; gaps in either or both sequences are permitted in making the alignment in order to optimize the number of shared nucleotides, although the nucleotides in each sequence must nonetheless remain in their proper order. Sequence similarity may be determined, for example, using sequence techniques such as GCG FastA (Genetics Computer Group, Madison, Wis.), MacVector 4.5 (Kodak/IBI software package) or other suitable sequencing programs or methods known in the art. Preferably, sequence similarity between two nucleotide sequences is determined using the Blastn program of the BLAST 2 search algorithm, as described by Tatusova, et al. (1999, *FEMS Microbiol Lett.*, 174:247-250), and available through the World Wide Web, for instance at the internet site maintained by the National Center for Biotechnology Information, National Institutes of Health. Preferably, the default values for all BLAST 2 search parameters are used. In the comparison of two nucleotide sequences using the BLAST search algorithm, sequence similarity is referred to as "identities." The sequence similarity is typically at least 50% identity, at least 55% identity, at least 60% identity, at least 65% identity, at least 70% identity, at least 75% identity, at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity.

Conditions that "allow" an event to occur or conditions that are "suitable" for an event to occur, such as an enzymatic reaction, or "suitable" conditions are conditions that do not prevent such events from occurring. Thus, these conditions permit, enhance, facilitate, and/or are conducive to the event. Such conditions, known in the art and described herein, may depend upon, for example, the enzyme being used.

As used herein, a "microbe" is a single celled organism that is a member of the domain Archaea or a member of the domain Bacteria.

As used herein, "genetically modified cell" refers to a cell into which has been introduced an exogenous polynucleotide, such as an expression vector. For example, a cell is a genetically modified cell by virtue of introduction into a suitable cell of an exogenous polynucleotide that is foreign to the cell. The cell can be a microbe or a eukaryotic cell. Examples of a eukaryotic cell include an animal cell, such as a human cell.

As used herein, a "detectable moiety" or "label" is a molecule that is detectable, either directly or indirectly, by spectroscopic, photochemical, biochemical, immunochemical, or chemical means. For example, useful labels include $^{32}P$, fluorescent dyes, electron-dense reagents, enzymes and their substrates (e.g., as commonly used in enzyme-linked immunoassays, e.g., alkaline phosphatase and horse radish peroxidase), biotin-streptavidin, digoxigenin, proteins such as antibodies, or haptens and proteins for which antisera or monoclonal antibodies are available. The label or detectable moiety is typically bound, either covalently, through a linker or chemical bound, or through ionic, van der Waals or hydrogen bonds to the molecule to be detected.

While most polynucleotide sequences described herein are listed as DNA sequences, it is understood that the complements, reverse sequences, and reverse complements of the DNA sequences can be easily determined by the skilled person. It is also understood that the sequences disclosed herein as DNA sequences can be converted from a DNA sequence to an RNA sequence by replacing each thymidine nucleotide with a uridine nucleotide, and that the sequences disclosed herein as RNA sequences can be converted from an RNA sequence to a DNA sequence by replacing each uridine nucleotide with a thymidine nucleotide.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

BRIEF DESCRIPTION OF THE FIGURES

FIG. 1 shows a schematic of CRISPR locus repeat and spacer (FIG. 1A), crRNA (FIG. 1B), actRNA (FIG. 1C), and relationship between these three polynucleotides. FIG. 1A. Portion of a CRISPR locus (a DNA polynucleotide) including part of an individual repeat (black) and a spacer (gray). The positions of the repeat nucleotides proximal to the spacer are numbered from 1-12, 3' to 5' from the junction with the downstream spacer. The short black lines perpendicular to the two strands denote base pairing between the two strands. The non-template strand of the DNA is shown in 5' to 3' orientation. FIG. 1B. An example of a CRISPR RNA or crRNA (an RNA polynucleotide) shown 5' to 3'. An example of a crRNA tag (5' tag) and guide region (Guide Sequence) are shown in black and gray, respectively. The positions of nucleotides 1-8 of the crRNA tag are indicated and are, in this example, identical to nucleotides 1-8 of the non-template strand (top strand, shown 5' to 3') of the CRISPR repeat DNA shown in FIG. 1A. The guide region at the 3' end of the crRNA has a nucleotide sequence that is, in this example, identical to the nucleotide sequence of the non-template strand (top strand, shown 5' to 3') of the spacer of the CRISPR locus in A. FIG. 1C. An example of (a portion of) an activating RNA or actRNA (an RNA polynucleotide). This RNA is shown 3' to 5'. An example of a PAM is indicated in white (outlined in black) at the 3' end of the shown region of the actRNA. An example of a target region (Target Sequence) is indicated in gray immediately upstream of the PAM. The Target Sequence of the activating RNA has a nucleotide sequence that is, in this example, complementary to the nucleotide sequence of the guide region of the crRNA in FIG. 1B (denoted by dashed lines perpendicular to the crRNA and actRNA). The dashed lines at the 3' end and the 5' end of the actRNA denote that additional nucleotides at either end of the actRNA are possible.

FIG. 2 depicts Cmr proteins and an example of a nucleotide sequence encoding each Cmr protein.

FIG. 3 depicts a Cmr complex. FIG. 3A. A non-limiting example of a structural model of a Cmr complex with an associated crRNA. In FIG. 3A, FIG. 3B, and FIG. 3C the tag of the crRNA is indicated in black and the guide region is indicated in gray. FIG. 3B. RNA-activated DNase. A Cmr complex with associated components when the Cmr complex has RNA-activated DNAse activity. The actRNA includes a PAM (indicated in white outlined in black) as well as a target region (indicated in gray). In some embodiments, the actRNA is also referred to as a predetermined actRNA. A substrate DNA is also shown. FIG. 3C. RNAse. A Cmr complex with associated components when the Cmr complex has RNAse activity. The substrate RNA (also referred to herein as a predetermined target RNA or a predetermined substrate RNA) is also shown (with the target region indicated in gray). Triangles indicate cleavage of the substrate DNA and RNA in FIG. 3B and FIG. 3C, respectively. The dashed lines at the 3' end and the 5' end of the actRNA in FIG. 3B and the substrate RNA in FIG. 3C denote that additional nucleotides at either end of the RNA molecules are possible.

FIG. 6A. Plasmid challenge assay. In the absence of CRISPR-Cas defense, plasmid infection results in colony formation (growth of cells transformed with a plasmid containing the pyrF gene in the absence of uracil). FIG. 6B. Target sequence transcription configuration of the various plasmids. The orientation of the 7.01 crRNA target sequence relative to the promoter and plasmid backbone is shown. Plasmids were designed for no transcription (none +/−), transcription of a target RNA complementary to the endogenous 7.01 crRNA (target [tar]), or transcription of an RNA that is not complementary to the 7.01 crRNA (reverse complement of target [rc]). FIG. 6C, FIG. 6D. Northern analysis of expression of the 7.01 target RNA (FIG. 6C) or the reverse complement RNA (FIG. 6D). The left lane is Decade marker RNA (Life Technologies). All other lanes contain 10 µg of total RNA isolated from P. furiosus TPF20 strains bearing plasmids configured to express the indicated RNA. The primary product is indicated with an asterisk. Blots were also probed for 5S rRNA as a loading control. FIG. 6E. Colonies produced by infection with five plasmids in Wild-type (three endogenous CRISPR-Cas systems), ΔCmr (lacking the Cmr system), Cmr (Cmr only), and Null (no system) strains (indicated by gray bars designated in key to right of graph). The presence of crRNA 7.01 target sequence on the plasmids is indicated by a dashed line (no target sequence) or 7.01 below the graph (Target:) and the presence and orientation of crRNA 7.01 target sequence on the plasmids are indicated by a thick gray arrow in diagrams above the graph. The presence and orientation of the promoter for target region transcription on the plasmid is indicated by a line arrow in diagrams above the graph, and the presence of a target region transcript is indicated below the graph as a dashed line, "none," "target," and "rc of target" (RNA:). Colony numbers are plotted with the standard deviation in nine replicates indicated by error bars.

FIG. 7A. Location of the specified tested flanking sequences (first 8 nucleotides of the upper strand of the base paired Target DNA duplex, immediately 3' of the target sequence) relative to the target sequence in the Target DNA, which is aligned with the guide sequence of the crRNA (gray). Potential complementarity between crRNA 5' tag sequence (black) and the flanking sequence also indicated. FIG. 7B. Colonies produced by infection of 12 plasmids (1-11 plus no target) in Wild-type (3 endogenous CRISPR-Cas systems), ΔCmr (lacking Cmr system), Cmr (Cmr only). Colony numbers are plotted with the standard deviation in 9 replicates indicated by error bars. All plasmids, except a negative control (No Target), produce a 7.01 target RNA, but vary in 3' flanking sequence. The 3' flanking sequence is mutated sequentially from fully complementary with the 5' tag (non-underlined nucleotides) to fully non-complementary (underlined nucleotides) in plasmids 1-9. Complementarity between 5' tag and target flanking region is also indicated graphically. Asterisks on the chart indicate intermediate silencing phenotypes FIG. 8A. The location of tested PAM sequences (PAM, dark gray) relative to the target sequence (medium gray) in the Target DNA and aligned crRNA. Dotted gray lines indicate complementarity between the crRNA guide region (light gray) and DNA target sequence (medium gray). FIGS. 8B, 8C. Results of plasmid infection assays for Cmr and wild-type strains, respectively. The plasmids contain the transcribed 7.01 target sequence and the indicated flanking (PAM) sequence. Colony numbers are the average of at least three replicates. Target-adjacent sequences that activated CRISPR-Cas targeting resulting in >100-fold reduction in colony numbers relative to negative control plasmid are shaded dark gray. Sequences that conferred 30-fold to 100-fold reduction in colony numbers are shaded light gray. The plasmid sequence downstream from the PAM (positions +4 to +8) in all plasmids is 5'-TTCCG-3'.

FIG. 10A. Target sequence transcription configuration of the various plasmids. Orientation of the 2.01/6.01 crRNA target sequence relative to the promoter and target-adjacent PAM region is shown. Plasmids are designed for transcription of a target RNA complementary to the endogenous 2.01/6.01 crRNAs (target) or transcription of an RNA that is not complementary to the 2.01/6.01 crRNAs (rc target). FIG. 10B. Colonies produced by infection with 11 plasmids in Wild-type and Cmr strains. Plasmids include 2.01 or 6.01 target sequences as indicated above (Target:). The presence of target region transcript is indicated below graph as "No target", "target", and "rc target" (RNA:) with the target-adjacent sequences indicated beneath (PAM:). Colony numbers are the average of three replicates with error bars indicating the standard deviation.

FIG. 11A. Plasmid infection of Csx1 deletion strain. Cmr strains with (Cmr) or without Csx1 (Cmr ΔCsx1) were infected with plasmids expressing no target RNA (---), crRNA 7.01 target RNA (tar), or the reverse complement RNA (rc). Colonies numbers are plotted with error bars indicating standard deviation in three replicates. Both target plasmids contain a GGG target-adjacent sequence. FIG. 11B. Western blot analysis of Csx1 expression. S20 extract containing 50 μg protein from either Cmr and Cmr ΔCsx1 strains were probed with polyclonal antibodies against Pfu Csx1. FIG. 11C. Cmr complex from Cmr and Cmr ΔCsx1 strains. Proteins immunoprecipitated with preimmune (PI, Cmr only) or immune (Im) antibodies again Cmr2 from Cmr strains with (Cmr) or without Csx1 (Cmr ΔCsx1) were analyzed by SDS-PAGE and silver staining. Cmr protein identities are indicated based on predicted molecular weights and mass spectrometry. FIG. 11D. RNA cleavage activity of Cmr complexes with (Cmr) or without (Cmr ΔCsx1) Csx1. Complexes immunopurified from Cmr strains were incubated with 5' end-labeled crRNA 7.01 target RNA. Products were analyzed by denaturing PAGE. Decade Marker RNAs (M) were included for size estimations. Asterisks mark primary RNA cleavage products.

FIGS. 12A-12D. Substrate analysis. Recombinant Cmr2 (50 or 500 nM) was incubated with (+) or without (−) added $NiCl_2$ (200 μM) in the presence of a 5' radiolabeled ssDNA oligo (FIG. 12A), a 5' radiolabeled dsDNA annealed from oligos (FIG. 12B), unlabeled circular ssM13 phage DNA (FIG. 12C), or a 5' radiolabeled "bubble" DNA substrate (with a central single-stranded region) annealed from two partially complementary ssDNA oligos (FIG. 12D). E. Mutant analysis. Wild-type (WT), HD domain putative active site mutant ($HD_m$), Palm domain GGDD motif mutant ($Palm_m$), or double-mutant ($HD_m,Palm_m$) Cmr2 proteins were incubated with 5' radiolabeled ssDNA with (+) or without (−) added $NiCl_2$. F. Activity in the context of the Cmr complex. Increasing amounts (50-200 nM) of either recombinant Cmr2 or preformed Cmr crRNP complexes (Cmr1-6+ crRNA) were incubated with 5' radiolabeled ssDNA oligo. Products were analyzed by denaturing PAGE (FIGS. 12A, 12B, 12D-12F) or agarose gel electrophoresis (FIG. 12C). Radiolabeled Decade markers (M) or New England Biolabs 1-kb ladder (L) were used for size estimation.

FIGS. 14A-14D. Substrate analysis. Cmr2 (50 nM) and Cmr crRNP complexes (~50 nM) were analyzed with (t) or without (−) the target RNA (complementary to the 7.01 crRNA) or with the reverse complement of the target RNA (rc). The substrates used were 5' radiolabeled ssDNA complementary to crRNA 7.01 (FIG. 14A), dsDNA with a crRNA 7.01 target sequence 5' radiolabeled on the target (FIG. 14B) or nontarget (FIG. 14C) strand, and dsDNA with a mutant 7.01 target sequence (FIG. 14D). FIG. 14E, FIG. 14F. Mutant analysis. Cmr crRNP complexes containing wild-type (WT), HD domain putative active site mutant ($HD_m$), Palm domain GGDD motif mutant ($Palm_m$), or double-mutant ($HD_m,Palm_m$) Cmr2 were incubated with dsDNA with the crRNA 7.01 target sequence 5' radiolabeled on the target (E) or nontarget (F) strand. Graphical representations of substrates are shown with the 7.01 target (gray, FIGS. 14A, 14B, 14C, 14E, and 14F) and mutant 7.01 target (gray, FIG. 14D) sequences and radiolabeled strands (asterisks) indicated. Products were analyzed by denaturing PAGE. Decade marker RNA (M) was included for size estimations.

FIG. 15A. Plasmid infection of strains with Cmr2 mutants. Cmr strains expressing the indicated Cmr2 proteins (wild type [WT], ΔHD, $Palm_m$, ΔHD,$Palm_m$, and $HD_m,Palm_m$) were infected with plasmids expressing no target RNA (none), crRNA 7.01 target RNA (7.01 target) or the reverse complement RNA (Reverse complement of 7.01 target). Colony numbers are plotted with error bars indicating the standard deviation in three replicates. FIG. 15B. Cmr complexes from Cmr2 mutant strains. Proteins immunoprecipitated with preimmune (PI; wild type only) or immune (Im) antibodies against Cmr2 from Cmr strains expressing the indicated Cmr2 proteins (wild type, ΔHD, $Palm_m$, ΔHD, $Palm_m$, and $HD_m,Palm_m$) were analyzed by SDS-PAGE and silver staining. Cmr protein identities are indicated based on predicted molecular weights and mass spectrometry. FIG. 15C. RNA cleavage activity of Cmr complexes in Cmr2 mutant strains. Complexes immunopurified from Cmr strains expressing the indicated Cmr2 proteins (wild type, ΔHD, $Palm_m$, ΔHD, $Palm_m$, and $HD_m,Palm_m$) were incubated with 5' end-labeled crRNA 7.01 target RNA. Products were analyzed by denaturing PAGE. Decade marker RNAs (M) were included for size estimations. Asterisks mark primary RNA cleavage products. Note that the top product migrates distinctly from the band in observed in preimmune sample in multiple experiments.

FIG. 16A. Model showing the Cmr complex (Cmr1-6 proteins and crRNA) activated by a target RNA containing a sequence recognized by crRNA and an rPAM (PAM sequence in the target RNA) sequence. The Cmr2 protein of the activated complex cleaves dsDNA. B,C. Target RNA binding and cleavage by Cmr4 mutant complexes. 5' radiolabeled 7.01 target RNA was incubated with Cmr crRNPs containing wild-type (WT) or mutant (D26N) Cmr4, and products were analyzed by native PAGE (FIG. 16B) or denaturing PAGE (FIG. 16C). FIG. 16D. DNA cleavage activity of the Cmr4 mutant complex. Wild-type and Cmr4 mutant Cmr complexes were incubated with target RNA and 5' radiolabeled dsDNA containing the crRNA 7.01 target sequence, and products were analyzed by denaturing PAGE. FIGS. 16E-16G. Analysis of RNA PAM (rPAM) sequences. Cmr crRNPs were incubated with target RNAs containing the indicated flanking sequences (as well as the crRNA 7.01 target sequence) and with 5' radiolabeled dsDNA substrates containing the crRNA 7.01 target sequence (FIG. 16E, 16G) or a mutated target sequence (FIG. 16F). Products were analyzed by denaturing PAGE. For FIG. 16G, reactions were analyzed at 5, 15, and 60 min. Flanking sequences corresponding to PAMs (identified in vivo) are indicated as light gray nucleotides. Graphical representations of substrates are shown with the 7.01 target (FIG. 16E, 16G, light gray) and mutant 7.01 target (FIG. 16F, dark gray) sequences and the radiolabeled strands (asterisks) indicated.

FIG. 17A. The Cmr complex DNA nuclease is activated and tethered by the nascent target RNA. The transcribed invader RNA containing the crRNA target sequence (light gray region of Invader RNA) and rPAM (dark gray region of Invader RNA) is recognized by the Cmr complex containing the crRNA with the guide sequence (light gray region of crRNA). The activated nuclease is tethered to and cleaves the invader DNA. FIG. 17B. As the length of the tether increases, the Cmr complex DNA nuclease is deactivated by cleavage of the target RNA.

FIG. 18A. Steps in Pfu strain construction by homologous recombination of transformed SOE-PCR (splicing by overlap extension polymerase chain reaction) constructs. FIG. 18B. Generic SOE-PCR construct with approximate sizes and primer locations indicated. Initially, four distinct PCR products are generated by PCR using primer pairs 1*/2*, 3/4, 5*/6*, and 7*/8*. The final product displayed is generated by two additional rounds of SOE-PCR with two PCR products acting as templates in a PCR reaction with the outer primers of the two products. Primers 3 and 4 are used to amplify the Pgdh-pyrF selection marker in all constructs. Primers 1*-2* & 5*-8* are specific for a given construct (primer numbers indicated in panel FIG. 18C). To mediate splicing events, primers 2*, 5* and 7* also contain sequences that overlap with the adjacent PCR products. FIG. 18C. Graphic representation of the individual SOE-PCR constructs used for strain construction in this study. Annotated Pf ORF numbers are indicated. Primer numbers refer to oligos in Table 4. For the Cmr2ΔHD strain, the deleted nucleotides are indicated next to the PF1129 (Cmr2) ORF. For amino acid substitution SOE_PCR products, a thin line indicates the mutated sequences.

DETAILED DESCRIPTION OF ILLUSTRATIVE EMBODIMENTS

Figure 4:
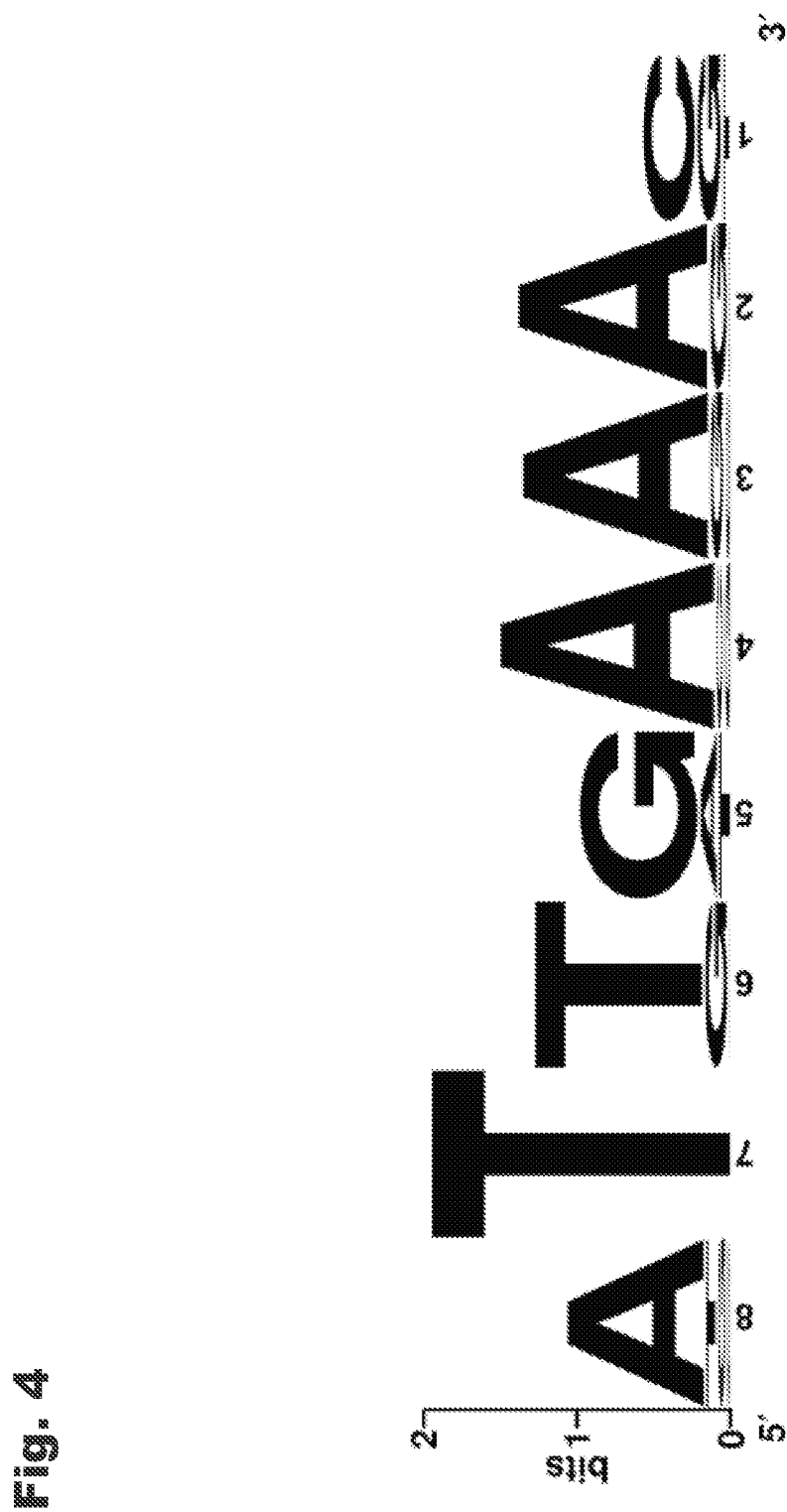
FIG. 4 shows a WebLogo representation of 8 nucleotide tag sequences found in the microbes listed in Table 2. The nucleotide identity(s) and position is shown on the X-axis, where the sequence is displayed 5' to 3'. The nucleotide at position 1 is immediately upstream of the guide region (as in FIG. 1B). The overall height plotted on the Y-axis indicates the sequence conservation at a given position, while the height of individual symbols within a stack indicates the conservation at that position. While the sequence discloses thymine nucleotides it is understood these nucleotides are uracil in an RNA molecule.

Provided herein is a complex that includes at least one polynucleotide (referred to herein as a crRNA) and at least 4 proteins (FIG. 3A) and has an RNase activity and an RNA-activated DNAse activity. In one embodiment, a complex can cleave a second RNA (RNA substrate), referred to herein as a predetermined target RNA (FIG. 3C). In one embodiment, a complex can interact with a second RNA, referred to herein as an activating RNA (actRNA), which causes the complex to also have an RNA-activated DNAse activity (DNA substrate) (FIG. 3B). The polynucleotide(s), the proteins, or the combination thereof, may be enriched or isolated.

crRNA

The polynucleotide that is part of the complex is referred to herein as a CRISPR RNA (crRNA). crRNAs are found in microbial cells that have a CRISPR locus, where a crRNA is a small noncoding RNA that is produced by transcription and processing of a CRISPR transcript derived from a CRISPR locus. A CRISPR locus is a regular array of copies of a short direct repeat (often 30 to 40 nucleotides in a wild-type microbial cell) interspaced with similarly sized sequences, referred to herein as spacers, that can originate from viruses or plasmids (Terns and Terns, 2014, Trends in Genetics, 30:111-118). In contrast to the repeats, each spacer of a CRISPR locus can be a different nucleotide sequence. A crRNA described herein includes a tag region and a guide region. The tag region is located immediately adjacent to and 5' of the guide region (FIGS. 1 and 3).

The crRNA tag region includes 5 to 12 nucleotides, for instance 5, 6, 7, 8, 9, 10, 11, or 12 nucleotides. The nucleotide sequence of a tag region is identical to or substantially identical to a series of nucleotides present in the repeat sequence present in a CRISPR locus; however, the tag region of a crRNA is RNA while a CRISPR locus is DNA. Specifically, the nucleotide sequence of a tag region is identical to or substantially identical to the 5 to 12 nucleotides of a CRISPR locus repeat that are immediately upstream of a spacer (FIG. 1), where the tag includes uracil nucleotides and the CRISPR locus includes thymine residues. In one embodiment, a tag having a "substantially identical" nucleotide sequence includes 1, 2, 3, 4, 5, or 6 nucleotides that are not the same as the nucleotides of a reference tag, such as a tag region described in Table 2. In one embodiment, a tag having a "substantially identical" nucleotide sequence has no greater than 50%, no greater than 38%, no greater than 25% or no greater than 13% nucleotides that are not the same as the nucleotides of a reference tag, such as a tag region described in Table 2. For instance, when a tag is 8 nucleotides in length it can include 1, 2, 3, or 4 nucleotides that are not the same as the nucleotides of a reference tag. The difference may be the result of a transition, transversion, deletion or insertion mutation.

The nucleotide sequence of a tag region that can be present in a crRNA described herein can easily be identified in microbes that include a CRISPR locus and a Type III-B CRISPR-Cas system (also referred to in the art as Cmr module or RAMP module). Examples of microbes that include a Type III-B CRISPR-Cas system include those listed in Table 1. The genomic sequences of these microbes are known, and the location of CRISPR loci in these microbes is known. A crRNA described herein includes a tag region identical to or substantially identical to the nucleotide sequence of the 3'-most 5 to 12 nucleotides of a repeat from a CRISPR locus that is immediately upstream of a spacer (see FIG. 1B).

TABLE 1

Examples of microbes that contain a Type III-B CRISPR-Cas system.*

Microbes that include a CRISPR locus and a Type III-B CRISPR-Cas system, and no other CRISPR-Cas system.

*Acidilobus* saccharovorans 345 15
*Alicyclobacillus acidocaldarius* DSM 446
*Alicyclobacillus acidocaldarius* Tc 4 1
*Allochromatium vinosum* DSM 180
Anabaena cylindrica PCC 7122
Anaerobaculum mobile DSM 13181
Arthrospira *platensis* NIES 39
*Azospirillum lipoferum* 4B
*Caldilinea aerophila* DSM 14535 NBRC 104270
Calothrix PCC 7507
Candidatus Accumulibacter phosphatis clade IIA UW 1
Candidatus Chloracidobacterium *thermophilum* B
*Chloroherpeton thalassium* ATCC 35110
*Clostridium botulinum* A ATCC 19397
*Clostridium botulinum* A ATCC 3502
*Clostridium botulinum* A Hall
*Clostridium botulinum* Ba4 657
*Clostridium botulinum* F 230613
*Clostridium botulinum* F Langeland
*Clostridium botulinum* H04402 065
Cyanobacterium PCC 10605
Cyanobacterium *stanieri* PCC 7202
Cyanothece ATCC 51142
Cyanothece PCC 7424
Cyanothece PCC 7425
Cyanothece PCC 7822
Cyanothece PCC 7822
Cylindrospermum stagnale PCC 7417
*Deinococcus geothermalis* DSM 11300
*Desulfotomaculum acetoxidans* DSM 771
*Desulfovibrio hydrothermalis* AM13 DSM 14728
*Flexibacter litoralis* DSM 6794
*Flexistipes sinusarabici* DSM 4947
Geobacillus HH01
Geobacillus thermoglucosidasius C56 YS93
Gloeobacter JS
*Haliangium ochraceum* DSM 14365
*Haliscomenobacter hydrossis* DSM 1100
*Halorhodospira halophila* SL1
Halothece PCC 7418
*Herpetosiphon aurantiacus* DSM 785

TABLE 1-continued

Examples of microbes that contain a Type III-B CRISPR-Cas system.*

*Hyperthermus butylicus* DSM 5456
*Ignicoccus hospitalis* KIN4 I
*Isosphaera pallida* ATCC 43644
*Kyrpidia tusciae* DSM 2912
*Marinithermus hydrothermalis* DSM 14884
*Marinitoga piezophila* KA3
*Marinomonas* MWYL1
*Marinomonas mediterranea* MMB 1
*Methanococcus vannielii* SB
*Methanosaeta harundinacea* 6Ac
*Myxococcus fulvus* HW 1
*Myxococcus xanthus* DK 1622
*Nostoc* PCC 7524
*Oscillatoria* PCC 7112
*Oscillatoria acuminata* PCC 6304
*Paenibacillus larvae* 04 309
*Pleurocapsa* PCC 7327
*Porphyromonas gingivalis* ATCC 33277
*Porphyromonas gingivalis* TDC60
*Porphyromonas gingivalis* W83
*Pyrobaculum* 1860
*Pyrobaculum calidifontis* JCM 11548
*Pyrobaculum neutrophilum* V24Sta
*Pyrococcus yayanosii* CH1
*Rhodospirillum centenum* SW
*Rivularia* PCC 7116
*Shewanella putrefaciens* 200
*Sorangium cellulosum* So ce 56
*Sulfolobus islandicus* HVE10 4
*Sulfolobus islandicus* LAL14 1
*Sulfolobus islandicus* L D 8 5
*Sulfolobus islandicus* L S 2 15
*Sulfolobus islandicus* M 14 25
*Sulfolobus islandicus* M 16 27
*Sulfolobus islandicus* M 16 4
*Sulfolobus islandicus* REY15A
*Sulfolobus islandicus* Y G 57 14
*Sulfolobus solfataricus* P2
*Sulfolobus tokodaii* 7
*Synechococcus* JA 2 3B a 2 13
*Synechococcus* JA 3 3Ab
*Synechococcus* PCC 6312
*Synechococcus* PCC 7002
*Synechococcus* PCC 7502
*Synechocystis* PCC 6803
*Synechocystis* PCC 6803
*Syntrophobotulus glycolicus* DSM 8271
*Syntrophus aciditrophicus* SB
*Teredinibacter turnerae* T7901
*Thermoanaerobacter italicus* Ab9
*Thermoanaerobacter mathranii* A3
*Thermoanaerobacter tengcongensis* MB4
*Thermoanaerobacterium thermosaccharolyticum* DSM 571
*Thermoanaerobacterium thermosaccharolyticum* M0795
Thermobaculum terrenum ATCC BAA 798
*Thermodesulfatator indicus* DSM 15286
*Thermofilum* 1910b
*Thermomicrobium roseum* DSM 5159
*Thermosipho africanus* TCF52B
*Thermus thermophilus* HB27
*Thermus thermophilus* HB8
*Thioalkalivibrio nitratireducens* DSM 14787
*Thioalkalivibrio sulfidophilus* HL EbGr7
*Thiocystis violascens* DSM 198
*Thioflavicoccus mobilis* 8321
*Treponema azotonutricium* ZAS 9
*Truepera radiovictrix* DSM 17093

Microbes that include a CRISPR locus, a Type III-B CRISPR-Cas system, and at least one other CRISPR-Cas system.

*Pyrobaculum neutrophilum* V24Sta
Candidatus Korarchaeum cryptofilum OPF8
*Desulfurococcus kamchatkensis* 1221n
*Fervidicoccus fontis* Kam940
*Pyrobaculum calidifontis* JCM 11548
*Pyrobaculum oguniense* TE7
*Anaerolinea thermophila* UNI 1

TABLE 1-continued

Examples of microbes that contain a Type III-B CRISPR-Cas system.*

*Aquifex aeolicus* VF5
*Caldicellulosiruptor obsidiansis* OB47
*Geobacillus* WCH70
*Geobacillus* Y412MC52
*Geobacillus* Y412MC61
*Methanococcus voltae* A3
*Methanosaeta thermophila* PT
*Myxococcus stipitatus* DSM 14675
*Pelotomaculum thermopropionicum* SI
*Pyrococcus furiosus* COM1
*Pyrococcus furiosus* DSM 3638
*Syntrophothermus lipocalidus* DSM 12680
*Meiothermus ruber* DSM 1279
*Paenibacillus terrae* HPL 003
*Truepera radiovictrix* DSM 17093
Candidatus Desulforudis audaxviator MP104C
*Thermotoga* RQ2
*Thermotoga maritima* MSB8
Comamonadaceae bacterium CR
*Vulcanisaeta distributa* DSM 14429
*Archaeoglobus fulgidus* DSM 4304
*Caldivirga maquilingensis* IC 167
*Pyrobaculum arsenaticum* DSM 13514
*Sulfolobus islandicus* Y G 57 14
*Sulfolobus solfataricus* P2
*Caldicellulosiruptor kronotskyensis* 2002
*Desulfotomaculum kuznetsovii* DSM 6115
*Halothermothrix orenii* H 168
*Mesotoga prima* MesG1 Ag 4 2
*Rubrobacter xylanophilus* DSM 9941
*Sulfurihydrogenibium* YO3AOP1
*Thermocrinis albus* DSM 14484
*Thermus* CCB US3 UF1
*Thermotoga maritima* MSB8
*Thermotoga maritima* MSB8
*Bacillus halodurans* C 125
*Meiothermus ruber* DSM 1279
*Meiothermus silvanus* DSM 9946
*Sulfolobus islandicus* LAL14 1
*Thermofilum pendens* Hrk 5
*Thermobifida fusca* YX
*Fervidobacterium pennivorans* DSM 9078
*Thermosipho melanesiensis* BI429
*Vulcanisaeta moutnovskia* 768 28
*Archaeoglobus fulgidus* DSM 4304

*Microbes extracted from Makarova et al. 2015, Nature Reviews Microbiology, 13:722-736, Supplemental Table 7.

Examples of predicted tag regions are listed in Table 2. The tag regions of these microbes were determined by: obtaining the CRISPR repeat sequences from CRISPRdb (crispr.u-psud.fr), orienting the repeat using the CRISPR-strand tool via the CRISPRmap web application v2.1 (rna.informatik.uni-freiburg.de/CRISPRmap) and extracting the eight 3'-most nucleotides of the CRISPR repeat. Using similar methods, a skilled person can easily identify tag regions in other microbes having a Type III-B CRISPR-Cas system. The conservation in tag sequences identified in the organisms listed in Table 1 is illustrated in the form of a weblogo in FIG. 4. A weblogo is a graphical representation of the sequence conservation of nucleotides (Schneider and Stephens, 1990, Nucleic Acids Res. 18:6097-6100, and Crooks et al., 2004, Genome Res. 14:1188-1190). As is readily apparent in FIG. 4, an A, U, G, or C is possible at position 8, but A is most prevalent; a U is present at position 7; an A, U, or G is possible at position 6, but U is most prevalent; an A, U, or G is possible at position 5; an A, G, or C is possible at position 4, 3, and 2, but A is most prevalent; and a U, G, or C is possible at position 1, but G and C are most prevalent. The most prevalent nucleotides found in the identified tag sequences (proceeding from position 8 to 1, and 5' to 3') are ATTGAAAC/G.

TABLE 2

Tag regions from microbes containing a Type III-B CRISPR-Cas system.

| Microbe | Predicted 5' tag |
|---|---|
| Alicyclobacillus acidocaldarius DSM 446 | ATTGAAGC |
| Alicyclobacillus acidocaldarius Tc 4 1 | ATTGAAGC |
| Allochromatium vinosum DSM 180 | ATTAAGAC |
| Anaerobaculum mobile DSM 13181 | ATGGAAAC |
| Aquifex aeolicus VF5 | GTTGAAAC |
| Archaeoglobus fulgidus DSM 4304 | ATTGAAAG |
| Azospirillum lipoferum 4B | ATTGAAGC |
| Bacillus halodurans C 125 | ATTGAAAT |
| Candidatus Korarchaeum cryptofilum OPF8 | ATTGAAAG |
| Chloroherpeton thalassium ATCC 35110 | ATTGAAAC |
| Clostridium botulinum A ATCC 19397 | ATTTAAAT |
| Clostridium botulinum A ATCC 3502 | ATTTAAAT |
| Clostridium botulinum A Hall | ATTTAAAT |
| Clostridium botulinum Ba4 657 | ATTTAAAT |
| Deinococcus geothermalis DSM 11300 | ATTGAAAC |
| Desulfurococcus kamchatkensis 1221n | ATTGAAAG |
| Fervidicoccus fontis Kam940 | ATTGAAAG |
| Fervidobacterium pennivorans DSM 9078 | ATGGAAAC |
| Flexibacter litoralis DSM 6794 | ATTGCGAC |
| Geobacillus HH01 | ATTGAAAC |
| Geobacillus Y412MC52 | ATTGAAAC |
| Geobacillus Y412MC61 | ATTGAAAC |
| Haliangium ochraceum DSM 14365 | ATTGAAGC |
| Halorhodospira halophila SL1 | ATTAAGAC |
| Halothermothrix orenii H 168 | ATTGAAAC |
| Herpetosiphon aurantiacus DSM 785 | ATTAAAAC |
| Hyperthermus butylicus DSM 5456 | ATTGCAAG |
| Isosphaera pallida ATCC 43644 | ATTGAAGC |
| Mesotoga prima MesG1 Ag 4 2 | ATTGAAAC |
| Methanococcus vannielii SB | ATTGAAAC |
| Methanosaeta harundinacea 6Ac | ATTGAAAC |
| Nostoc PCC 7524 | ATTGAAAC |
| Pelotomaculum thermopropionicum SI | ATTGAAAC |
| Pyrobaculum arsenaticum DSM 13514 | ATTGAAAG |
| Pyrococcus furiosus COM1 | ATTGAAAG |
| Shewanella putrefaciens 200 | CTTAGAAA |
| Sulfolobus islandicus L D 8 5 | ATTGAAAG |
| Sulfolobus islandicus M 16 4 | ATTGAAAG |
| Sulfolobus islandicus REY15A | ATTGAAAG |
| Sulfolobus islandicus Y G 57 14 | ATTGAAAG |
| Sulfolobus solfataricus P2 | ATTGAAAG |
| Sulfolobus tokodaii 7 | ATTGAAAG |
| Sulfurihydrogenibium YO3AOP1 | TTATAAAG |
| Synechococcus JA 2 3B a 2 13 | TTGGAAAC |
| Synechococcus PCC 6312 | TTGAGCAC |
| Synechococcus PCC 7502 | TTGGAAAC |
| Thermoanaerobacter tengcongensis MB4 | ATTGAAAC |
| Thermoanaerobacterium thermosaccharolyticum DSM 571 | ATTGAAAC |
| Thermoanaerobacterium thermosaccharolyticum M0795 | ATTGAAAC |
| Thermobaculum terrenum ATCC BAA 798 | GTGAACCG |
| Thermocrinis albus DSM 14484 | GTTGAAAG |
| Thermomicrobium roseum DSM 5159 | CTTGAAAC |
| Thermotoga RQ2 | ATTGAAAC |
| Thermotoga maritima MSB8 | ATTGAAAC |
| Thermotoga thermarum DSM 5069 | ATGGAAAC |
| Treponema azotonutricium ZAS 9 | ATTAAGAC |

A crRNA also includes a guide region (FIGS. 1 and 3). The guide region includes a number of nucleotides that is an integer greater than 14 (e.g., at least 15, at least 16, at least 17). In some aspects, the guide region may be an integer less than 76 (e.g., no greater than 75, no greater than 74, no greater than 73, and so on). In some embodiments, the guide region of a crRNA is at least 28, at least 29, at least 30, at least 31, at least 32, at least 33, at least 34, at least 35, at least 36, at least 37, at least 38, or at least 39 nucleotides. Thus, in one embodiment, a crRNA described herein may be at least 20 nucleotides in length (a 5 nucleotide tag region and a 15 nucleotide guide region), or greater. In some aspects, a crRNA described herein may be 39 nucleotides or 45 nucleotides in length, for instance, an 8 nucleotide tag and a guide of 31 or 37 nucleotides. The guide region of a crRNA may be any nucleotide sequence. In one embodiment, the nucleotide sequence of a guide region includes nucleotides that are not naturally present downstream of a CRISPR repeat that is present in a wild-type cell, where the thymine nucleotides downstream of a CRISPR repeat are uracil nucleotides in a guide region. For instance, the nucleotide sequence of a guide region is not derived from the types of invaders that are typically the source for spacer sequences, such as nucleotide sequences from a virus or a transposon. In one embodiment, the nucleotide sequence of a guide region is a nucleotide sequence (or complementary to such a nucleotide sequence) present in a eukaryotic cell and typically not present in a microbe. For instance, a nucleotide sequence from a eukaryotic virus, or a nucleotide sequence expressed by a eukaryotic cell, such as a nucleotide sequence that can be used as a biomarker.

Activating RNA

The second polynucleotide that is optionally a part of the complex is referred to herein as an activating RNA (actRNA). An actRNA includes, 5' to 3', a target region and a protospacer adjacent motif (PAM) region. The target region and PAM region are located immediately adjacent to each other, with the target region present 5' of the PAM region (FIGS. 1 and 3). The target region includes a nucleotide sequence that is complementary or substantially complementary to the nucleotide sequence of the guide region of a crRNA. The target region may be shorter than the guide region of a crRNA. In one embodiment, a target region of an actRNA includes at least 12, at least 13, at least 14, at least 15, at least 16, at least 17, or at least 18 nucleotides that are complementary or substantially complementary to the guide region of a crRNA. Thus, the region that is complementary or substantially complementary between an actRNA target region and a guide region of a crRNA may be as few as 12 nucleotides or may be much longer, e.g., in one embodiment no greater than 75. In one embodiment, a target region that is "substantially complementary" to a crRNA guide region includes 1, 2, 3, 4, 5, 6, 7, 8, 9, or 10 nucleotides that are not complementary to the nucleotides of a crRNA guide region. In one embodiment, a target region that is "substantially complementary" to a crRNA guide region includes no less than 50% complementarity, no less than 60%, no less than 70%, or no less than 80% nucleotides that are not complementary to the nucleotides of a crRNA guide region. In one embodiment, a target region and crRNA guide region that are "substantially complementary" have a melting temperature (Tm) of no less than 24° C. under standard conditions of 50 nM primer, 50 mM Na$^+$, and pH 7.0. The Tm of two strands of RNA that are less than 14 nucleotides in length can be determined using the equation $Tm=(wA+xT)*2+(yG+zC)*4$ where w, x, y, z are the number of the bases A,T,G,C in the sequence, respectively (Marmur and Doty, 1962, J Mol Biol., 5:109-118). The Tm of two strands of RNA that are longer than 13 nucleotides can be determined using the equation $Tm=64.9+41*(yG\pm zC-16.4)/(wA+xT+yG+zC)$. Both equations assume that the annealing occurs under the standards conditions of 50 nM primer, 50 mM Na$^+$, and pH 7.0.

In one embodiment, an actRNA may include other nucleotides on the 5' side (i.e., immediately upstream of the target region, see FIG. 1). These additional nucleotides are not complementary or substantially complementary to the crRNA guide region because they extend beyond the crRNA guide region (see FIG. 17A of Example 1). No upper limit of the length of a target region is known, however, in one embodiment an actRNA is no greater than 1,000 nucleotides, no greater than 500 nucleotides, no greater than 250 nucleotides, or no greater than 100 nucleotides.

An actRNA also includes a PAM region. A PAM is a short secondary activation element located immediately adjacent the 3' end of the target region of an actRNA (FIG. 1). A PAM region is from 1 to 5 nucleotides in length, such as 1, 2, 3, 4, or 5 nucleotides. In one embodiment, a PAM is 5'-NGN, 5'-NNG, 5'-NAA, or 5'-NAC, where N is any nucleotide (A, G, U, or C), and the first nucleotide of each trimer is immediately downstream of the 3' end of the target sequence (FIG. 1). In another embodiment, a PAM may be 5'-NAU, 5'-NAG, 5'-NUA, 5'-NUG, 5'-NUC, 5'-NUU, 5'-NGA, 5'-NGG, 5'-NGC, 5'-NGU, 5'-NCA, 5'-NCG, 5'-NCU, or 5'-NCC. An actRNA can include additional nucleotides on the 3' side (i.e., immediately downstream of the PAM region (see FIG. 1, and FIG. 17A of Example 1).

Proteins

In one embodiment, a complex described herein includes at least 4, at least 5, or at least 6 proteins. When the complex interacts with an actRNA, the complex has an RNA-activated DNAse activity (FIG. 3B). The complex also has an RNAse activity; the complex cleaves a substrate RNA, also referred to herein as a predetermined substrate RNA (FIG. 3C). A complex having one of these activities when an actRNA and substrate DNA, or substrate RNA is present is referred to herein as a Cmr complex, and the activity of the Cmr complex is endonucleolytic. In one embodiment, a Cmr complex has RNA-activated DNAse activity in the absence of a Csx1 protein (Deng et al., 2013, Mol. Microbiol., 87(5):1088-1099).

A complex described herein having RNA-activated DNAse activity catalytically cleaves under suitable conditions a substrate DNA molecule (also referred to herein as a target DNA). The cleavage can occur in a region that is double stranded or single stranded. A substrate DNA molecule may be circular or linear. In one embodiment, a substrate DNA molecule may be part of a double stranded DNA-RNA hybrid. A substrate DNA may include a detectable moiety.

A complex described herein does not have a specific nucleotide sequence that it targets, thus there are no sequence requirements of a substrate DNA, and a substrate DNA may have any nucleotide sequence. Likewise, there are no requirements regarding length of a substrate DNA molecule. In one embodiment, a substrate DNA molecule is a chromosome present in a microbial cell, and microbial chromosomes can be greater than 4,000 kilobases in length. In one embodiment, a substrate DNA molecule is at least 2, at least 10, at least 25, at least 50, at least 75, at least 110, or at least 117 nucleotides. A Cmr2 protein may also have an DNAse activity under different conditions.

Whether a complex has RNA-activated DNAse activity may be determined by in vitro assays. In one embodiment, an in vitro assay is carried out as described herein (see Example 1). The results of the reaction may be determined by standard methods, such as electrophoretic separation using a denaturing polyacrylamide gel.

In one embodiment described in greater detail herein, a Cmr complex has RNAse activity (FIG. 3C). Whether a Cmr complex has RNAse activity may be determined by in vitro assays. In one embodiment, an in vitro assay is carried out as described by Hale et al. (2009, Cell, 139(5):945-56). The results of the reaction may be determined by standard methods, such as electrophoretic separation using a denaturing polyacrylamide gel.

The complex of Cmr proteins includes at least one Cmr2 protein, at least one Cmr3 protein, at least one Cmr4 protein, and at least one Cmr5 protein. In one embodiment, the complex includes at least one Cmr1 protein. In one embodiment, the complex includes at least one Cmr6 protein. In one embodiment, the complex includes at least one of each Cmr protein 1-6. Cmr proteins 2-5, optionally Cmr proteins 1-5, Cmr proteins 2-6, or Cmr proteins 1-6, form a complex under suitable conditions (see, for instance, Example 1) with a crRNA and an optional actRNA (FIG. 3B).

An example of a Cmr1 protein is depicted at SEQ ID NO:1, an example of a Cmr2 protein is depicted at SEQ ID NO:2, an example of a Cmr3 protein is depicted at SEQ ID NO:3, an example of a Cmr4 protein is depicted at SEQ ID NO:4, an example of a Cmr5 protein is depicted at SEQ ID NO:5, and an example of a Cmr6 protein is depicted at SEQ ID NO:6 (see FIG. 2). Other examples of Cmr1, Cmr2, Cmr3, Cmr4, Cmr5, and Cmr6 proteins include those having sequence similarity with the known Cmr1, Cmr2, Cmr3, Cmr4, Cmr5, and Cmr6 proteins, such as the amino acid sequence of SEQ ID NO:1, SEQ ID NO:2, SEQ ID NO:3, SEQ ID NO:4, SEQ ID NO:5, and SEQ ID NO:6. A Cmr1, Cmr2, Cmr3, Cmr4, Cmr5, and Cmr6 protein having sequence similarity with the amino acid sequence of SEQ ID NO:1, SEQ ID NO:2, SEQ ID NO:3, SEQ ID NO:4, SEQ ID NO:5, and SEQ ID NO:6, respectively, has RNA-activated DNAse activity when used in a complex with a crRNA, an actRNA, and the other members of the complex.

The amino acid sequence of a Cmr1, Cmr2, Cmr3, Cmr4, Cmr5, or a Cmr6 protein having sequence similarity to SEQ ID NO:1, Cmr2, SEQ ID NO:3, SEQ ID NO:4, SEQ ID NO:5, or SEQ ID NO:6, respectively, may include conservative substitutions. A conservative substitution is typically the substitution of one amino acid for another that is a member of the same class. For example, it is well known in the art of protein biochemistry that an amino acid belonging to a grouping of amino acids having a particular size or characteristic (such as charge, hydrophobicity, and/or hydrophilicity) may generally be substituted for another amino acid without substantially altering the secondary and/or tertiary structure of a protein. For the purposes of this invention, conservative amino acid substitutions are defined to result from exchange of amino acids residues from within one of the following classes of residues: Class I: Gly, Ala, Val, Leu, and Ile (representing aliphatic side chains); Class II: Gly, Ala, Val, Leu, Ile, Ser, and Thr (representing aliphatic and aliphatic hydroxyl side chains); Class III: Tyr, Ser, and Thr (representing hydroxyl side chains); Class IV: Cys and Met (representing sulfur-containing side chains); Class V: Glu and Asp,(carboxyl group containing acidic side chains); Class VI: His, Arg and Lys (representing basic side chains); Class VII: Gly, Ala, Pro, Trp, Tyr, Ile, Val, Leu, Phe and Met (representing hydrophobic side chains); Class VIII: Phe, Trp, and Tyr (representing aromatic side chains); and Class IX: Asn and Gln (representing amide side chains). The classes are not limited to naturally occurring amino acids, but also include artificial amino acids, such as beta or gamma amino acids and those containing non-natural side chains, and/or other similar monomers such as hydroxyacids.

A Cmr2 protein is a member of the Cas10 superfamily of proteins (Makarova et al., 2011, Nat. Rev. Microbiol. 9, 467-477) and the COG1353 group of polypeptides (Haft et al., 2005, PLoS Comput. Biol. 1, e60; Makarova et al., 2002, Nucleic Acids Res. 30, 482-496). Information on the COG1353 group of polypeptides is available at the Clusters of Orthologous Groups of proteins (COGs) web page through the National Center for Biotechnology Information internet site, see also Tatusov et al., 1997, Science, 278:631-637, and Tatusov et al. 2003, BMC Bioinformatics, 4(1):41). A Cmr2 protein includes a predicted nuclease domain (often referred to as a permuted histidine-aspartate (HD) superfamily hydrolase domain) at the amino terminus, a zinc finger domain, and a ferredoxin-like fold similar to the catalytic domain of many polymerases and nucleotide cyclases (Makarova et al., 2011, Nat. Rev. Microbiol. 9, 467-477). The ferredoxin-like fold contains a degenerate GGDEF (SEQ ID NO:13) (GGDD, SEQ ID NO:14) motif similar to that found in nucleotide cyclases (Anantharaman et al., 2010, Biol. Direct 5, 43). The acidic residues of the GGDEF (SEQ ID NO:13) motif are known to bind divalent metal ions in these enzymes (Anantharaman et al., 2010, Biol. Direct 5,43, Wang et al., 2011, Structure 19, 257-264).

The crystal structures of Cmr1, Cmr2, the Cmr2 and 3 subcomplex, Cmr4, Cmr5, and Cmr6 have been determined (Sun et al., 2014, Acta crystallographica Section D, Biological crystallography 70:535-543; Osawa et al., 2013, J. Mol. Biol. 425:3811-3823; Shao et al., 2013, Structure 21:376-384; Benda et al., 2014, Mol. Cell 56:43-54; and Park et al., 2013, FEBS Lett. 587:562-568). In addition, the crystal structure of a Cmr complex without Cmr1 (Cmr2, Cmr2, Cmr3, Cmr4, Cmr5, and Cmr6 with a crRNA) is known (Osawa et al., 2015, Molecular Cell 58:418-430). The crystal structure of a Cmr2 protein is disclosed by Benda et al. (Benda et al., 2014, Molecular Cell 56:43-54). The amino acid sequence of the Cmr2 protein of Benda et al. is identical to amino acids 1-871 of SEQ ID NO:2, with the exception that the Cmr2 protein of Benda also includes a small 6× His tag and linker on the amino terminus. As shown in the sequence alignment of the amino terminal regions of SEQ ID NO:2 and archaeal and bacterial Cmr2 proteins at Figure S1 of Cocozaki et al. (2012, Structure, 20:545-553), the amino terminal 215 amino acids include the HD superfamily hydrolase domain, secondary structures include α-helices, β-strands, and loops are shown above the alignment, and four domains are present. Also shown are regions of conserved amino acids. Sequence alignments with associated structural features between Cmr proteins 1 and 3-5 showing structural information are available (Cmr1, Sun et al., 2014, Acta crystallographica Section D, Biological crystallography 70:535-543; Cmr3, Shao et al., 2013, Structure 21:376-384; Cmr4, Benda et al., 2014, Mol. Cell 56:43-54; and Cmr5, Park et al., 2013, FEBS Lett. 587:562-568). Based on the structural and functional data available to the skilled person, the skilled person can predict with a reasonable expectation of success which amino acids may be substituted, and what sorts of substitutions (e.g., conservative or non-conservative) can be made to a Cmr1, Cmr2, Cmr3, Cmr4, Cmr5, and Cmr6 protein without altering the RNA-activated DNase activity of the Cmr1-6 complex.

Further guidance concerning how to make phenotypically silent amino acid substitutions is provided in Bowie et al. (1990, Science, 247:1306-1310), wherein the authors indicate proteins are surprisingly tolerant of amino acid substitutions. For example, Bowie et al. disclose that there are two main approaches for studying the tolerance of a protein sequence to change. The first method relies on the process of evolution, in which mutations are either accepted or rejected by natural selection. The second approach uses genetic engineering to introduce amino acid changes at specific positions of a cloned gene and selects or screens to identify sequences that maintain functionality. As stated by the authors, these studies have revealed that proteins are surprisingly tolerant of amino acid substitutions. The authors further indicate which changes are likely to be permissive at a certain position of the protein. For example, most buried amino acid residues require non-polar side chains, whereas few features of surface side chains are generally conserved. Other such phenotypically silent substitutions are described in Bowie et al, and the references cited therein.

Other examples of Cmr1, Cmr2, Cmr3, Cmr4, Cmr5, and Cmr6 proteins are readily available in microbes that include a CRISPR locus and a Type III-B CRISPR-Cas system. Type III systems are characterized by the presence of cas10 superfamily genes (such as cmr2) and are further classified into two subtypes, III-A (also known as Mtube subtype or Csm module) and III-B (also known as Cmr module or RAMP module), that can be distinguished by the presence of distinct genes for "small subunits", csm2 (in the case of subtype III-A) and cmr5 (in the case of subtype III-B) (Makarova et al., 2015, Nature Reviews Micriobiol., 13:722-736). Type III-B CRISPR-Cas systems also include a cas5 superfamily (Cmr 3) gene, and cas7 superfamily (Cmr1, Cmr4, Cmr6) genes. The term "Cmr" is used herein to describe proteins that are members of the III-B system.

Cmr proteins of a Type III-B subtype that can be used in a Cmr complex described herein can be identified in other microbes. The steps a skilled person can take to identify Cmr proteins in a microbe are described in Makarova (2015, Nature Reviews Micriobiol., 13:722-736). Briefly, a portion of a genome such as a partially assembled genomic sequence, or a whole genomic sequence is evaluated for the presence of a gene encoding a candidate Cas10 superfamily (Cmr2) protein, where the candidate Cas10 (Cmr2) protein includes an HD superfamily hydrolase domain and a ferredoxin-like fold containing a degenerate GGDEF (GGDD) motif similar to that found in nucleotide cyclases. If the genome does not include a gene encoding a candidate Cas10 (Cmr2) protein, then the genome does not include the set of Cmr proteins that make up a Cmr complex described herein. If the genome includes a gene encoding a candidate Cas10 (Cmr2) protein, the genome is evaluated for the presence of a gene encoding a candidate "small subunit" superfamily Cmr5 protein. If the genome includes a gene encoding a candidate "small subunit" Cmr5 protein, the genome is evaluated for the presence of genes encoding candidate Cas5 superfamily (Cmr3) and Cas7 superfamily (Cmr1, Cmr4, Cmr6) proteins. Genes identified as described above are Cmr1, Cmr2, Cmr3, Cmr4, Cmr5 and Cmr6 genes and can be used in the methods described herein.

Other examples of Cmr1, Cmr2, Cmr3, Cmr4, Cmr5, and Cmr6 proteins are readily available in microbes that include a CRISPR locus and a Type III-B CRISPR-Cas system (also known as Cmr module or RAMP module). Examples of microbes that include a Type III-B CRISPR-Cas system include a member of the genus *Pyrococcus*, such as *P. furiosus*, and any of the microbes listed in Table 1. The microbes in Table 1 are also listed at Supplemental Table 7 of Makarova et al. (2015, Nature Reviews Microbiol., 13:722-736) as having a Type III-B CRISPR-Cas system. The Cmr2 proteins in Supplemental Table 7 of Makarova et al. are referred to as Cas10, and the GI sequence identification number for each Cmr1, Cmr2, Cmr3, Cmr4, Cmr5, and Cmr6 protein that is a Type III-B CRISPR-Cas system is included in Supplemental Table 7 of Makarova et al. A Cmr1, Cmr2, Cmr3, Cmr4, Cmr5, and Cmr6 protein may be isolated from a microbe, or may be produced using recombinant techniques, or chemically or enzymatically synthesized using routine methods. In one embodiment, a composition includes a crRNA tag region and a complex of proteins from the same microbe. For example, when a composition includes a crRNA with a tag region from a *P. furiosus*, the Cmr proteins are also from a *P. furiosus*.

In one embodiment a Cmr2 protein includes at least one mutation that reduces RNA-activated DNAse activity. In one embodiment, the mutation completely abolishes detectable RNA-activated DNAse activity. In one embodiment, a mutation is in the HD superfamily hydrolase domain of Cmr2. For example, a mutation of this region may be altering the H of the domain (at residue 13 in SEQ ID NO:2), the D of the domain (at residue 14 in SEQ ID NO:2), or the combination thereof. A person of ordinary skill in the art recognizes that this numbering system can vary between different Cmr2 proteins, thus the location of these residues may vary in other Cmr2 proteins. The alteration may be a non-conservative substitution, such as replacement of the H, the D, or both H and D with an alanine. A Cmr2 protein having such a mutation reduces the DNA cleavage activity of the Cmr2 protein but retains RNAse activity. Such a mutated Cmr2 protein can be used in situations where the RNAse activity of a complex described herein is useful. Examples of such situations are described in greater detail herein.

In one embodiment a Cmr4 protein includes at least one mutation that reduces RNAse activity of the Cmr complex. In one embodiment, the mutation completely abolishes detectable RNAse activity. In one embodiment, the mutation is in the active site, which includes the L1 loop of Cmr4, for instance, amino acids 11-41 of SEQ ID NO:4. For example, a mutation of this region may alter the D of the active site (at residue 26 of SEQ ID NO:4). A person of ordinary skill in the art recognizes that this numbering system can vary between different Cmr4 proteins, thus the location of these residues may vary in other Cmr4 proteins. The alteration may be a non-conservative substitution, such as replacement of the D with an N. A Cmr4 protein having such a mutation reduces the single stranded RNA cleavage activity of the Cmr4 protein but retains DNAse activity. In one embodiment, elimination of the RNase activity through mutation of Cmr4 makes the complex a more potent DNase.

Also provided are fusion proteins, such as fusion between a protein disclosed herein and an additional amino acid sequence. For instance, the additional amino acid sequence may be useful for purification of the fusion polypeptide by affinity chromatography. An example of such an additional amino acid sequence is a polyhistidine-tag (his-tag). In one embodiment, two proteins disclosed herein may be fused to result in a single protein.

Also provided herein is a genetically modified cell that has been engineered to include one or more exogenous polynucleotides, where the polynucleotides include a coding region encoding a Cmr1 protein, Cmr2 protein, Cmr3 protein, Cmr4 protein, Cmr5 protein, Cmr6 protein, or a combination thereof. In one embodiment, the genetically modified cell includes an exogenous polynucleotide encoding a Cmr2 protein having a mutation in the HD superfamily hydrolase domain, such as an alteration of the H of the domain (at residue 13 in SEQ ID NO:2), the D of the domain (at residue 14 in SEQ ID NO:2), or the combination thereof. In one embodiment, the genetically modified cell includes an exogenous polynucleotide encoding a Cmr4 protein having a mutation in the active site, such as an alteration of the D of the active site (at residue 26 of SEQ ID NO:4). A genetically modified cell may be engineered to include an exogenous polynucleotide that encodes a crRNA. An exogenous polynucleotide may be present in the cell on a vector, or integrated in the genomic DNA of the cell.

Methods of Use

Provided herein are methods of using a composition that includes a crRNA and a Cmr complex of at least 4 Cmr proteins. In one embodiment, a method includes causing cleavage of DNA or triggered cell death in response to the presence or expression of a specific RNA. The method may be in vitro or in vivo. In those embodiments where DNA is cleaved by the complex, the Cmr4 protein may include a mutation that reduces RNAse activity of the complex.

In one embodiment, a method includes cleavage of DNA to determine whether a predetermined actRNA is present or absent in a sample. The method includes incubating a composition with a sample that is being tested to determine if a predetermined actRNA is present. The composition includes a crRNA, the proteins of the complex, and a substrate DNA. The substrate DNA is cleaved if the predetermined actRNA target is present. Thus, the cleavage of substrate DNA can act as a biosensor for the presence of a predetermined actRNA. In one embodiment, transcription of the substrate DNA is not required.

The predetermined actRNA includes a region of known nucleotide sequence. Examples of RNAs that can be detected are those present in a biological sample and include, but are not limited to, a viral RNA, a disease-associated RNA, and an RNA in a subject's plasma, such as a fetal RNA in maternal plasma. For instance, if the method is to determine whether a virus is present in a sample, the predetermined actRNA is selected from an RNA known to be expressed by virus and having a nucleotide sequence that is known. In another example, if the method is to cleave DNA when a disease-associated RNA is present in a sample, the predetermined actRNA is selected from a disease-associated RNA known to be expressed in a diseased cell and having a nucleotide sequence that is known. The predetermined actRNA includes a target region at its 5' end and a PAM region at its 3' end (see FIG. 1). In one embodiment, a biological sample includes, but is not limited to, a sample of tissue or fluid isolated from a subject, including but not limited to, for example, blood, plasma, serum, fecal matter, urine, bone marrow, bile, spinal fluid, lymph tissue and lymph fluid, samples of the skin, external secretions of the skin, respiratory, intestinal, and genitourinary tracts, tears, saliva, milk, blood cells, organs, and biopsies. In one embodiment, the biological sample includes a cell, such as a microbial cell, or a eukaryotic cell, or an extract of a cell. Examples of a eukaryotic cell include an animal cell, such as a human cell, and the predetermined actRNA is present in the cell or in an extract of the cell.

The DNA substrate may be at least 2 nucleotides in length, and may be any nucleotide sequence. The substrate DNA may include a label. A "label" refers to a detectable moiety attached (covalently or non-covalently), or capable of being attached, to a substrate DNA, which provides or is capable of providing information about the substrate DNA (e.g., whether the substrate DNA in intact or cleaved). Labels can be used to provide a detectable (and optionally quantifiable) signal. Exemplary labels include, but are not limited to, fluorophore labels (including, e.g., quenchers or absorbers), non-fluorescent labels, colorimetric labels, chemiluminescent labels, bioluminescent labels, radioactive labels, mass-modifying groups, affinity labels, magnetic particles, antigens, enzymes (including, e.g., peroxidase, phosphatase), substrates, and the like. Labels may provide signals detectable by fluorescence, radioactivity, colorimetry, X-ray diffraction or absorption, magnetism, enzymatic activity, mass spectrometry, and the like. Affinity labels provide for a specific interaction with another molecule. Examples of affinity labels include, for instance, biotin, avidin, streptavidin, dinitrophenyl, digoxigenin, cholesterol, polyethyleneoxy, haptens, and peptides such as antibodies.

In one embodiment a label is a fluorophore. A "fluorophore" is a moiety that can emit light of a particular wavelength following absorbance of light of shorter wavelength. The wavelength of the light emitted by a particular fluorophore is characteristic of that fluorophore. Thus, a particular fluorophore can be detected by detecting light of an appropriate wavelength following excitation of the fluorophore with light of shorter wavelength. Fluorophore labels include, but are not limited to, dyes of the fluorescein family, the carboxyrhodamine family, the cyanine family, and the rhodamine family. Other families of dyes that can be used in the invention include, e.g., polyhalofluorescein-family dyes, hexachlorofluorescein-family dyes, coumarin-family dyes, oxazine-family dyes, thiazine-family dyes, squaraine-family dyes, chelated lanthanide-family dyes, the family of dyes available under the trade designation Alexa Fluor™, from Molecular Probes, and the family of dyes available under the trade designation Bodipy™, from Invitrogen (Carlsbad, Calif.). Dyes of the fluorescein family include, e.g., 6-carboxyfluorescein (FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED), 2'-chloro-7'-phenyl-1,4-dichloro-6-carboxyfluorescein (VIC), 6-carboxy-X-rhodamine (ROX), and 2',4',5',7'-tetrachloro-5-carboxyfluorescein (ZOE). Dyes of the carboxyrhodamine family include tetramethyl-6-carboxyrhodamine (TAMRA), tetrapropano-6-carboxyrhodamine (ROX), Texas Red, R110, and R6G. Dyes of the cyanine family include Cy2, Cy3, Cy3.5, Cy5, Cy5.5, and Cy7. Fluorophores are readily available commercially from, for instance, Perkin-Elmer (Foster City, Calif.), Molecular Probes, Inc. (Eugene, Oreg.), and Amersham GE Healthcare (Piscataway, N.J.).

The label may be a quencher. The term "quencher" as used herein refers to a moiety that absorbs energy emitted from a fluorophore, or otherwise interferes with the ability of the fluorescent dye to emit light. A quencher can re-emit the energy absorbed from a fluorophore in a signal characteristic for that quencher, and thus a quencher can also act as a fluorophore (a fluorescent quencher). This phenomenon is generally known as fluorescent resonance energy transfer (FRET). Alternatively, a quencher can dissipate the energy absorbed from a fluorophore as heat (a non-fluorescent quencher). Quenchers may be fluorescent quenchers or non-fluorescent quenchers. Fluorescent quenchers include, but are not limited to, TAN/IRA, DABCYL, DAB SYL, cyanine dyes including nitrothiazole blue (NTB), anthraquinone, malachite green, nitrothiazole, and nitroimidazole compounds. Exemplary non-fluorescent quenchers that dissipate energy absorbed from a fluorophore include those available under the trade designation Black Hole™, from Biosearch Technologies, Inc. (Novato, Calif.), those available under the trade designation Eclipse Dark™, from Epoch Biosciences (Bothell, Wash.), those available under the trade designation Qx1™, from Anaspec, Inc. (San Jose, Calif.), and those available under the trade designation Iowa Black™, from Integrated DNA Technologies (Coralville, Iowa).

Typically, a fluorophore and a quencher are used together, and may be on the same substrate DNA. When paired together, a fluorophore and fluorescent quencher can be referred to as a donor fluorophore and acceptor fluorophore, respectively. A number of convenient fluorophore/quencher pairs are known in the art (see, for example, Glazer et al, Current Opinion in Biotechnology, 1997;8:94-102; Tyagi et al., 1998, Nat. Biotechnol., 16:49-53) and are readily available commercially from, for instance, Molecular Probes (Junction City, Oreg.), and Applied Biosystems (Foster City, Calif.). Examples of donor fluorophores that can be used with various acceptor fluorophores include, but are not limited to, fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2-,2'-disulfonic acid derivatives. Acceptor fluorophores typically depend upon the donor fluorophore used. Examples of acceptor fluorophores include, but are not limited to, LC™-Red 640, LC™-Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate or other chelates of Lanthanide ions (e.g., Europium, or Terbium). Donor and acceptor fluorophores are readily available commercially from, for instance, Molecular Probes or Sigma Chemical Co. (St. Louis, Mo.).

The nucleotide sequence of the guide region of a crRNA is complementary or substantially complementary to nucleotides of the predetermined actRNA (i.e., the target region) (FIG. 1). The region of complementarity between the predetermined actRNA and the crRNA does not include the PAM region and, in one embodiment, does include the nucleotide of the predetermined actRNA immediately adjacent to the PAM region.

Any method for measuring the presence or absence of cleavage of the substrate DNA may be used. For instance, if the substrate DNA is labeled with a fluorophore and fluorescent quencher pair, the presence of the predetermined actRNA is inferred from an increase in fluorescence, and the absence of the predetermined actRNA is inferred from fluorescence remaining constant.

In one embodiment, the method for cleaving a DNA target is in vivo, such as in a microbial cell or in a eukaryotic cell. One or more exogenous coding regions encoding and expressing the Cmr proteins and optionally the crRNA can be introduced into the cell, for instance, as part of one or more vectors. In one embodiment, an exogenous coding region encoding one or more Cmr proteins or a crRNA can be integrated into the genome of a cell. When a predetermined actRNA is present in the cell, the RNA activates the DNAse activity of the Cmr complex, resulting in cleavage of DNA in the cell. In such an embodiment, cleavage of substrate DNA can result in cell death, thus detecting the presence or absence of substrate DNA cleavage can be determining whether the cell continues to survive.

In one embodiment, a method includes cleaving a predetermined target RNA (e.g., the complex has RNAse activity, see FIG. 3C). The method may be in vitro or in vivo. In those embodiments where RNA is cleaved by the Cmr complex, the Cmr2 protein may include a mutation that reduces DNAse activity of the Cmr2 protein.

A method for cleaving a predetermined target RNA includes incubating a composition with a sample that includes a predetermined target RNA. The composition includes a crRNA and a Cmr complex. The Cmr2 protein may include a mutation that reduces DNAse activity of the Cmr2 protein. In this embodiment, the predetermined target RNA is cleaved by the Cmr complex, thus the predetermined target RNA can be referred to as a target RNA.

The predetermined target RNA includes a target region of known nucleotide sequence, and the sequence of the target region is complementary or substantially complementary to the nucleotide sequence of the guide region of the crRNA. In one embodiment, a predetermined target RNA includes a PAM region, thus, an actRNA can be one type of target RNA for a Cmr complex. Cleaving a target RNA using the methods described herein permits a level of flexibility that is not available with many other methods for cleaving an RNA molecule. Cleavage of an RNA substrate by a Cmr complex is known to occur within the region of crRNA-substrate RNA complementarity, 5 nucleotides from the 5' end of the guide region of the crRNA or the 3' end of the target region of the substrate RNA (FIG. 3C). Cleavages can also occur at 6 nucleotide intervals further into the crRNA-target duplex (Hale et al., 2014, Genes & Development, 28:2432-2443, Staals et al., 2013, Molecular cell, 52:135-145). Using the methods presented herein, the skilled worker can determine what RNA is to be cleaved and where cleavage of the target RNA is desired, and then design a crRNA that will guide the proteins described herein to cleave the target at that specific location.

In one embodiment, the method for cleaving a target RNA is in vivo, such as in a microbial cell or in a eukaryotic cell. One or more vectors encoding and expressing the Cmr proteins and optionally the crRNA can be introduced in the cell. In one embodiment, an exogenous coding region encoding one or more Cmr proteins or a crRNA can be integrated into the genome of a cell. When a predetermined target RNA is present in the cell, it is cleaved by the complex of Cmr proteins and the crRNA.

Kits

Also provided herein are kits. A kit may include one or more of the polynucleotides or proteins described herein. For instance, a kit may include a crRNA or a vector encoding a crRNA, or a Cmr1 protein, a Cmr2 protein, a Cmr3 protein, a Cmr4 protein, a Cmr5 protein, a Cmr6 protein, or a combination thereof, or a vector encoding one or more Cmr protein. In another aspect, a kit may include more than one vector encoding one or more of the protein described herein. Kits may be used, for instance, for modifying a cell to express proteins described herein, or for in vitro cleaving of a DNA or RNA molecule. The kit components can be present in separate containers, in a suitable packaging material in an amount sufficient for at least one use or assay. Optionally, other reagents such as buffers and solutions needed to practice the invention are also included. Instructions for use of the packaged polypeptide or primer pair are also typically included.

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

The present invention is illustrated by the following examples. It is to be understood that the particular examples, materials, amounts, and procedures are to be interpreted broadly in accordance with the scope and spirit of the invention as set forth herein.

Example 1

Bipartite Recognition of Target RNAs Activates DNA Cleavage by the Type III-B CRISPR-Cas System CRISPR-Cas systems eliminate nucleic acid invaders in bacteria and archaea. The effector complex of the Type III-B Cmr system cleaves invader RNAs recognized by the CRISPR RNA (crRNA) of the complex. Here it is shown that invader RNAs also activate the Cmr complex to cleave DNA. As has been observed for other Type III systems, Cmr eliminates plasmid invaders in *Pyrococcus furiosus* by a mechanism that depends on transcription of the crRNA target sequence within the plasmid. Notably, it was found that the target RNA per se induces DNA cleavage by the Cmr complex in vitro. DNA cleavage activity does not depend on cleavage of the target RNA but notably does require the presence of a short sequence adjacent to the target sequence within the activating target RNA (rPAM [RNA protospacer-adjacent motif]). The activated complex does not require a target sequence (or a PAM) in the DNA substrate. Plasmid elimination by the *P. furiosus* Cmr system also does not require the Csx1 (CRISPR-associated Rossman fold [CARF] superfamily) protein. Plasmid silencing depends on the HD nuclease and Palm domains of the Cmr2 (Cas10 superfamily) protein. The results establish the Cmr complex as a DNA nuclease activated by invader RNAs containing a crRNA target sequence and a rPAM. This example was published as Elmore et al., (Feb. 4, 2016), Genes & Development, 30:447-459.

Introduction

CRISPR-Cas systems eliminate nucleic acid invaders in bacteria and archaea by means of crRNA-guided nuclease effector complexes (Terns and Terns 2013; Barrangou and Marraffini 2014; van der Oost et al. 2014; Jackson and Wiedenheft 2015). The CRISPR RNAs (crRNAs) include target recognition sequences captured from invaders and cached between the repeat elements of the CRISPR locus (Bolotin et al. 2005; Mojica et al. 2005; Pourcel et al. 2005). crRNAs guide Cas proteins to identify and destroy corresponding invader nucleic acid.

There are multiple CRISPR-Cas systems made up of distinct modules of Cas proteins that effect invader sequence acquisition, crRNA production, and invader destruction. The systems are classified into three broad types (Types I, II, and III), and each includes a signature superfamily protein (Cas3, Cas9, and Cas10, respectively) (Makarova et al. 2011). The characterized Type I and Type II systems cleave DNAs complementary to the crRNA guide sequences (Jinek et al. 2012; Westra et al. 2012). To prevent damage to the host genome (e.g., at the CRISPR where the invader sequences are cached), these systems depend on detection of a second signal to trigger cleavage activity; in addition to the sequence recognized by the crRNA, the Type I and II effector complexes require the presence of a short protospacer-adjacent motif (PAM) adjoining the target sequence in order to activate cleavage. The PAM sequence is found adjacent to the invader target sequences that these systems acquire but not in the CRISPR repeat sequence adjacent to the target sequence integrated in the host genome (Mojica et al. 2009; Shah et al. 2013).

Interestingly, the Type III systems have been found to target RNA and DNA (Hale et al. 2009; Zhang et al. 2012; Deng et al. 2013; Staals et al. 2013; 2014; Tamulaitis et al. 2014; Samai et al. 2015). In particular, the Type III-B Cmr complex from *Pyrococcus furiosus* cleaves target RNAs at 6-nucleotide (nt) intervals in the region of crRNA complementarity by means of a series of Cmr4 protein subunits that line the region of crRNA-target RNA base pairing (Hale et al. 2009, 2014; Benda et al. 2014; Ramia et al. 2014a; Osawa et al. 2015). At the 5' end of the crRNA, Cmr3 recognizes the common crRNA tag sequence (derived from the repeat sequence in the CRISPR), and, near the 3' end of the crRNA, Cmr1 and Cmr6 function in target RNA capture (Spilman et al. 2013; Hale et al. 2014; Osawa et al. 2015). The HD nuclease domain of the signature Cas10 superfamily protein Cmr2, also found at the 5' end of the crRNA, is not required for RNA cleavage activity (Cocozaki et al. 2012; Spilman et al. 2013; Osawa et al. 2015). Type III-A Csm systems have also been shown to target RNA (Staals et al. 2014; Tamulaitis et al. 2014; Samai et al. 2015).

DNA silencing by the Type III-B Cmr (and Type III-A Csm) systems requires directional transcription of the invader DNA, which has been hypothesized to facilitate access of the crRNA to the target DNA strand (Deng et al. 2013; Goldberg et al. 2014). Csx1, an auxiliary protein associated with Cmr systems (Garrett et al. 2011; Makarova and Koonin 2013), was additionally found to be necessary for plasmid elimination in *Sulfolobus islandicus* (Deng et al. 2013). In the Csm complex, the Palm domain of the Cas10 superfamily protein Csm1 has been shown to be important for plasmid silencing (Hatoum-Aslan et al. 2014; Ramia et al. 2014b; Samai et al. 2015). Rather than requiring a PAM sequence in the invader DNA to trigger specific destruction of the invader, it has been proposed that the characterized Type III systems are inhibited from cleaving the host genome CRISPR by the base-pairing potential between the CRISPR repeat sequence and the corresponding crRNA 5' tag sequence (Marraffini and Sontheimer 2010; Deng et al. 2013).

In this study, the mechanism of DNA silencing by the Cmr system in *P. furiosus* is investigated. Our results reveal a significant new paradigm for CRISPR-Cas silencing (illustrated in FIG. 16A, below): The Cmr complex is a DNA nuclease activated by the presence of an invader RNA containing the crRNA target sequence and a PAM (without a requirement for the crRNA target sequence and PAM in the DNA itself).

Materials and Methods

Strains and Growth Conditions

The strains and plasmids used in this study are listed in Table 3. *P. furiosus* strains were grown under strict anaerobic conditions at 90° C. in defined medium or complex medium (cell extract preparation only). Cultures and media were prepared as described previously (Lipscomb et al. 2011), with medium pH adjusted to ~6.5. Cultures were inoculated with 1%-2% inoculum or a single colony and grown anaerobically. Medium was supplemented with 20 μM uracil and/or 2.75 mM 5-FOA as needed for selection.

TABLE 3

| *E. coli* Strains | Relevant Characteristics | Source Reference |
|---|---|---|
| Top10 | F-mcrA Δ(mrr-hsdRMS-mcrBC) Φ80lacZΔM15 ΔlacX74 recA1 araD139 Δ(ara leu) 7697 galU galK rpsL (StrR) endA1 nupG | Invitrogen |
| BL21-CodonPlus(DE3)-RIPL | *E. coli* B F-ompT hsdS(r-m-) dcm+ Tetr gal λ(DE3) endA Hte [argU proL Camr] [argU ileY leuW Strep/Specr] | Novagen |

| *P. furiosus* Strains | Relevant Characteristics | Source or Reference |
|---|---|---|
| JFW02 (WT) | ΔpyrF ΔtrpAB | (Farkas et al. 2011) |
| TPF06 (ΔCmr) | JFW02 Δcmr(ΔPF1124-PF1130) | This study |
| TPF15 (Cmr) | JFW02 Δcsa(ΔPF0637-0644) Δcst (ΔPF1121-1123) | This study |
| TPF20 (null) | JFW02 Δcmr+ cst(ΔPF1121-PF1130) Δcsa (ΔPF0637-0644) | This study |

TABLE 3-continued

| | | |
|---|---|---|
| TPF24 (ΔCsx1) | TPF15 Δcsx1 (ΔPF1127) | This study |
| TPF25 (Cmr2ΔHD) | TPF15 cmr2::cmr2ΔHD | This study |
| TPF27 (Cmr2-DD-AA) | TPF15 cmr2::cmr2-D673A,D674A | This study |
| TPF35 (Cmr2::Cmr2ΔHD, DD-AA) | TPF27 cmr2::cmr2ΔHD | This study |
| TPF37 (Cmr2::Cmr2-HD-AA, DD-AA) | TPF27 cmr2: : cmr2-H13A,D14A | This study |

| Plasmids | Relevant Characteristics | Source or Reference |
|---|---|---|
| pJFW17 | AprR general cloning vector with E. coli OriT, and Pfu Pgdh-pyrF cassette | (Farkas et al. 2011) |
| pJFW18 | pJFW17 derivative; Pfu OriC for replication in P. furiosus | (Farkas et al. 2011) |
| pJE47 | pJFW18 derivative; Tk-csg promoter/Tk-chiA terminator expression cassette | This study |
| pJE65 | pJE47 derivative; 7.01 spacer, GGG flank, target strand transcribed | This study |
| pJE66 | pJE47 derivative; 7.01 spacer, GGG flank, non-target strand transcribed | This study |
| pJE75 | pJE47 derivative; 7.01 spacer, flank pos +1-8 are 5' tag comp., target strand trans. | This study |
| pJE76 | pJE47 derivative; 7.01 spacer, flank pos +1-7 are 5' tag comp., target strand | This study |
| pJE77 | pJE47 derivative; 7.01 spacer, flank pos +1-6 are 5' tag comp., target strand | This study |
| pJE78 | pJE47 derivative; 7.01 spacer, flank pos +1-5 are 5' tag comp., target strand | This study |
| pJE79 | pJE47 derivative; 7.01 spacer, flank pos +1-4 are 5' tag comp., target strand | This study |
| pJE80 | pJE47 derivative; 7.01 spacer, flank pos +1-3 are 5' tag comp., target strand | This study |
| pJE81 | pJE47 derivative; 7.01 spacer, flank pos +1-2 are 5' tag comp., target strand | This study |
| pJE82 | pJE47 derivative; 7.01 spacer, flank pos +1 is 5' tag comp., target strand trans. | This study |
| pJE83 | pJE47 derivative; 7.01 spacer, flank pos +1-8 are 5' tag reversed target strand trans. | This study |
| pJE84 | pJE47 derivative; 7.01 spacer, flank pos +4-8 are 5' tag comp., target strand | This study |
| pJE85 | pJE47 derivative; 7.01 spacer, flank pos +2-3 are 5' tag comp., target strand | This study |
| pJE186 | pJE47 derivative; 7.01 spacer, TTT flank, target strand transcribed | This study |
| pJE187 | pJE47 derivative; 7.01 spacer, TTC flank, target strand transcribed | This study |
| pJE188 | pJE47 derivative; 7.01 spacer, TTA flank, target strand transcribed | This study |
| pJE189 | pJE47 derivative; 7.01 spacer, TTG flank, target strand transcribed | This study |
| pJE190 | pJE47 derivative; 7.01 spacer, TCT flank, target strand transcribed | This study |
| pJE191 | pJE47 derivative; 7.01 spacer, TCC flank, target strand transcribed | This study |
| pJE192 | pJE47 derivative; 7.01 spacer, TCA flank, target strand transcribed | This study |
| pJE193 | pJE47 derivative; 7.01 spacer, TCG flank, target strand transcribed | This study |
| pJE194 | pJE47 derivative; 7.01 spacer, TAT flank, target strand transcribed | This study |
| pJE195 | pJE47 derivative; 7.01 spacer, TAC flank, target strand transcribed | This study |
| pJE196 | pJE47 derivative; 7.01 spacer, TAA flank, target strand transcribed | This study |
| pJE197 | pJE47 derivative; 7.01 spacer, TAG flank, target strand transcribed | This study |
| pJE198 | pJE47 derivative; 7.01 spacer, TGT flank, target strand transcribed | This study |
| pJE199 | pJE47 derivative; 7.01 spacer, TGC flank, target strand transcribed | This study |
| pJE200 | pJE47 derivative; 7.01 spacer, TGA flank, target strand transcribed | This study |
| pJE201 | pJE47 derivative; 7.01 spacer, TGG flank, target strand transcribed | This study |
| pJE202 | pJE47 derivative; 7.01 spacer, CTT flank, target strand transcribed | This study |
| pJE203 | pJE47 derivative; 7.01 spacer, CTC flank, target strand transcribed | This study |
| pJE204 | pJE47 derivative; 7.01 spacer, CTA flank, target strand transcribed | This study |
| pJE205 | pJE47 derivative; 7.01 spacer, CTG flank, target strand transcribed | This study |
| pJE206 | pJE47 derivative; 7.01 spacer, CCT flank, target strand transcribed | This study |
| pJE207 | pJE47 derivative; 7.01 spacer, CCC flank, target strand transcribed | This study |
| pJE208 | pJE47 derivative; 7.01 spacer, CCA flank, target strand transcribed | This study |
| pJE209 | pJE47 derivative; 7.01 spacer, CCG flank, target strand transcribed | This study |
| pJE210 | pJE47 derivative; 7.01 spacer, CAT flank, target strand transcribed | This study |
| pJE211 | pJE47 derivative; 7.01 spacer, CAC flank, target strand transcribed | This study |
| pJE212 | pJE47 derivative; 7.01 spacer, CAA flank, target strand transcribed | This study |
| pJE213 | pJE47 derivative; 7.01 spacer, CAG flank, target strand transcribed | This study |
| pJE214 | pJE47 derivative; 7.01 spacer, CGT flank, target strand transcribed | This study |
| pJE215 | pJE47 derivative; 7.01 spacer, CGC flank, target strand transcribed | This study |
| pJE216 | pJE47 derivative; 7.01 spacer, CGA flank, target strand transcribed | This study |
| pJE217 | pJE47 derivative; 7.01 spacer, CGG flank, target strand transcribed | This study |
| pJE218 | pJE47 derivative; 7.01 spacer, ATT flank, target strand transcribed | This study |
| pJE219 | pJE47 derivative; 7.01 spacer, ATC flank, target strand transcribed | This study |
| pJE220 | pJE47 derivative; 7.01 spacer, ATA flank, target strand transcribed | This study |
| pJE221 | pJE47 derivative; 7.01 spacer, ATG flank, target strand transcribed | This study |
| pJE222 | pJE47 derivative; 7.01 spacer, ACT flank, target strand transcribed | This study |
| pJE223 | pJE47 derivative; 7.01 spacer, ACC flank, target strand transcribed | This study |
| pJE224 | pJE47 derivative; 7.01 spacer, ACA flank, target strand transcribed | This study |
| pJE225 | pJE47 derivative; 7.01 spacer, ACG flank, target strand transcribed | This study |
| pJE226 | pJE47 derivative; 7.01 spacer, AAT flank, target strand transcribed | This study |
| pJE227 | pJE47 derivative; 7.01 spacer, AAC flank, target strand transcribed | This study |
| pJE228 | pJE47 derivative; 7.01 spacer, AAA flank, target strand transcribed | This study |
| pJE229 | pJE47 derivative; 7.01 spacer, AAG flank, target strand transcribed | This study |
| pJE230 | pJE47 derivative; 7.01 spacer, AGT flank, target strand transcribed | This study |
| pJE231 | pJE47 derivative; 7.01 spacer, AGC flank, target strand transcribed | This study |
| pJE232 | pJE47 derivative; 7.01 spacer, AGA flank, target strand transcribed | This study |
| pJE233 | pJE47 derivative; 7.01 spacer, AGG flank, target strand transcribed | This study |
| pJE234 | pJE47 derivative; 7.01 spacer, GTT flank, target strand transcribed | This study |
| pJE235 | pJE47 derivative; 7.01 spacer, GTC flank, target strand transcribed | This study |
| pJE236 | pJE47 derivative; 7.01 spacer, GTA flank, target strand transcribed | This study |

TABLE 3-continued

| | | |
|---|---|---|
| pJE237 | pJE47 derivative; 7.01 spacer, GTG flank, target strand transcribed | This study |
| pJE238 | pJE47 derivative; 7.01 spacer, GCT flank, target strand transcribed | This study |
| pJE239 | pJE47 derivative; 7.01 spacer, GCC flank, target strand transcribed | This study |
| pJE240 | pJE47 derivative; 7.01 spacer, GCA flank, target strand transcribed | This study |
| pJE241 | pJE47 derivative; 7.01 spacer, GCG flank, target strand transcribed | This study |
| pJE242 | pJE47 derivative; 7.01 spacer, GAT flank, target strand transcribed | This study |
| pJE243 | pJE47 derivative; 7.01 spacer, GAC flank, target strand transcribed | This study |
| pJE244 | pJE47 derivative; 7.01 spacer, GAA flank, target strand transcribed | This study |
| pJE245 | pJE47 derivative; 7.01 spacer, GAG flank, target strand transcribed | This study |
| pJE246 | pJE47 derivative; 7.01 spacer, GGT flank, target strand transcribed | This study |
| pJE247 | pJE47 derivative; 7.01 spacer, GGC flank, target strand transcribed | This study |
| pJE248 | pJE47 derivative; 7.01 spacer, GGA flank, target strand transcribed | This study |
| pJE249 | pJE47 derivative; 7.01 spacer, GGG flank, target strand transcribed | This study |
| pJE271 | pJE65 derivative; Pcsg deleted | This study |
| pJE272 | pJE66 derivative; Pcsg deleted | This study |
| pJE275 | pJE47 derivative; 6.01 spacer, GGG flank, target strand transcribed | This study |
| pJE276 | pJE47 derivative; 6.01 spacer, GGG flank, non-target (guide) strand transcribed | This study |
| pJE294 | pJE47 derivative; mutated non-target spacer, GGG flank either end | This study |
| pJE299 | pJE47 derivative; 6.01 spacer, AAA flank, target strand transcribed | This study |
| pJE300 | pJE47 derivative; 6.01 spacer, CCC flank, target strand transcribed | This study |
| pJE301 | pJE47 derivative; 6.01 spacer, TTT flank, target strand transcribed | This study |
| pJE302 | pJE47 derivative; 2.01 spacer, GGG flank, target strand transcribed | This study |
| pJE303 | pJE47 derivative; 2.01 spacer, GGG flank, non-target (guide) strand transcribed | This study |
| pJE304 | pJE47 derivative; 2.01 spacer, AAA flank, target strand transcribed | This study |
| pJE305 | pJE47 derivative; 2.01 spacer, CCC flank, target strand transcribed | This study |
| pJE306 | pJE47 derivative; 2.01 spacer, TTT flank, target strand transcribed | This study |
| pLC64-ChiA | *T. kodakaraensa* shuttle vector with Pcsg-ChiA expression cassette | (Elmore et al. 2013) |

*Escherichia coli* strains TOP10 and BL21-CodonPlus (DE3)-RIPL were used for plasmid DNA manipulation and protein expression, respectively. Cultures were grown at 37° C. or 25° C. in Luria broth (Millers) or Terrific broth supplemented with 50 μg/mL apramycin sulfate, 50 μg/mL kanamycin sulfate, or 100 μg/mL ampicillin.

Northern Analysis

Northern analysis was carried out as previously described (Hale et al. 2008). Following initial probing, membranes were reprobed for the 5S rRNA loading control. The probe sequences used are listed in Table 4.

TABLE 4

Oligos

Northern Probe Oligos

| Northern Probe | Sequence (5'-3') |
|---|---|
| 7.01 antisense | GCTCTCAGCCGCAAGGACCGCATAC (SEQ ID NO: 15) |
| 7.01 sense | GTATGCGGTCCTTGCGGCTGAGAGC (SEQ ID NO: 16) |
| Pfu 5S rRNA antisense | CCCGGCTTCCCGCCCCCTCT (SEQ ID NO: 17) |

SOE-PCR Construct Primer Oligos

| Primer | Sequence (5'-3') |
|---|---|
| Pgdh_PyrF_F [3] | GATTGAAAATGGAGTGAGCTGAG (SEQ ID NO: 18) |
| Pdgh_PyrF_R [4] | TTATCTTGAGCTCCATTCTTTCACC (SEQ ID NO: 19) |
| 4Csx1_1 [1] | GGCAGAATTTACCCCCTTCC (SEQ ID NO: 20) |
| 4Csx1_2 [2] | CTCAGCTCACTCCATTTTCAATCTCATTCCCATATCCCTCCTAAAGC (SEQ ID NO: 21) |
| 4Csx1_5 [5] | GGTGAAAGAATGGAGCTCAAGATAATCCCACAATAGGGAAAGTTGG (SEQ ID NO: 22) |
| 4Csx1_6 [6] | TCATTCCCATATCCCTCCTAAAGC (SEQ ID NO: 23) |
| 4Csx1_7 [7] | GCTTTAGGAGGGATATGGGAATGACTGCAAATCTCGCTTATGAAG (SEQ ID NO: 24) |
| 4Csx1_8 [8] | CCTTTGCCCTGGGAGTTACA (SEQ ID NO: 25) |
| Cmr2ΔHD_1 [9] | TGTTACACCGCTTAGTTCTCCA (SEQ ID NO: 26) |
| Cmr2ΔHD_2 [10] | CTCAGCTCACTCCATTTTCAATCGTTAACCACTCCAACCACC (SEQ ID NO: 27) |
| Cmr2ΔHD_5 [11] | GGTGAAAGAATGGAGCTCAAGATAATGGATTGCCTCGATTTAAGC (SEQ ID NO: 28) |
| Cmr2ΔHD_6 [12] | GTTAACCACTCCAACCACC (SEQ ID NO: 29) |
| Cmr2ΔHD_7 [13] | GGTGGTTGGAGTGGTTAACGTTAAGGATCCCACTTTGCTC (SEQ ID NO: 30) |
| Cmr2ΔHD_8 [14] | GGCACTTCCATCCTTTGAGT (SEQ ID NO: 31) |
| Cmr2-D673A, D674A_1 [15] | TGGATAGCCTGGGAGAGAGA (SEQ ID NO: 32) |
| Cmr2-D673A, D674A_2 [16] | CTCAGCTCACTCCATTTTCAATCCCCTCCAGCGTATATTAGC (SEQ ID NO: 33) |
| Cmr2-D673A, D674A 5 [17] | GGTGAAAGAATGGAGCTCAAGATAATTATGGATGGCGACGATATG (SEQ ID NO: 34) |

TABLE 4-continued

| Oligos | |
|---|---|
| Cmr2-D673A, D674A_6 [18] | CCCTCCAGCGTATATTAGC (SEQ ID NO: 35) |
| Cmr2-D673A, D674A_7 [19] | GCTAATATACGCTGGAGGGGCAGCAGTCCTAGCAATTTTGCCAGTC (SEQ ID NO: 36) |
| Cmr2-D673A, D674A_8 [20] | AAATTCGGGTTCCTCCTCAC (SEQ ID NO: 37) |
| Cmr2-H13A, D14A_1 [21] | ATCCTCCTGGGAGCAGATTT (SEQ ID NO: 38) |
| Cmr2-H13A, D14A_2 [22] | CTCAGCTCACTCCATTTTCAATCAAGGTATACAAAAAGTTTCTCTTTGATG (SEQ ID NO: 39) |
| Cmr2-H13A, D14A_5 [23] | GGTGAAAGAATGGAGCTCAAGATAAAGGAGAGCTTCTCCCCTTTG (SEQ ID NO: 40) |
| Cmr2-H13A, D14A_6 [24] | AAGGTATACAAAAAGTTTCTCTTTGATG (SEQ ID NO: 41) |
| Cmr2-H13A, D14A_7 [25] | CATCAAAGAGAAACTTTTTGTATACCTTGCAGCACCACCAGACAAGGCTCTAA (SEQ ID NO: 42) |
| Cmr2-H13A, D14A_8 [26] | CCGAACTTGTCCACTATCACC (SEQ ID NO: 43) |
| ΔCmr_1 [27] | TCCAATCCGAAGCTTGCAACATA (SEQ ID NO: 44) |
| ΔCmr_2 [28] | CTCAGCTCACTCCATTTTCAATCGCTACCTCACCGAGCCAAATAAAGTG (SEQ ID NO: 45) |
| ΔCmr_5 [29] | GGTGAAAGAATGGAGCTCAAGATAACTGGGCTTCGGAATGGTTAAGG (SEQ ID NO: 46) |
| ΔCmr_6 [30] | GCTACCTCACCGAGCCAAATAAAGTG (SEQ ID NO: 47) |
| ΔCmr_7 [31] | CACTTTATTTGGCTCGGTGAGGTAGCTTGCCGTTGGTGGCAGAGATAG (SEQ ID NO: 48) |
| ΔCmr_8 [32] | GCCTTTGGTACCCTCTCCCAGA (SEQ ID NO: 49) |
| ΔCmr + Cst_7 [33] | CACTTTATTTGGCTCGGTGAGGTAGCATGAAACCGTGCTTTGCAAAATTTCTTC (SEQ ID NO: 50) |
| ΔCst_1 [34] | TCGTTGCCAATTGAAACTAAGGT (SEQ ID NO: 51) |
| ΔCst_2 [35] | CTCAGCTCACTCCATTTTCAATCCTAAACATATTCAACAAGCCTCCCATAG (SEQ ID NO: 52) |
| ΔCst_5 [36] | GGTGAAAGAATGGAGCTCAAGATAAATGTCCCACCTCCTGGGGACT (SEQ ID NO: 53) |
| ΔCst_6 [37] | CTAAACATATTCAACAAGCCTCCCATAG (SEQ ID NO: 54) |
| ΔCst_7 [38] | CTATGGGAGGCTTGTTGAATATGTTTAGATGAAACCGTGCTTTGCAAAATTTCTTC (SEQ ID NO: 55) |
| ΔCst_8 [39] | GGGCCGCTTCAGTCTTTCCATA (SEQ ID NO: 56) |
| ΔCsa_1 [40] | GGATTTTGTATTGCCTCACGGTTA (SEQ ID NO: 57) |
| ΔCsa_2 [41] | CTCAGCTCACTCCATTTTCAATCGTTTTCTGTATCGAATATTCCCCGAATG (SEQ ID NO: 58) |
| ΔCsa_5 [42] | GGTGAAAGAATGGAGCTCAAGATAATCCCAGGTTCTGGTTTGACAAG (SEQ ID NO: 59) |
| ΔCsa_6 [43] | GTTTTTCTGTATCGAATATTCCCCGAATG (SEQ ID NO: 60) |
| ΔCsa_7 [44] | CATTCGGGGAATATTCGATACAGAAAAACAGCTTTATCTTTTCCCATAACCATTAGG (SEQ ID NO: 61) |
| ΔCsa_8 [45] | TGGCTCCCTTAACTCGCTGGA (SEQ ID NO: 62) |

*numbers in brackets refer to FIG. 18C.

| PCR Screening Oligos | |
|---|---|
| Primer | Sequence (5' to 3') |
| ΔCsx1_seq_For | GTGTTGGAGTGGGTGAGGAG (SEQ ID NO: 63) |
| ΔCsx1_seq_Rev | TCTGGAGATATTTGCCGTTAATC (SEQ ID NO: 64) |
| ΔCsx1_seq_Int | TCCCACAATAGGGAAAGTTGG (SEQ ID NO: 65) |
| Cmr2ΔHD_seq_For | GTTTTTGGGAGCACAAAGGA (SEQ ID NO: 66) |
| Cmr2ΔHD_seq_Rev | GGTTCCTCATCAAGCCACAA (SEQ ID NO: 67) |
| Cmr2ΔHD_seq_Int | TGGATTGCCTCGATTTAAGC (SEQ ID NO: 68) |
| Cmr2-D673A, D674A_seq_For | GGGTCTCTCGGATGAAGATG (SEQ ID NO: 69) |
| Cmr2-D673A, D674A_seq_Rev | TTCTGCCTTTCTCTGTTCCAA (SEQ ID NO: 70) |
| Cmr2-D673A, D674A_seq_Int | TTATGGATGGCGACGATATG (SEQ ID NO: 71) |
| Cmr2-D673A, D674A_scr_Mu | GACTGGCAAAATTGCTAGGACTGCTGC (SEQ ID NO: 72) |
| Cmr2-D673A, D674A_scr_WT | GACTGGCAAAATTGCTAGGACATCATC (SEQ ID NO: 73) |
| Cmr2-H13A, D14A_seq_For | GTTTTTGGGAGCACAAAGGA (SEQ ID NO: 74) |
| Cmr2-H13A, D14A_seq_Rev | TTCAGCCTCCTTTCCTGAGA (SEQ ID NO: 75) |
| Cmr2-H13A, D14A_seq_Int | AGGAGAGCTTCTCCCCTTTG (SEQ ID NO: 76) |
| Cmr2-H13A, D14A_scr_Mu | TTAGAGCCTTGTCTGGTGGTGCTGC (SEQ ID NO: 77) |
| Cmr2-H13A, D14A_scr_WT | TTAGAGCCTTGTCTGGTGGATCATG (SEQ ID NO: 78) |
| ΔCmr + Cst_seq_For | TTGGAGATAGGTTCACGTGGT (SEQ ID NO: 79) |
| ΔCmr + Cst_seq_Rev | AAATCCCTGATGAGCTGTGG (SEQ ID NO: 80) |
| ΔCmr + Cst_seq_Int | CTGGGCTTCGGAATGGTTAAGG (SEQ ID NO: 81) |
| ΔCmr_seq_For | TTGGAGATAGGTTCACGTGGT (SEQ ID NO: 82) |
| ΔCmr_seq_Rev | GCGTGAGCCACAAATCTAGTC (SEQ ID NO: 83) |
| ΔCsa_seq_For | CGAGATTGAAACAGGAGCTG (SEQ ID NO: 84) |
| ΔCsa_seq_Rev | TTGGGAGGAGCTGTAATTGG (SEQ ID NO: 85) |

TABLE 4-continued

| Oligos | |
|---|---|
| ΔCsa_seq_Int | TCCCAGGTTCTGGTTTGACAAG (SEQ ID NO: 86) |
| ΔCst_seq_For | CCTGGGGGAGAGACAGAACT (SEQ ID NO: 87) |
| ΔCst_seq_Rev | AAATCCCTGATGAGCTGTGG (SEQ ID NO: 88) |
| ΔCst_seq_Int | ATGTCCCACCTCCTGGGGACT (SEQ ID NO: 89) |

| Oligos for Target Plasmid Cloning | |
|---|---|
| Oligos | Sequence (5'-3') |
| 7.01_TT_GGG + | [phos]TATGGGATCCTCTGAAGTGCTCTCAGCCGCAAGGACCGCATACTACAAgggAT CCGAGG (SEQ ID NO: 90) |
| 7.01_TT_GGG - | [phos]GATCCCTCGGATcccTTGTAGTATGCGGTCCTTGCGGCTGAGAGCACTTCAGA GGATCCCA (SEQ ID NO: 91) |
| 7.01_GT_GGG + | [phos]TATGCTCGGATcccTTGTAGTATGCGGTCCTTGCGGCTGAGAGCACTTCAGAG GATCCG (SEQ ID NO: 92) |
| 7.01_GT_GGG - | [phos]GATCCGGATCCTCTGAAGTGCTCTCAGCCGCAAGGACCGCATACTACAAgggA TCCGAGCA (SEQ ID NO: 93) |
| 7.01_TT_tagc_1-8 + | [phos]TATGGGATCCTCTGAAGTGCTCTCAGCCGCAAGGACCGCATACTACAActttc aatAGG (SEQ ID NO: 94) |
| 7.01_TT_tagc_1-8 - | [phos]GATCCCTattgaaagTTGTAGTATGCGGTCCTTGCGGCTGAGAGCACTTCAGA GGATCCCA (SEQ ID NO: 95) |
| 7.01_TT_tagc_1-7 + | [phos]TATGGGATCCTCTGAAGTGCTCTCAGCCGCAAGGACCGCATACTACAActttc aaAAGG (SEQ ID NO: 96) |
| 7.01_TT_tagc_1-7 - | [phos]GATCCCTTttgaaagTTGTAGTATGCGGTCCTTGCGGCTGAGAGCACTTCAGA GGATCCCA (SEQ ID NO: 97) |
| 7.01_TT_tagc_1-6 + | [phos]TATGGGATCCTCTGAAGTGCTCTCAGCCGCAAGGACCGCATACTACAActttc aTAAGG (SEQ ID NO: 98) |
| 7.01_TT_tagc_1-6 - | [phos]GATCCCTTAtgaaagTTGTAGTATGCGGTCCTTGCGGCTGAGAGCACTTCAGA GGATCCCA (SEQ ID NO: 99) |
| 7.01_TT_tagc_1-5 + | [phos]TATGGGATCCTCTGAAGTGCTCTCAGCCGCAAGGACCGCATACTACAActttc TTAAGG (SEQ ID NO: 100) |
| 7.01_TT_tagc_1-5 - | [phos] GATCCCTTAAgaaagTTGTAGTATGCGGTCCTTGCGGCTGAGAGCACTTCAG AGGATCCCA (SEQ ID NO: 101) |
| 7.01_TT_tagc_1-4 + | [Phos]TATGGGATCCTCTGAAGTGCTCTCAGCCGCAAGGACCGCATACTACAActttG TTAAGG (SEQ ID NO: 102) |
| 7.01_TT_tagc_1-4 - | [phos] GATCCCTTAACaaagTTGTAGTATGCGGTCCTTGCGGCTGAGAGCACTTCAG AGGATCCCA (SEQ ID NO: 103) |
| 7.01_TT_tagc_1-3 + | [phos]TATGGGATCCTCTGAAGTGCTCTCAGCCGCAAGGACCGCATACTACAActtAG TTAAGG (SEQ ID NO: 104) |
| 7.01_TT_tagc_1-3 - | [phos] GATCCCTTAACTaagTTGTAGTATGCGGTCCTTGCGGCTGAGAGCACTTCAG AGGATCCCA (SEQ ID NO: 105) |
| 7.01_TT_tagc_1-2 + | [phos]TATGGGATCCTCTGAAGTGCTCTCAGCCGCAAGGACCGCATACTACAActAAG TTAAGG (SEQ ID NO: 106) |
| 7.01_TT_tagc_1-2 - | [phos] GATCCCTTAACTTagTTGTAGTATGCGGTCCTTGCGGCTGAGAGCACTTCAG AGGATCCCA (SEQ ID NO: 107) |
| 7.01_TT_tagc_1-1 + | [phos]TATGGGATCCTCTGAAGTGCTCTCAGCCGCAAGGACCGCATACTACAAcAAAG TTAAGG (SEQ ID NO: 108) |
| 7.01_TT_tagc_1-1 - | [phos] GATCCCTTAACTTTgTTGTAGTATGCGGTCCTTGCGGCTGAGAGCACTTCAG AGGATCCCA (SEQ ID NO: 109) |
| 7.01_TT_rtag + | [phos]TATGGGATCCTCTGAAGTGCTCTCAGCCGCAAGGACCGCATACTACAAGAAAG TTAAGG (SEQ ID NO: 110) |
| 7.01_TT_rtag - | [phos] GATCCCTTAACTTTCTTGTAGTATGCGGTCCTTGCGGCTGAGAGCACTTCAG AGGATCCCA (SEQ ID NO: 111) |
| 7.01_TT_tagc_4-8 + | [phos]TATGGGATCCTCTGAAGTGCTCTCAGCCGCAAGGACCGCATACTACAAGAAtc aatAGG (SEQ ID NO: 112) |
| 7.01_TT_tagc_4-8 - | [phos] GATCCCTattgaTTCTTGTAGTATGCGGTCCTTGCGGCTGAGAGCACTTCAG AGGATCCCA (SEQ ID NO: 113) |
| 7.01_TT_tagc_2-3 + | [phos]TATGGGATCCTCTGAAGTGCTCTCAGCCGCAAGGACCGCATACTACAAGttAG TTAAGG (SEQ ID NO: 114) |
| 7.01_TT_tagc_2-3 - | [phos] GATCCCTTAACTaaCTTGTAGTATGCGGTCCTTGCGGCTGAGAGCACTTCAG AGGATCCCA (SEQ ID NO: 115) |
| pJE47_nontarg_ + | [phos]TATGCTCGGATcccAGTCCTGTAGAGACTAATACCTTCAATACGCAGCACCAG GATCCG (SEQ ID NO: 116) |
| pJE47_nontarg_ + | [phos] GATCCGGATCCTGGTGCTGCGTATTGAAGGTATTAGTCTCTACAGGACTggg ATCCGAGCA (SEQ ID NO: 117) |
| 6.01_GT_GGG + | [phos]TATGCTCGGATCCCAGTGAAGAATTTGACGTACAAATGTCCTTAGTGGAACAG GATCCG (SEQ ID NO: 118) |
| 6.01_GT_GGG - | [phos] GATCCGGATCCTGTTCCACTAAGGACATTTGTACGTCAAATTCTTCACTGGG ATCCGAGCA (SEQ ID NO: 119) |
| 2.01_GT_GGG + | [phos]TATGCTCGGATCCCTGTTCATCGCACTTCTTCTTCTGACTCTGCTCCACTTAG AGGATCCG (SEQ ID NO: 120) |
| 2.01_GT_GGG - | [phos] GATCCGGATCCTCTAAGTGGAGCAGAGTCAGAAGAAGAAGTGCGATGAACAG GGATCCGAGCA (SEQ ID NO: 121) |
| 701_NNN_F | GGTGTTGTCATATGGGTTCCTCTGAAGTGCTCTCAGCCGCAAGGACCGCATACTACAAN NNTTCCGAGGGATCCCCCCTCT (SEQ ID NO: 122) |
| 701_NNN_R | AGAGGGGGGATCCCTCGGA (SEQ ID NO: 123) |
| 701_NNN_TCC + | [Phos]TATGGGtTCCTCTGAAGTGCTCTCAGCCGCAAGGACCGCATACTACAAtcctT CCGAGG (SEQ ID NO: 124) |

TABLE 4-continued

| Oligos | |
|---|---|
| 701_NNN_TCC - | [Phos]GATCCCTCGGAaggaTTGTAGTATGCGGTCCTTGCGGCTGAGAGCACTTCAGA GGAaCCCA (SEQ ID NO: 125) |
| 701_NNN_CCT + | [Phos]TATGGGtTCCTCTGAAGTGCTCTCAGCCGCAAGGACCGCATACTACAAccttT CCGAGG (SEQ ID NO: 126) |
| 701_NNN_CCT | [Phos]GATCCCTCGGAaaggTTGTAGTATGCGGTCCTTGCGGCTGAGAGCACTTCAGA GGAaCCCA (SEQ ID NO: 127) |
| 701_NNN_CAC + | [Phos]TATGGGtTCCTCTGAAGTGCTCTCAGCCGCAAGGACCGCATACTACAAcactT CCGAGG (SEQ ID NO: 128) |
| 701_NNN_CAC - | [Phos]GATCCCTCGGAagtgTTGTAGTATGCGGTCCTTGCGGCTGAGAGCACTTCAGA GGAaCCCA (SEQ ID NO: 129) |
| 701_NNN_ATC + | [Phos]TATGGGtTCCTCTGAAGTGCTCTCAGCCGCAAGGACCGCATACTACAAatctT CCGAGG (SEQ ID NO: 130) |
| 701_NNN_ATC - | [Phos]GATCCCTCGGAagatTTGTAGTATGCGGTCCTTGCGGCTGAGAGCACTTCAGA GGAaCCCA (SEQ ID NO: 131) |
| 701_NNN_ACC + | [Phos]TATGGGtTCCTCTGAAGTGCTCTCAGCCGCAAGGACCGCATACTACAAcctT CCGAGG (SEQ ID NO: 132) |
| 701_NNN_ACC- | [Phos]GATCCCTCGGAaggtTTGTAGTATGCGGTCCTTGCGGCTGAGAGCACTTCAGA GGAaCCCA (SEQ ID NO: 133) |
| 701_NNN_AAT + | [Phos] TATGGGtTCCTCTGAAGTGCTCTCAGCCGCAAGGACCGCATACTACAAaatt TCCGAGG (SEQ ID NO: 134) |
| 701_NNN_AAT - | [Phos]GATCCCTCGGAaattTTGTAGTATGCGGTCCTTGCGGCTGAGAGCACTTCAGA GGAaCCCA (SEQ ID NO: 135) |
| 701_NNN_TAC + | [Phos]TATGGGtTCCTCTGAAGTGCTCTCAGCCGCAAGGACCGCATACTACAAtactT CCGAGG (SEQ ID NO: 136) |
| 701 NNN_TAC - | [Phos]GATCCCTCGGAagtaTTGTAGTATGCGGTCCTTGCGGCTGAGAGCACTTCAGA GGAaCCCA (SEQ ID NO: 137) |
| 701 NNN_CTT + | [Phos]TATGGGtTCCTCTGAAGTGCTCTCAGCCGCAAGGACCGCATACTACAActttT CCGAGG (SEQ ID NO: 138) |
| 701 NNN_CTT - | [Phos]GATCCCTCGGAaaagTTGTAGTATGCGGTCCTTGCGGCTGAGAGCACTTCAGA GGAaCCCA (SEQ ID NO: 139) |
| 701 NNN_CCA + | [Phos]TATGGGtTCCTCTGAAGTGCTCTCAGCCGCAAGGACCGCATACTACAAccatT CCGAGG (SEQ ID NO: 140) |
| 701 NNN_CCA - | [Phos]GATCCCTCGGAatggTTGTAGTATGCGGTCCTTGCGGCTGAGAGCACTTCAGA GGAaCCCA (SEQ ID NO: 141) |
| 701 NNN_CAG + | [Phos]TATGGGtTCCTCTGAAGTGCTCTCAGCCGCAAGGACCGCATACTACAAcagtT CCGAGG (SEQ ID NO: 142) |
| 701 NNN_CAG - | [Phos]GATCCCTCGGAactgTTGTAGTATGCGGTCCTTGCGGCTGAGAGCACTTCAGA GGAaCCCA (SEQ ID NO: 143) |
| 701 NNN_ACT + | [Phos]TATGGGtTCCTCTGAAGTGCTCTCAGCCGCAAGGACCGCATACTACAAacttT CCGAGG (SEQ ID NO: 144) |
| 701_NNN_ACT - | [Phos]GATCCCTCGGAaagtTTGTAGTATGCGGTCCTTGCGGCTGAGAGCACTTCAGA GGAaCCCA (SEQ ID NO: 145) |
| 701_NNN_ACA + | [Phos]TATGGGtTCCTCTGAAGTGCTCTCAGCCGCAAGGACCGCATACTACAAacatT CCGAGG (SEQ ID NO: 146) |
| 701_NNN_ACA - | [Phos]GATCCCTCGGAatgtTTGTAGTATGCGGTCCTTGCGGCTGAGAGCACTTCAGA GGAaCCCA (SEQ ID NO: 147) |
| 701_NNN_AAA + | [Phos]TATGGGtTCCTCTGAAGTGCTCTCAGCCGCAAGGACCGCATACTACAAaaatT CCGAGG (SEQ ID NO: 148) |
| 701_NNN_AAA - | [Phos]GATCCCTCGGAatttTTGTAGTATGCGGTCCTTGCGGCTGAGAGCACTTCAGA GGAaCCCA (SEQ ID NO: 149) |
| 701_NNN_AAG + | [Phos]TATGGGtTCCTCTGAAGTGCTCTCAGCCGCAAGGACCGCATACTACAAaagtT CCGAGG (SEQ ID NO: 150) |
| 701_NNN_AAG - | [Phos]GATCCCTCGGAacttTTGTAGTATGCGGTCCTTGCGGCTGAGAGCACTTCAGA GGAaCCCA (SEQ ID NO: 151) |
| 701_NNN_AGT + | [Phos]TATGGGtTCCTCTGAAGTGCTCTCAGCCGCAAGGACCGCATACTACAAagttT CCGAGG (SEQ ID NO: 152) |
| 701_NNN_AGT - | [Phos]GATCCCTCGGAaactTTGTAGTATGCGGTCCTTGCGGCTGAGAGCACTTCAGA GGAaCCCA (SEQ ID NO: 153) |
| 701_NNN_GTT + | [Phos]TATGGGtTCCTCTGAAGTGCTCTCAGCCGCAAGGACCGCATACTACAAgtttT CCGAGG (SEQ ID NO: 154) |
| 701_NNN_GTT - | [Phos] GATCCCTCGGAaaacTTGTAGTATGCGGTCCTTGCGGCTGAGAGCACTTCAG AGGAaCCCA (SEQ ID NO: 155) |
| 701_NNN_GAC + | [Phos]TATGGGtTCCTCTGAAGTGCTCTCAGCCGCAAGGACCGCATACTACAAgactT CCGAGG (SEQ ID NO: 156) |
| 701_NNN_GAC - | [Phos]GATCCCTCGGAagtcTTGTAGTATGCGGTCCTTGCGGCTGAGAGCACTTCAGA GGAaCCCA (SEQ ID NO: 157) |
| 701_NNN_GAA + | [Phos]TATGGGtTCCTCTGAAGTGCTCTCAGCCGCAAGGACCGCATACTACAAgaatT CCGAGG (SEQ ID NO: 158) |
| 701_NNN_GAA - | [Phos]GATCCCTCGGAattcTTGTAGTATGCGGTCCTTGCGGCTGAGAGCACTTCAGA GGAaCCCA (SEQ ID NO: 159) |
| 601_GGG + | [Phos]TATGGGATCCTGTTCCACTAAGGACATTTGTACGTCAAATTCTTCACTgggAT CCGAGG (SEQ ID NO: 160) |
| 601_GGG - | [Phos]GATCCCTCGGATcccAGTGAAGAATTTGACGTACAAATGTCCTTAGTGGAACA GGATCCCA (SEQ ID NO: 161) |
| 601_AAA + | [phos]TATGGGATCCTGTTCCACTAAGGACATTTGTACGTCAAATTCTTCACTaaaAT CCGAGG (SEQ ID NO: 162) |
| 601_AAA - | [phos]GATCCCTCGGATtttAGTGAAGAATTTGACGTACAAATGTCCTTAGTGGAACA GGATCCCA (SEQ ID NO: 163) |

TABLE 4-continued

| Oligos | |
|---|---|
| 601_CCC + | [phos]TATGGGATCCTGTTCCACTAAGGACATTTGTACGTCAAATTCTTCACTcccAT<br>CCGAGG (SEQ ID NO: 164) |
| 601_CCC - | [phos]GATCCCTCGGATgggAGTGAAGAATTTGACGTACAAATGTCCTTAGTGGAACA<br>GGATCCCA (SEQ ID NO: 165) |
| 601_TTT + | [phos]TATGGGATCCTGTTCCACTAAGGACATTTGTACGTCAAATTCTTCACTtttAT<br>CCGAGG (SEQ ID NO: 166) |
| 601_TTT - | [phos]GATCCCTCGGATaaaAGTGAAGAATTTGACGTACAAATGTCCTTAGTGGAACA<br>GGATCCCA (SEQ ID NO: 167) |
| Pcsg_F | AACGAAGCGGCCGCTATCGGCAAAAGG (SEQ ID NO: 168) |
| Term_R | AACGAAGATATCGAGGAAGCGGAGGTTCCAAG (SEQ ID NO: 169) |
| Pcsg_R | GGATCCGATTCGTTCATATGACAACACCTCCTTGGGTTG (SEQ ID NO: 170) |
| Term_F | GTTGTCATATGAACGAATCGGATCCCCCCTCTCTTCTCCTCTTTTG<br>(SEQ ID NO: 171) |

Oligos for in vitro Cmr2/Cmr4 Mutations

| Oligos | Sequence (5'-3') |
|---|---|
| Cmr2_D673A, D674A_qc_F | GCTAATATACGCTGGAGGGGCAGCAGTCCTAGCAATTTTGCCAGTC<br>(SEQ ID NO: 172) |
| Cmr2_D673A, D674A_qc_R | GACTGGCAAAATTGCTAGGACTGCTGCCCCTCCAGCGTATATTAGC<br>(SEQ ID NO: 173) |
| Cmr2_H13A, D14A_qc_F | CATCAAAGAGAAACTTTTTGTATACCTTGCAGCACCACCAGACAAGGCTCTAA<br>(SEQ ID NO: 174) |
| Cmr2 H13A, D14A qc R | TTAGAGCCTTGTCTGGTGGTGCTGCAAGGTATACAAAAAGTTTCTCTTTGATG<br>(SEQ ID NO: 175) |

Figure 12:
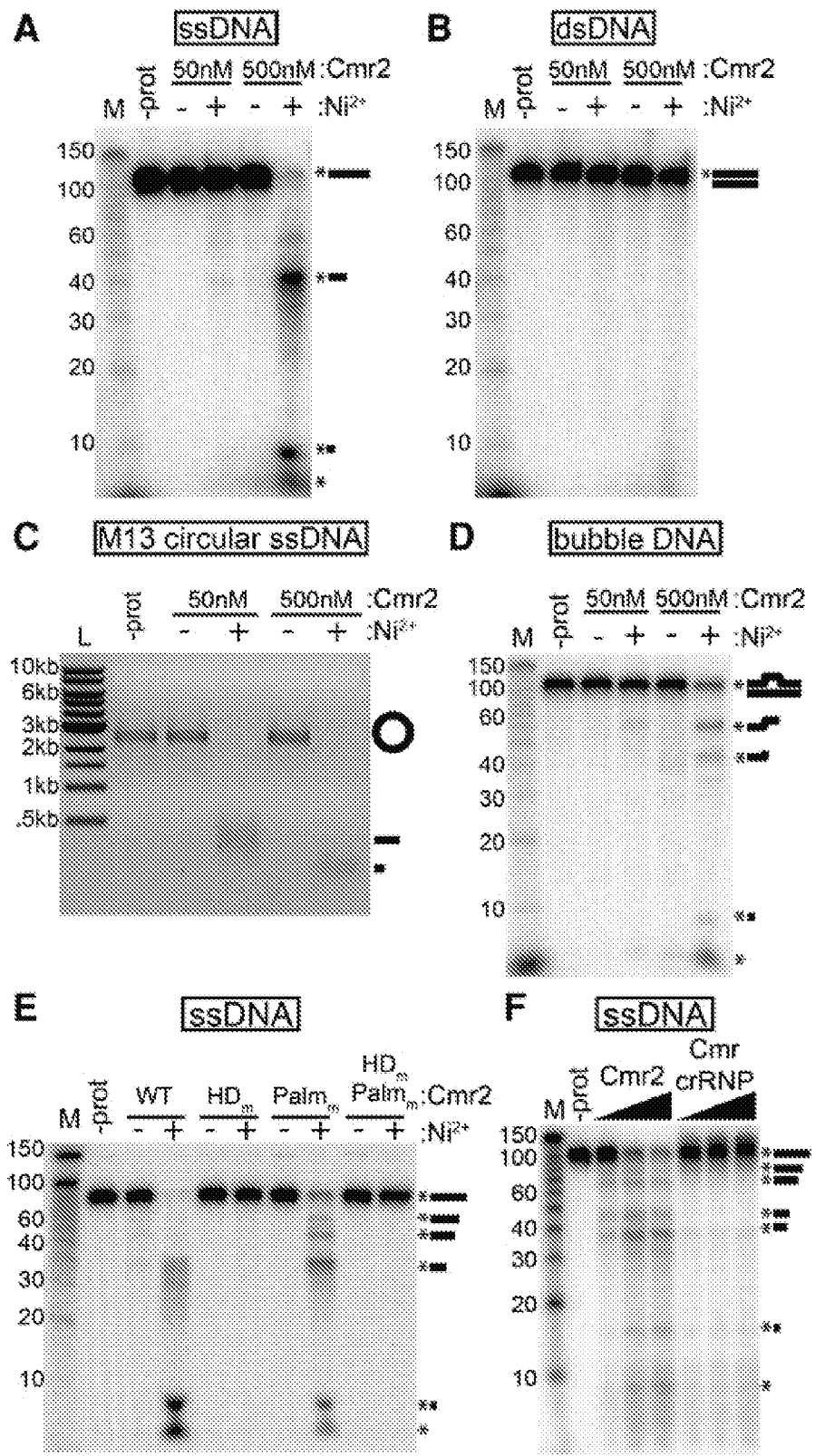
FIG. 12 shows Cmr2 is a ssDNA endonuclease.
Figure 15:
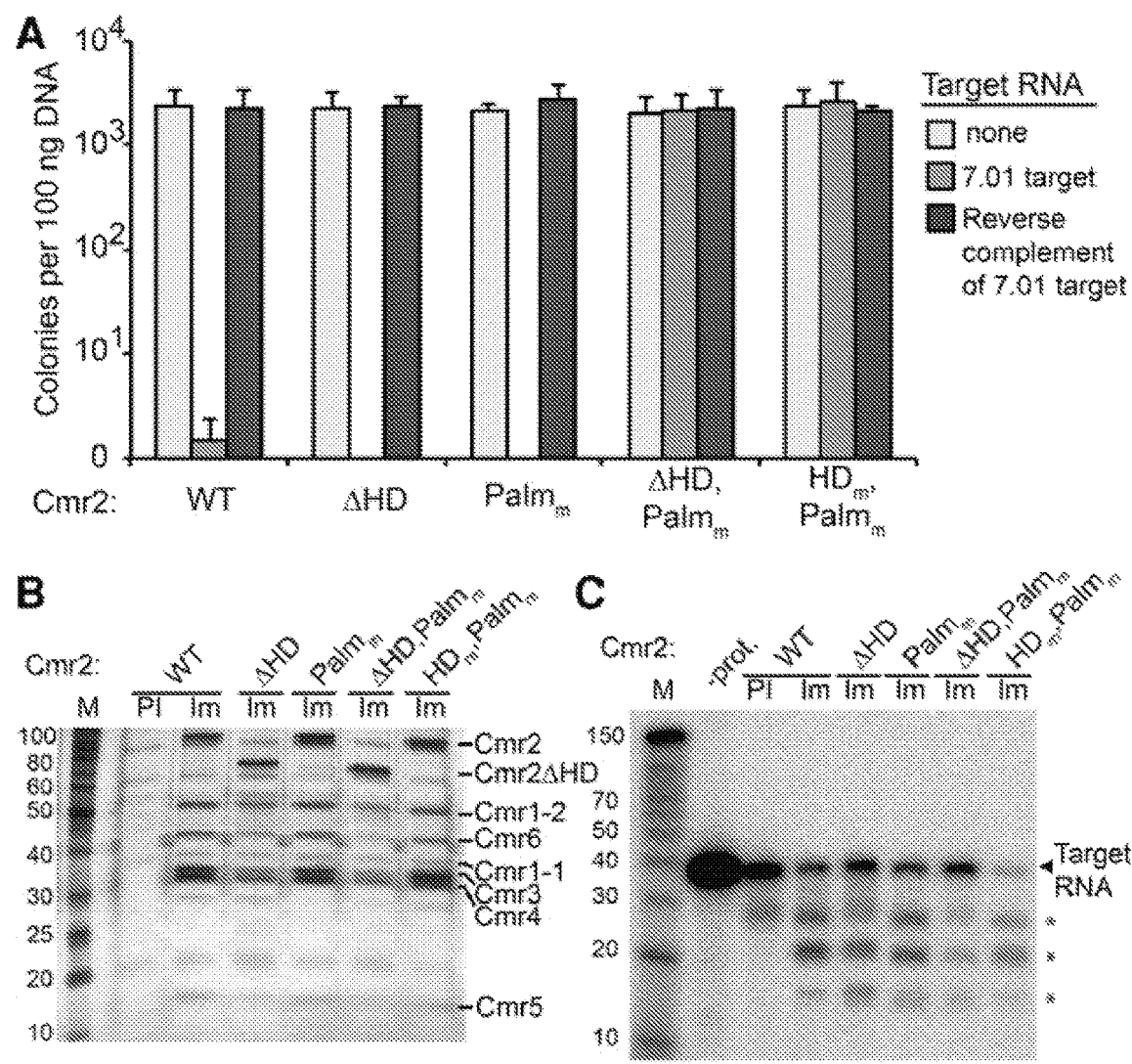
FIG. 15 shows mutation of both the HD and Palm domains of Cmr2 is required to abolish Type III-B plasmid silencing in vivo.
Figure 16:
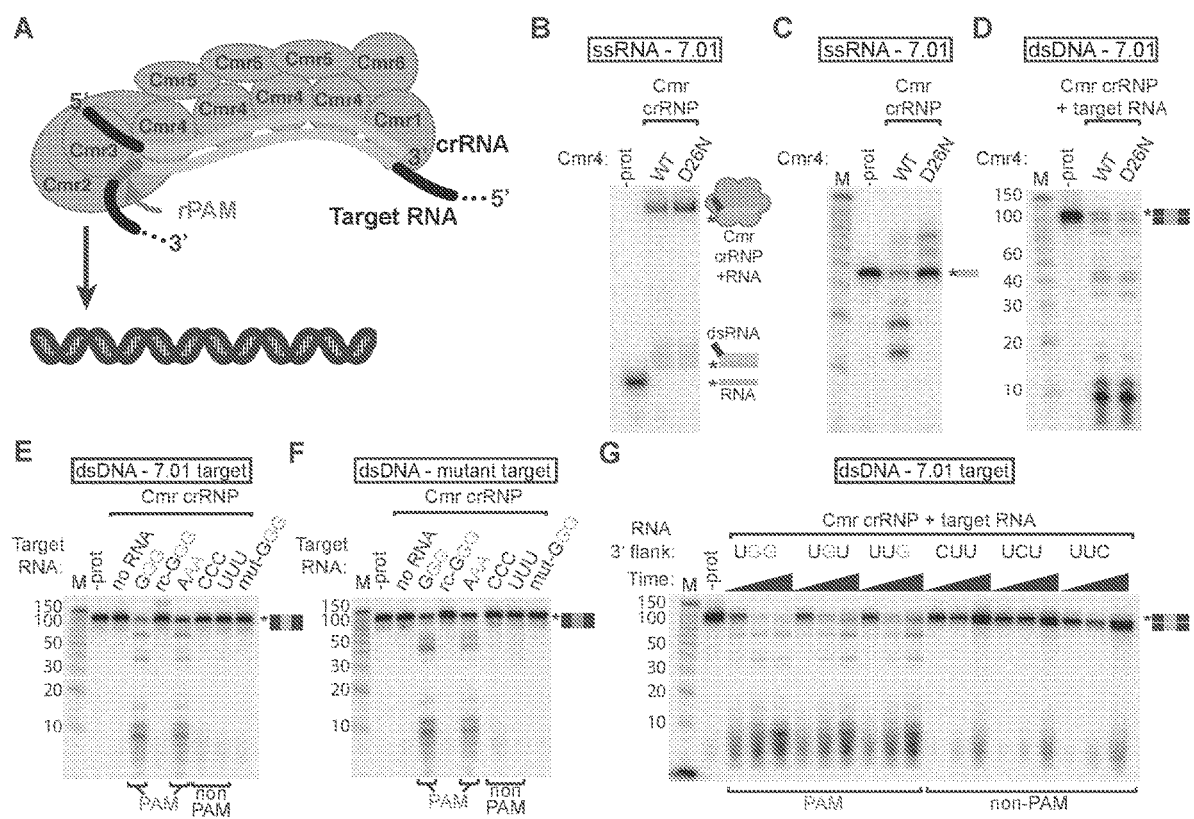
FIG. 16 shows target RNAs containing a PAM sequence trigger Cmr dsDNA cleavage activity.

Assay Oligos for FIGS. 12, 15 & 16

| Oligos | Sequence (5'-3') |
|---|---|
| 7.01_DNA_target [se]<br>(2397) | GGCGACCGTATGCGCGTAGTGCCGTGCAGTCGCCGTACCCCTGAAGTGCTCTCAGCCGC<br>AAGGACCGCATACTACAAGGGAGTTACTCGCGTGCACTCCGCCTTGGTGGAGCACTGA<br>(SEQ ID NO: 176) |
| 7.01 DNA target [as]<br>(2398) | TCAGTGCTCCACCAAGGCGGAGTGCACGCGAGTAACTCCCTTGTAGTATGCGGTCCTTG<br>CGGCTGAGAGCACTTCAGGGGTACGGCGACTGCACGGCACTACGCGCATACGGTCGCC<br>(SEQ ID NO: 177) |
| 7.01_DNA_bubble [as]<br>(3124) | TCAGTGCTCCACCAAGGCGGAGTGCACGCGAGTAACTCCCAACATCATACGCCAGGAAC<br>GCCGACTCTCGTGAAGTCGGGTACGGCGACTGCACGGCACTACGCGCATACGGTCGCC<br>(SEQ ID NO: 178) |
| non-target_DNA [se] (2765) | GGCGACCGTATGCGCGTAGTGCCGTGCAGTCGCCGTACCCAGTCCTGTAGAGACTAATA<br>CCTTCAATACGCAGCACCGGGAGTTACTCGCGTGCACTCCGCCTTGGTGGAGCACTGA<br>(SEQ ID NO: 179) |
| non-target_DNA [as] (2766) | TCAGTGCTCCACCAAGGCGGAGTGCACGCGAGTAACTCCCGGTGCTGCGTATTGAAGGT<br>ATTAGTCTCTACAGGACTGGGTACGGCGACTGCACGGCACTACGCGCATACGGTCGCC<br>(SEQ ID NO: 180) |
| 45-mer 7.01 crRNA (RNA 1) | AUUGAAAGUUGUAGUAUGCGGUCCUUGCGGCUGAGAGCACUUCAG<br>(SEQ ID NO: 181) |
| 37-mer 7.01 target (RNA 2) | CUGAAGUGCUCUCAGCCGCAAGGACCGCAUACUACAA<br>(SEQ ID NO: 182) |

Figure 13:
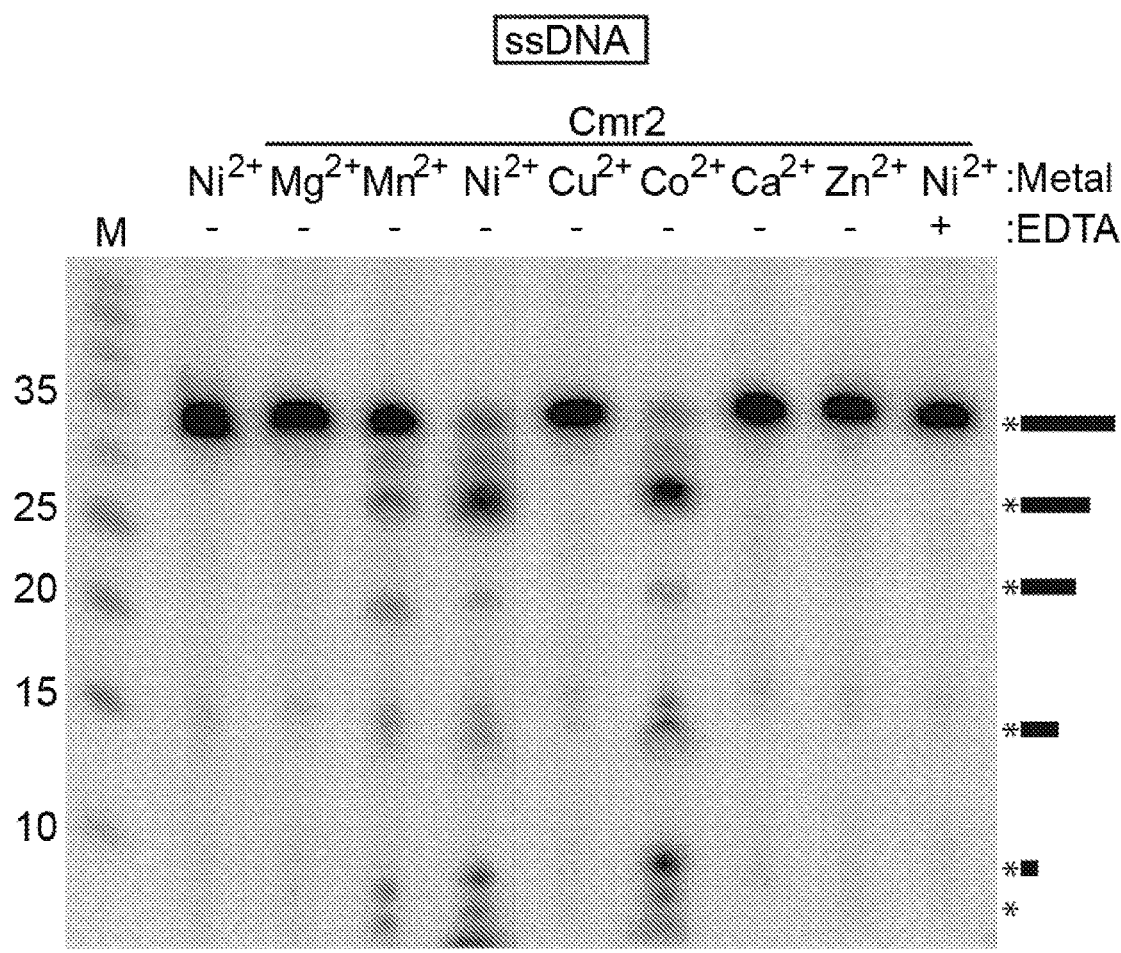
FIG. 13 shows Cmr2 ssDNA cleavage is divalent cation dependent. Wild-type Cmr2 protein was incubated with a 5' radiolabeled single stranded DNA and several different metal chlorides (indicated herein) in the absence (−) or presence of EDTA (+). The resulting products were separated by denaturing PAGE, and visualized by phosphorimaging. A DNA size ladder (M) is used in the left-most lane for sized identification, and graphical representation of cleavage products is indicated on the right

FIG. 13 Assay Oligos

| Oligos | Sequence (5'-3') |
|---|---|
| DNA 1 | TCGATGTAACGTATGCAAATGACAATTATTACTA (SEQ ID NO: 183) |

IVT Template PCR Primers

| Oligos | Sequence (5'-3') |
|---|---|
| 117-mer F T7 (3110) | aagcaagaattcTAATACGACTCACTATAGGGAGAGGCGACCGTATGCG<br>(SEQ ID NO: 184) |
| 117-mer R (3112) | TCAGTGCTCCACCAAG (SEQ ID NO: 185) |
| 117-mer F (3114) | GGCGACCGTATGCG (SEQ ID NO: 186) |
| 117-mer R T7 (3115) | aagcaaggatccTAATACGACTCACTATAGGGAGATCAGTGCTCCACCAAG<br>(SEQ ID NO: 187) |
| pJE47_IVT_T7_F (2798) | TAATACGACTCACTATAGGGAGACAACACTTAGTAGGGGCTA<br>(SEQ ID NO: 188) |
| pJE47_IVT_R (2801) | GCTTCCTTAGCTGTTTCTCCA (SEQ ID NO: 189) |

General DNA Manipulation and Target Plasmid Construction

Plasmids were isolated from Top10 with QIAprep Spin Miniprep (Qiagen) for routine analysis and Zyppy Plasmid Maxiprep kit (Zymo Research) for plasmid construction and assays. Plasmids were isopropanol-precipitated following initial isolation. Phusion polymerase (New England Biolabs) was used for all PCR cloning. *P. furiosus* gDNA was isolated from 1-mL overnight cultures with Zymo Quick gDNA kit (Zymo Research).

The expression cassette in pJE47 was constructed by amplifying the Pcsg promoter and ChiA terminator of pLC64-ChiA. Products were spliced by SOE-PCR and cloned into NotI/EcoRV sites of pJFW18 (Farkas et al. 2011).

Plasmids pJE65-85, pJE275-276, pJE294, and pJE299-306 were generated by ligation of annealed 5' phosphorylated oligos with NdeI/BamHI-linearized pJE47. Plasmids pJE186-249 were constructed by a combination of two methods. The majority of the plasmid inserts was constructed by extension of 701_NNN_F, containing degenerate PAM nucleotides, with primer 701_NNN_R. The remainder was generated with annealed oligos. Products were cloned into NdeI/BamHI sites of pJE47. Plasmids pJE271/272 were constructed by NotI/NdeI digestion of pJE65/66 (respectively) to remove the Pcsg promoter and treated with Quick Blunting kit (New England Biolabs). Oligo sequences are listed in Table 4, with "+" oligos annealed with cognate "−" oligos to generate inserts.

*P. furiosus* Strain Construction

Figure 18:
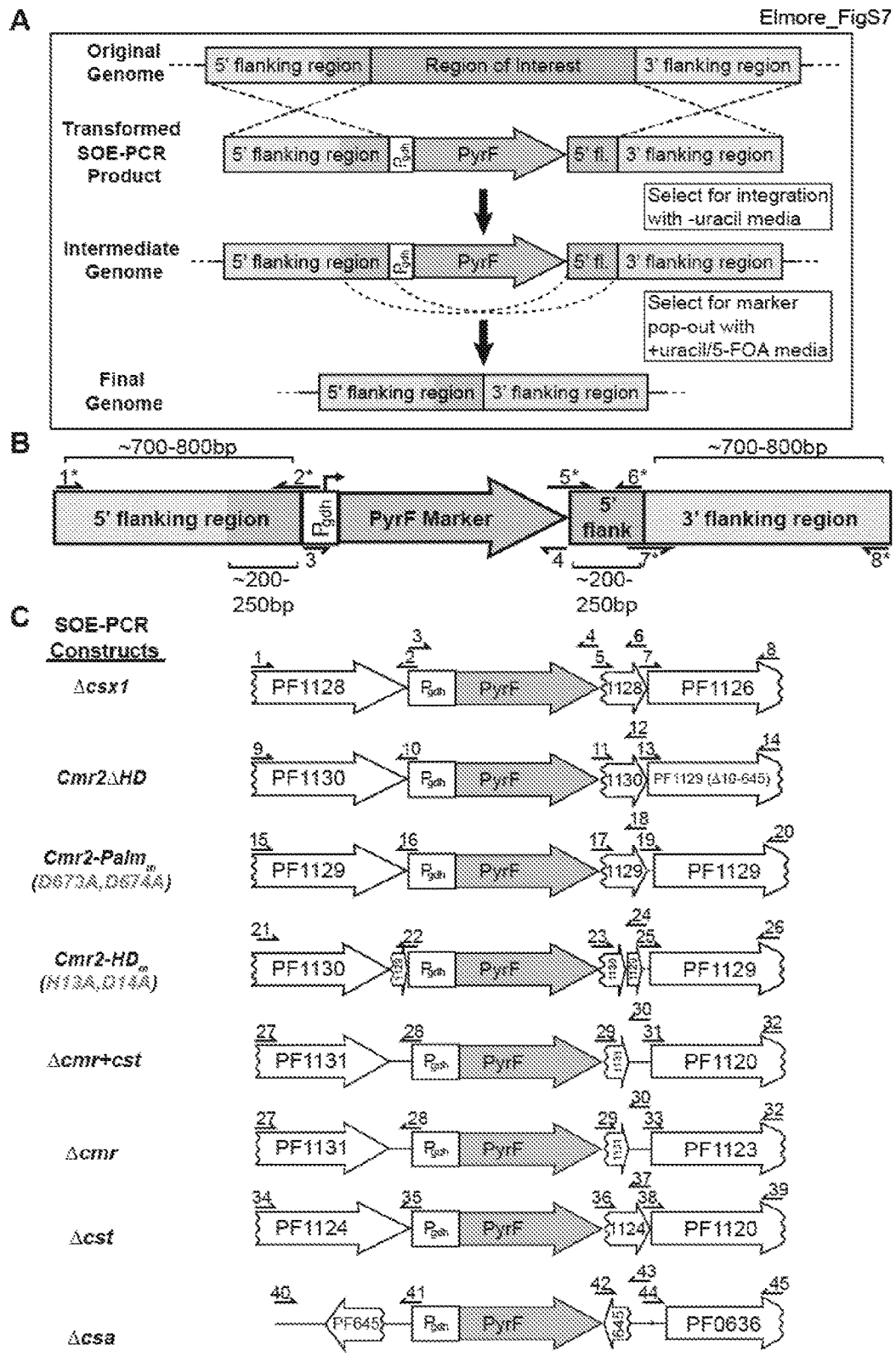
FIG. 18 shows construction of Pfu strains.

*P. furiosus* strains were constructed using a variant of the previously described pop-in/pop-out marker replacement technique (FIG. 18; Lipscomb et al. 2011; Farkas et al. 2012).

Plasmid Transformation Assay in *P. furiosus*

Incubations were performed anaerobically at 90° C. with defined *P. furiosus* medium. Liquid cultures were grown to mid to late log phase, and 33.3 µL of culture was mixed with 66.7 ng of plasmid DNA (in 1.66 µL) and incubated briefly (5-60 min) at room temperature during plating. The mixtures were spread on solid defined medium and incubated for ~64 h. Following incubation, colonies per plate were enumerated. All assays were carried out with a minimum of three replicates.

*P. furiosus* Cell Extract Preparation and Coimmunoprecipitation (co-IP) Reactions Cultures were grown to late log phase, harvested by centrifugation, and weighed. Lysis buffer (50 mM Tris-Cl at pH 8, 30 U/mL SUPERase In [Life Technologies], 1× Complete-mini EDTA-free protease inhibitor [Roche]) was added (3 mL per 1 g of cells). Cells were lysed by sonication and centrifuged at 20,000 g for 30 min at 4° C. The soluble fraction was collected as S20 cell extract, with protein quantified by Qubit assay (Life Technologies). IgY antibodies previously raised against recombinant Cmr2 (Hale et al. 2012) were used for co-IPs. Co-IPs were carried out as previously described (Hale et al. 2012) with the following modifications: Each immunoprecipitation (30 µL of resin) used S20 cell extract containing 2 mg of protein. UltraLink hydrazide (Pierce) resin was used for silver stain analysis of immunoprecipitations, and anti-IgY agarose resin (Gallus Immunotech) was used for RNA cleavage assays.

Co-IP RNA Cleavage Activity Assays

Co-IP RNA cleavage assays were carried out as described (Hale et al. 2012).

Co-IP Silver Staining

Co-IP samples (30 µL resin) were resuspended in 60 µL of non-reducing Laemmli buffer and heated for 5 min at 60° C. to elute samples from UltraLink beads. An equal fraction of each elution (one-half of a co-IP) was separated on 11% SDS-polyacrylamide gels, and subjected to silver staining.

Protein Expression and Purification

Cmr2 mutants $HD_m$ (H13A, D14A) and $Palm_m$ (D673A, D674A) were generated by PCR mutagenesis (primers in Table 4). Expression and purification of both recombinant wild type and mutants, including Cmr4-D26N (Ramia et al. 2014a), was performed as described (Hale et al. 2009, 2014) with the following modifications: Cells were lysed, and protein was purified in buffer containing 40 mM Tris-Cl (pH 7.5), 500 mM NaCl, and 0.2 mM PMSF. Purified proteins were dialyzed into 40 mM Tris-Cl (pH 7.5) and 500 mM NaCl and quantified by Qubit assay (Life Technologies).

Preparation of DNA and RNA Substrates

DNA oligos were purchased from IDT (DNA 1) (FIG. 13) or Operon (all others). RNAs for in vitro Cmr crRNP formation (45-mer 7.01 crRNA) or cleavage assay substrate (37-mer 7.01 target RNA) were purchased from IDT. DNA and RNA substrates used in cleavage assays were 5' end labeled with 32P using T4 polynucleotide kinase (New England Biolabs). Annealing 5' radiolabeled DNA oligos with 2× molar excess of gel-purified, unlabeled oligos generated radiolabeled dsDNA substrates. To form a bubble substrate, oligos 2397 and 3124 (Table 4) were annealed for Cmr2 assays (FIG. 12). Annealing oligos 2397 and 2398 (7.01 target) or 2765 and 2766 (mutant nontarget) generated full-length dsDNA substrates. All substrates were gel-purified prior to use on nondenaturing (dsDNA) or denaturing (ssDNA/RNA) PAGE.

Cmr Complex Assembly and in vitro Cmr2/Cmr Complex Assays

Cmr complex (Cmr1-6+crRNA) assembly was performed as described (Hale et al. 2009, 2012, 2014) with modifications. The reconstitution buffer used was 20 mM Tris-Cl (pH 7.5 at 25° C.), 250 mM NaCl, 10% glycerol, 2.5 mM MgCl2, and 200 µM NiCl2; the protein concentrations were 500 nM with the exception of 50 nM Cmr2, and the crRNA concentration was 50 nM.

Figure 14:
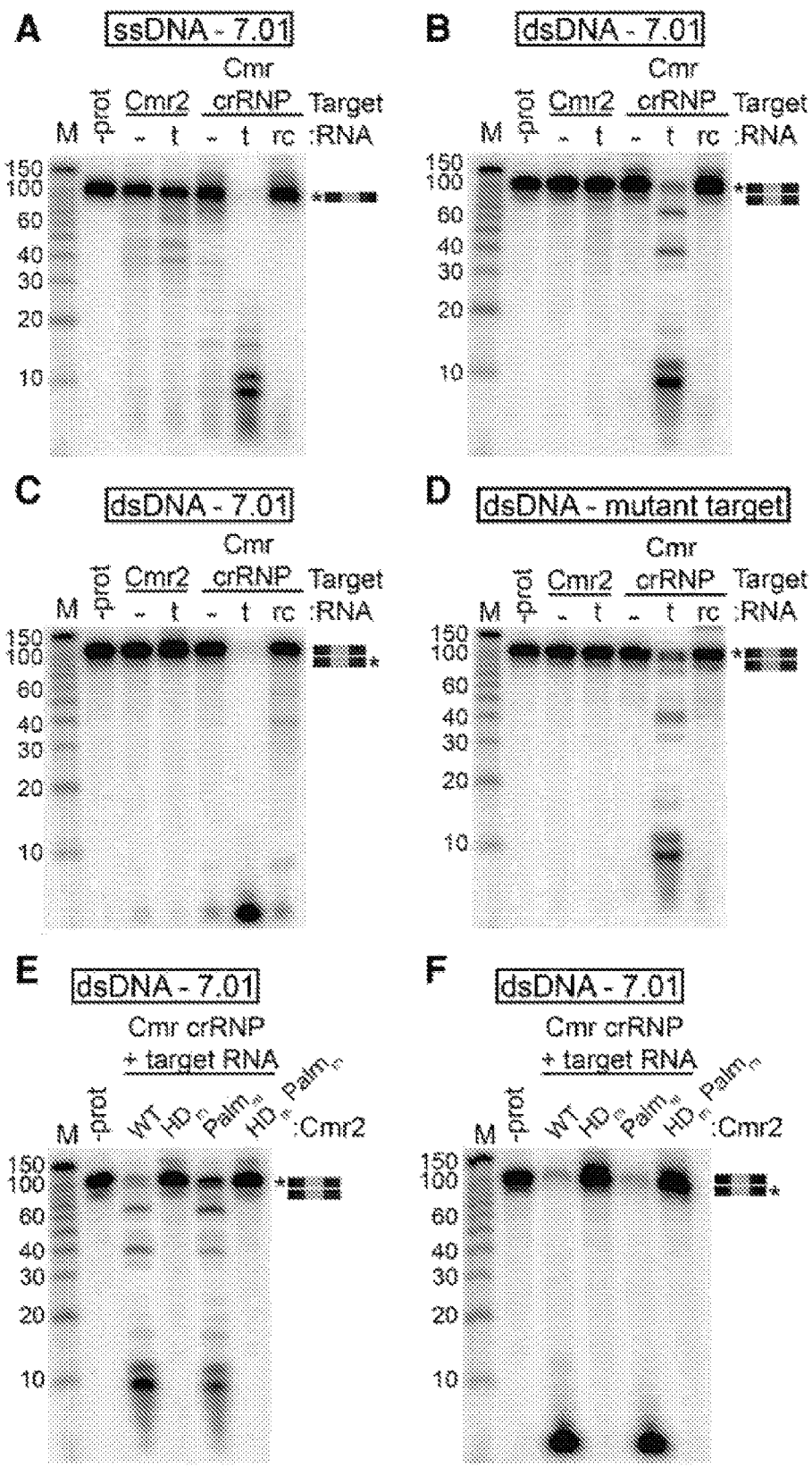
FIG. 14 shows the Cmr complex cleaves dsDNA in the presence of target RNA.

Assays were performed with either Cmr2 or assembled Cmr complex. All samples were preincubated in reconstitution buffer (-crRNA for Cmr2 alone) prior to the addition of substrates. Cleavage reactions were initiated by addition of either 5000 cpm (~0.05 pmol) 5' radiolabeled DNA/RNA or 0.21 pmol of M13 circular ssDNA (New England Biolabs). Unless otherwise indicated, substrates were incubated with 500 nM (FIG. 3) or 50 nM (FIG. 4) Cmr2 or ~50 nM Cmr complex (FIGS. 14, 16). Unless indicated, assays were incubated for 1 h at 70° C. Following incubation (cleavage assays), reactions were treated with proteinase K (New England Biolabs) for 15 min at 37° C., denatured in gel loading buffer II (ThermoFisher) at 95° C., and separated on either 15% TBE-UREA PAGE or 0.7% TAE-agarose. For target binding, following 70° C. incubation, half of the reaction was separated on 6% TBE-PAGE with 4% glycerol. Agarose gels were visualized by SYBR Gold (Thermofisher) stain. PAGE gels were dried and imaged by phosphorimaging.

The substrates (asterisks indicate labeled oligos) used for FIGS. 12, 14, 16 were as follows: oligo *2397 in FIGS. 12, A, E, and F; annealed *2397/2398 in FIG. 12B; M13 in FIG. 12C; annealed *2397/3124 in FIG. 12D; *2397 in FIG. 14A; *2397/2398 in FIGS. 14, B and F; 2397/*2398 in FIGS. 14, C and G; *2765/2766 in FIG. 14D; RNA oligo *2 in FIGS. 16, B and C; *2397/2398 in FIGS. 16, D, E, and G; and *2765/2766 in FIG. 16F.

Assay-specific details are as follows: FIG. 12F assays used 50, 100, or 200 nM Cmr2 or assembled Cmr2 complex as indicated. For RNA target-dependent DNA cleavage assays (FIGS. 14, 16), following preincubation, 22.5 nM of target RNA was added immediately before DNA substrates.

In vitro Transcription (IVT) of Target RNAs

Target RNAs were generated using MEGAshortscript T7 kit (ThermoFisher) with PCR templates. Products were gel-purified and quantified by Qubit analysis (ThermoFisher). IVT templates for FIGS. 14 and 16C target RNAs were made by PCR of the annealed oligos 2397/2398 with primers 3110/3112 (t) or 3115/3114 (rc). For FIG. 16E-G IVT templates, target plasmids were amplified with primers 2798/2801. Plasmids pJE65 (GGG), pJE66 (rc-GGG), pJE67 (AAA), pJE69 (CCC), pJE71 (UUU), pJE294 (mut-GGG), pJE201 (UGG), pJE189 (UUG), pJE198 (UGU), pJE202 (CUU), pJE190 (UCU), and pJE187 (UUC) were used as PCR templates.

P. furiosus (Pfu) Strain Construction

Pfu strains were constructed using a variant of the previously described pop-in/pop-out marker replacement technique (FIG. 18)(Lipscomb et al. 2011; Farkas et al. 2012). The transformed PCR products were generated by splicing 4 PCR products together with Splicing by Overlap Extension PCR (SOE-PCR). A schema of the SOE-PCR products guiding each mutation is shown in FIG. 18C. PCR primers used to generate SOE-PCR products are listed in Table 4. Strains were constructed as follows. TPF06 (ΔCmr) was constructed by deletion of PF1130-PF1124 from wild-type CRISPR-Cas strain JFW02. TPF15 (Cmr; ΔcsaΔcst) and TPF20 (null; ΔcsaΔcmr+cst) were each constructed from JFW02 by stepwise deletion of PF0637-0644 (ΔCsa) and either PF1121-PF1123 (Δcst) for TPF15 or PF1121-1130 (ΔCmr+cst) for TPF20. TPF24 (ΔCsx1) was constructed by deletion of PF1127 from TPF15. Cmr2 mutant strains TPF25 (Cmr2ΔHD) and TPF27 (Cmr2-Palmm) were constructed via mutation of Cmr2 in TPF15. Double Cmr2 mutant strains TPF35 (Cmr2ΔHD) and TPF37 (Cmr2-HDm) were constructed via further mutation of Cmr2 in TPF27. PCR constructs used in each case are denoted in parentheses.

Protein Expression and Purification

Csx1 antigen (PF1127) was cloned from Pf gDNA into a modified pET24D vector with an N-terminal 6× His-tag. Protein expression and purification was performed as previously described for Cmr proteins (Hale et al. 2009; Hale et al. 2014).

Western Blot Analysis

As previously described, antibodies against recombinant Pf Csx1 were generated (Carte et al. 2010). Western blot analysis was carried out as previously described (Hale et al. 2012) with the following modifications: S20 cell extracts containing 50 μg of protein were boiled in Laemmli buffer for 5 minutes, centrifuged briefly, and separated on 12.5% SDS-PAGE. Pf Csx1 antibody was used for primary antibody incubation at 0.5 μg/mL in TBST.

Cmr2 DNA Cleavage Assay

Metal utilization by Cmr2 for DNA cleavage was assayed using conditions described in the main text with the following modifications. Other metals are substituted for NiC12 at 2 mM where noted. 5'-radiolabeled DNA1 (Table 4) was used as a substrate for ssDNA cleavage.

Results

Figure 5:
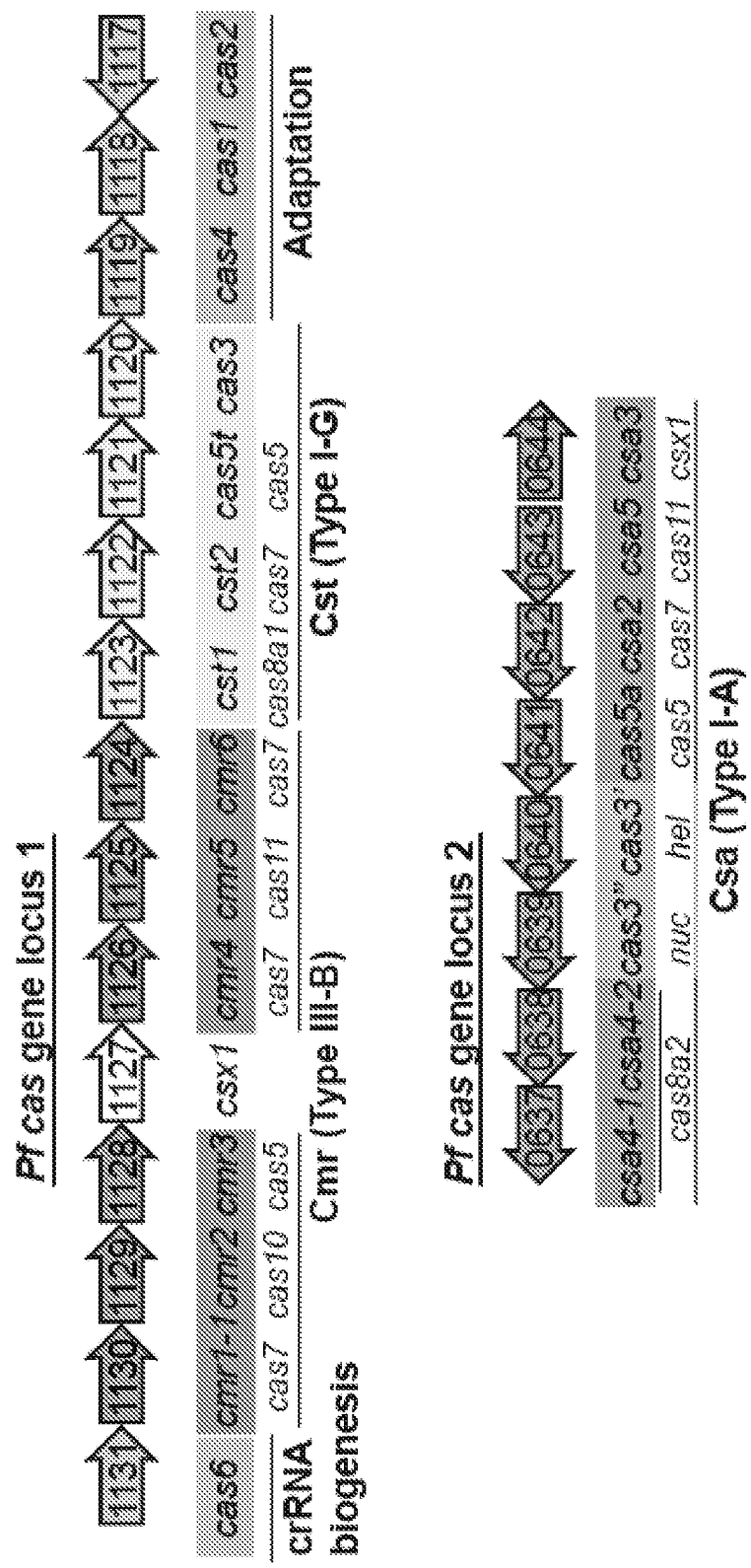
FIG. 5 depicts Pyrococcus furiosus cas gene locus organization. The genome organization and annotations of the predicted cas genes were adapted from the NCBI database. Type III-B Cmr, Type I-G Cst, Type I-A Csa, and adaptation/biogenesis cas genes are indicated with cas gene superfamily designations indicated below relevant csa, cst, and cmr genes. The csx1 gene is often found in association with Type III-B systems and is encoded in between the cmr genes in Pf.
Figure 6:
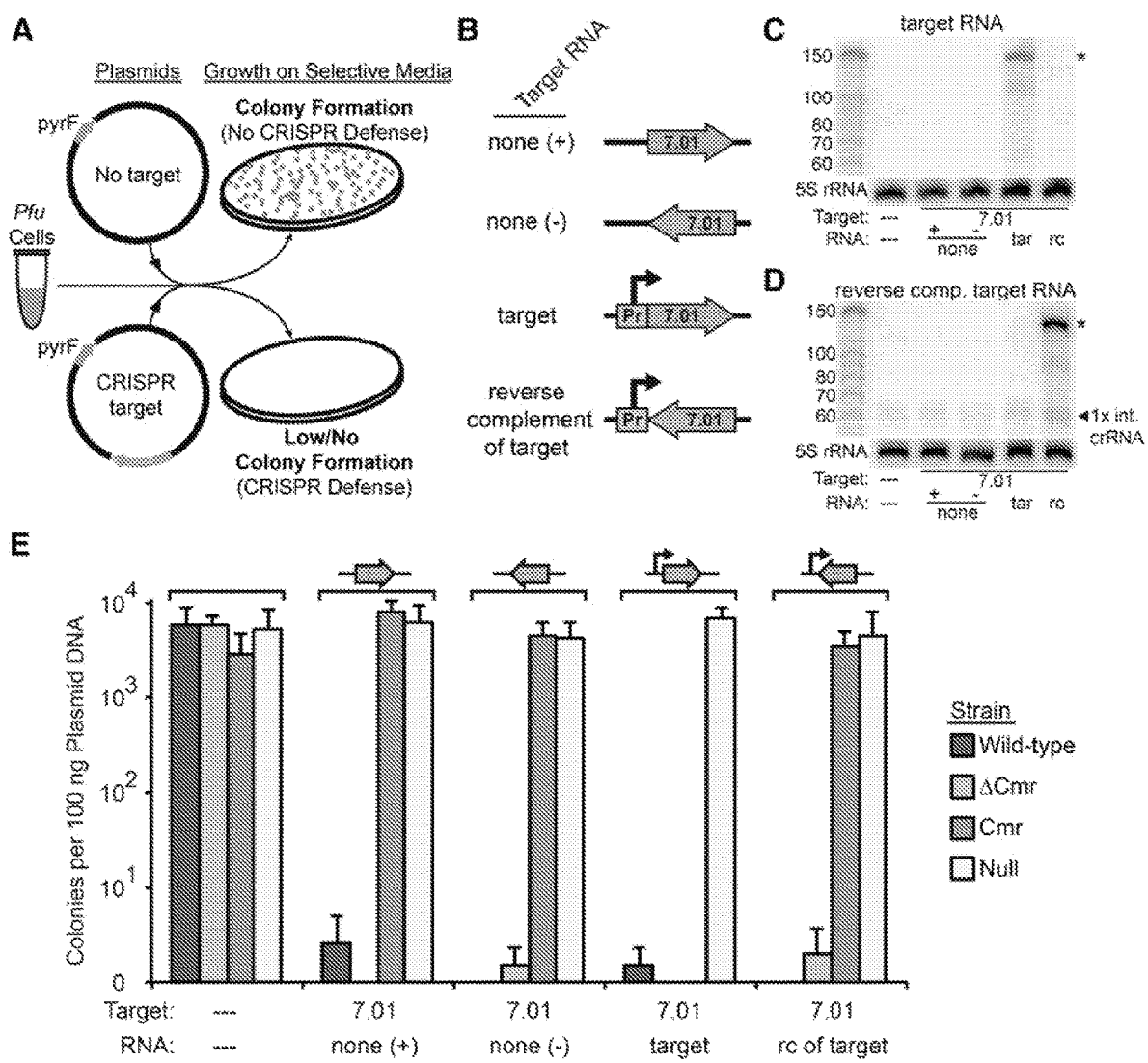
FIG. 6 shows the P. furiosus (Pfu) Cmr system silences plasmid DNA in a transcription-dependent manner.

The P. furiosus Type III-B Cmr System Silences Plasmid DNA in a Transcription-Dependent Manner The hyperthermophilic archaeon P. furiosus has three CRISPR-Cas systems: a Type III-B Cmr system as well as Type I-A Csa and Type I-G Cst systems (FIG. 5). The effector complexes in P. furiosus use crRNAs produced from seven shared CRISPR loci (Majumdar et al. 2015). Using deletion strains containing a single CRISPR-Cas system, it was found that the P. furiosus Type I-A Csa and Type I-G Cst systems silence plasmid DNA invaders in a PAM-dependent manner (Elmore et al. 2015). Here the plasmid targeting capability of the P. furiosus Type III-B Cmr system is examined. We generated and infected strains containing various combinations of CRISPR-Cas systems with plasmids containing either no target or a target sequence complementary to endogenous P. furiosus crRNA 7.01 (FIG. 1A). The 7.01 target sequence was included in both orientations relative to the plasmid backbone with or without a constitutive promoter in order to assess the dependence of any observed silencing on transcription and crRNA complementarity (FIG. 6B). Northern analysis confirmed expression of the "target RNA" (complementary to crRNA 7.01) (FIG. 6C, indicated by an asterisk) or the reverse complement of the target RNA (same sequence as crRNA 7.01) (FIG. 6D, indicated by an asterisk) from the respective constructs. The plasmid confers uracil prototrophy on P. furiosus, so successful infection of the plasmid would be observed as colony formation on selective media, and CRISPR-Cas defense would be observed as a reduction in colony formation (FIG. 6A).

In addition to the wild-type P. furiosus strain with three CRISPR-Cas systems (FIG. 5), strains containing only the Cmr system (Cmr), lacking the Cmr system (ΔCmr), and lacking all CRISPR-Cas modules (null) (FIG. 6E) were tested. Transformation with the plasmid lacking the target sequence resulted in the formation of $5.81 \times 10^3$ to $2.86 \times 10^3$ uracil prototroph colonies per 100 ng of plasmid DNA (FIG. 6E, wild-type and Cmr strains, respectively). The Csa and Cst CRISPR-Cas systems in P. furiosus provide orientation-independent and transcription-independent defense against plasmids with crRNA target sequences (Elmore et al. 2015), and thus, as expected, the presence of a target sequence on the plasmid reduced colony formation to <1% of the negative control plasmid in both the wild-type strain and the ΔCmr strain (fewer than two uracil prototroph colonies per 100 ng of plasmid DNA) (FIG. 6E, wild-type [dark gray bars] and ΔCmr [light-gray bars]). In the absence of CRISPR-Cas defense, plasmids containing the target sequence are not silenced and produce colony numbers indistinguishable from the negative control plasmid (FIG. 6E, null, white bars).

Notably, the Cmr strain does not silence plasmids in which the target sequence is not transcribed (RNA: none [+] or none [−]) or in which the transcribed RNA is not complementary to the crRNA (reverse complement of target); however, the Cmr strain effectively silences plasmids that transcribe a target RNA recognized by the crRNA (target RNA) (FIG. 6E, Cmr). The results indicate that the P. furiosus Type III-B Cmr system performs transcription-dependent plasmid silencing.

The Type III-B Cmr System in P. furiosus Recognizes a PAM in the Invader (Rather than Repeat Tag Complementarity in the Host) to Distinguish Invader from Host Evidence indicates that the Type III-A Csm system does not target DNA (such as the host's own CRISPR locus) that has complementarity to the 5' tag sequence of the crRNA adjacent to the crRNA target site (see FIG. 7A, gray dashed line; Marraffini and Sontheimer 2010; Samai et al. 2015), while Type I systems specifically target DNA (such as the invader DNA) that has a PAM sequence adjacent to the crRNA target site (see FIG. 8A; Almendros et al. 2012; Fischer et al. 2012; Sinkunas et al. 2013; Westra et al. 2013; Plagens et al. 2014). In order to determine the mechanism of host protection by the P. furiosus Cmr system, cells with plasmids possessing various sequences 3' of the crRNA target site (where both tag complementarity and PAMs occur) were challenged.

Figure 7:
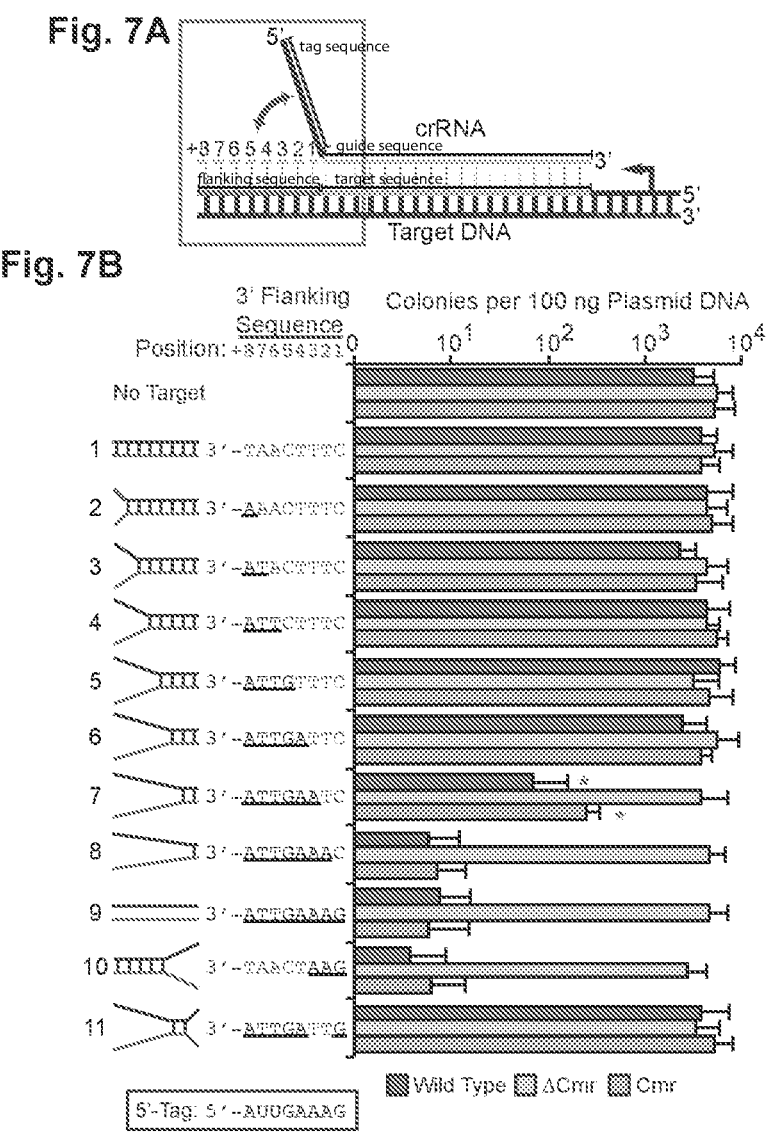
FIG. 7 shows 3' flanking positions +1/2/3 are relevant for self versus non-self discrimination by Cmr.

In FIG. 7, silencing of several transcribed 7.01 target plasmids containing varying degrees of complementarity to the P. furiosus crRNA 5' tag sequence were tested. Note that the Csa and Cst systems present in the ΔCmr strain (FIG. 7, light-gray bars) require a PAM sequence that is not present in any of the tested plasmids, so the plasmids were not silenced in the control strain containing these two systems (FIG. 7B, ΔCmr, light-gray bars). In the Cmr strain (FIG. 7B, gray bars), full complementarity of the plasmid sequence to the crRNA tag sequence conferred protection on the plasmid, resulting in colony formation similar to the control plasmid lacking crRNA target sequence (FIG. 7B, variant 1 and no target). Moreover, in the absence of 5' crRNA tag complementarity, the plasmid is not protected (FIG. 7B, variant 9). However, analysis of further variants suggests a specific role for the target site-proximal 3 nucleotides of the flanking DNA. Three nucleotides of complementarity proximal to the crRNA target site protected the plasmid (FIG. 7B, variant 6); however, modification of these three proximal nucleotides, even in the context of five remaining nucleotides of complementarity, resulted in loss of protection (FIG. 7B, variant 10, see also variants 7 and 8), suggesting that the identity of these nucleotides may be more important than tag complementarity. Note that, as expected, plasmids silenced by the Cmr system in the Cmr strain were also silenced in the wild-type strain (FIG. 7B, dark-gray bars).

Figure 8:
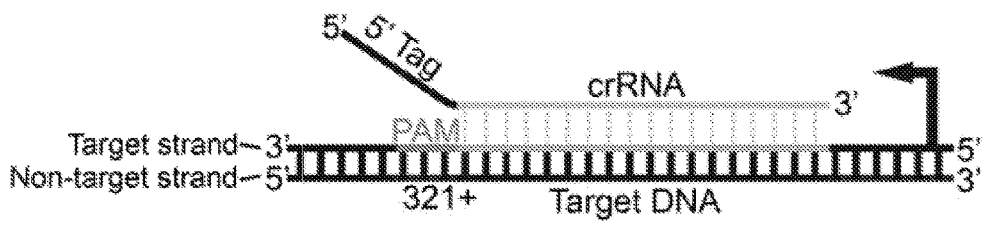
FIG. 8 shows the Cmr system in P. furiosus (Pfu) uses a PAM to distinguish invader from host.
Figure 9:
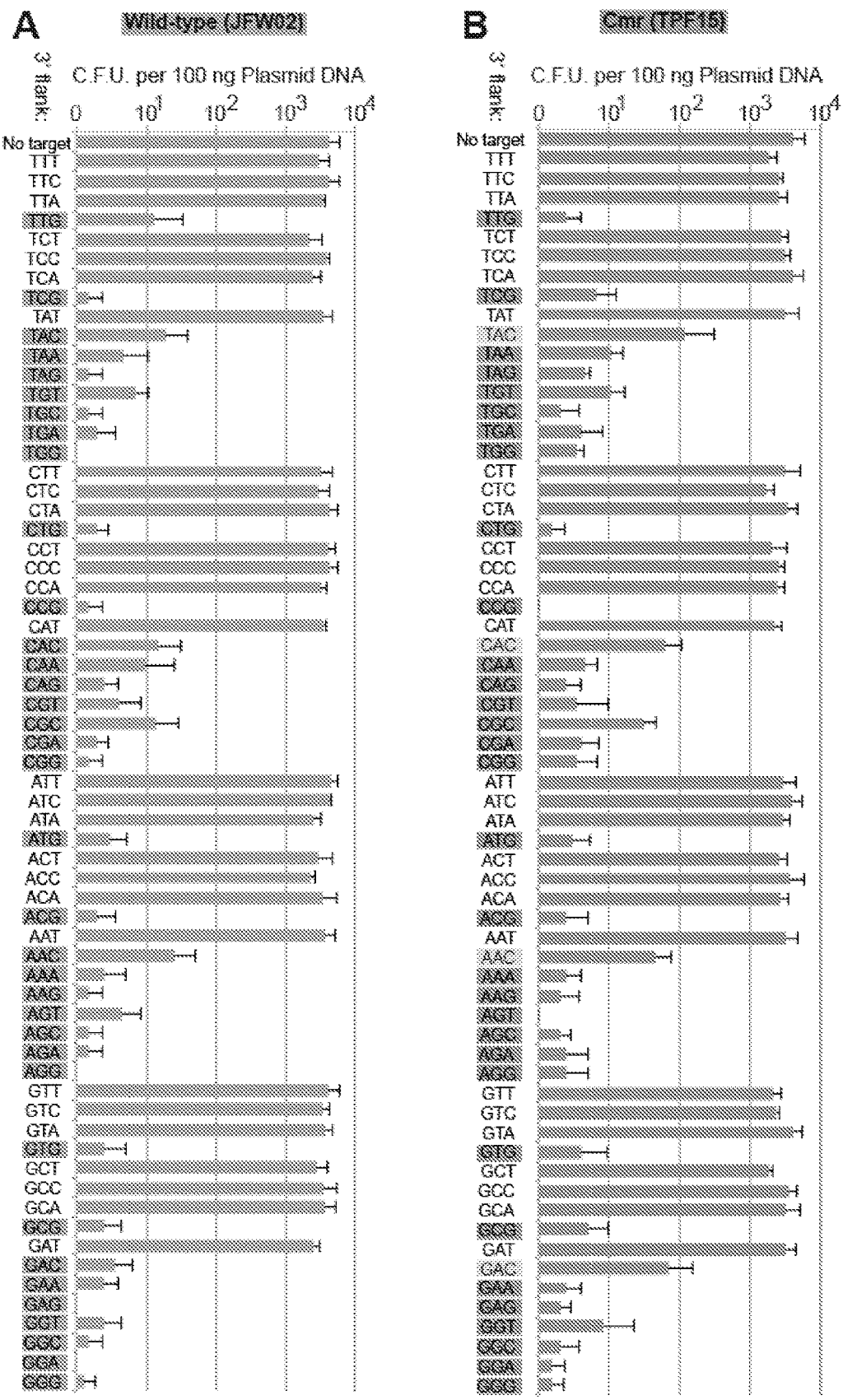
FIG. 9 shows the Cmr system in Pfu utilizes a protospacer adjacent motif (PAM) to distinguish invader from host. Colonies produced by infection with 65 plasmids in wild-type (FIG. 9A) and Cmr (FIG. 9B) strains. Colony numbers are the average of at least 3 replicates with the standard deviation indicated by error bars. All plasmids, except a negative control (no target), produce 7.01 target RNAs that differ by the 3 nucleotides immediately 3' of the 7.01 target sequence (see FIG. 8A), as indicated. Target-adjacent sequences that activated CRISPR-Cas targeting resulting in greater than 100-fold reduction in colony numbers relative to negative control plasmid are shaded dark gray. Sequences that conferred 30-fold to 100-fold reduction in colony numbers are shaded light gray.

To more clearly determine whether the host protection mechanism was complementarity-driven protection of the host or PAM-driven targeting of the invader and comprehensively delineate the Cmr system-flanking sequence requirement, we tested the complete series of variations in the proximal 3 nucleotides of the 3' adjacent region (FIG. 8; FIG. 9). The negative control plasmid (no target) produced an average of $4.34 \times 10^3$ and $4.06 \times 10^3$ uracil prototroph colonies per 100 ng of plasmid DNA in the wild-type and Cmr strains, respectively, as expected. It was found that plasmids with various trinucleotide sequences completely lacking tag complementarity were not targeted in the Cmr (and wild-type) strain (e.g., TCC, ACC, and GCC) (FIG. 8B), indicating that potential targets are not simply protected by crRNA tag complementarity in this region. On the other hand, plasmids with a contiguous series of 32 trinucleotide sequences were effectively silenced in the Cmr (and wild-type) strain (>100-fold reduction in colony formation relative to negative control plasmid) (FIG. 8B, C, dark-gray shading). (Another four trinucleotide sequences were weakly silenced in the Cmr strain [30-fold to 100-fold reduction in colony formation] [FIG. 8B, light-gray shading].)

Figure 10:
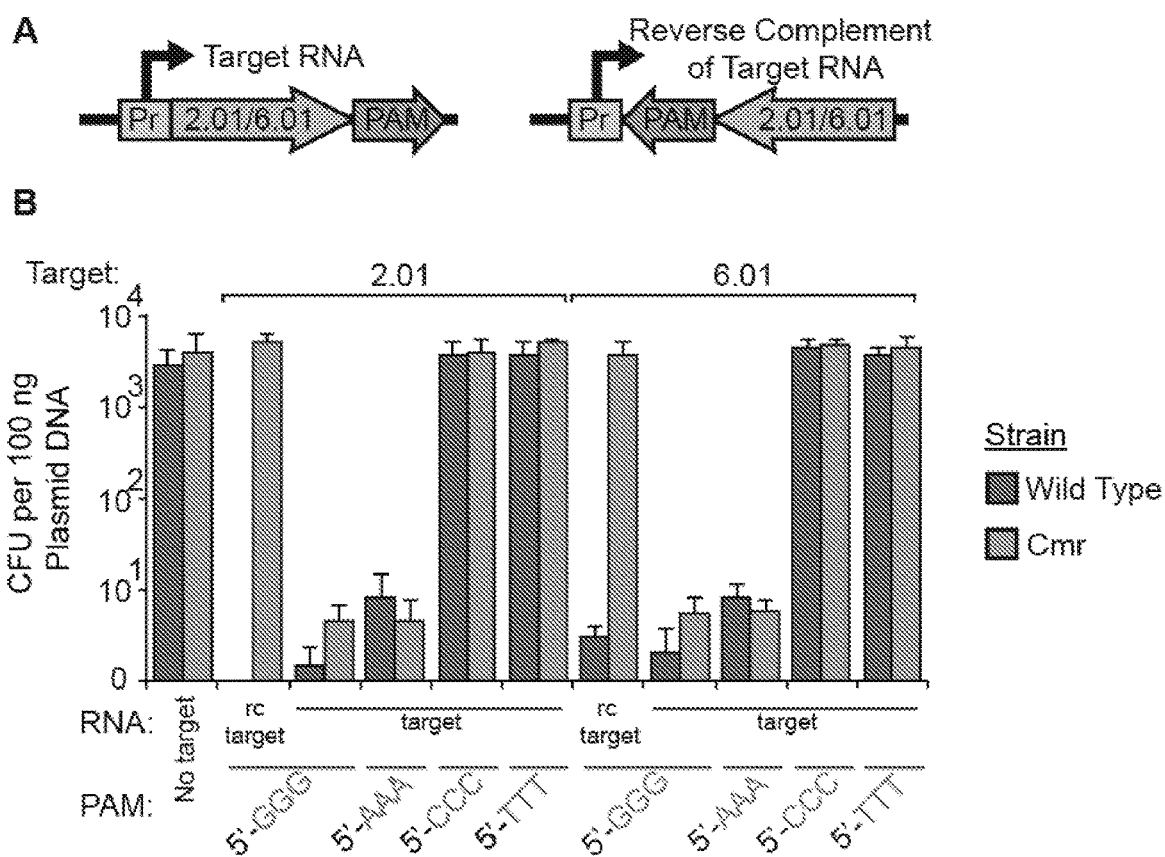
FIG. 10 shows Cmr silences additional CRISPR target sequences in a target transcription- and PAM-dependent manner.

To confirm the generality of these observations, we tested for targeting of plasmids by P. furiosus crRNAs 2.01 and 6.01 (FIG. 10). As expected, plasmids containing the 2.01 or 6.01 target sequences were silenced when the plasmids included the PAMs identified by crRNA 7.01 targeting (GGG or AAA) and not non-PAM sequences (CCC or TTT) (FIG. 10).

The results indicate that the P. furiosus Cmr system requires a PAM in addition to the crRNA target sequence in order to target DNA for silencing. Functional Cmr PAM sequences include NGN, NNG, and NAA (and NAC) (FIG. 8C). The crRNA target sequences stored in the seven P. furiosus CRISPR loci do not contain a functional PAM in their adjacent CRISPR repeats (CTT). The range of PAM sequences recognized by the Cmr system in P. furiosus fully encompasses and significantly extends beyond the combined set recognized by the P. furiosus Type I-A Csa and Type I-G Cst systems (NGG, NGA, NAG, and HCG) (Elmore et al. 2015). Our findings indicate that the Type III-B Cmr system in P. furiosus depends on a PAM sequence to activate silencing (rather than on complementarity to inhibit silencing) in order to protect against self-destruction at CRISPR loci.

Figure 11:
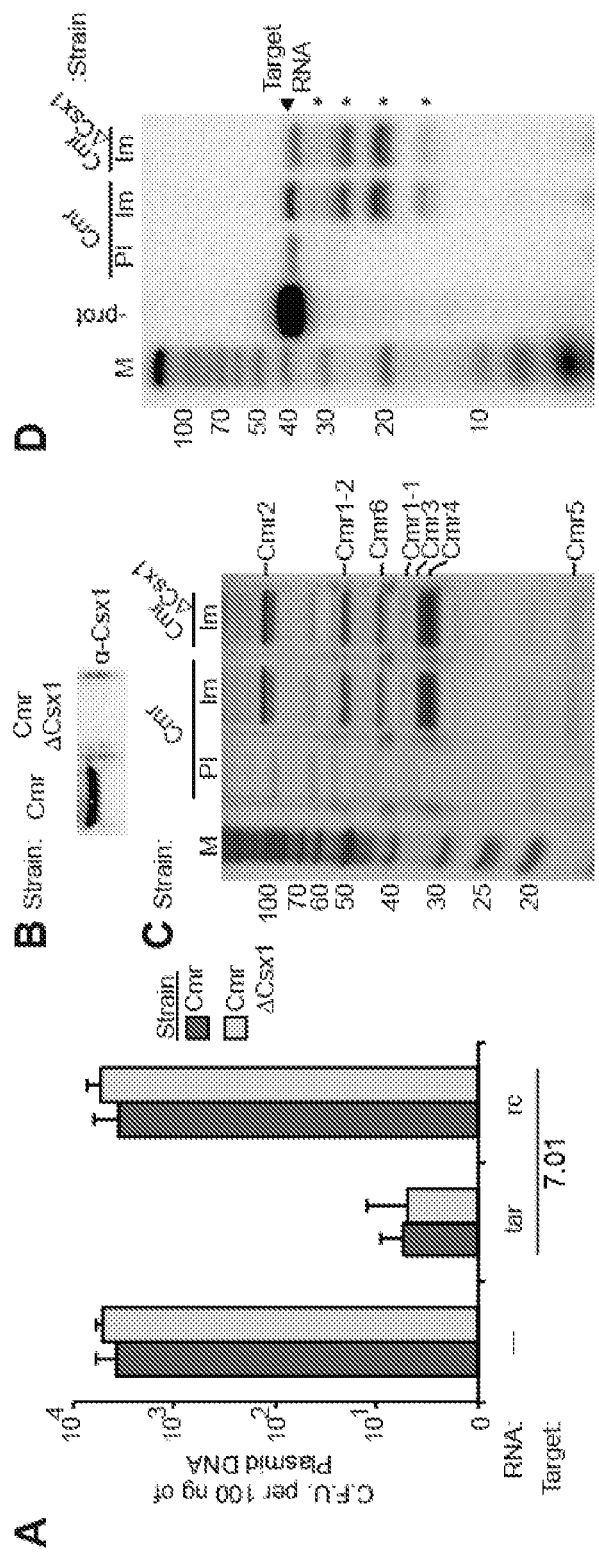
FIG. 11 shows Csx1 is not required for plasmid interference by Cmr in Pfu.

Csx1 is Not Essential for Transcription-Dependent DNA Silencing by the Type III-B Cmr System in P. furiosus Csx1 and Csm6 are CARF (CRISPR-associated Rossman fold) domain proteins often associated with Type III CRISPR-Cas systems, which were recently identified as important for transcription-dependent silencing by the S. islandicus Type III-B Cmr and Staphylococcus epidermidis Type III-A Csm systems, respectively (Deng et al. 2013; Goldberg et al. 2014; Hatoum-Aslan et al. 2014; Makarova et al. 2014). P. furiosus harbors a csx1 gene within the Cmr module (FIG. 5). To test whether Csx1 is required for P. furiosus Cmr transcription-dependent DNA silencing, csx1 in the Cmr strain (Cmr ΔCsx1) were deleted. The csx1 deletion strain was infected with plasmids that produce 7.01 target RNA, its reverse complement, or no target RNA; however, we observed no change in plasmid silencing in the absence of Csx1 (FIG. 11A). The absence of Csx1 in the deletion strain by Western analysis (FIG. 11B) was confirmed. The protein composition and RNA cleavage activity of immunopurified Cmr complexes were also not disrupted by deletion of csx1 (FIG. 11C, 11D). Furthermore, crRNA maturation and accumulation were not observably affected by the absence of Csx1 (Northern analysis) (data not shown). Our results indicate that Csx1 is not essential for Cmr crRNP formation, RNA cleavage activity or, unlike Csx1/Csm6 in other characterized Type III systems (Deng et al. 2013; Goldberg et al. 2014; Hatoum-Aslan et al. 2014), transcription-dependent plasmid silencing activity by the Cmr system in P. furiosus in our assay.

The Cmr2 Protein Cleaves ssDNA Via its HD Nuclease Domain

Cmr2 is a member of the Cas10 superfamily—the signature protein family of the Type III CRISPR-Cas systems—with characteristic Palm and N-terminal HD nuclease domains (Makarova et al. 2011). Csm1, the Cas10 protein of the Type III-A Csm complex, is essential for plasmid elimination (Hatoum-Aslan et al. 2014) and has been shown to have 3'-5' ssDNA exonuclease activity via the Palm domain in S. epidermidis and ssDNA endonuclease activity via the HD domain in Thermococcus onnurineus (Ramia et al. 2014b; Jung et al. 2015). Cmr2 is an essential component of the P. furiosus Cmr RNA targeting complex; however, the HD domain is not required for the RNA cleavage activity of the complex in vitro (Hale et al. 2009; Cocozaki et al. 2012).

To test whether Cmr2 is a DNA nuclease, we incubated purified P. furiosus Cmr2 with linear ssDNA and dsDNA, a "bubble" dsDNA (having a ssDNA internal sequence), and circular ssDNA. Cmr2 efficiently cleaved linear 5' radiolabeled ssDNA (FIG. 12A) but not dsDNA (FIG. 12B). Cleavage of linear ssDNA by Cmr2 is metal-dependent: Cleavage was most efficient in the presence of Ni2+ (included in assays shown in FIG. 12) and Co2+, less efficient with Mn2+, and blocked by addition of EDTA (FIG. 13). Cmr2 also cleaves circular single-stranded M13 (ssM13) phage DNA (FIG. 12C) and within the single-stranded region of a bubble DNA substrate (FIG. 12D), revealing that Cmr2 can act endonucleolytically to cleave ssDNA.

Mutation of the HD domain active site abolishes the ssDNA cleavage activity of Cmr2 (alanine substitution of residues H13 and D14) (FIG. 12E, $HD_m$). Mutation of the GGDD motif in the Palm domain has no effect on activity (alanine substitution of residues D673 and D674) (FIG. 3E, $Palm_m$). Additional assays indicate that deletion of the HD domain also abolishes ssDNA cleavage activity and that the HD domain alone is insufficient for ssDNA cleavage (data not shown).

Interestingly, the observed ssDNA nuclease activity of the Cmr2 protein is significantly attenuated within the Cmr crRNP complex. The reconstituted Cmr complex (including Cmr1-6 and crRNA) displays very little ssDNA nuclease activity in comparison with approximately equimolar concentrations of Cmr2 alone (FIG. 12F). Our results indicate that Cmr2 is a latent DNA nuclease present within the Cmr effector complex.

Binding of a Target RNA Activates Generic DNA Cleavage Activity of the Type III-B Cmr Complex Plasmid targeting by the Cmr complex depends on directional transcription of the target region of the plasmid in vivo (FIG. 6), suggesting that activity of the complex may depend on transcription-induced access to a ssDNA target site and/or on the RNA product of transcription of the target site. To test for stimulation of DNA cleavage activity by the target RNA, we assayed DNA cleavage in the presence of the 7.01 target RNA (complementary to the 7.01 crRNA guide region) or the reverse complement of the target RNA (FIG. 14).

We found that the Cmr complex cleaves both ssDNA and dsDNA specifically upon addition of the target RNA (complementary to the crRNA guide sequence) (FIG. 14A, 14B, Cmr crRNP, t lanes). Activity was not stimulated by the reverse complement of the target RNA (FIG. 14A, 14B, rc lanes). Notably, while stimulation of the complex is specifically dependent on the complementary target RNA (both in vivo and in vitro) (FIGS. 6,14), cleavage by the complex is independent of complementarity of the DNA to the crRNA: dsDNA lacking the crRNA target sequence is also efficiently cleaved by the activated complex (dsDNA mutant target) (FIG. 14D, Cmr crRNP, t lane). Both strands of the dsDNA are cleaved (individual strands 5' radiolabeled in FIG. 14B, 14C). The ssDNA cleavage activity of the Cmr complex stimulated by the target RNA was greater than the ssDNA cleavage activity of an approximately equimolar concentration of Cmr2 alone (FIG. 14A).

Cmr2 is the DNA Nuclease of the Target RNA-Activated Cmr Complex

The importance of Cmr2 nuclease activity in the observed dsDNA cleavage by the activated Cmr complex was determined using complexes reconstituted with Cmr2 active site mutants. As with the free Cmr2 protein, mutation of the Palm domain GGDD motif ($Palm_m$) did not significantly affect cleavage of either strand of the DNA, but mutation of the HD domain of Cmr2 ($HD_m$) abolishes cleavage of both strands of dsDNA by the activated Cmr complex in vitro (FIG. 14E, 14F). The results indicate that Cmr2 mediates DNA cleavage by the Cmr complex. Furthermore, Cmr2 is inactive in the Cmr complex except in the presence of a target RNA complementary to the crRNA (FIG. 14A-D).

To test the importance of Cmr2 in plasmid silencing in vivo, we generated *P. furiosus* Cmr strains with various Cmr2 mutations. Each strain was assayed for transcription-dependent plasmid silencing activity (using plasmids that produce 7.01 target RNA, its reverse complement, or no target RNA) (FIG. 15A). While mutation of the HD domain abolishes DNA cleavage activity of the activated Cmr complex and the Cmr2 protein in vitro (FIGS. 12,14), deletion of the HD domain did not disrupt plasmid silencing in vivo (FIG. 15A, ΔHD). Mutation of the Palm domain also did not disrupt silencing (FIG. 15A, $Palm_m$). However, simultaneous mutation of both the Palm domain and the HD domain (either deletion or active site mutation) abolished Cmr plasmid silencing (FIG. 15A, ΔHD-$Palm_m$ and $HD_m$-$Palm_m$), suggesting that both the HD and Palm domains can mediate plasmid silencing in vivo. The silencing mediated by the HD and Palm domains in vivo was dependent on transcription of the target sequence (FIG. 15A, ΔHD and $Palm_m$), consistent with the requirement for the target RNA for DNA cleavage in vitro (FIG. 14). The lack of DNA cleavage activity supported by the Palm domain in vitro (FIG. 14) suggests that an additional requirement for Palm domain activity is provided in vivo (which could be related to other aspects of transcription or numerous other differences). Analysis of complexes immunoprecipitated from each strain indicates that the Cmr2 mutations did not prevent formation of the Cmr effector complex (FIG. 15B) or target RNA cleavage by the Cmr complex (FIG. 15C). The results indicate that Cmr2 plays an essential function in DNA cleavage activity of the Cmr complex that can be mediated by its Palm or HD nuclease domain in vivo.

Cleavage of the Target RNA is Not Required for DNA Cleavage

The Cmr complex cleaves complementary target RNAs in vitro and in vivo (Hale et al. 2009, 2012). To determine whether target RNA cleavage is required to stimulate Cmr DNA cleavage activity, we disrupted RNA cleavage with a Cmr4 active site mutation. Cmr complexes containing either wild-type or mutant Cmr4 (RNA cleavage active site mutant D26N) were incubated with radiolabeled target RNA (complementary to crRNA guide sequence). Target RNA binding (assessed by native PAGE) was not affected by the Cmr4 mutations (FIG. 16B), but target RNA cleavage was abolished (FIG. 16C). To examine DNA cleavage activity, we incubated the Cmr complexes containing the Cmr4 mutant with the target RNA and radiolabeled dsDNA. The Cmr4 mutations had no observable effect on DNA cleavage activity of the complex (FIG. 16D), indicating that Cmr DNA cleavage activity does not require cleavage of the target RNA.

A PAM Sequence in the Target RNA (rPAM) is Required to Activate the Type III-B Cmr Complex DNA Cleavage Activity Many Type I and Type II CRISPR-Cas effector complexes depend on the bipartite PAM sequence/crRNA recognition sequence in the target DNA to activate target DNA cleavage (Jinek et al. 2012; Westra et al. 2012; Sinkunas et al. 2013; Plagens et al. 2014). We identified a series of PAM sequences required in vivo for transcription-dependent plasmid silencing by the Cmr system (FIG. 8; FIG. 9). However, we found that the target RNA-activated Cmr complex does not depend on recognition of the crRNA target site in the target DNA (FIG. 14D), suggesting that the identified PAM sequences may also not be recognized in the invader DNA.

As the PAM sequences are also found adjacent to the crRNA recognition site in the target RNAs in vivo, we tested the ability of target RNAs with and without identified PAMs (FIG. 8) to stimulate DNA cleavage. We found that target RNAs containing a PAM 3' of the 7.01 crRNA recognition sequence (GGG and AAA) (see FIG. 16A) effectively activated DNA cleavage, but, strikingly, RNAs lacking PAMs (CCC and UUU) did not (FIG. 16E). FIG. 16G shows the time course of DNA cleavage stimulated by a further series of target RNAs. Again, the target RNAs containing Cmr PAMs defined by in vivo plasmid silencing assays (FIG. 8) stimulated DNA cleavage (FIG. 16G, UGG, UGU, and UUG). RNAs lacking PAMs failed to activate DNA cleavage despite having the crRNA recognition sequence and, notably, despite the presence of an identified PAM and crRNA recognition sequence in the DNA substrate included in the assay (FIG. 16G [CUU, UCU, and UUC], E [CCC and UUU]).

DNA cleavage activity was only stimulated by target RNAs containing both the crRNA recognition sequence and a PAM (FIG. 16A). RNAs with a GGG PAM but the reverse complement (rc-GGG) or a mutated version (mut-GGG) of the 7.01 crRNA recognition sequence failed to activate DNA cleavage (FIG. 16E). Also consistent with our previous findings (FIG. 14D), DNA cleavage stimulated by the 7.01-GGG and 7.01-AAA target RNAs is independent of a crRNA recognition site in the DNA: Cmr complexes activated by both target RNAs cleave DNA with and without the crRNA recognition sequence (FIG. 16E, 16F, respectively).

Discussion

The findings presented here reveal novel mechanisms for CRISPR-Cas effector complex activation and invader specificity: The Cmr effector complex is activated to cleave DNA by RNAs that contain an rPAM sequence and crRNA target sequence (FIG. 16A).

Transcription-Dependent Invader Silencing: DNA Nuclease Activity is Triggered by the Ttarget RNA Plasmid silencing by the Cmr system in *P. furiosus* requires transcription of the crRNA target region (FIG. 6; FIG. 10). Invader silencing had also previously been observed to be transcription-dependent for the Type III-A Csm system in *S. epidermidis* (Goldberg et al. 2014) and the Type III-B Cmr system in *S. islandicus* (Deng et al. 2013). A leading hypothesis is that transcription is important to allow access of the CRISPR-Cas DNA nuclease to the target DNA sequence; however, our findings indicate that the product of transcription, rather than the physical process of transcription, is essential for function. We found that exogenously supplied target RNA is sufficient to activate Cmr DNA nuclease activity in vitro (FIGS. 14,16). The *S. epidermidis* Csm crRNP was observed to nick target strand DNA in vitro when coupled with target transcription (Samai et al. 2015). Notably, the Csm in vitro DNA-nicking activity and the previously observed in vivo invader silencing by both the Csm and Cmr systems (like the Cmr system in *P. furiosus*) (FIG. 6; FIG. 10; Deng et al. 2013; Goldberg et al. 2014) specifically require transcription of the target strand, consistent with a requirement for the target RNA product. Invader silencing likely involves a complex biochemical mechanism; our findings indicate that target RNA detection is one essential aspect.

rPAM: Recognition of the PAM Sequence in the Target RNA Licenses DNA Cleavage

CRISPR-Cas systems use mechanisms to distinguish invader targets from host CRISPR loci. To date, two mechanisms have been described: deactivation of the DNA nuclease by complementarity of the crRNA 5' tag region with the potential CRISPR target for the Type III-A Csm system (see FIG. 7; Marraffini and Sontheimer 2010) and requisite activation of the nuclease by a PAM sequence (in addition to the target sequence) in the invader DNA for Type I and II systems (see FIG. 2; Mojica et al. 2009; Shah et al. 2013). Notably, we found that the Type III-B Cmr system in *P. furiosus* is activated by PAMs rather than deactivated by 5' tag complementarity (FIGS. 8,9, 10). Note that plasmids with the 5' tag complementary sequence are not targeted, but neither are plasmids with many flanking sequences lacking 5' tag complementarity; i.e., GCC (FIGS. 8, 9, 10). (Although there is no discernable pattern to suggest interaction between the crRNA tag sequence and non-PAM sequences, we cannot exclude a role for miscellaneous non-Watson-Crick interactions in function.) The PAM that activates the *P. furiosus* Cmr complex is very flexible, requiring only a single G (or two As) in one of two positions (FIG. 8) to induce silencing, and includes the PAM that was bioinformatically predicted (5'-NGG-3') for the CRISPR repeat sequence found in *P. furiosus* (Kunin et al. 2007; Mojica et al. 2009).

Remarkably, the DNA cleavage activity of the *P. furiosus* Cmr complex depends on the presence of the discriminating PAM sequence within the target RNA molecule. This contrasts the well-characterized Type I and II CRISPR-Cas systems, in which the PAM sequence is recognized in the DNA substrate (Jinek et al. 2012; Westra et al. 2012; Sinkunas et al. 2013; Rollins et al. 2015). We expect that further analysis will reveal that other Type III systems use an rPAM to effect invader silencing. Based on the orientation of the target RNA by the crRNA within the Cmr complex (Spilman et al. 2013; Osawa et al. 2015), we predict that Cmr2 and/or Cmr3 are involved in rPAM recognition (see FIG. 16). Electron microscopic studies of the architecturally similar Type I and Type III CRISPR-Cas complexes have demonstrated that interaction with a target DNA or RNA can effect concerted structural changes across multiple subunits of these effector complexes (Wiedenheft et al. 2011; Hochstrasser et al. 2014; Taylor et al. 2015). Our findings indicate that bipartite recognition of an invader—both the crRNA target sequence and the discriminating PAM sequence within the invader RNA—activates DNA cleavage activity of the Type III-B CRISPR-Cas complex.

Target RNA Cleavage by Type III Complexes: Possible Role in the Limitation of DNA Nuclease Activity Cleavage of invader RNAs (complementary to the crRNA) has been observed for numerous Type III systems (Hale et al. 2009; Zhang et al. 2012; Staals et al. 2013, 2014; Tamulaitis et al. 2014; Samai et al. 2015) and, prior to detection of DNA nuclease activity, was thought to be the mechanism of invader resistance by Cmr systems. Indeed, RNA cleavage can silence RNA viruses (Tamulaitis et al. 2014). DNA and RNA cleavage activities of the Type III CRISPR-Cas systems may function in parallel to eliminate DNA invaders and their transcripts.

Cleavage of the target RNA is not required for transcription-dependent DNA interference associated with Type III systems (FIG. 16D; Samai et al. 2015). Nonetheless, RNA cleavage may play an important role in the regulation of the function of Type III DNA nucleases in vivo. As outlined below, cleavage of the target RNA may be important for deactivation or turnover of complexes activated by the target RNA, which will be an interesting area of future investigation.

Cmr2 is the DNA Nuclease of the Type III-B CRISPR-Cas System

In this study, we determined that the Cas10 superfamily protein of the *P. furiosus* Cmr effector complex, Cmr2 (Makarova et al. 2011), is a latent DNA endonuclease (FIGS. 12,14,16). Our results revealed that the activity of Cmr2 is curbed in the context of the Cmr crRNP (FIG. 12F) and indicate that it is activated by interaction of the complex with target RNAs containing rPAMs (FIG. 16). Although other silencing mechanisms are possible, Cmr2-mediated DNA cleavage likely effects plasmid silencing by the Type III-B CRISPR-Cas system, which is target RNA transcription-dependent and PAM-dependent and was not observed when the HD and Palm domains of the Cmr2 nuclease were inactivated (FIG. 15).

The Cas10 proteins of the Type III CRISPR-Cas systems are characterized by the presence of two Palm domains (one of which is typically predicted to be inactive) (Cocozaki et al. 2012) and often contain a fused HD nuclease domain (Makarova et al. 2006). The evidence regarding the roles of the HD and Palm domains of Cas10 proteins in DNA targeting is complex.

Our findings indicate that both the Palm domain and the HD domain of Cmr2 can mediate silencing in the *P. furiosus* Type III-B Cmr complex. We found that mutation of the HD domain (but not the Palm domain) of Cmr2 disrupts cleavage of both DNA strands by the complex in vitro (FIG. 14). While the Palm domain does not function in the in vitro assay, mutation of both domains is required to disrupt silencing in vivo (FIG. 15), indicating that both domains can mediate silencing in vivo.

At the same time, current evidence implicates one or the other of the domains in Type III-A Csm systems from different organisms. For the Type III-A Csm1 protein from *S. epidermidis*, mutation of the Palm domain GGDD motif disrupts DNA cleavage by the complex (and by the isolated protein) in vitro (Ramia et al. 2014b; Samai et al. 2015). (The HD domain mutant was not tested in Samai et al. 2015.) In addition, mutation of the Palm domain alone (and not of the HD domain alone) of *S. epidermidis* Csm1 disrupts silencing in vivo (Hatoum-Aslan et al. 2014). However, mutation of the HD domain alone of *T. onnurineus* Csm1 disrupts DNA cleavage in vitro (Jung et al. 2015). (The Palm domain mutant was not tested in Jung et al. 2015.)

Cmr2 crystal structures indicate that both domains coordinate divalent metals in their active sites (Cocozaki et al. 2012; Osawa et al. 2015). However, some Cas10 proteins appear to contain only one or the other of the two nuclease domains (Makarova et al. 2006; Vestergaard et al. 2014). Collectively, the data suggest that either or both the Palm and HD domains of Cas10 superfamily nucleases may catalyze DNA cleavage within Type III CRISPR-Cas effector complexes.

Models for Function of DNA Nuclease in Invader Silencing by Type III-B Cmr Systems A DNA nuclease activity that does not require a crRNA target sequence within the DNA is a novel mechanism in CRISPR-Cas invader silencing that presents challenges in understanding its function. We propose two models to describe how the Cmr system may function in invader defense, in which the DNA nuclease acts locally in cis or more broadly in trans.

Figure 17:
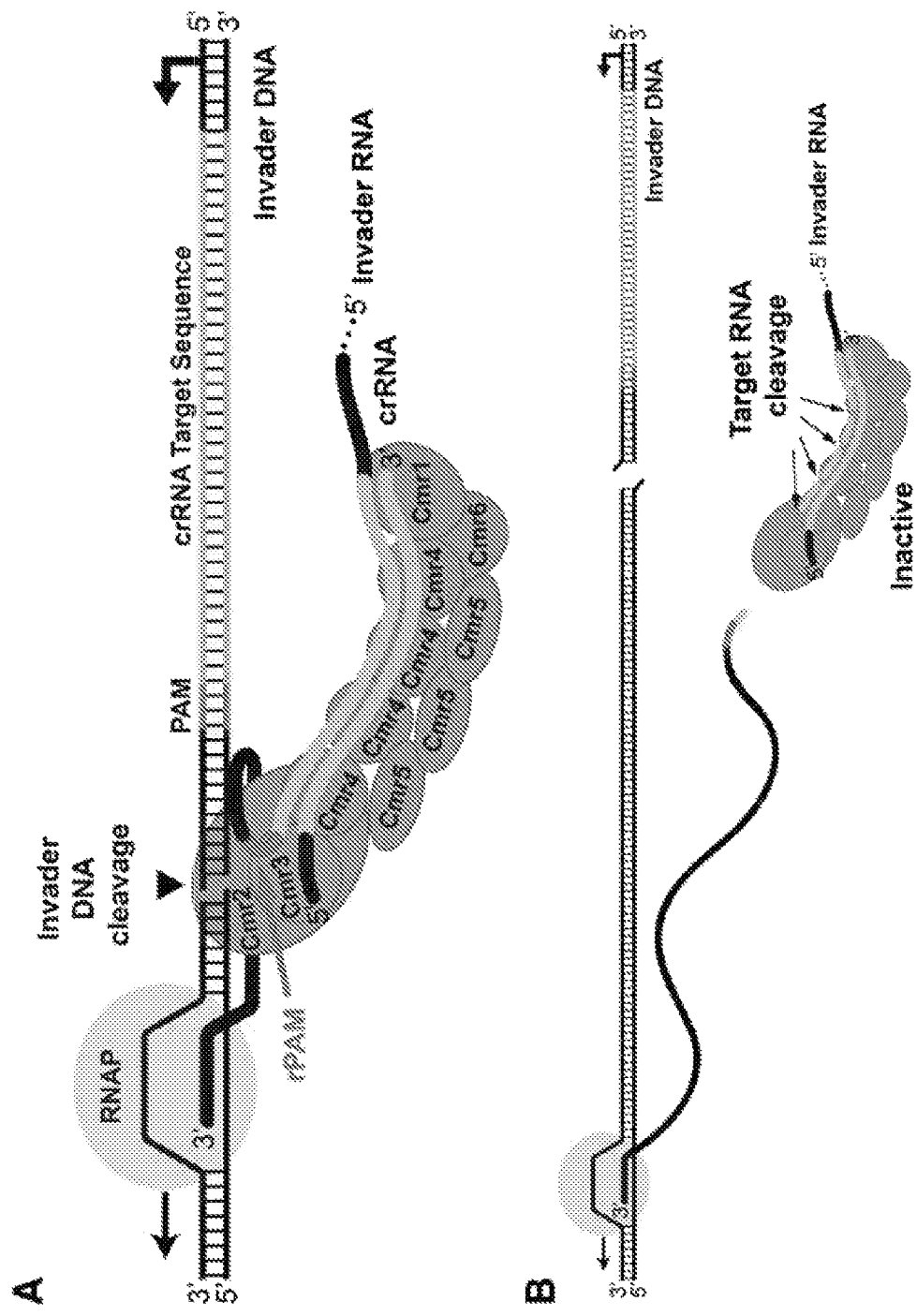
FIG. 17 depicts a model for limitation of Cmr nuclease activity to invader DNA.

The DNA nuclease activity of the Cmr complex depends on the target RNA, and interaction with the nascent invader RNA may physically tether the nuclease and limit its activity to the invader DNA (illustrated in FIG. 17A). Regulation of the DNA nuclease activity by cleavage of the target RNA could further function to limit nuclease activity to the invader DNA. For example, cleavage of the target RNA may terminate the activity of the DNA nuclease as it drifts away from the site of transcription (illustrated in FIG. 17B). Consistent with this model, disruption of target RNA cleavage by the *S. epidermidis* Csm complex results in a hyperactive DNA silencing activity phenotype in vivo (Samai et al. 2015).

Alternatively, the Cmr system may act as a sophisticated abortive infection system that, when activated by invader RNA, destroys host cell DNA to curb the spread of the infection: the altruistic sacrifice of the individual cell for the benefit of the population. Such an immune response would be analogous to bacterial abortive infection systems (Labrie et al. 2010; Samson et al. 2013) or the hypersensitive response in plants (Spoel and Dong 2012). For a CRISPR-Cas immune system, this mode of action (destruction of the cell in which the system is activated) might be expected to eliminate the relevant CRISPR-acquired invader targeting sequence from the population, which might be an acceptable cost for survival of the population. However, notably, Cmr systems are rarely found in the absence of another CRISPR-Cas system (Haft et al. 2005) that may act as the first line of defense and, when successful, preserve the invader-directed spacer for rapid elimination of infection in future generations. The Cmr system may be activated, and the cell may be eliminated, when infection progresses to the point where invader sequence transcription is rampant.

Citations in Example 1

Almendros C, Guzman N M, Diez-Villasenor C, Garcia-Martinez J, Mojica F J. 2012. Target motifs affecting natural immunity by a constitutive CRISPR-Cas system in *Escherichia coli*. PLoS One 7: e50797.

Barrangou R, Marraffini L A. 2014. CRISPR-Cas systems: prokaryotes upgrade to adaptive immunity. Mol Cell 54: 234-244.

Benda C, Ebert J, Scheltema R A, Schiller H B, Baumgartner M, Bonneau F, Mann M, Conti E. 2014. Structural model of a CRISPR RNA-silencing complex reveals the RNA-target cleavage activity in Cmr4. Mol Cell 56: 43-54.

Bolotin A, Quinquis B, Sorokin A, Ehrlich S D. 2005. Clustered regularly interspaced short palindrome repeats (CRISPRs) have spacers of extrachromosomal origin. Microbiology 151: 2551-2561.

Carte J, Pfister N T, Compton M M, Terns R M, Terns M P. 2010. Binding and cleavage of CRISPR RNA by Cash. RNA 16: 2181-2188.

Cocozaki A I, Ramia N F, Shao Y, Hale C R, Terns R M, Terns M P, Li H. 2012. Structure of the Cmr2 subunit of the CRISPR-Cas RNA silencing complex. Structure 20: 545-553.

Deng L, Garrett R A, Shah S A, Peng X, She Q. 2013. A novel interference mechanism by a Type IIIB CRISPR-Cmr module in *Sulfolobus*. Mol Microbiol 87: 1088-1099.

Elmore J, Deighan T, Westpheling J, Terns R M, Terns M P. 2015. DNA targeting by the Type I-G and Type I-A CRISPR-Cas systems of *Pyrococcus furiosus*. Nucleic Acids Res 43: 10353-10363.

Elmore J R, Yokooji Y, Sato T, Olson S, Glover C V, 3rd, Graveley B R, Atomi H, Terns R M, Terns M P. 2013. Programmable plasmid interference by the CRISPR-Cas system in *Thermococcus kodakarensis*. RNA biology 10: 828-840.

Farkas J, Chung D, DeBarry M, Adams M W, Westpheling J. 2011. Defining components of the chromosomal origin of replication of the hyperthermophilic archaeon *Pyrococcus furiosus* needed for construction of a stable replicating shuttle vector. Appl Environ Microbiol 77: 6343-6349.

Farkas J, Stirrett K, Lipscomb G L, Nixon W, Scott R A, Adams M W, Westpheling J. 2012. Recombinogenic properties of *Pyrococcus furiosus* strain COM1 enable rapid selection of targeted mutants. Appl Environ Microbiol 78: 4669-4676.

Fischer S, Maier L K, Stoll B, Brendel J, Fischer E, Pfeiffer F, Dyall-Smith M, Marchfelder A. 2012. An archaeal immune system can detect multiple protospacer adjacent motifs (PAMs) to target invader DNA. J Biol Chem 287: 33351-33363.

Garrett R A, Vestergaard G, Shah S A. 2011. Archaeal CRISPR-based immune systems: exchangeable functional modules. Trends Microbiol 19: 549-556.

Goldberg G W, Jiang W, Bikard D, Marraffini L A. 2014. Conditional tolerance of temperate phages via transcription-dependent CRISPR-Cas targeting. Nature 514: 633-637.

Haft D H, Selengut J, Mongodin E F, Nelson K E. 2005. A guild of 45 CRISPR-associated (Cas) protein families and multiple CRISPR/Cas subtypes exist in prokaryotic genomes. PLoS Comput Biol 1: e60.

Hale C, Kleppe K, Terns R M, Terns M P. 2008. Prokaryotic silencing (psi)RNAs in *Pyrococcus furiosus*. RNA 14: 2572-2579.

Hale C R, Zhao P, Olson S, Duff M O, Graveley B R, Wells L, Terns R M, Terns M P. 2009. RNA-guided RNA cleavage by a CRISPR RNA-Cas protein complex. Cell 139: 945-956.

Hale C R, Majumdar S, Elmore J, Pfister N, Compton M, Olson S, Resch A M, Glover C V III, Graveley B R, Terns R M, et al. 2012. Essential features and rational design of CRISPR RNAs that function with the Cas RAMP module complex to cleave RNAs. Mol Cell 45: 292-302.

Hale C R, Cocozaki A, Li H, Terns R M, Terns M P. 2014. Target RNA capture and cleavage by the Cmr Type III-B CRISPR-Cas effector complex. Genes Dev 28: 2432-2443.

Hatoum-Aslan A, Maniv I, Samai P, Marraffini L A. 2014. Genetic characterization of antiplasmid immunity through a Type III-A CRISPR-Cas system. J Bacteriol 196: 310-317.

Hochstrasser M L, Taylor D W, Bhat P, Guegler C K, Sternberg S H, Nogales E, Doudna J A. 2014. CasA mediates Cas3-catalyzed target degradation during CRISPR RNA-guided interference. Proc Natl Acad Sci 111: 6618-6623.

Jackson R N, Wiedenheft B. 2015. A conserved structural chassis for mounting versatile CRISPR RNA-guided immune responses. Mol Cell 58: 722-728.

Jinek M, Chylinski K, Fonfara I, Hauer M, Doudna J A, Charpentier E. 2012. A programmable dual-RNA-guided DNA endonuclease in adaptive bacterial immunity. Science 337: 816-821.

Jung T Y, An Y, Park K H, Lee M R, Oh B H, Woo E. 2015. Crystal structure of the Csm1 subunit of the Csm complex and its single-stranded DNA-specific nuclease activity. Structure 23: 782-790.

Kunin V, Sorek R, Hugenholtz P. 2007. Evolutionary conservation of sequence and secondary structures in CRISPR repeats. Genome Biol 8: R61.

Labrie S J, Samson J E, Moineau S. 2010. Bacteriophage resistance mechanisms. Nat Rev Microbiol 8: 317-327.

Lipscomb G L, Stirrett K, Schut G J, Yang F, Jenney F E Jr, Scott R A, Adams M W, Westpheling J. 2011. Natural competence in the hyperthermophilic archaeon *Pyrococcus furiosus* facilitates genetic manipulation: construction of markerless deletions of genes encoding the two cytoplasmic hydrogenases. Appl Environ Microbiol 77: 2232-2238.

Majumdar S, Zhao P, Pfister N T, Compton M, Olson S, Glover C V III, Wells L, Graveley B R, Terns R M, Terns M P. 2015. Three CRISPR-Cas immune effector complexes coexist in *Pyrococcus furiosus*. RNA 21: 1147-1158.

Makarova K S, Koonin E V. 2013. Evolution and classification of CRISPR-Cas systems and Cas protein families. In CRISPR-Cas systems (ed. Barrangou R, van der Oost J), pp. 61-91. Springer, Berlin.

Makarova K S, Grishin N V, Shabalina S A, Wolf Y I, Koonin E V. 2006. A putative RNA-interference-based immune system in prokaryotes: computational analysis of the predicted enzymatic machinery, functional analogies with eukaryotic RNAi, and hypothetical mechanisms of action. Biol Direct 1: 7.

Makarova K S, Haft D H, Barrangou R, Brouns S J, Charpentier E, Horvath P, Moineau S, Mojica F J, Wolf Y I, Yakunin A F, et al. 2011. Evolution and classification of the CRISPR-Cas systems. Nat Rev Microbiol 9: 467-477.

Makarova K S, Anantharaman V, Grishin N V, Koonin E V, Aravind L. 2014. CARF and WYL domains: ligand-binding regulators of prokaryotic defense systems. Front Genet 5: 102.

Marraffini L A, Sontheimer E J. 2010. Self versus non-self discrimination during CRISPR RNA-directed immunity. Nature 463: 568-571.

Mojica F J, Diez-Villasenor C, Garcia-Martinez J, Soria E. 2005. Intervening sequences of regularly spaced prokaryotic repeats derive from foreign genetic elements. J Mol Evol 60: 174-182.

Mojica F J, Diez-Villasenor C, Garcia-Martinez J, Almendros C. 2009. Short motif sequences determine the targets of the prokaryotic CRISPR defence system. Microbiology 155: 733-740.

Osawa T, Inanaga H, Sato C, Numata T. 2015. Crystal structure of the CRISPR-Cas RNA silencing Cmr complex bound to a target analog. Mol Cell 58: 418-430.

Plagens A, Tripp V, Daume M, Sharma K, Klingl A, Hrle A, Conti E, Urlaub H, Randau L. 2014. In vitro assembly and activity of an archaeal CRISPR-Cas Type I-A cascade interference complex. Nucleic Acids Res 42: 5125-5138.

Pourcel C, Salvignol G, Vergnaud G. 2005. CRISPR elements in Yersinia pestis acquire new repeats by preferential uptake of bacteriophage DNA, and provide additional tools for evolutionary studies. Microbiology 151: 653-663.

Ramia N F, Spilman M, Tang L, Shao Y, Elmore J, Hale C, Cocozaki A, Bhattacharya N, Terns R M, Terns M P, et al. 2014a. Essential structural and functional roles of the Cmr4 subunit in RNA cleavage by the Cmr CRISPR-Cas complex. Cell Rep 9: 1610-1617.

Ramia N F, Tang L, Cocozaki A I, Li H. 2014b. *Staphylococcus epidermidis* Csm1 is a 3'-5' exonuclease. Nucleic Acids Res 42: 1129-1138.

Rollins M F, Schuman J T, Paulus K, Bukhari H S, Wiedenheft B. 2015. Mechanism of foreign DNA recognition by a CRISPR RNA-guided surveillance complex from *Pseudomonas aeruginosa*. Nucleic Acids Res 43: 2216-2222.

Samai P, Pyenson N, Jiang W, Goldberg G W, Hatoum-Aslan A, Marraffini L A. 2015. Co-transcriptional DNA and RNA cleavage during Type III CRISPR-Cas immunity. Cell 161: 1164-1174.

Samson J E, Magadan A H, Sabri M, Moineau S. 2013. Revenge of the phages: defeating bacterial defences. Nat Rev Microbiol 11: 675-687.

Shah S A, Erdmann S, Mojica F J, Garrett R A. 2013. Protospacer recognition motifs: mixed identities and functional diversity. RNA Biol 10: 891-899.

Sinkunas T, Gasiunas G, Waghmare S P, Dickman M J, Barrangou R, Horvath P, Siksnys V. 2013. In vitro reconstitution of cascade-mediated CRISPR immunity in *Streptococcus thermophilus*. EMBO J 32: 385-394.

Spilman M, Cocozaki A, Hale C, Shao Y, Ramia N, Terns R, Terns M, Li H, Stagg S. 2013. Structure of an RNA silencing complex of the CRISPR-Cas immune system. Mol Cell 52: 146-152.

Spoel S H, Dong X. 2012. How do plants achieve immunity? Defence without specialized immune cells. Nat Rev Immunol 12: 89-100.

Staals R H, Agari Y, Maki-Yonekura S, Zhu Y, Taylor D W, van Duijn E, Barendregt A, Vlot M, Koehorst J J, Sakamoto K, et al. 2013. Structure and activity of the RNA-targeting Type III-B CRISPR-Cas complex of *Thermus thermophilus*. Mol Cell 52: 135-145.

Staals R H, Zhu Y, Taylor D W, Kornfeld J E, Sharma K, Barendregt A, Koehorst J J, Vlot M, Neupane N, Varossieau K, et al. 2014. RNA targeting by the Type III-A CRISPR-Cas Csm complex of *Thermus thermophilus*. Mol Cell 56: 518-530.

Tamulaitis G, Kazlauskiene M, Manakova E, Venclovas C, Nwokeoji A O, Dickman M J, Horvath P, Siksnys V. 2014. Programmable RNA shredding by the Type III-A CRISPR-Cas system of *Streptococcus thermophilus*. Mol Cell 56: 506-517.

Taylor D W, Zhu Y, Staals R H, Kornfeld J E, Shinkai A, van der Oost J, Nogales E, Doudna J A. 2015. Structures of the CRISPR-Cmr complex reveal mode of RNA target positioning. Science 348: 581-585.

Terns R M, Terns M P. 2013. The RNA- and DNA-targeting CRISPR-Cas immune systems of *Pyrococcus furiosus*. Biochem Soc Trans 41: 1416-1421.

van der Oost J, Westra E R, Jackson R N, Wiedenheft B. 2014. Unravelling the structural and mechanistic basis of CRISPR-Cas systems. Nat Rev Microbiol 12: 479-492.

Vestergaard G, Garrett R A, Shah S A. 2014. CRISPR adaptive immune systems of archaea. RNA Biol 11: 156-167.

Westra E R, van Erp P B, Kunne T, Wong S P, Staals R H, Seegers C L, Bollen S, Jore M M, Semenova E, Severinov K, et al. 2012. CRISPR immunity relies on the consecutive binding and degradation of negatively supercoiled invader DNA by cascade and Cas3. Mol Cell 46: 595-605.

Westra E R, Semenova E, Datsenko K A, Jackson R N, Wiedenheft B, Severinov K, Brouns S J. 2013. Type I-E CRISPR-Cas systems discriminate target from non-target DNA through base pairing-independent PAM recognition. PLoS Genet 9: e1003742.

Wiedenheft B, Lander G C, Zhou K, Jore M M, Brouns S J, van der Oost J, Doudna J A, Nogales E. 2011. Structures of the RNA-guided surveillance complex from a bacterial immune system. Nature 477: 486-489.

Zhang J, Rouillon C, Kerou M, Reeks J, Brugger K, Graham S, Reimann J, Cannone G, Liu H, Albers S V, et al. 2012. Structure and mechanism of the CMR complex for CRISPR-mediated antiviral immunity. Mol Cell 45: 303-313.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

---

What is claimed is:

1. A non-naturally occurring composition comprising:
   a) a CRISPR-RNA (crRNA), wherein the crRNA is a single stranded RNA comprising:
      a tag region comprising at least 5 to no greater than 12 nucleotides, and
      a guide region comprising a nucleotide sequence of at least 15 nucleotides,
      wherein the tag region is immediately upstream of the guide region;
   b) a Cmr complex, wherein the Cmr complex comprises at least 6 proteins comprising Cmr1, Cmr2, Cmr3, Cmr4, Cmr5, and Cmr6, and wherein the Cmr2 protein comprises a mutation that reduces RNA-activated DNAse activity of the Cmr complex, wherein the mutation comprises a substitution of the histidine of the HD superfamily hydrolase domain, a substitution of the aspartic acid of the HD superfamily hydrolase domain, or the combination thereof.

2. The composition of claim 1 wherein the mutation of the histidine comprises a mutation to an alanine, and wherein the mutation of the aspartic acid comprises a mutation to an alanine.

3. The composition of claim 1 wherein the tag is selected from a combination of microbe and predicted 5' tag chosen from *Alicyclobacillus acidocaldarius* DSM 446, ATTGAAGC; *Alicyclobacillus acidocaldarius* Tc 4 1, ATTGAAGC; *Allochromatium vinosum* DSM 180, ATTAAGAC; *Anaerobaculum mobile* DSM 13181, ATGGAAAC; *Aquifex aeolicus* VF5, GTTGAAAC; *Archaeoglobus fulgidus* DSM 4304, ATTGAAAG; *Azospirillum lipoferum* 4B, ATTGAAGC; *Bacillus halodurans* C 125, ATTGAAAT; *Candidatus Korarchaeum cryptofilum* OPF8, ATTGAAAG; *Chloroherpeton thalassium* ATCC 35110, ATTGAAAC;

*Clostridium botulinum* A ATCC 19397, ATTTAAAT; *Clostridium botulinum* A ATCC 3502, ATTTAAAT; *Clostridium botulinum* A Hall, ATTTAAAT; *Clostridium botulinum* Ba4 657, ATTTAAAT; *Deinococcus geothermalis* DSM 11300, ATTGAAAC; *Desulfurococcus kamchatkensis* 1221n, ATTGAAAG; *Fervidicoccus fontis* Kam940, ATTGAAAG; *Fervidobacterium pennivorans* DSM 9078, ATGGAAAC; *Flexibacter litoralis* DSM 6794, ATTGCGAC; *Geobacillus* HH01, ATTGAAAC; *Geobacillus* Y412MC52, ATTGAAAC; *Geobacillus* Y412MC61, ATTGAAAC; *Haliangium ochraceum* DSM 14365, ATTGAAGC; *Halorhodospira halophila* SL1, ATTAAGAC; *Halothermothrix orenii* H 168, ATTGAAAC; *Herpetosiphon aurantiacus* DSM 785, ATTAAAAC; *Hyperthermus butylicus* DSM 5456, ATTGCAAG; *Isosphaera pallida* ATCC 43644, ATTGAAGC; *Mesotoga prima* MesG1 Ag 4 2, ATTGAAAC; *Methanococcus vannielii* SB, ATTGAAAC; *Methanosaeta harundinacea* 6Ac, ATTGAAAC; *Nostoc* PCC 7524, ATTGAAAC; *Pelotomaculum thermopropionicum* SI, ATTGAAAC; *Pyrobaculum arsenaticum* DSM 13514, ATTGAAAG; *Pyrococcus furiosus* COM1, ATTGAAAG; *Shewanella putrefaciens* 200, CTTAGAAA; *Sulfolobus islandicus* L D 8 5, ATTGAAAG; *Sulfolobus islandicus* M 16 4, ATTGAAAG; *Sulfolobus islandicus* REY15A, ATTGAAAG; *Sulfolobus islandicus* Y G 57 14, ATTGAAAG; *Sulfolobus solfataricus* P2, ATTGAAAG; *Sulfolobus tokodaii* 7, ATTGAAAG; *Sulfurihydrogenibium* YO3AOP1, TTATAAAG; *Synechococcus* JA 2 3B a 2 13, TTGGAAAC; *Synechococcus* PCC 6312, TTGAGCAC; *Synechococcus* PCC 7502, TTGGAAAC; *Thermoanaerobacter tengcongensis* MB4, ATTGAAAC; *Thermoanaerobacterium thermosaccharolyticum* DSM 571, ATTGAAAC; *Thermoanaerobacterium thermosaccharolyticum* M0795, ATTGAAAC; *Thermobaculum terrenum* ATCC BAA 798, GTGAACCG; *Thermocrinis albus* DSM 14484, GTTGAAAG; *Thermomicrobium roseum* DSM 5159, CTTGAAAC; *Thermotoga* RQ2, ATTGAAAC; *Thermotoga maritima* MSB8, ATTGAAAC; *Thermotoga thermarum* DSM 5069, ATGGAAAC; and *Treponema azotonutricium* ZAS 9, ATTAAGAC, and the proteins of the Cmr complex are selected from the same microbe as described in Table 1.

4. The composition of claim 1 wherein the tag is selected from a combination of microbe and predicted 5' tag chosen from *Alicyclobacillus acidocaldarius* DSM 446, ATTGAAGC; *Alicyclobacillus acidocaldarius* Tc 4 1, ATTGAAGC; *Allochromatium vinosum* DSM 180, ATTAAGAC; *Anaerobaculum mobile* DSM 13181, ATGGAAAC; *Aquifex aeolicus* VF5, GTTGAAAC; *Archaeoglobus fulgidus* DSM 4304, ATTGAAAG; *Azospirillum lipoferum* 4B, ATTGAAGC; *Bacillus halodurans* C 125, ATTGAAAT; *Candidatus Korarchaeum cryptofilum* OPF8, ATTGAAAG; *Chloroherpeton thalassium* ATCC 35110, ATTGAAAC; *Clostridium botulinum* A ATCC 19397, ATTTAAAT; *Clostridium botulinum* A ATCC 3502, ATTTAAAT; *Clostridium botulinum* A Hall, ATTTAAAT; *Clostridium botulinum* Ba4 657, ATTTAAAT; *Deinococcus geothermalis* DSM 11300, ATTGAAAC; *Desulfurococcus kamchatkensis* 1221n, ATTGAAAG; *Fervidicoccus fontis* Kam940, ATTGAAAG; *Fervidobacterium pennivorans* DSM 9078, ATGGAAAC; *Flexibacter litoralis* DSM 6794, ATTGCGAC; *Geobacillus* HH01, ATTGAAAC; *Geobacillus* Y412MC52, ATTGAAAC; *Geobacillus* Y412MC61, ATTGAAAC; *Haliangium ochraceum* DSM 14365, ATTGAAGC; *Halorhodospira halophila* SL1, ATTAAGAC; *Halothermothrix orenii* H 168, ATTGAAAC; *Herpetosiphon aurantiacus* DSM 785, ATTAAAAC; *Hyperthermus butylicus* DSM 5456, ATTGCAAG; *Isosphaera pallida* ATCC 43644, ATTGAAGC; *Mesotoga prima* MesG1 Ag 4 2, ATTGAAAC; *Methanococcus vannielii* SB, ATTGAAAC; *Methanosaeta harundinacea* 6Ac, ATTGAAAC; *Nostoc* PCC 7524, ATTGAAAC; *Pelotomaculum thermopropionicum* SI, ATTGAAAC; *Pyrobaculum arsenaticum* DSM 13514, ATTGAAAG; *Pyrococcus furiosus* COM1, ATTGAAAG; *Shewanella putrefaciens* 200, CTTAGAAA; *Sulfolobus islandicus* L D 8 5, ATTGAAAG; *Sulfolobus islandicus* M 16 4, ATTGAAAG; *Sulfolobus islandicus* REY15A, ATTGAAAG; *Sulfolobus islandicus* Y G 57 14, ATTGAAAG; *Sulfolobus solfataricus* P2, ATTGAAAG; *Sulfolobus tokodaii* 7, ATTGAAAG; *Sulfurihydrogenibium* YO3AOP1, TTATAAAG; *Synechococcus* JA 2 3B a 2 13, TTGGAAAC; *Synechococcus* PCC 6312, TTGAGCAC; *Synechococcus* PCC 7502, TTGGAAAC; *Thermoanaerobacter tengcongensis* MB4, ATTGAAAC; *Thermoanaerobacterium thermosaccharolyticum* DSM 571, ATTGAAAC; *Thermoanaerobacterium thermosaccharolyticum* M0795, ATTGAAAC; *Thermobaculum terrenum* ATCC BAA 798, GTGAACCG; *Thermocrinis albus* DSM 14484, GTTGAAAG; *Thermomicrobium roseum* DSM 5159, CTTGAAAC; *Thermotoga* RQ2, ATTGAAAC; *Thermotoga maritima* MSB8, ATTGAAAC; *Thermotoga thermarum* DSM 5069, ATGGAAAC; and *Treponema azotonutricium* ZAS 9, ATTAAGAC.

5. The composition of claim 1 wherein the Cmr1, Cmr2, Cmr3, Cmr4, Cmr5, and Cmr6 protein are selected from either (i) a microbe that includes a CRISPR locus and a Type III-B CRISPR-Cas system, and no other CRISPR-Cas system, the microbe chosen from *Acidilobus saccharovorans* 345 15, *Alicyclobacillus acidocaldarius* DSM 446, *Alicyclobacillus acidocaldarius* Tc 4 1, *Allochromatium vinosum* DSM 180, *Anaebaena cylindrica* PCC 7122, *Anaerobaculum mobile* DSM 13181, *Arthrospira platensis* NIES 39, *Azospirillum lipoferum* 4B, *Caldilinea aerophila* DSM 14535 NBRC 104270, *Calothrix* PCC 7507, *Candidatus Accumulibacter phosphatis* clade IIA UW 1, *Candidatus Chloracidobacterium thermophilum* B, *Chloroherpeton thalassium* ATCC 35110, *Clostridium botulinum* A ATCC 19397, *Clostridium botulinum* A ATCC 3502, *Clostridium botulinum* A Hall, *Clostridium botulinum* Ba4 657, *Clostridium botulinum* F 230613, *Clostridium botulinum* F Langeland, *Clostridium botulinum* H04402 065, *Cyanobacterium* PCC 10605, *Cyanobacterium stanieri* PCC 7202, *Cyanothece* ATCC 51142, *Cyanothece* PCC 7424, *Cyanothece* PCC 7425, *Cyanothece* PCC 7822, *Cyanothece* PCC 7822, *Cylindrospermum stagnale* PCC 7417, *Deinococcus geothermalis* DSM 11300, *Desulfotomaculum acetoxidans* DSM 771, *Desulfovibrio hydrothermalis* AM13 DSM 14728, *Flexibacter litoralis* DSM 6794, *Flexistipes sinusarabici* DSM 4947, *Geobacillus* HH01, *Geobacillus thermoglucosidasius* C56 YS93, *Gloeobacter* JS, *Haliangium ochraceum* DSM 14365, *Haliscomenobacter hydrossis* DSM 1100, *Halorhodospira halophila* SL1, *Halothece* PCC 7418, *Herpetosiphon aurantiacus* DSM 785, *Hyperthermus butylicus* DSM 5456, *Ignicoccus hospitalis* KIN4 I, *Isosphaera pallida* ATCC 43644, *Kyrpidia tusciae* DSM 2912, *Marinithermus hydrothermalis* DSM 14884, *Marinitoga piezophila* KA3, *Marinomonas* MWYL1, *Marinomonas mediterranea* MMB 1, *Methanococcus vannielii* SB, *Methanosaeta harundinacea* 6Ac, *Myxococcus fulvus* HW 1, *Myxococcus xanthus* DK 1622, *Nostoc* PCC 7524, *Oscillatoria* PCC 7112, *Oscillatoria acuminata* PCC 6304, *Paenibacillus larvae* 04 309, *Pleurocapsa* PCC 7327, *Porphyromonas gingivalis* ATCC 33277, *Porphyromonas gingivalis* TDC60, *Porphyromonas gingivalis* W83, *Pyro-* baculum 1860, *Pyrobaculum calidifontis* JCM 11548, *Pyrobaculum neutrophilum* V24Sta, *Pyrococcus yayanosii* CH1, *Rhodospirillum centenum* SW, *Rivularia* PCC 7116, *Shewanella putrefaciens* 200, *Sorangium cellulosum* So ce 56, *Sulfolobus islandicus* HVE10 4, *Sulfolobus islandicus* LAL14 1, *Sulfolobus islandicus* L D 8 5, *Sulfolobus islandicus* L S 2 15, *Sulfolobus islandicus* M 14 25, *Sulfolobus islandicus* M 16 27, *Sulfolobus islandicus* M 16 4, *Sulfolobus islandicus* REY15A, *Sulfolobus islandicus* Y G 57 14, *Sulfolobus solfataricus* P2, *Sulfolobus tokodaii* 7, *Synechococcus* JA 2 3B a 2 13, *Synechococcus* JA 3 3Ab, *Synechococcus* PCC 6312, *Synechococcus* PCC 7002, *Synechococcus* PCC 7502, *Synechocystis* PCC 6803, *Synechocystis* PCC 6803, *Syntrophobotulus glycolicus* DSM 8271, *Syntrophus aciditrophicus* SB, *Teredinibacter turnerae* T7901, *Thermoanaerobacter italicus* Ab9, *Thermoanaerobacter mathranii* A3, *Thermoanaerobacter tengcongensis* MB4, *Thermoanaerobacterium thermosaccharolyticum* DSM 571, *Thermoanaerobacterium thermosaccharolyticum* M0795, *Thermobaculum terrenum* ATCC BAA 798, *Thermodesulfatator indicus* DSM 15286, *Thermofilum* 1910b, *Thermomicrobium roseum* DSM 5159, *Thermosipho africanus* TCF52B, *Thermus thermophilus* HB27, *Thermus thermophilus* HB8, *Thioalkalivibrio nitratireducens* DSM 14787, *Thioalkalivibrio sulfidophilus* HL EbGr7, *Thiocystis violascens* DSM 198, *Thioflavicoccus mobilis* 8321, *Treponema azotonutricium* ZAS 9, and *Truepera radiovictrix* DSM 17093, or (ii) a microbe that includes a CRISPR locus, a Type III-B CRISPR-Cas system, and at least one other CRISPR-Cas system, the microbe chosen from *Pyrobaculum neutrophilum* V24Sta, *Candidatus Korarchaeum cryptofilum* OPF8, *Desulfurococcus kamchatkensis* 1221n, *Fervidicoccus fontis* Kam940, *Pyrobaculum calidifontis* JCM 11548, *Pyrobaculum oguniense* TE7, *Anaerolinea thermophila* UNI 1, *Aquifex aeolicus* VF5, *Caldicellulosiruptor obsidiansis* OB47, *Geobacillus* WCH70, *Geobacillus* Y412MC52, *Geobacillus* Y412MC61, *Methanococcus voltae* A3, *Methanosaeta thermophila* PT, *Myxococcus stipitatus* DSM 14675, *Pelotomaculum thermopropionicum* SI, *Pyrococcus furiosus* COM1, *Pyrococcus furiosus* DSM 3638, *Syntrophothermus lipocalidus* DSM 12680, *Meiothermus ruber* DSM 1279, *Paenibacillus terrae* HPL 003, *Truepera radiovictrix* DSM 17093, *Candidatus Desulforudis audaxviator* MP104C, *Thermotoga* RQ2, *Thermotoga maritima* MSB8, *Comamonadaceae bacterium* CR, *Vulcanisaeta distributa* DSM 14429, *Archaeoglobus fulgidus* DSM 4304, *Caldivirga maquilingensis* IC 167, *Pyrobaculum arsenaticum* DSM 13514, *Sulfolobus islandicus* Y G 57 14, *Sulfolobus solfataricus* P2, *Caldicellulosiruptor kronotskyensis* 2002, *Desulfotomaculum kuznetsovii* DSM 6115, *Halothermothrix orenii* H 168, *Mesotoga prima* MesG1 Ag 4 2, *Rubrobacter xylanophilus* DSM 9941, *Sulfurihydrogenibium* YO3AOP1, *Thermocrinis albus* DSM 14484, *Thermus* CCB US3 UF1, *Thermotoga maritima* MSB8, *Thermotoga maritima* MSB8, *Bacillus halodurans* C 125, *Meiothermus ruber* DSM 1279, *Meiothermus silvanus* DSM 9946, *Sulfolobus islandicus* LAL14 1, *Thermofilum pendens* Hrk 5, *Thermobifida fusca* YX, *Fervidobacterium pennivorans* DSM 9078, *Thermosipho melanesiensis* B1429, *Vulcanisaeta moutnovskia* 768 28, and *Archaeoglobus fulgidus* DSM 4304.

6. The composition of claim 1 further comprising an activating RNA, wherein the activating RNA comprises a target region, wherein the nucleotide sequence of the target region is complementary to the entire guide region of the crRNA.

7. The composition of claim 1 wherein the Cmr1, Cmr2, Cmr3, Cmr4, Cmr5, and Cmr6 protein are selected from either (i) a microbe that includes a CRISPR locus and a Type III-B CRISPR-Cas system, and no other CRISPR-Cas system, the microbe chosen from *Acidilobus saccharovorans* 345 15, *Alicyclobacillus acidocaldarius* DSM 446, *Alicyclobacillus acidocaldarius* Tc 4 1, *Allochromatium vinosum* DSM 180, *Anabaena cylindrica* PCC 7122, *Anaerobaculum mobile* DSM 13181, *Arthrospira platensis* NIES 39, *Azospirillum lipoferum* 4B, *Caldilinea aerophila* DSM 14535 NBRC 104270, *Calothrix* PCC 7507, *Candidatus Accumulibacter phosphatis* Glade IIA UW 1, *Candidatus Chloracidobacterium thermophilum* B, *Chloroherpeton thalassium* ATCC 35110, *Clostridium botulinum* A ATCC 19397, *Clostridium botulinum* A ATCC 3502, *Clostridium botulinum* A Hall, *Clostridium botulinum* Ba4 657, *Clostridium botulinum* F 230613, *Clostridium botulinum* F Langeland, *Clostridium botulinum* H04402 065, *Cyanobacterium* PCC 10605, *Cyanobacterium stanieri* PCC 7202, *Cyanothece* ATCC 51142, *Cyanothece* PCC 7424, *Cyanothece* PCC 7425, *Cyanothece* PCC 7822, *Cyanothece* PCC 7822, *Cylindrospermum stagnale* PCC 7417, *Deinococcus geothermalis* DSM 11300, *Desulfotomaculum acetoxidans* DSM 771, *Desulfovibrio hydrothermalis* AM13 DSM 14728, *Flexibacter litoralis* DSM 6794, *Flexistipes sinusarabici* DSM 4947, *Geobacillus* HH01, *Geobacillus thermoglucosidasius* C56 YS93, *Gloeobacter* JS, *Haliangium ochraceum* DSM 14365, *Haliscomenobacter hydrossis* DSM 1100, *Halorhodospira halophila* SL1, *Halothece* PCC 7418, *Herpetosiphon aurantiacus* DSM 785, *Hyperthermus butylicus* DSM 5456, *Ignicoccus hospitalis* KIN4 I, *Isosphaera pallida* ATCC 43644, *Kyrpidia tusciae* DSM 2912, *Marinithermus hydrothermalis* DSM 14884, *Marinitoga piezophila* KA3, *Marinomonas* MWYL1, *Marinomonas mediterranea* MMB 1, *Methanococcus vannielii* SB, *Methanosaeta harundinacea* 6Ac, *Myxococcus fulvus* HW 1, *Myxococcus xanthus* DK 1622, *Nostoc* PCC 7524, *Oscillatoria* PCC 7112, *Oscillatoria acuminata* PCC 6304, *Paenibacillus larvae* 04 309, *Pleurocapsa* PCC 7327, *Porphyromonas gingivalis* ATCC 33277, *Porphyromonas gingivalis* TDC60, *Porphyromonas gingivalis* W83, *Pyrobaculum* 1860, *Pyrobaculum calidifontis* JCM 11548, *Pyrobaculum neutrophilum* V24Sta, *Pyrococcus yayanosii* CH1, *Rhodospirillum centenum* SW, *Rsivularia* PCC 7116, *Shewanella putrefaciens* 200, *Sorangium cellulosum* So ce 56, *Sulfolobus islandicus* HVE10 4, *Sulfolobus islandicus* LAL14 1, *Sulfolobus islandicus* L D 8 5, *Sulfolobus islandicus* L S 2 15, *Sulfolobus islandicus* M 14 25, *Sulfolobus islandicus* M 16 27, *Sulfolobus islandicus* M 16 4, *Sulfolobus islandicus* REY15A, *Sulfolobus islandicus* Y G 57 14, *Sulfolobus solfataricus* P2, *Sulfolobus tokodaii* 7, *Synechococcus* JA 2 3B a 2 13, *Synechococcus* JA 3 3Ab, *Synechococcus* PCC 6312, *Synechococcus* PCC 7002, *Synechococcus* PCC 7502, *Synechocystis* PCC 6803, *Synechocystis* PCC 6803, *Syntrophobotulus glycolicus* DSM 8271, *Syntrophus aciditrophicus* SB, *Teredinibacter turnerae* T7901, *Thermoanaerobacter italicus* Ab9, *Thermoanaerobacter mathranii* A3, *Thermoanaerobacter tengcongensis* MB4, *Thermoanaerobacterium thermosaccharolyticum* DSM 571, *Thermoanaerobacterium thermosaccharolyticum* M0795, *Thermobaculum terrenum* ATCC BAA 798, *Thermodesulfatator indicus* DSM 15286, *Thermofilum* 1910b, *Thermomicrobium roseum* DSM 5159, *Thermosipho africanus* TCF52B, *Thermus thermophilus* HB27, *Thermus thermophilus* HB8, *Thioalkalivibrio nitratireducens* DSM 14787, *Thioalkalivibrio sulfidophilus* HL EbGr7, *Thiocystis violascens* DSM 198, *Thioflavicoccus mobilis* 8321, *Treponema* azotonutricium ZAS 9, and *Truepera radiovictrix* DSM 17093, or (ii) a microbe that includes a CRISPR locus, a Type III-B CRISPR-Cas system, and at least one other CRISPR-Cas system, the microbe chosen from *Pyrobaculum neutrophilum* V24Sta, *Candidatus Korarchaeum cryptofilum* OPF8, *Desulfurococcus kamchatkensis* 1221n, *Fervidicoccus fontis* Kam940, *Pyrobaculum calidifontis* JCM 11548, *Pyrobaculum oguniense* TE7, *Anaerolinea thermophila* UNI 1, *Aquifex aeolicus* VF5, *Caldicellulosiruptor obsidiansis* OB47, *Geobacillus* WCH70, *Geobacillus* Y412MC52, *Geobacillus* Y412MC61, *Methanococcus voltae* A3, *Methanosaeta thermophila* PT, *Myxococcus stipitatus* DSM 14675, *Pelotomaculum thermopropionicum* SI, *Pyrococcus furiosus* COM1, *Pyrococcus furiosus* DSM 3638, *Syntrophothermus lipocalidus* DSM 12680, *Meiothermus ruber* DSM 1279, *Paenibacillus terrae* HPL 003, *Truepera radiovictrix* DSM 17093, *Candidatus Desulforudis audaxviator* MP104C, *Thermotoga* RQ2, *Thermotoga maritima* MSB8, *Comamonadaceae bacterium* CR, *Vulcanisaeta distributa* DSM 14429, *Archaeoglobus fulgidus* DSM 4304, *Caldivirga maquilingensis* IC 167, *Pyrobaculum arsenaticum* DSM 13514, *Sulfolobus islandicus* Y G 57 14, *Sulfolobus solfataricus* P2, *Caldicellulosiruptor kronotskyensis* 2002, *Desulfotomaculum kuznetsovii* DSM 6115, *Halothermothrix orenii* H 168, *Mesotoga prima* MesG1 Ag 4 2, *Rubrobacter xylanophilus* DSM 9941, *Sulfurihydrogenibium* YO3AOP1, *Thermocrinis albus* DSM 14484, *Thermus* CCB US3 UF1, *Thermotoga maritima* MSB8, *Thermotoga maritima* MSB8, *Bacillus halodurans* C 125, *Meiothermus ruber* DSM 1279, *Meiothermus silvanus* DSM 9946, *Sulfolobus islandicus* LAL14 1, *Thermofilum pendens* Hrk 5, *Thermobifida fusca* YX, *Fervidobacterium pennivorans* DSM 9078, *Thermosipho melanesiensis* BI429, *Vulcanisaeta moutnovskia* 768 28, and *Archaeoglobus fulgidus* DSM 4304, and wherein the nucleotide sequence of the tag comprises no greater than 25% nucleotides that are not the same as the nucleotide sequence of the tag from the same microbe selected from a combination of microbe and predicted 5' tag chosen from *Alicyclobacillus acidocaldarius* DSM 446, ATTGAAGC, *Alicyclobacillus acidocaldarius* Tc 4 1, ATTGAAGC, *Allochromatium vinosum* DSM 180, ATTAAGAC, *Anaerobaculum mobile* DSM 13181, ATGGAAAC, *Aquifex aeolicus* VF5, GTTGAAAC, *Archaeoglobus fulgidus* DSM 4304, ATTGAAAG, *Azospirillum lipoferum* 4B, ATTGAAGC, *Bacillus halodurans* C 125, ATTGAAAT, *Candidatus Korarchaeum cryptofilum* OPF8, ATTGAAAG, *Chloroherpeton thalassium* ATCC 35110, ATTGAAAC, *Clostridium botulinum* A ATCC 19397, ATTTAAAT, *Clostridium botulinum* A ATCC 3502, ATTTAAAT, *Clostridium botulinum* A Hall, ATTTAAAT, *Clostridium botulinum* Ba4 657, ATTTAAAT, *Deinococcus geothermalis* DSM 11300, ATTGAAAC, *Desulfurococcus kamchatkensis* 1221n, ATTGAAAG, *Fervidicoccus fontis* Kam940, ATTGAAAG, *Fervidobacterium pennivorans* DSM 9078, ATGGAAAC, *Flexibacter litoralis* DSM 6794, ATTGCGAC, *Geobacillus* HH01, ATTGAAAC, *Geobacillus* Y412MC52, ATTGAAAC, *Geobacillus* Y412MC61, ATTGAAAC, *Haliangium ochraceum* DSM 14365, ATTGAAGC, *Halorhodospira halophila* SL1, ATTAAGAC, *Halothermothrix orenii* H 168, ATTGAAAC, *Herpetosiphon aurantiacus* DSM 785, ATTAAAAC, *Hyperthermus butylicus* DSM 5456, ATTGCAAG, *Isosphaera pallida* ATCC 43644, ATTGAAGC, *Mesotoga prima* MesG1 Ag 4 2, ATTGAAAC, *Methanococcus vannielii* SB, ATTGAAAC, *Methanosaeta harundinacea* 6Ac, ATTGAAAC, *Nostoc* PCC 7524, ATTGAAAC, *Pelotomaculum thermopropionicum* SI, ATTGAAAC, *Pyrobaculum arsenaticum* DSM 13514, ATTGAAAG, *Pyrococcus furiosus* COM1, ATTGAAAG, *Shewanella putrefaciens* 200, CTTAGAAA, *Sulfolobus islandicus* L D 8 5, ATTGAAAG, *Sulfolobus islandicus* M 16 4, ATTGAAAG, *Sulfolobus islandicus* REY15A, ATTGAAAG, *Sulfolobus islandicus* Y G 57 14, ATTGAAAG, *Sulfolobus solfataricus* P2, ATTGAAAG, *Sulfolobus tokodaii* 7, ATTGAAAG, *Sulfurihydrogenibium* YO3A0P1, TTATAAAG, *Synechococcus* JA 2 3B a 2 13, TTGGAAAC, *Synechococcus* PCC 6312, TTGAGCAC, *Synechococcus* PCC 7502, TTGGAAAC, *Thermoanaerobacter tengcongensis* MB4, ATTGAAAC, *Thermoanaerobacterium thermosaccharolyticum* DSM 571, ATTGAAAC, *Thermoanaerobacterium thermosaccharolyticum* M0795, ATTGAAAC, *Thermobaculum terrenum* ATCC BAA 798, GTGAACCG, *Thermocrinis albus* DSM 14484, GTTGAAAG, *Thermomicrobium roseum* DSM 5159, CTTGAAAC, *Thermotoga* RQ2, ATTGAAAC, *Thermotoga maritima* MSB8, ATTGAAAC, *Thermotoga thermarum* DSM 5069, ATGGAAAC, and *Treponema azotonutricium* ZAS 9, ATTAAGAC.

8. A non-naturally occurring composition comprising:
a) a CRISPR-RNA (crRNA), wherein the crRNA is a single stranded RNA comprising:
   a tag region comprising at least 5 to no greater than 12 nucleotides, and
   a guide region comprising a nucleotide sequence of at least 15 nucleotides, wherein the tag region is immediately upstream of the guide region, and wherein the nucleotide sequence of the tag comprises no greater than 50% of nucleotides that are not the same as the nucleotide sequence of the tag selected from a combination of microbe and predicted 5' tag chosen from *Alicyclobacillus acidocaldarius* DSM 446, ATTGAAGC, *Alicyclobacillus acidocaldarius* Tc 4 1, ATTGAAGC, *Allochromatium vinosum* DSM 180, ATTAAGAC, *Anaerobaculum mobile* DSM 13181, ATGGAAAC, *Aquifex aeolicus* VF5, GTTGAAAC, *Archaeoglobus fulgidus* DSM 4304, ATTGAAAG, *Azospirillum lipoferum* 4B, ATTGAAGC, *Bacillus halodurans* C 125, ATTGAAAT, *Candidatus Korarchaeum cryptofilum* OPF8, ATTGAAAG, *Chloroherpeton thalassium* ATCC 35110, ATTGAAAC, *Clostridium botulinum* A ATCC 19397, ATTTAAAT, *Clostridium botulinum* A ATCC 3502, ATTTAAAT, *Clostridium botulinum* A Hall, ATTTAAAT, *Clostridium botulinum* Ba4 657, ATTTAAAT, *Deinococcus geothermalis* DSM 11300, ATTGAAAC, *Desulfurococcus kamchatkensis* 1221n, ATTGAAAG, *Fervidicoccus fontis* Kam940, ATTGAAAG, *Fervidobacterium pennivorans* DSM 9078, ATGGAAAC, *Flexibacter litoralis* DSM 6794, ATTGCGAC, *Geobacillus* HH01, ATTGAAAC, *Geobacillus* Y412MC52, ATTGAAAC, *Geobacillus* Y412MC61, ATTGAAAC, *Haliangium ochraceum* DSM 14365, ATTGAAGC, *Halorhodospira halophila* SL1, ATTAAGAC, *Halothermothrix orenii* H 168, ATTGAAAC, *Herpetosiphon aurantiacus* DSM 785, ATTAAAAC, *Hyperthermus butylicus* DSM 5456, ATTGCAAG, *Isosphaera pallida* ATCC 43644, ATTGAAGC, *Mesotoga prima* MesG1 Ag 4 2, ATTGAAAC, *Methanococcus vannielii* SB, ATTGAAAC, *Methanosaeta harundina-* cea 6Ac, ATTGAAAC; *Nostoc* PCC 7524, ATTGAAAC; *Pelotomaculum thermopropionicum* SI, ATTGAAAC; *Pyrobaculum arsenaticum* DSM 13514, ATTGAAAG; *Pyrococcus furiosus* COM1, ATTGAAAG; *Shewanella putrefaciens* 200, CTTAGAAA; *Sulfolobus islandicus* L D 8 5, ATTGAAAG; *Sulfolobus islandicus* M 16 4, ATTGAAAG; *Sulfolobus islandicus* REY15A, ATTGAAAG; *Sulfolobus islandicus* Y G 57 14, ATTGAAAG; *Sulfolobus solfataricus* P2, ATTGAAAG; *Sulfolobus tokodaii* 7, ATTGAAAG; *Sulfurihydrogenibium* YO3AOP1, TTATAAAG; *Synechococcus* JA 2 3B a 2 13, TTGGAAAC; *Synechococcus* PCC 6312, TTGAGCAC; *Synechococcus* PCC 7502, TTGGAAAC; *Thermoanaerobacter tengcongensis* MB4, ATTGAAAC; *Thermoanaerobacterium thermosaccharolyticum* DSM 571, ATTGAAAC; *Thermoanaerobacterium thermosaccharolyticum* M0795, ATTGAAAC; *Thermobaculum terrenum* ATCC BAA 798, GTGAACCG; *Thermocrinis albus* DSM 14484, GTTGAAAG; *Thermomicrobium roseum* DSM 5159, CTTGAAAC; *Thermotoga* RQ2, ATTGAAAC; *Thermotoga maritima* MSB8, ATTGAAAC; *Thermotoga thermarum* DSM 5069, ATGGAAAC; and *Treponema azotonutricium* ZAS 9, ATTAAGAC; and b) a Cmr complex, wherein the Cmr complex comprises at least 6 proteins comprising Cmr1, Cmr2, Cmr3, Cmr4, Cmr5, and Cmr6, wherein the Cmr2 protein comprises a mutation that reduces RNA-activated DNAse activity of the Cmr complex, wherein the mutation comprises a substitution of the histidine of the HD superfamily hydrolase domain, a substitution of the aspartic acid of the HD superfamily hydrolase domain, or the combination thereof, and wherein the Cmr1, Cmr2, Cmr3, Cmr4, Cmr5, and Cmr6 proteins of the Cmr complex have at least 80% identity with the Cmr1, Cmr2, Cmr3, Cmr4, Cmr5, and Cmr6 protein of the same microbe.

9. A method for determining whether a predetermined RNA is present or absent in a sample, comprising:
incubating a composition with a sample,
wherein the composition comprises
a) the CRISPR-RNA (crRNA) and the Cmr complex of claim 1 and a substrate DNA,
wherein the sample is suspected of including a predetermined RNA that comprises a nucleotide sequence that is substantially complementary to at least a portion of the guide region of the crRNA, and
wherein the incubating comprises incubating the sample under suitable conditions for cleavage of the substrate DNA when the predetermined RNA is present.

* * * * *

UNITED STATES PATENT AND TRADEMARK OFFICE
CERTIFICATE OF CORRECTION

PATENT NO. : 11,193,127 B2
APPLICATION NO. : 16/065236
DATED : December 7, 2021
INVENTOR(S) : Rebecca M. Terns, Michael P. Terns and Joshua R. Elmore It is certified that error appears in the above-identified patent and that said Letters Patent is hereby corrected as shown below:

In the Claims

Column 135, Line 42: 'same microbe as described in Table 1.' should be replaced with -same microbe.-

Column 137, Line 61: 'B1429' should be replaced with -BI429-

Column 138, Line 12: 'Glade IIA' should be replaced with -clade IIA-

Column 138, Line 23: 'acetoxidans' should be italicized

Column 138, Line 44: 'Rsivularia' should be replaced with -Rivularia-

Column 140, Line 12: 'YO3A0P1' should be replaced with -YO3AOP1-

Column 140, Line 41: 'mobile' should be italicized

Signed and Sealed this
Ninth Day of May, 2023

Katherine Kelly Vidal
*Director of the United States Patent and Trademark Office*